(12) United States Patent
Shemesh

(10) Patent No.: US 11,517,731 B2
(45) Date of Patent: Dec. 6, 2022

(54) LUER LOCK ADAPTOR

(71) Applicant: SIMPLIVIA HEALTHCARE LTD., Kiryat Shmona (IL)

(72) Inventor: Eli Shemesh, Ashdod (IL)

(73) Assignee: SIMPLIVIA HEALTHCARE LTD., Kiryat Shmona (IL)

( * ) Notice: Subject to any disclaimer, the term of this patent is extended or adjusted under 35 U.S.C. 154(b) by 325 days.

(21) Appl. No.: 16/877,640

(22) Filed: May 19, 2020

(65) Prior Publication Data

US 2020/0338330 A1    Oct. 29, 2020

Related U.S. Application Data

(63) Continuation of application No. 16/006,936, filed on Jun. 13, 2018, now Pat. No. 10,682,505, which is a continuation of application No. 15/003,170, filed on Jan. 21, 2016, now Pat. No. 10,022,531.

(51) Int. Cl.
   *A61M 39/10* (2006.01)

(52) U.S. Cl.
   CPC ........ *A61M 39/10* (2013.01); *A61M 39/1011* (2013.01); *A61M 2039/1027* (2013.01); *A61M 2039/1033* (2013.01); *A61M 2039/1066* (2013.01); *A61M 2039/1077* (2013.01)

(58) Field of Classification Search
   None
   See application file for complete search history.

(56) References Cited

U.S. PATENT DOCUMENTS

| | | | |
|---|---|---|---|
| 2,842,276 A | 7/1958 | Butler |
| 3,359,977 A | 12/1967 | Burke |
| 3,853,158 A | 12/1974 | Whitty |
| 3,872,867 A | 3/1975 | Killinger |
| 4,128,098 A | 12/1978 | Bloom et al. |

(Continued)

FOREIGN PATENT DOCUMENTS

| | | |
|---|---|---|
| CN | 2126081 U | 12/1992 |
| CN | 2452515 | 10/2001 |

(Continued)

OTHER PUBLICATIONS

First Office Action dated Feb. 15, 2021 issued in Australian Application No. 2017208955.

(Continued)

*Primary Examiner* — Manuel A Mendez
(74) *Attorney, Agent, or Firm* — David Postolski; Gearhart Law LLC

(57) ABSTRACT

A luer lock adaptor including a housing defining an axis, an internal luer lock element having a threading, the internal luer lock element being located internally of the housing and being rotatably mounted thereto for rotation about the axis relative to the housing, in a manner which permits rotation of the luer lock element relative to the housing in a first rotation direction about the axis and limits rotation of the luer lock element relative to the housing in a second rotation direction about the axis, opposite to the first rotation direction, whereby the location of the internal luer lock element internally of the housing prevents manual access to the internal luer lock element for limiting rotation thereof in the first rotation direction.

20 Claims, 116 Drawing Sheets

(56) References Cited

U.S. PATENT DOCUMENTS

| | | |
|---|---|---|
| 4,576,211 A | 3/1986 | Valentini et al. |
| 4,588,403 A | 5/1986 | Weiss et al. |
| 4,600,040 A | 7/1986 | Naslund |
| 4,619,651 A | 10/1986 | Kopfer et al. |
| 4,673,404 A | 6/1987 | Gustavsson |
| 4,743,243 A | 5/1988 | Vaillancourt |
| 4,759,756 A | 7/1988 | Forman et al. |
| 4,775,376 A | 10/1988 | Strung |
| 4,834,149 A | 5/1989 | Fournier et al. |
| 4,834,152 A | 5/1989 | Howson et al. |
| 4,919,658 A | 4/1990 | Badia |
| 5,100,010 A | 3/1992 | Waters |
| 5,100,394 A | 3/1992 | Dudar et al. |
| 5,137,524 A | 8/1992 | Lynn et al. |
| 5,167,816 A | 12/1992 | Kruger et al. |
| 5,184,652 A | 2/1993 | Fan |
| 5,238,031 A | 8/1993 | Baeumer et al. |
| 5,340,359 A | 8/1994 | Badia |
| 5,354,287 A | 10/1994 | Wacks |
| 5,501,676 A | 3/1996 | Niedospial et al. |
| 5,549,566 A | 8/1996 | Elias et al. |
| 5,647,409 A | 7/1997 | Christ et al. |
| 5,647,845 A | 7/1997 | Haber et al. |
| 5,738,663 A | 4/1998 | Lopez |
| 5,810,792 A | 9/1998 | Fangrow, Jr. et al. |
| 5,827,262 A | 10/1998 | Neftel et al. |
| 6,022,339 A | 2/2000 | Fowles et al. |
| 6,063,068 A | 5/2000 | Fowles et al. |
| 6,070,623 A | 6/2000 | Aneas |
| 6,120,490 A | 9/2000 | Neftel |
| 6,146,362 A | 11/2000 | Turnbull et al. |
| 6,221,041 B1 | 4/2001 | Russo |
| 6,258,078 B1 | 7/2001 | Thilly |
| 6,378,576 B2 | 4/2002 | Thibault et al. |
| 6,394,979 B1 | 5/2002 | Sharp et al. |
| 6,409,708 B1 | 6/2002 | Wessman |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,571,837 B2 | 6/2003 | Jansen et al. |
| 6,591,876 B2 | 7/2003 | Safabash |
| 6,626,309 B1 | 9/2003 | Jansen et al. |
| 6,715,520 B2 | 4/2004 | Andréasson et al. |
| 6,776,776 B2 | 8/2004 | Alchas et al. |
| 6,875,205 B2 | 4/2005 | Leinsing |
| 6,948,522 B2 | 9/2005 | Newbrough et al. |
| 7,086,431 B2 | 8/2006 | D'Antonio et al. |
| 7,470,258 B2 | 12/2008 | Barker et al. |
| 7,867,215 B2 | 1/2011 | Åkerlund et al. |
| 8,122,923 B2 | 2/2012 | Kraus et al. |
| 8,177,772 B2 | 5/2012 | Christensen et al. |
| 8,196,614 B2 | 6/2012 | Kriheli |
| 8,267,127 B2 | 9/2012 | Kriheli |
| 8,317,743 B2 | 11/2012 | Denenburg |
| 8,377,039 B2 | 2/2013 | Utterberg et al. |
| 8,511,352 B2 | 8/2013 | Kraus et al. |
| 8,752,598 B2 | 6/2014 | Denenburg et al. |
| 9,345,641 B2 | 5/2016 | Kraus et al. |
| 10,022,531 B2 * | 7/2018 | Shemesh ............ A61M 39/1011 |
| 10,682,505 B2 * | 6/2020 | Shemesh ............ A61M 39/1011 |
| 2002/0087118 A1 | 7/2002 | Reynolds et al. |
| 2002/0189712 A1 | 12/2002 | Safabash |
| 2002/0193777 A1 | 12/2002 | Aneas |
| 2003/0055395 A1 | 3/2003 | Manera |
| 2003/0153895 A1 | 8/2003 | Leinsing |
| 2003/0181863 A1 | 9/2003 | Ackley et al. |
| 2004/0024354 A1 | 2/2004 | Reynolds |
| 2005/0131357 A1 | 6/2005 | Denton et al. |
| 2007/0079894 A1 | 4/2007 | Kraus et al. |
| 2007/0088327 A1 | 4/2007 | Guala |
| 2007/0106244 A1 | 5/2007 | Mosler et al. |
| 2008/0103485 A1 | 5/2008 | Kruger |
| 2008/0172039 A1 | 7/2008 | Raines |
| 2009/0036764 A1 | 2/2009 | Rivas et al. |
| 2010/0204670 A1 | 8/2010 | Kraushaar et al. |
| 2012/0123381 A1 | 5/2012 | Kraus et al. |
| 2013/0066293 A1 | 3/2013 | Garfield et al. |
| 2013/0072893 A1 | 3/2013 | Takemoto |
| 2013/0231630 A1 | 9/2013 | Kraus et al. |
| 2014/0020792 A1 | 1/2014 | Kraus et al. |
| 2016/0243001 A1 | 8/2016 | Kraus et al. |
| 2017/0209682 A1 | 7/2017 | Shemesh |

FOREIGN PATENT DOCUMENTS

| | | |
|---|---|---|
| CN | 1237892 C | 1/2004 |
| CN | 1931388 A | 3/2007 |
| CN | 102958558 A | 3/2013 |
| EP | 0126718 A2 | 11/1984 |
| EP | 1181921 A2 | 2/2002 |
| EP | 1145702 A3 | 5/2003 |
| EP | 1323403 A1 | 7/2003 |
| EP | 1228776 B1 | 11/2003 |
| EP | 1257419 B1 | 2/2008 |
| EP | 2259839 A2 | 12/2010 |
| EP | 2463201 B1 | 2/2014 |
| EP | 2712652 A2 | 4/2014 |
| FR | 2560049 A1 | 8/1985 |
| FR | 2815328 A1 | 4/2002 |
| JP | 60501294 A | 8/1985 |
| JP | H0278798 A | 3/1990 |
| JP | S60222059 B | 4/1990 |
| JP | H07213585 A | 8/1995 |
| JP | 2002511445 A | 4/2002 |
| JP | 2005524497 A | 8/2005 |
| JP | 4832585 B2 | 12/2011 |
| WO | 8404673 A1 | 12/1984 |
| WO | 8504801 A1 | 11/1985 |
| WO | 9105581 A1 | 5/1991 |
| WO | 1997046203 A1 | 12/1997 |
| WO | 9813006 A1 | 4/1998 |
| WO | 1998019724 A1 | 5/1998 |
| WO | 9927886 A1 | 6/1999 |
| WO | 9943282 A1 | 9/1999 |
| WO | 0035517 A1 | 6/2000 |
| WO | 0211794 A1 | 2/2002 |
| WO | 02053087 A2 | 7/2002 |
| WO | 02072173 A2 | 9/2002 |
| WO | 03051761 A2 | 6/2003 |
| WO | 2003086529 A1 | 10/2003 |
| WO | 2003086530 A1 | 10/2003 |
| WO | 2004004806 A1 | 1/2004 |
| WO | 2005041846 A2 | 5/2005 |
| WO | 2007124926 A1 | 11/2007 |
| WO | 2009111596 A2 | 9/2009 |
| WO | 2011122296 A1 | 10/2011 |
| WO | 2012002316 A1 | 1/2012 |
| WO | 2015164413 A1 | 10/2015 |
| WO | 2015173612 A1 | 11/2015 |
| WO | 2017125920 A1 | 7/2017 |

OTHER PUBLICATIONS

A communication dated Aug. 11, 2011, which issued during the prosecution of Applicant's European Patent Application No. 04791853.7.

3rd party observations dated May 28, 2009, which issued during the prosecution of Applicant's European Patent Application No. 047918853.7.

A Notice of Allowance dated Feb. 3, 2020 issued in U.S. Appl. No. 16/006,936.

A Notice of Allowance dated Mar. 20, 2018, which issued during the prosecution of U.S. Appl. No. 15/003,170.

A Supplementary European Search Report dated Jan. 20, 2009, which issued during the prosecution of Applicant's European Patent Application No. 04791853.7.

An English Translation of an Office Action dated Dec. 31, 2008, which issued during the prosecution of Applicant's Chinese Patent Application No. 200480035389.8.

An Examination Report dated Jan. 31, 2013, which issued during the prosecution of Indian Patent Application No. 1213/MUMNP/2008.

(56) References Cited

OTHER PUBLICATIONS

An International Preliminary Report on Patentability dated Feb. 15, 2006, which issued during the prosecution of Applicant's PCT/IL2004/000993.
An International Preliminary Report on Patentability dated Jul. 24, 2018, which issued during the prosecution of Applicant's PCT/IL2017/050063.
An International Search Report and a Written Opinion both dated Apr. 26, 2017, which issued during the prosecution of Applicant's PCT/IL2017/050063.
An International Search Report and a Written Opinion both dated Jun. 6, 2005, which issued during the prosecution of Applicant's PCT/IL2004/000993.
An International Search Report dated Oct. 1, 2008, which issued during the prosecution of Applicant's PCT/IL2008/000077.
An Office Action dated Apr. 12, 2011, which issued during the prosecution of Applicant's Japanese Patent Application No. JP 2010-188726, including an English translation.
An Office Action dated Aug. 7, 2019 issued in U.S. Appl. No. 16/006,936.
An Office Action dated Feb. 21, 2014, which issued during the prosecution of Canadian Patent Application No. 2,792,014.
An Office Action dated Feb. 8, 2011, which issued during the prosecution of U.S. Appl. No. 10/577,618.
An Office Action dated Jan. 11, 2016, which issued during the prosecution of U.S. Appl. No. 13/955,375.
An Office Action dated Jan. 30, 2015, which issued during the prosecution of Canadian Patent Application No. 2.792.014.
An Office Action dated Jan. 4, 2016, which issued during the prosecution of Canadian Patent Application No. 2,792,014.
An Office Action dated Jul. 11, 2011, which issued during the prosecution of Canadian Patent Application No. 2,541,615.
An Office Action dated Jul. 4, 2011, which issued during the prosecution of Japanese Patent Application No. 2010-200146.
An Office Action dated Jun. 12, 2019, which was issued during the prosecution of Brazil Patent Application No. PII0073841.
An Office Action dated Mar. 24, 2011, which issued during the prosecution of U.S. Appl. No. 10/577,618.
An Office Action dated Mar. 24, 2017, which issued during the prosecution of U.S. Appl. No. 15/175,385.
An Office Action dated May 11, 2015, which issued during the prosecution of U.S. Appl. No. 13/854,348.
An Office Action dated May 15, 2015, which issued during the prosecution of U.S. Appl. No. 13/955,375.
An Office Action dated May 4, 2016, which issued during the prosecution of U.S. Appl. No. 13/955,375.
An Office Action dated Nov. 15, 2010, which issued during the prosecution of Applicant's Japanese Patent Application No. JP2010-188726, including an English Translation.
An Office Action dated Nov. 16, 2015, which issued during the prosecution of U.S. Appl. No. 13/854,348.
An Office Action dated Oct. 1, 2012, which issued during the prosecution of U.S. Appl. No. 13/357,004.
An Office Action together with English comments dated Apr. 23, 2010, which issued during the prosecution of Applicant's Japanese Patent Application No. JP2006-537556.
European Search Report dated Nov. 18, 2016, which issued during the prosecution of Applicant's European Application No. 16173568.3.
European Search Report dated Oct. 11, 2013, which issued during the prosecution of Applicant's European Application No. 13179757.3.
Extended European Search Report dated May 15, 2012, which issued during the prosecution of European Application No. 12154647.7.
Microfilm of Utility application S61-176496 (Publication of Unexamined Utility Model Application No. S63-84239) draft on Apr. 23, 2020.
Notice of Allowance dated Apr. 15, 2013, which issued during the prosecution of U.S. Appl. No. 13/357,004.
Notice of Allowance dated Aug. 24, 2016, which issued during the prosecution of U.S. Appl. No. 13/955,375.
Notice of Allowance dated Feb. 19, 2016, which issued during the prosecution of U.S. Appl. No. 13/854,348.
Notice of Allowance dated Jan. 26, 2016, which issued during the prosecution of U.S. Appl. No. 13/854,348.
Notice of Allowance dated Nov. 8, 2016, which issued during the prosecution of U.S. Appl. No. 15/143,845.
Notice of Allowance dated Oct. 28, 2011, which issued during the prosecution of U.S. Appl. No. 10/577,618.
Supplementary European Search Report dated Jun. 30, 2014, which issued during the prosecution of Applicant's European Application No. 13179757.3.
U.S. Appl. No. 60/516,613, filed Oct. 30, 2003.
European Search Report dated Aug. 14, 2019 issued in PCT/IL2017050063.

\* cited by examiner

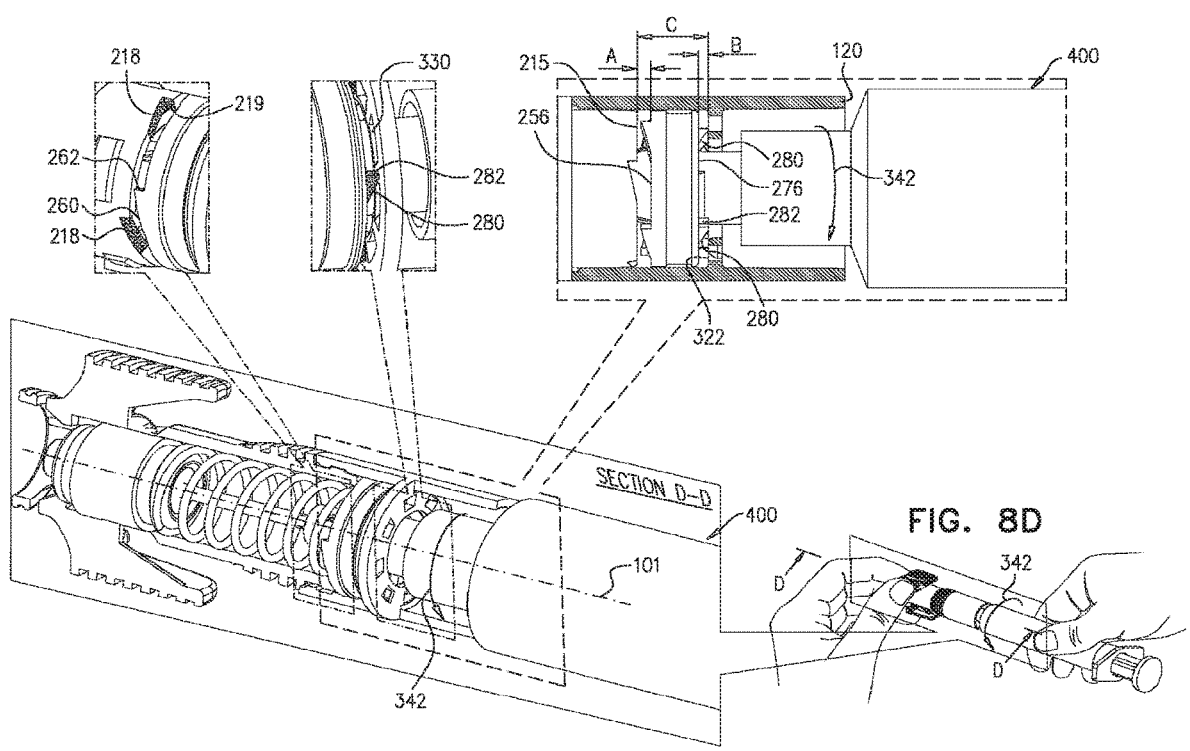

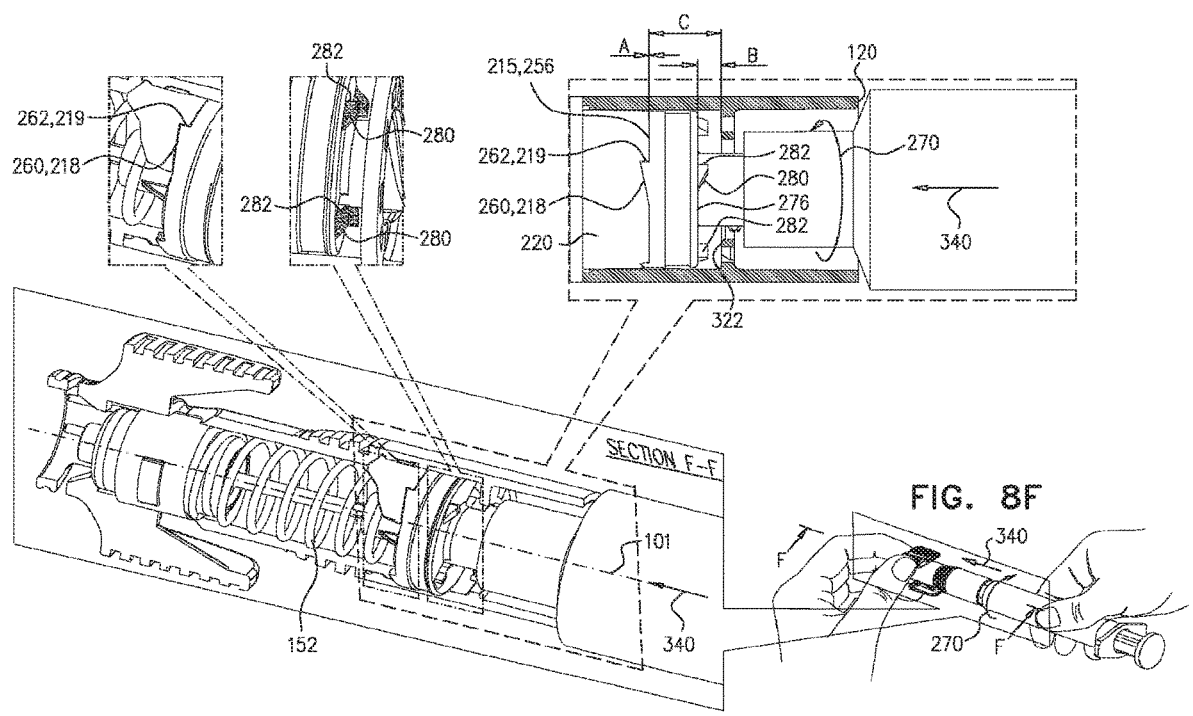

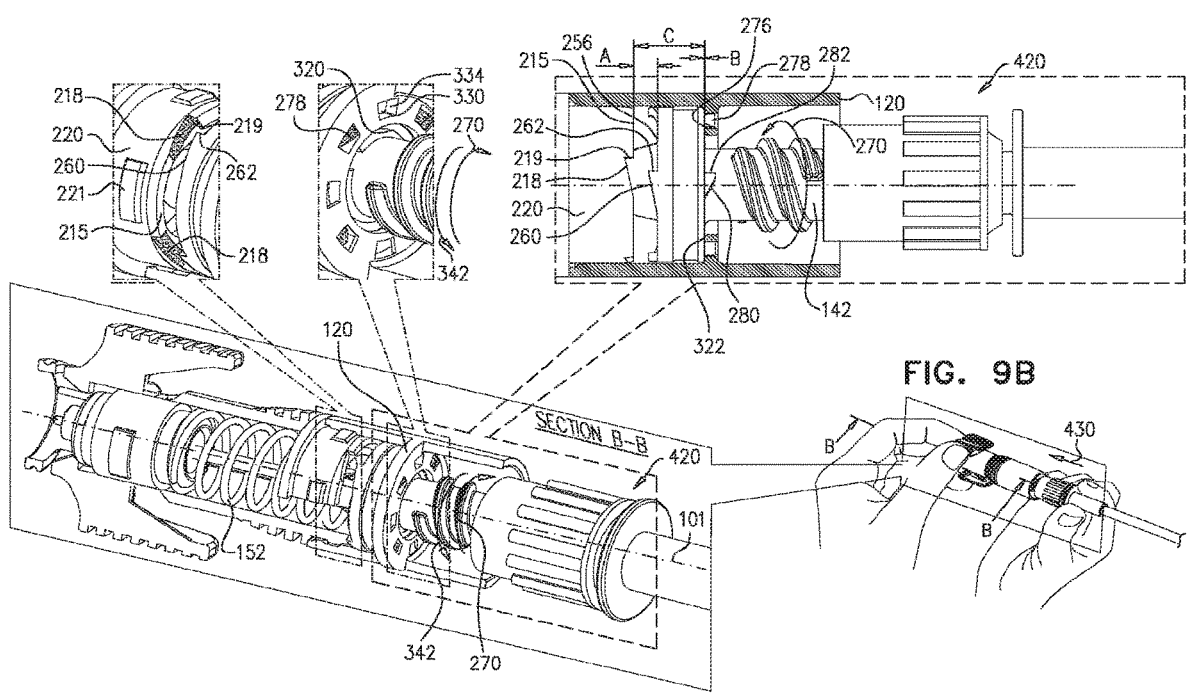

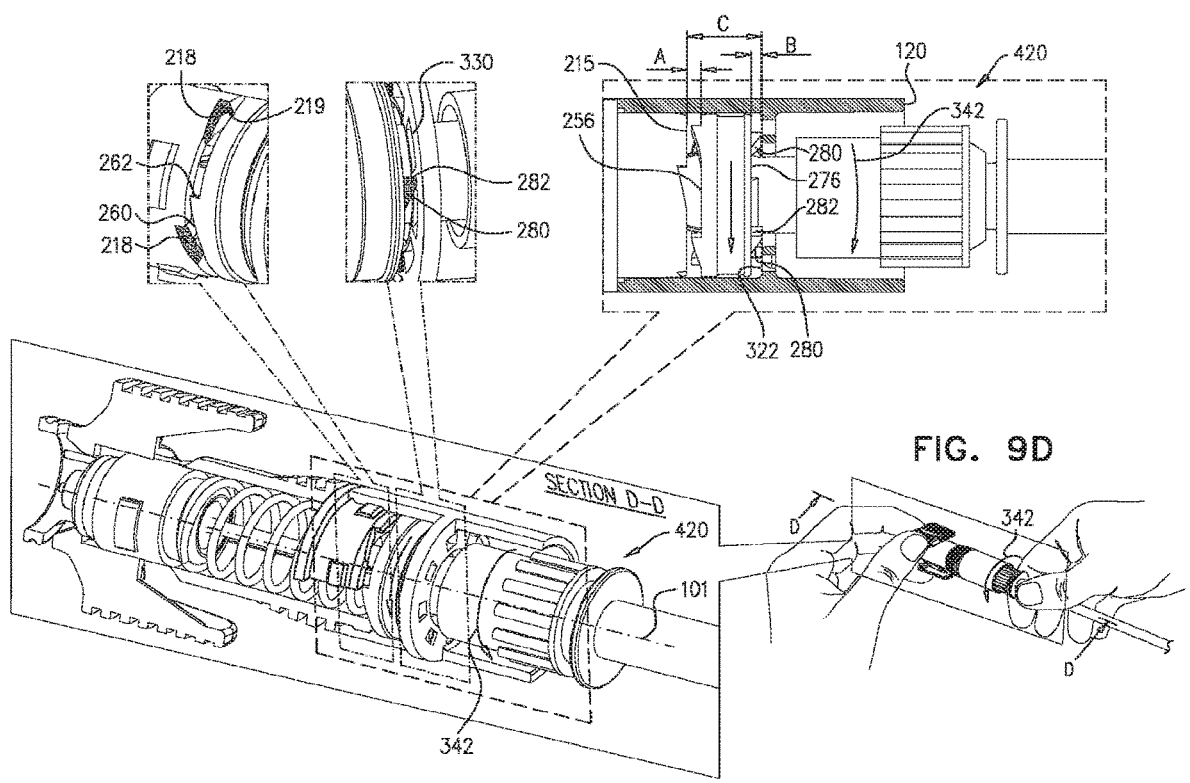

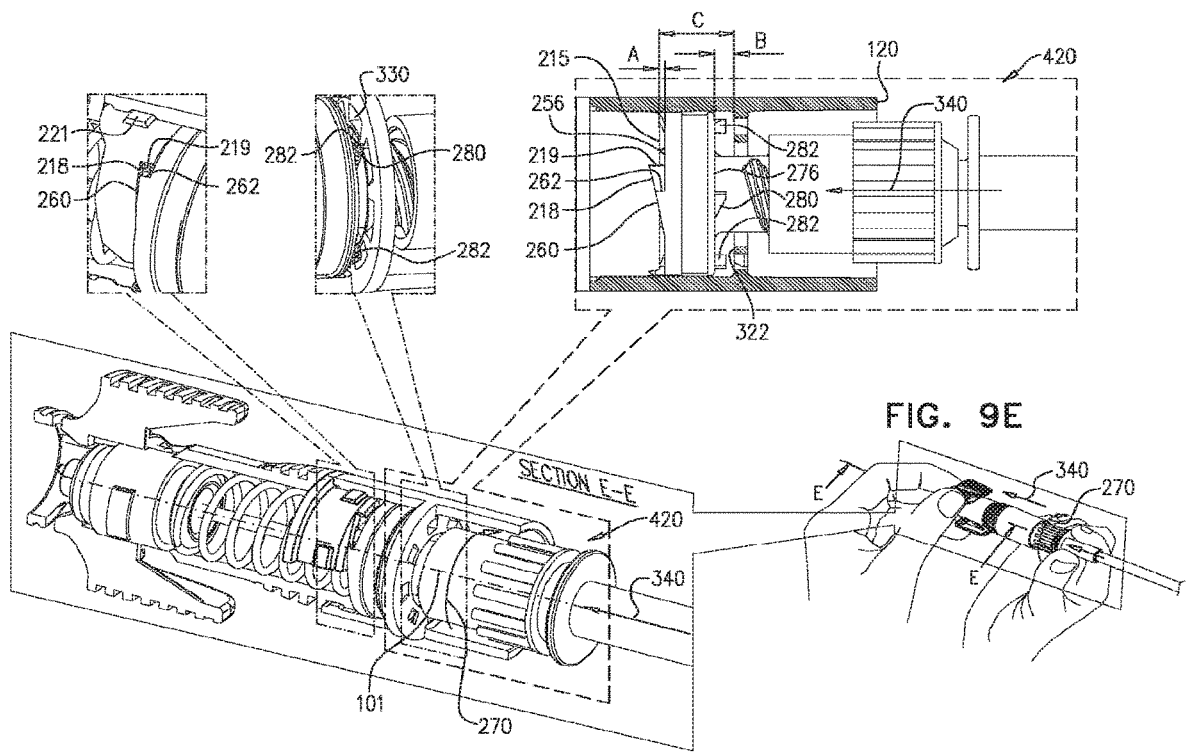

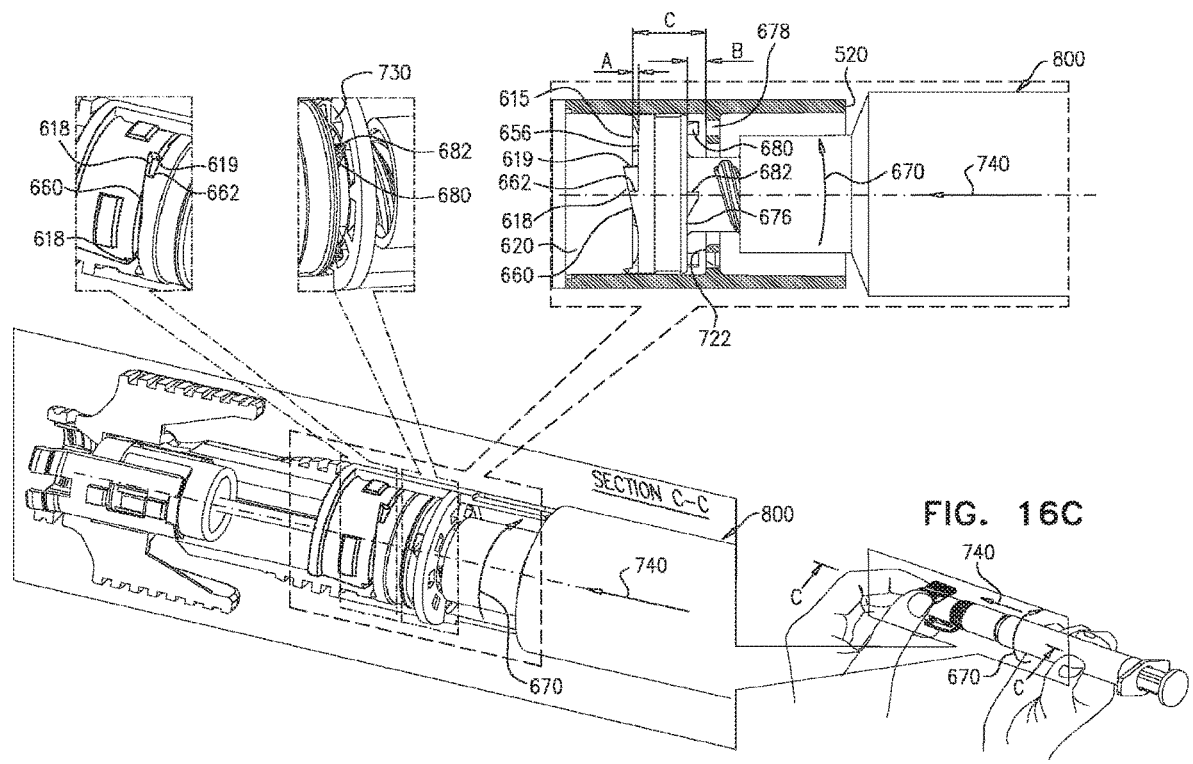

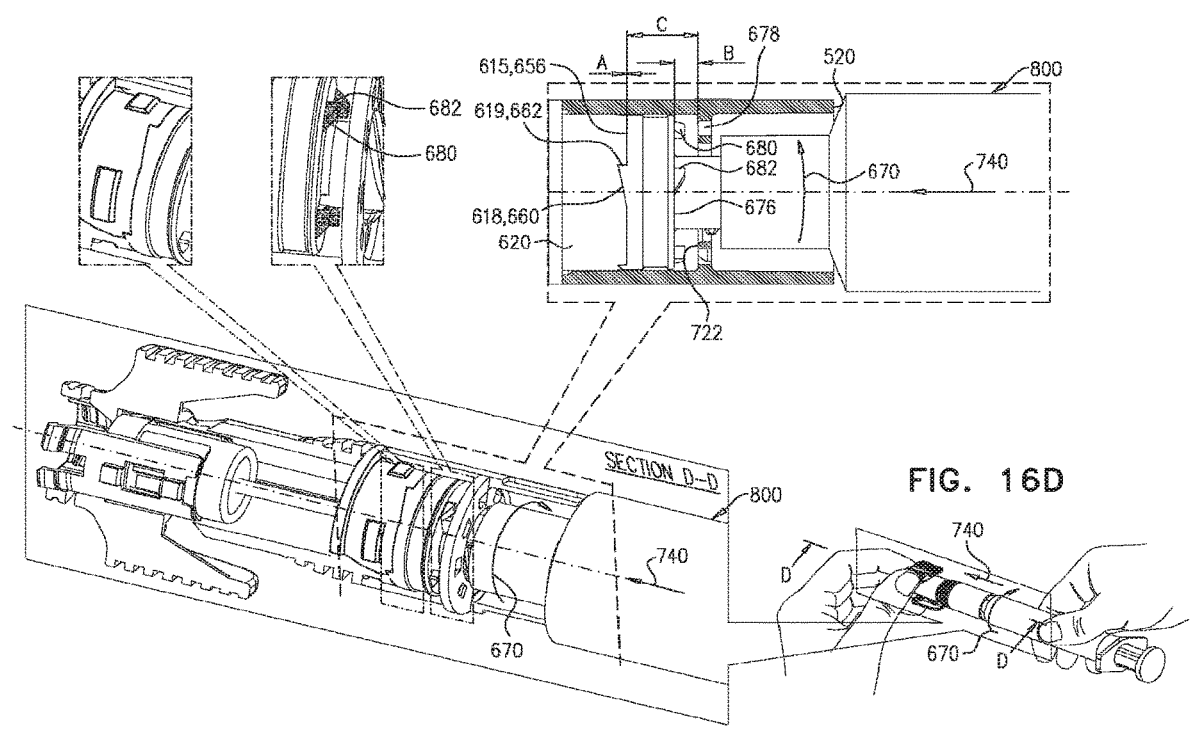

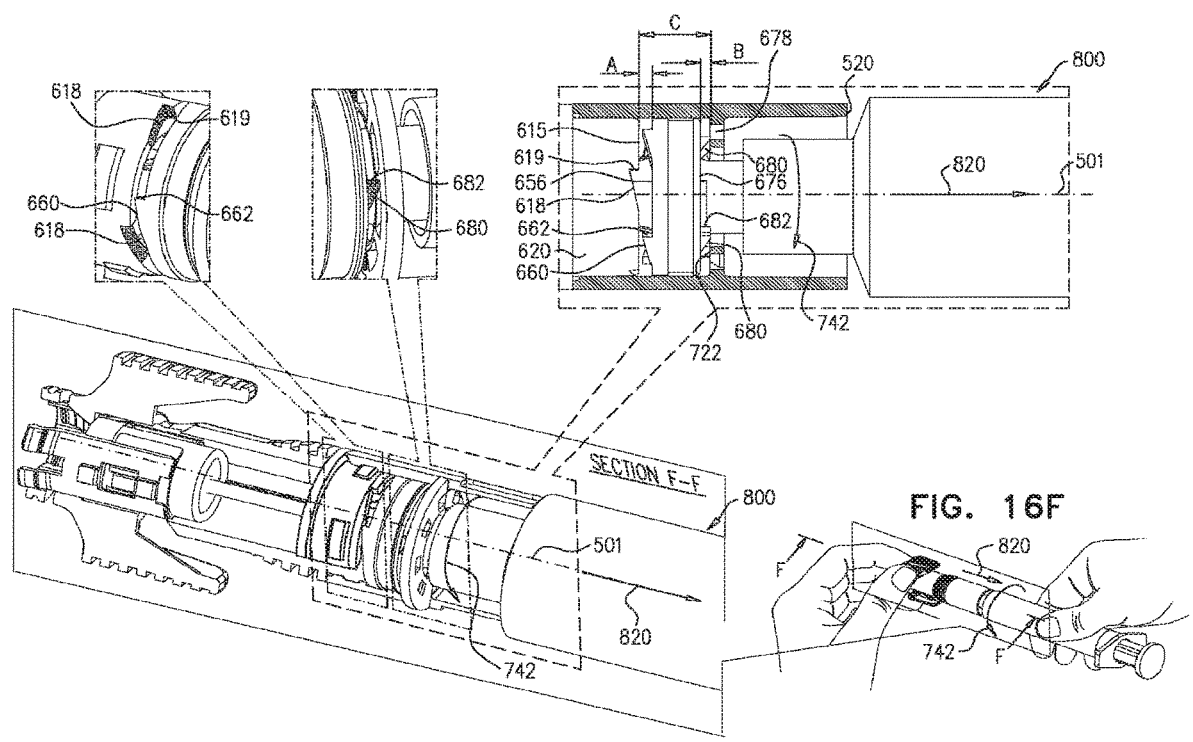

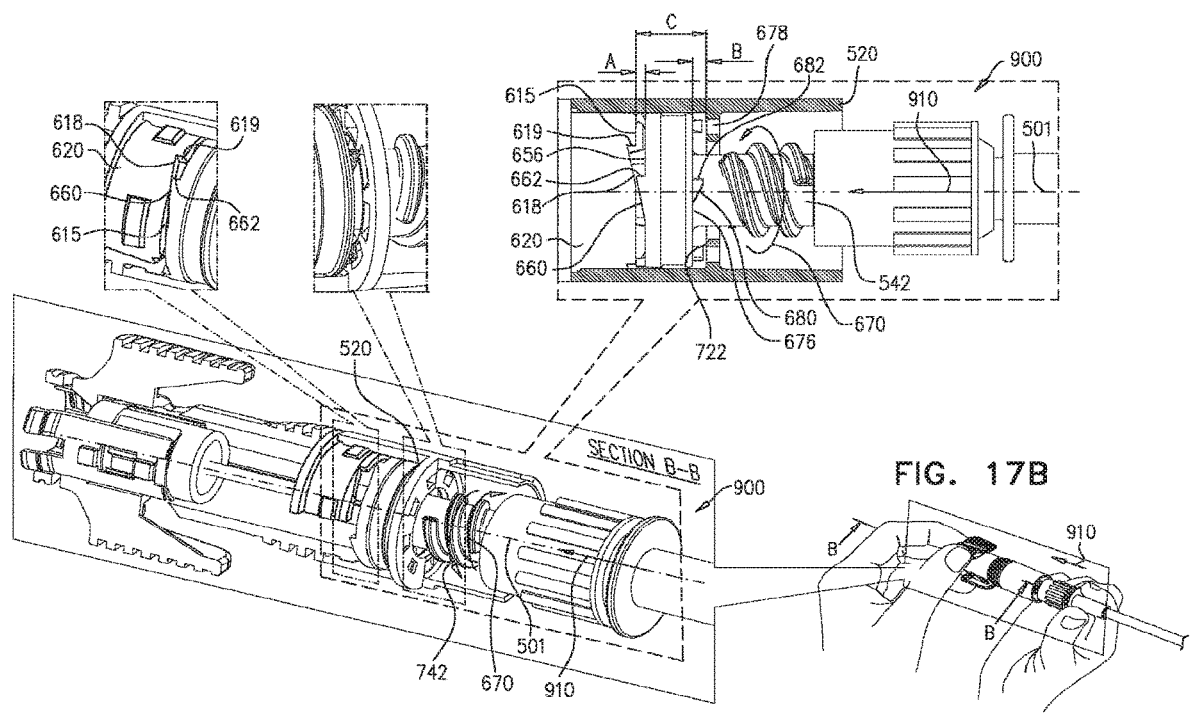

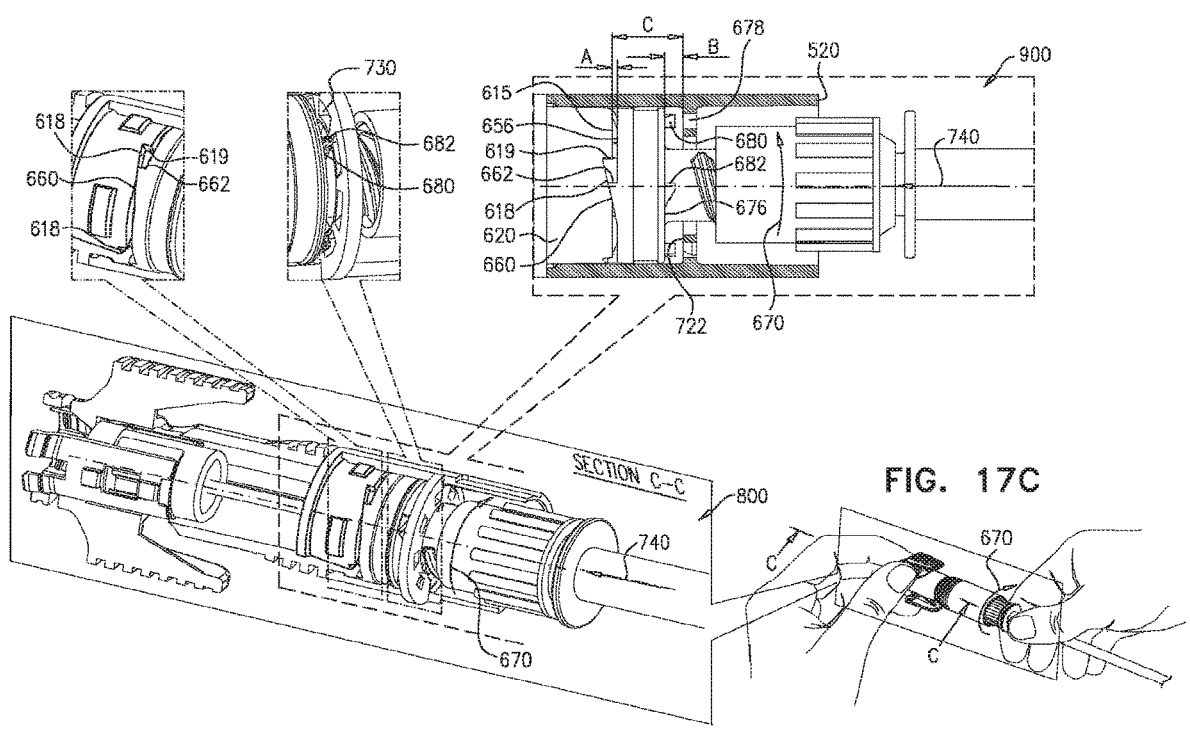

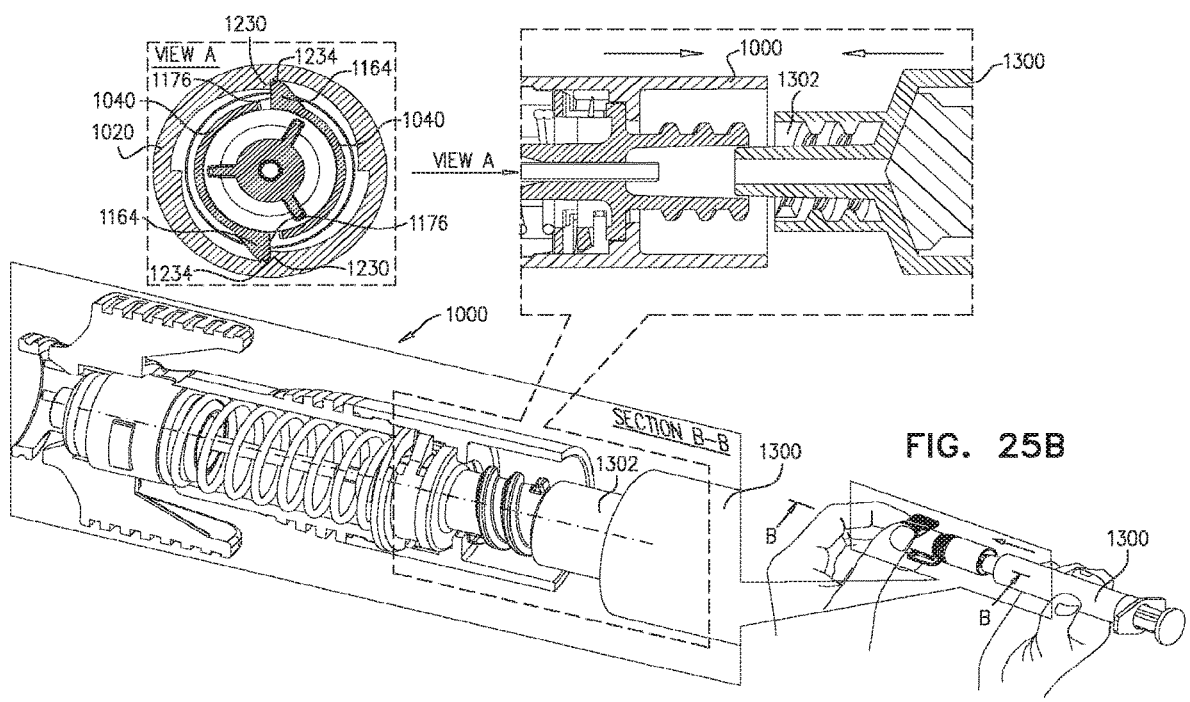

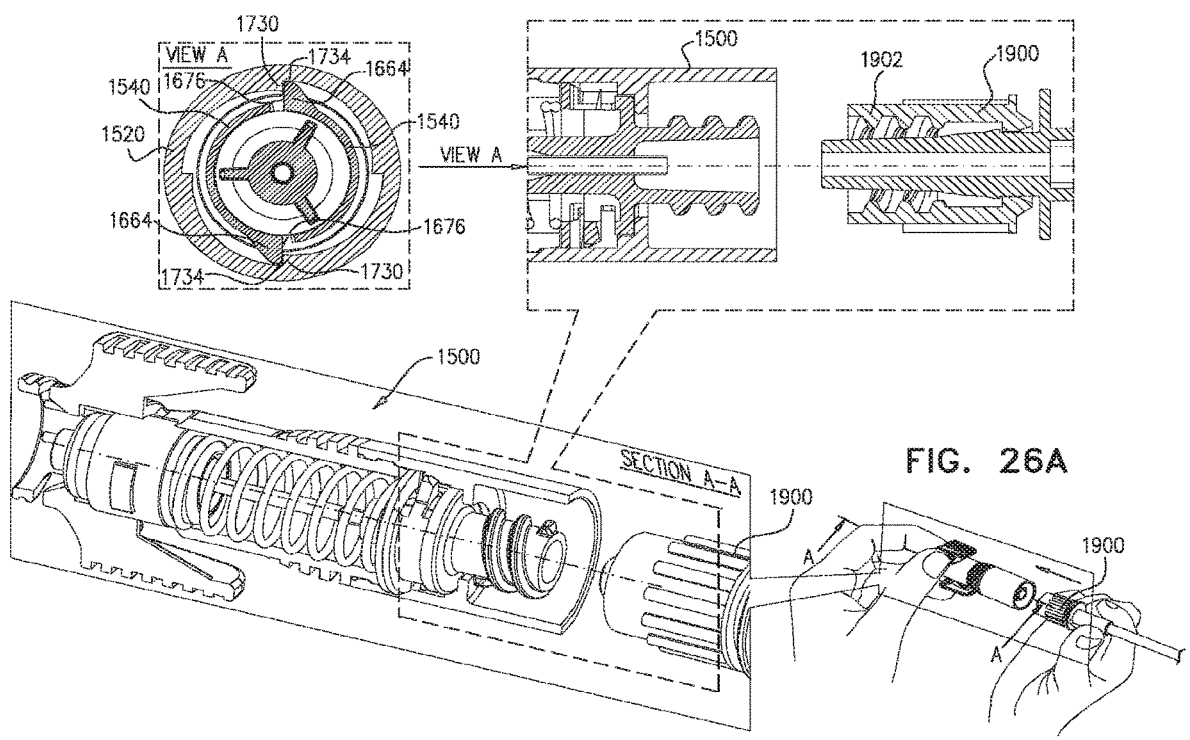

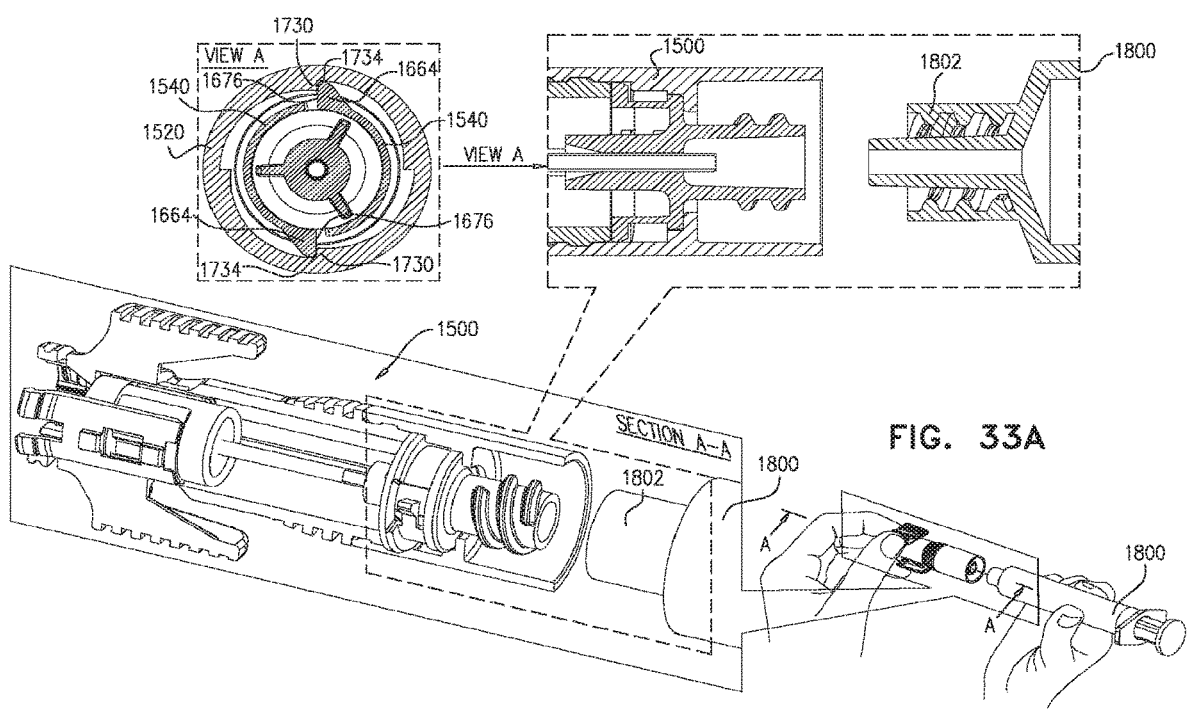

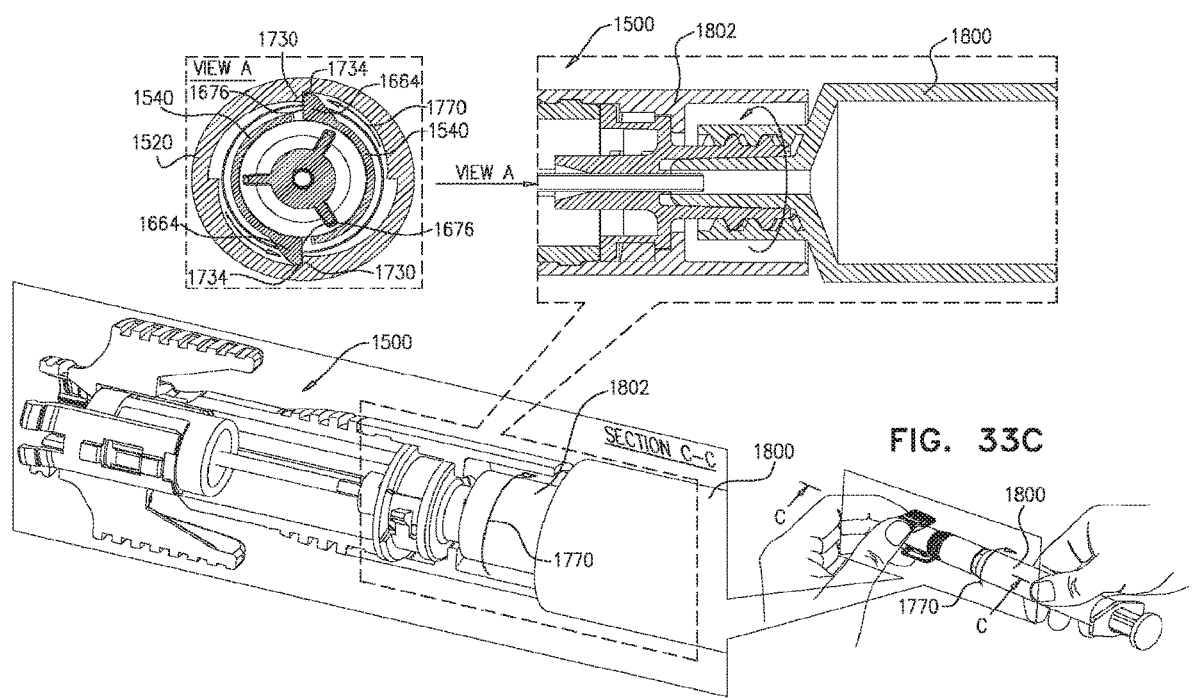

LUER LOCK ADAPTOR

CROSS-REFERENCE TO RELATED APPLICATIONS

This application is a U.S. Continuation Application of U.S. Non-Provisional patent application Ser. No. 16/006,936 filed on Jun. 13, 2018 and patented as U.S. Pat. No. 10,682,505 on Jun. 16, 2020, which is a U.S. Continuation Application of U.S. Non-Provisional patent application Ser. No. 15/003,170 filed on Jan. 21, 2016 and patented as U.S. Pat. No. 10,022,531, the contents of which are hereby fully incorporated by reference.

FIELD OF THE INVENTION

The present invention relates to medical connectors generally and more particularly to luer lock adaptors.

BACKGROUND OF THE INVENTION

Various types of luer lock adaptors are known in the art.

SUMMARY OF THE INVENTION

The present invention seeks to provide an improved luer lock adaptor.

There is thus provided in accordance with a preferred embodiment of the present invention, a luer lock adaptor including a housing defining an axis, an internal luer lock element having a threading, the internal luer lock element being located internally of the housing and being rotatably mounted thereto for rotation about the axis relative to the housing, in a manner which permits rotation of the luer lock element relative to the housing in a first rotation direction about the axis and limits rotation of the luer lock element relative to the housing in a second rotation direction about the axis, opposite to the first rotation direction, whereby the location of the internal luer lock element internally of the housing prevents manual access to the internal luer lock element for limiting rotation thereof in the first rotation direction.

In accordance with a preferred embodiment of the present invention an external luer lock element can be threadably locked to the internal luer lock element in frictional threaded engagement therewith by rotation of the external luer lock element in the second rotation direction in threading engagement with the internal luer lock element, since rotation of the internal luer lock element in the second rotation direction is limited and subsequent to locking of the external luer lock element to the internal luer lock element, the external luer lock element cannot be threadably disconnected from the internal luer lock element by rotation of the external luer lock element in the first rotation direction, since rotation of the internal luer lock in the first rotation direction is not limited and since the frictional engagement between the external luer lock element and the internal luer lock element causes the internal luer lock element to rotate in the first rotation direction together with the external luer lock element when the external luer lock element is rotated in the first rotation direction.

Preferably, the housing includes a forward housing portion defining a port connection end and a rearward housing portion defining a luer connection end. Additionally, the forward housing portion and the rearward housing portion are fixedly attached to each other so as to prevent both relative axial movement and relative azimuthal movement therebetween with respect to the axis.

In accordance with a preferred embodiment of the present invention the luer lock adaptor also includes a septa housing portion disposed within the forward housing portion. Additionally, the luer lock adaptor also includes a compression spring which urges the septa housing forwardly with respect to the internal luer lock element.

Preferably, the internal luer lock element includes a hub element, including a female luer connector portion at a rearward-facing end thereof. Additionally, the hub element includes, at a forward-facing end thereof, a needle mounting portion and a needle having a sharp tip is mounted onto the needle mounting portion and extends axially forwardly along the axis into the forward housing portion, such that in the absence of a port connection, the sharp tip of the needle is located within the septa housing.

In accordance with a preferred embodiment of the present invention the housing and the internal luer lock element each include ratchet-type portions which cooperate to permit free rotation of the internal luer lock element relative to the housing about the axis in the first rotation direction and limit rotation of the internal luer lock element relative to the housing in the second rotation direction. Additionally, the ratchet-type portions include at least one toothed edge formed on the housing and at least one toothed edge formed on the internal luer lock element, the at least one toothed edge formed on the internal luer lock element being arranged to cooperate with the at least one toothed edge formed on the housing for limiting relative rotation about the axis between the internal luer lock element and the housing in the second rotation direction.

Preferably, the at least one toothed edge formed on the internal luer lock element and the at least one toothed edge formed on the housing each include a single toothed edge. Alternatively, the at least one toothed edge formed on the internal luer lock element and the at least one toothed edge formed on the housing each include a pair of toothed edges.

In accordance with a preferred embodiment of the present invention the internal luer lock element is axially displaceable along the axis relative to the housing between a first relative axial position and a second relative axial position and the at least one toothed edge formed on the housing and at least one toothed edge formed on the internal luer lock element cooperate for limiting relative rotation about the axis between the internal luer lock element and the housing in the second rotation direction when the internal luer lock element is in either of the first relative axial position and the second relative axial position. Additionally, the at least one toothed edge formed on the housing and at least one toothed edge formed on the internal luer lock element cooperate for permitting relative rotation about the axis between the internal luer lock element and the housing in the first rotation direction when the internal luer lock element is in any position relative to the housing between and including the first relative axial position and the second relative axial position.

Preferably, the ratchet-type portions include at least one radially extending tooth formed on at least one of the housing and the internal luer lock element and at least one socket formed on another of the housing and the internal luer lock element for limiting relative rotation about the axis between the internal luer lock element and the housing in the second rotation direction. Additionally, the at least one radially extending tooth is formed on the housing and the at least one socket is formed on the internal luer lock element.

BRIEF DESCRIPTION OF THE DRAWINGS

The present invention will be understood and appreciated more fully from the following detailed description, taken in conjunction with the drawings in which:

FIGS. 8A, 8B, 8C, 8D, 8E, 8F and 8G are simplified illustrations of the luer lock adaptor of FIGS. 1A-7C in respective first, second, third, fourth, fifth, sixth and seventh operative orientations with respect to a conventional luer lock syringe;

FIGS. 9A, 9B, 9C, 9D, 9E, 9F and 9G are simplified illustrations of the luer lock adaptor of FIGS. 1A-7C in respective first, second, third, fourth, fifth, sixth and seventh operative orientations with respect to a conventional luer lock connector;

FIGS. 16A, 16B, 16C, 16D, 16E and 16F are simplified illustrations of the luer lock adaptor of FIGS. 10A-16C in respective first, second, third, fourth, fifth and sixth operative orientations with respect to a conventional luer lock syringe;

FIGS. 17A, 17B, 17C, 17D, 17E and 17F are simplified illustrations of the luer lock adaptor of FIGS. 10A-15C in respective first, second, third, fourth, fifth and sixth operative orientations with respect to a conventional luer lock connector;

FIGS. 25A, 25B, 25C, 25D, 25E and 25F are simplified illustrations of the luer lock adaptor of FIGS. 18A-24C in respective first, second, third, fourth, fifth and sixth operative orientations with respect to a conventional luer lock syringe;

FIGS. 26A, 26B, 26C, 26D, 26E and 26F are simplified illustrations of the luer lock adaptor of FIGS. 1A-7C in respective first, second, third, fourth, fifth and sixth operative orientations with respect to a conventional luer lock connector;

FIGS. 33A, 33B, 33C, 33D, 33E and 33F are simplified illustrations of the luer lock adaptor of FIGS. 18A-24C in respective first, second, third, fourth, fifth and sixth operative orientations with respect to a conventional luer lock syringe.

DETAILED DESCRIPTION OF PREFERRED EMBODIMENTS

Figure 1A:
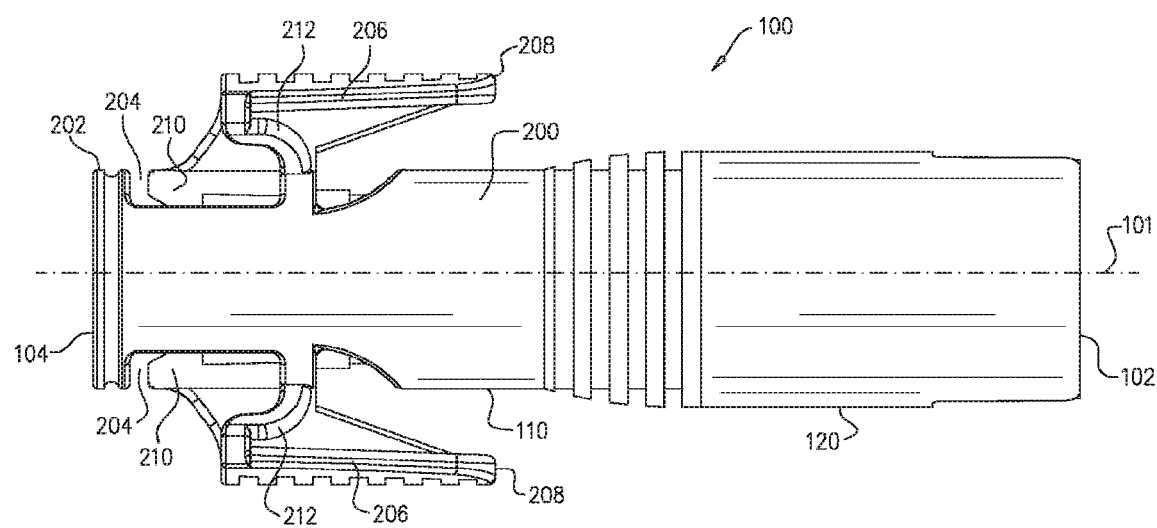
FIGS. 1A, 1B, 1C, 1D and 1E are simplified respective first and second side view, first and second end view illustrations and a sectional illustration, taken along lines IE-IE in FIG. 1D, of a luer lock adaptor constructed and operative in accordance with a preferred embodiment of the present invention.
Figure 1B:
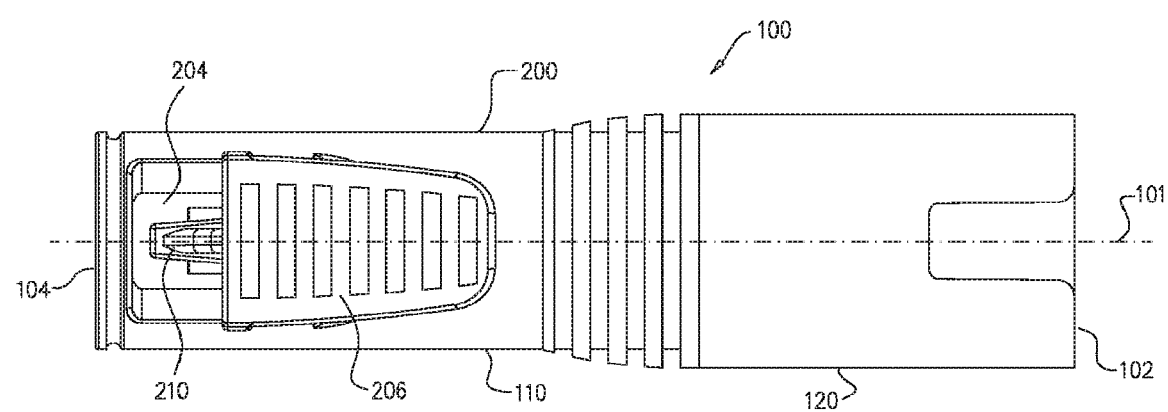
Figure 1C:
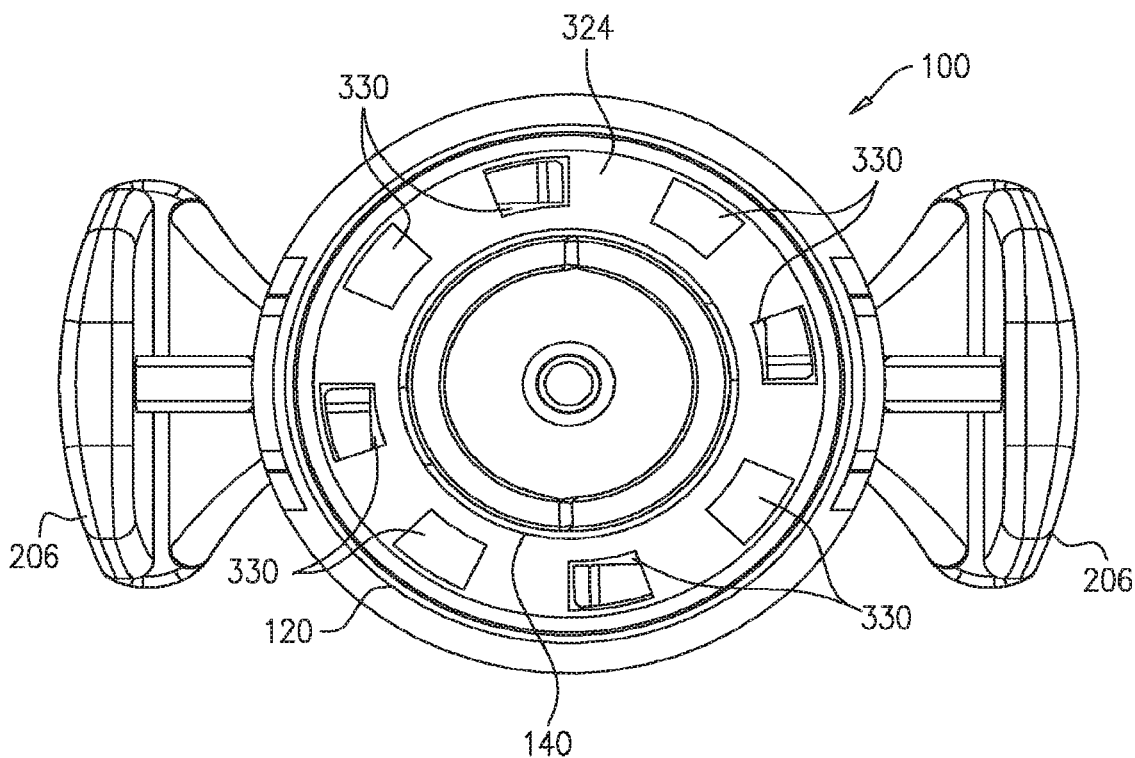
Figure 1D:
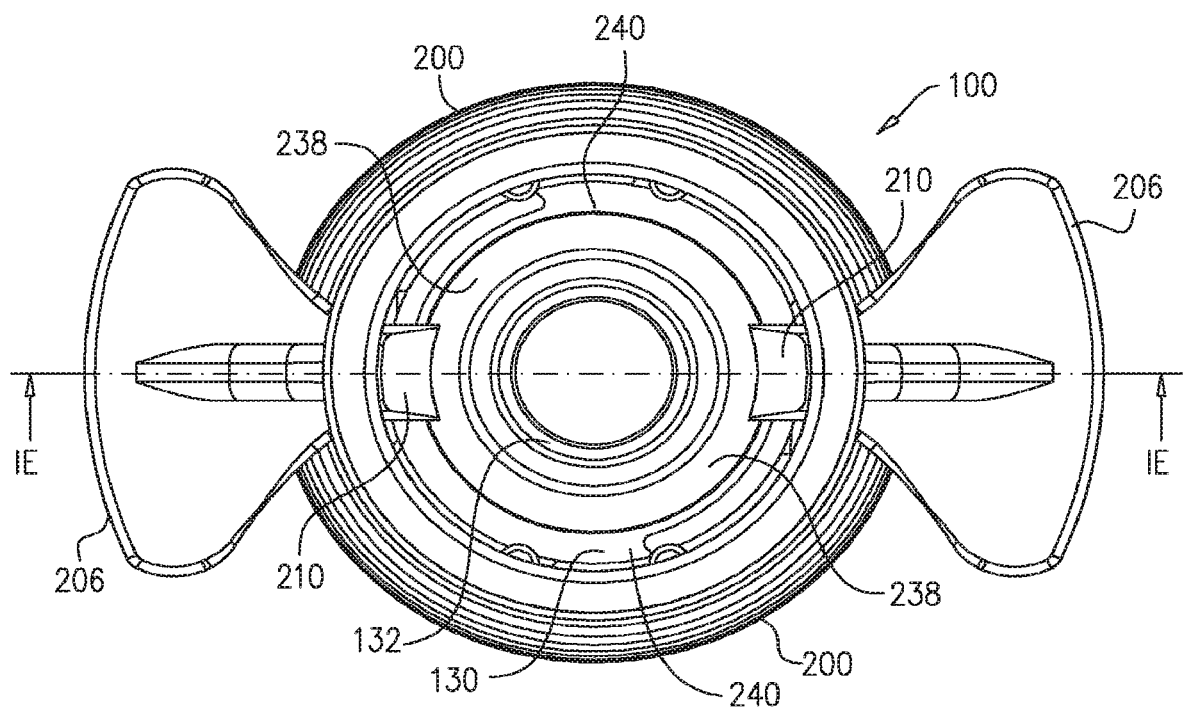
Figure 1E:
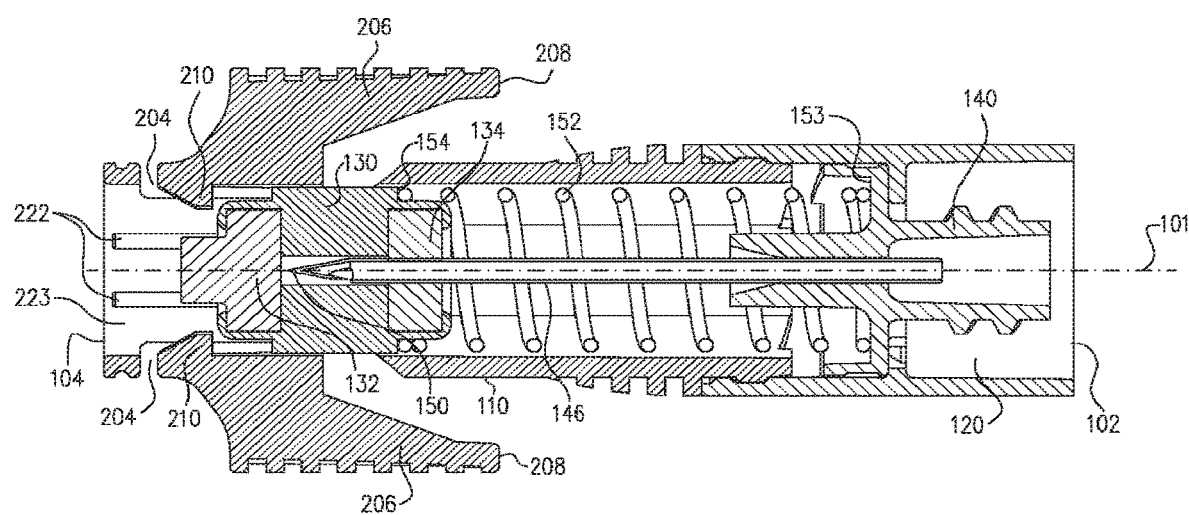
Figure 2:
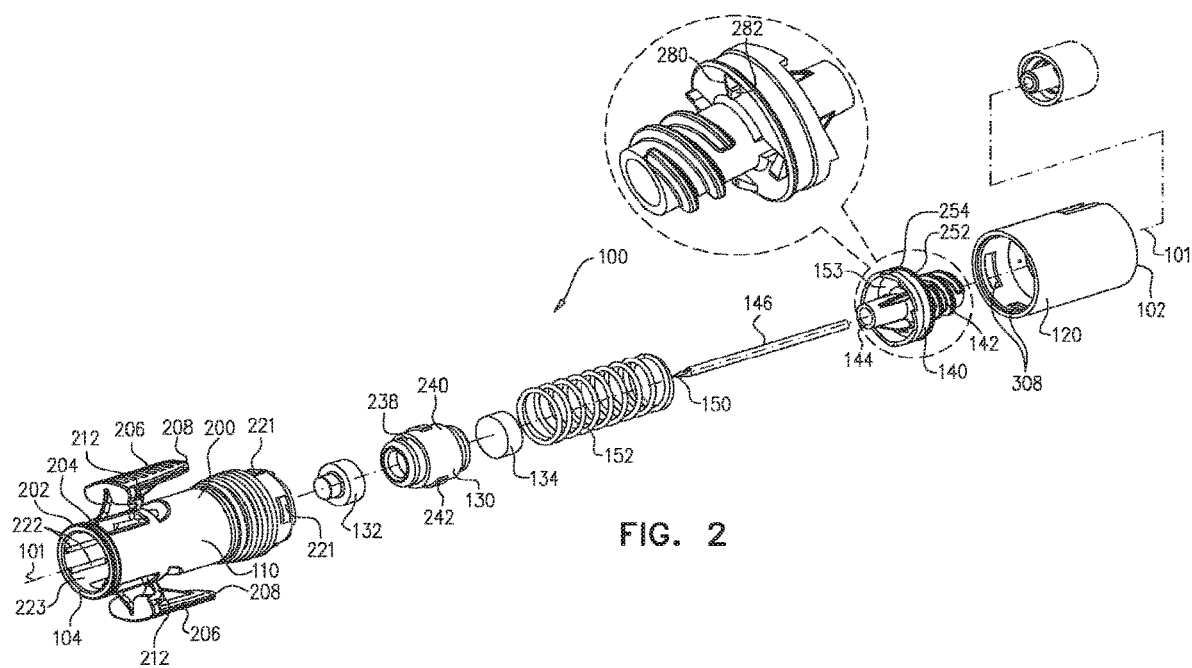
FIG. 2 is a simplified exploded view illustration of the luer lock adaptor of FIGS. 1A-1E.

Reference is now made to FIGS. 1A, 1B, 1C, 1D and 1E, which are simplified respective first and second side view and first and second end view illustrations and a sectional illustration, taken along lines IE-IE in FIG. 1D, of a luer lock adaptor constructed and operative in accordance with a preferred embodiment of the present invention, and to FIG. 2, which is a simplified exploded view illustration of the luer lock adaptor of FIGS. 1A-1E.

As seen in FIGS. 1A-1E and 2, there is provided a luer lock adaptor 100, which extends generally along a longitudinal axis 101 and has a luer connection end 102 and a port connection end 104. Although a female luer connection end 102 is shown, the luer connection end may be any suitable luer connection end. Although a specific port connection end 104 is shown, the port connection end 104 may be any suitable port connection end 104. Various examples of port connections are described in applicant/assignees U.S. Pat. No. 8,122,923, the contents of which are hereby incorporated by reference. The luer lock adaptor 100 preferably includes a forward housing portion 110 and a rearward housing portion 120, which are preferably fixedly snap-fit to each other so as to prevent both relative axial movement and relative azimuthal movement about axis 101 therebetween. Alternatively, forward housing portion 110 and rearward housing portion 120 may be formed as a single integral unit. The forward-facing direction is facing to the left in FIG. 1A.

Disposed within forward housing portion 110 is a septa housing portion 130 onto which is fixedly mounted a forward septum 132 and a rearward septum 134, which are retained in the septa housing portion 130, preferably by ultrasonic swaging of forward and rearward edges of the septa housing portion 130.

Disposed within rearward housing portion 120 is a hub element 140, defining a female luer connector portion 142, at a rearward-facing end thereof, and, at a forward-facing end thereof, a needle mounting portion 144. A needle 146, mounted onto needle mounting portion 144, extends axially forwardly along longitudinal axis 101 into forward housing portion 110, such that in the absence of a port connection at the port connection end 104, a sharp tip 150 of needle 146 is located within the septa housing 130 between rearward septum 134 and forward septum 132. A compression spring 152 urges septa housing 130 forwardly with respect to hub element 140 and needle 146. Compression spring 152 is seated between a forward-facing surface 153 of hub element 140 and a rearward facing surface 154 of septa housing 130.

It is a particular feature of an embodiment of the present invention that there is provided a luer lock adaptor, here luer lock adaptor 100, which includes a housing, here housing portions 110 and 120, which define an axis, here axis 101, and an internal luer lock element, here hub element 140, the internal luer lock element being located internally of the housing and being rotatably mounted thereto for rotation about the axis relative to the housing, in a manner which permits rotation of the luer lock element relative to the housing in a first rotation direction about the axis and limits rotation of the luer lock element relative to the housing in a second rotation direction about the axis, opposite to the first rotation direction, whereby the location of the internal luer lock element internally of the housing prevents manual access to the internal luer lock element for limiting rotation thereof in the first rotation direction.

Reference is now additionally made to FIGS. 3A, 3B, 3C and 3D, which are simplified respective first and second side view, perspective luer connection end view, and sectional view illustrations of forward housing portion 110, forming part of the luer lock adaptor of FIGS. 1A-2.

As seen in FIGS. 3A-3D, the forward housing portion 110 comprises a generally circular cylindrical main portion 200 having a forward circumferential rim 202 and a pair of opposite side cut outs 204 adjacent which are mounted a pair of oppositely directed port connector engagement portions 206.

Each of port connector engagement portions 206 preferably includes a ribbed finger engagement surface 208, which is connected to a retractable port connector engagement tooth 210. Each of port connector engagement portions 206 is flexibly mounted onto main portion 200 by means of a flexible mounting arch 212 which spans a corresponding cut out 204. Manual pressing on engagement surface 208 causes retraction of port connector engagement tooth 210, such that simultaneous manual pressing on engagement surfaces 208 of both of port connector engagement portions 206 enables disengagement of a port connector (not shown) from the interior of cylindrical main portion 200.

Figure 3A:
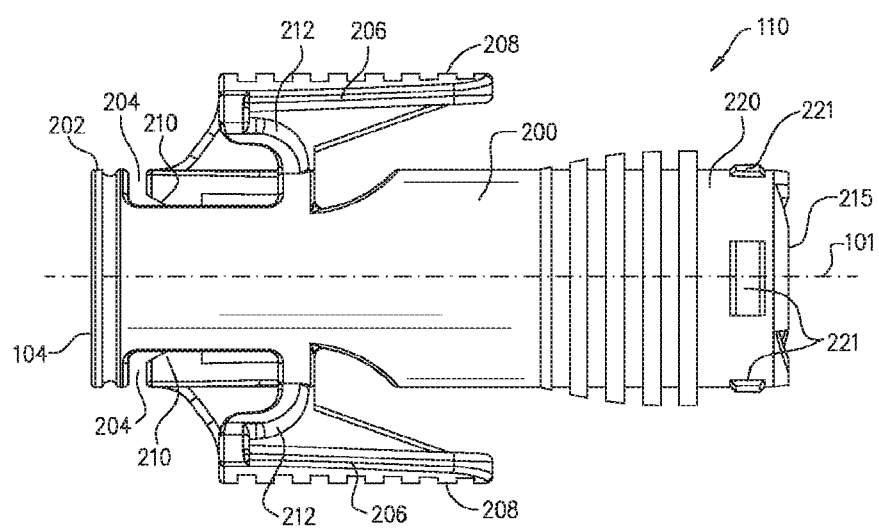
FIGS. 3A, 3B, 3C and 3D are simplified respective first and second side view, perspective luer connection end view and sectional view illustrations of a forward housing portion forming part of the luer lock adaptor of FIGS. 1A-2, FIG. 3D being taken along lines IIID-IIID in FIG. 3C.
Figure 3B:
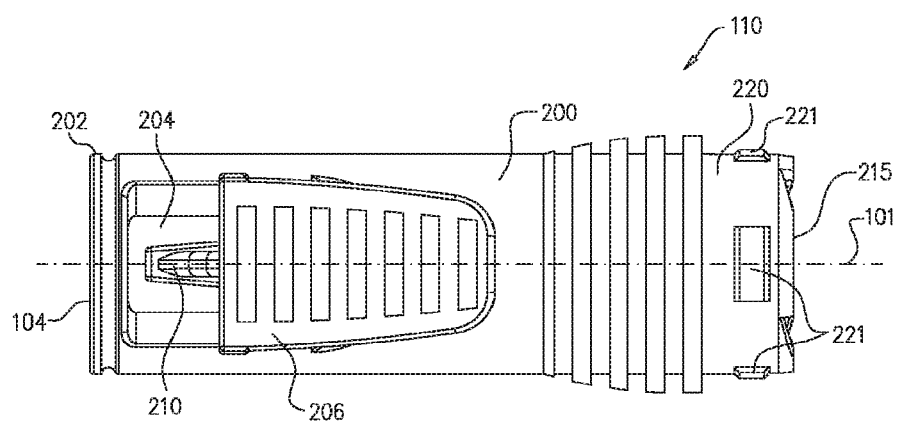
Figure 3C:
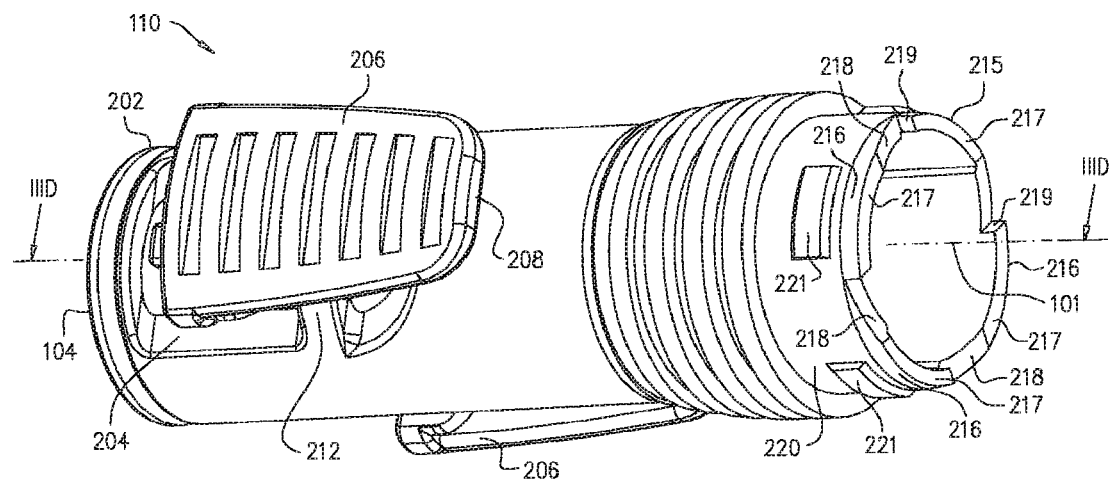
Figure 3D:
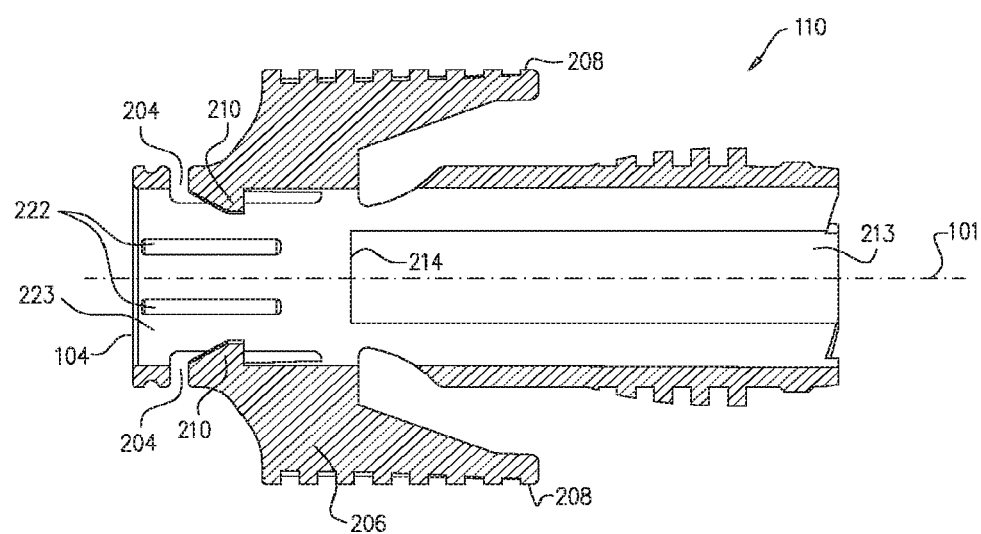

As seen clearly in FIG. 3D, opposite interior surfaces of main portion 200 each define a septa housing guiding recess 213 having a forward stop-defining wall surface 214, which limits the forward displacement of the septa housing 130 relative to the forward housing portion 110.

As seen particularly clearly in FIG. 3C, forward housing portion 110 includes a rearwardly-facing toothed edge 215 having formed thereon a plurality of teeth 216, typically four in number, each including a rearwardly-facing partially circumferential surface 217, a rearwardly and clockwise-facing inclined surface 218 and an axially extending, counter-clockwise facing, locking surface 219 from a forwardly-facing perspective.

Adjacent rearwardly-facing toothed edge 215 on a radially outward surface 220 of main portion 200 are a plurality of mutually spaced circumferential elongate protrusions 221.

As seen in FIG. 3D, a plurality of protrusions 222, preferably a pair on either side, lie on opposite sides of an inwardly-facing circumferential wall surface 223 of the hollow port connection end 104 of the luer lock adaptor 100.

Figure 4A:
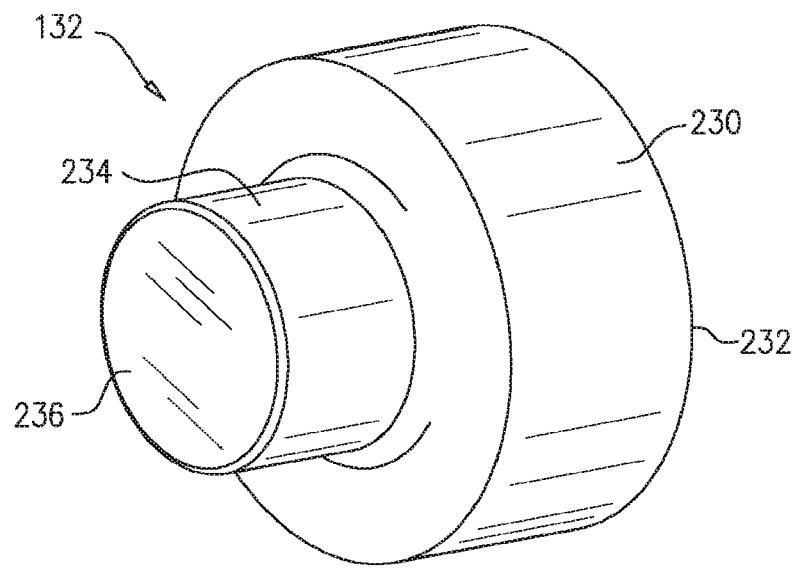
FIGS. 4A and 4B are simplified pictorial illustrations of a forward septum, forming part of the luer lock adaptor of FIGS. 1A-2.
Figure 4B:
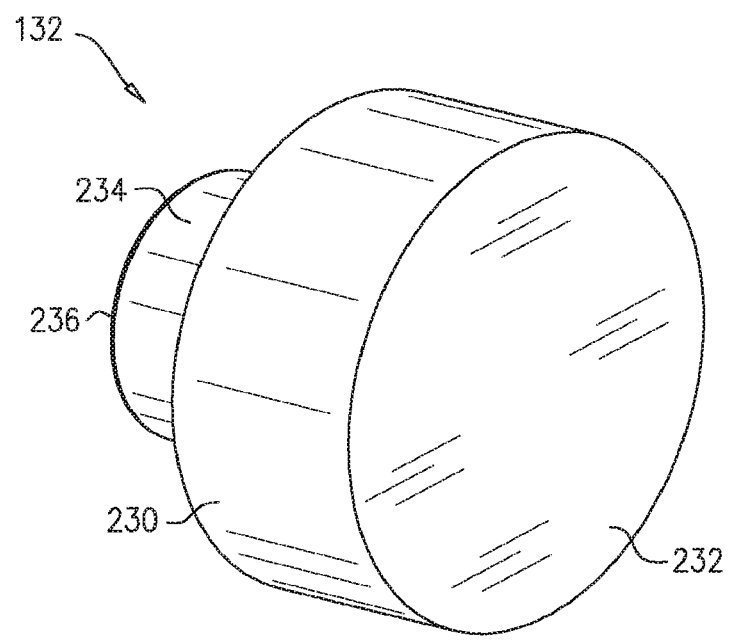
Figure 5A:
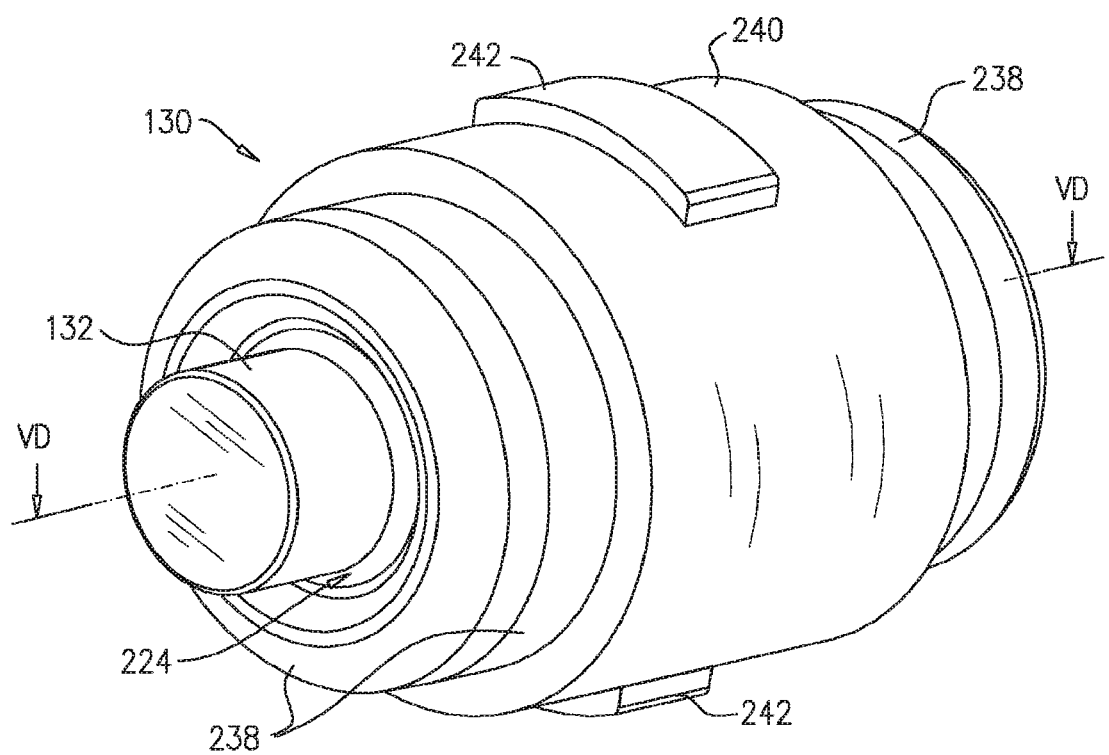
FIGS. 5A, 5B, 5C and 5D are simplified respective first and second side view, end view and sectional view illustrations of a septa housing portion forming part of the luer lock adaptor of FIGS. 1A-2, FIG. 5D being taken along lines VD-VD in FIG. 5A.
Figure 5B:
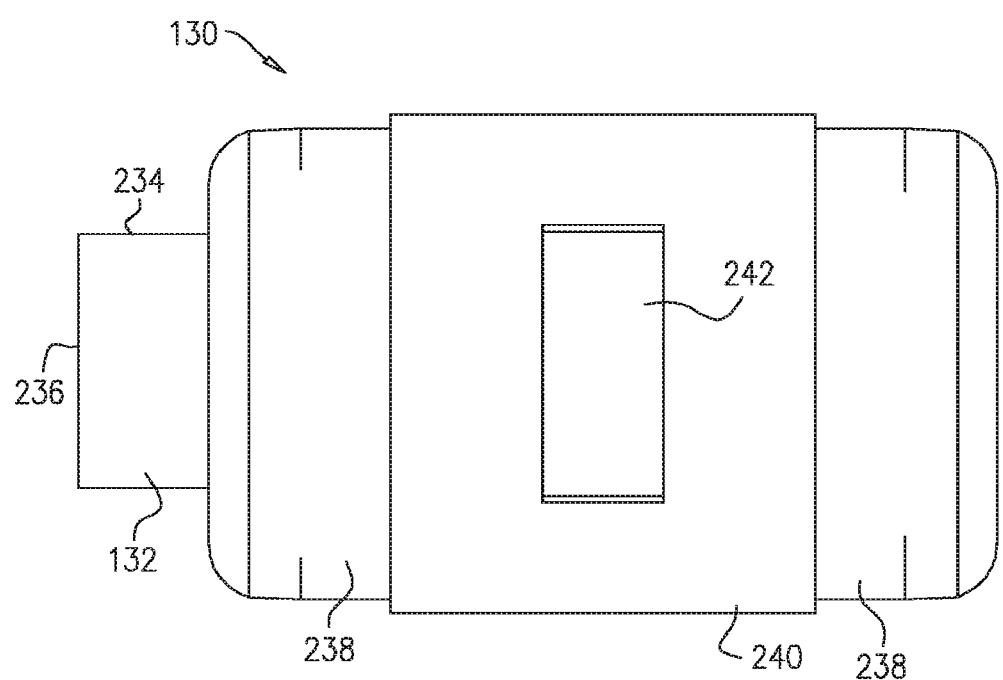
Figure 5C:
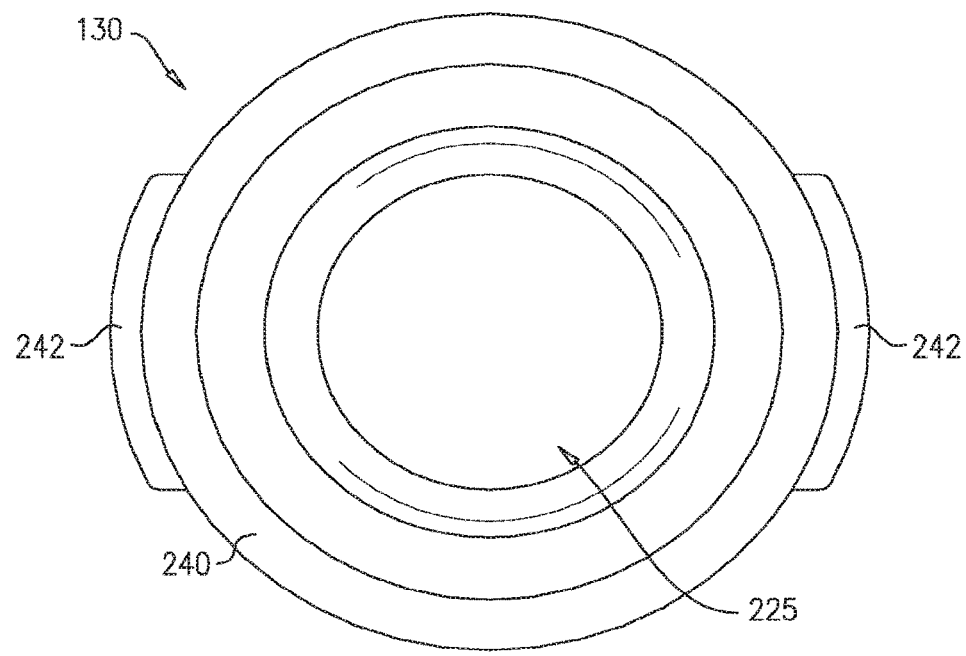
Figure 5D:
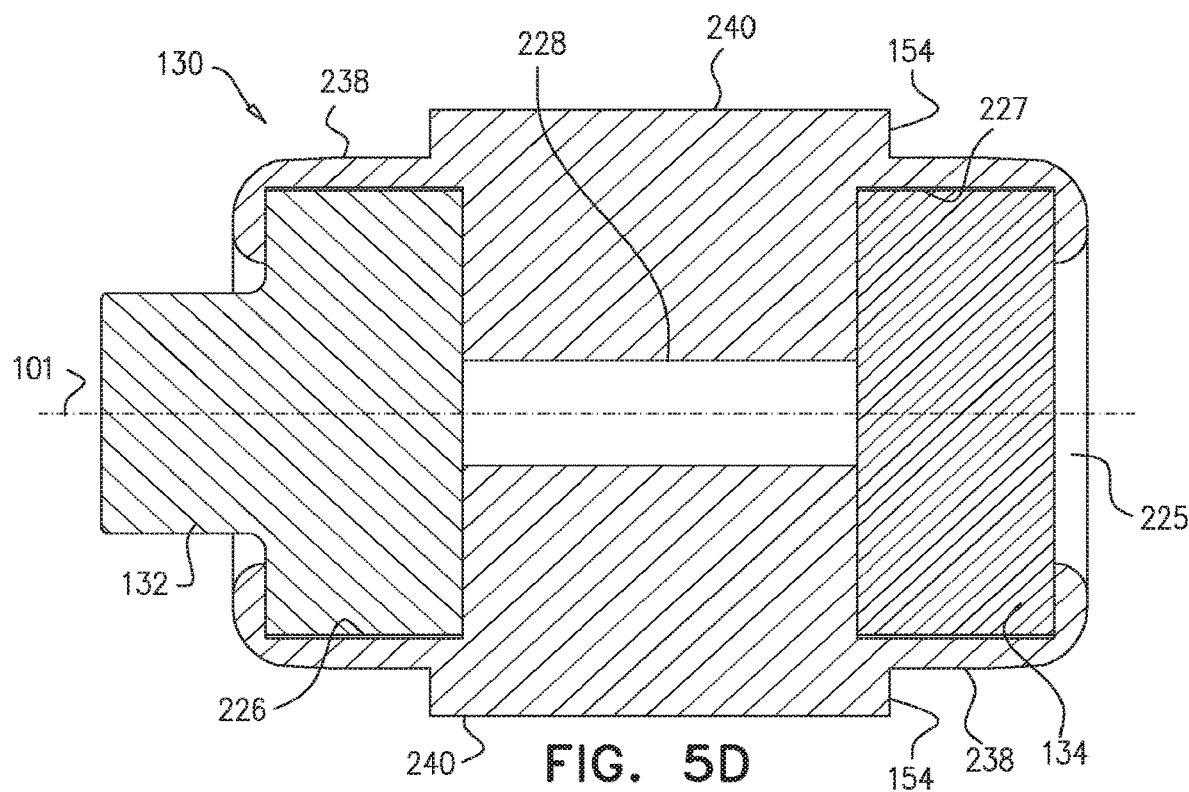

Reference is now additionally made to FIGS. 4A and 4B, which are simplified pictorial illustrations of forward septum 132, and to FIGS. 5A, 5B, 5C and 5D, which are simplified respective first and second side view, end view, and a sectional view, taken along lines VD-VD in FIG. 5A, illustrations of septa housing portion 130.

As seen in FIGS. 4A-5D, the septa housing portion 130 is a generally cylindrical element having generally rounded respective forward and rearward openings 224 and 225 leading to respective forward and rearward recesses 226 and 227, which accommodate respective forward and rearward septa 132 and 134. An open needle accommodating channel 228 extends longitudinally along axis 101 between forward and rearward recesses 226 and 227.

As seen particularly in FIGS. 4A & 4B, forward septum 132 preferably is an integrally formed element formed of a polymer, such as polyisoprene, and includes a relatively wide, rearward cylindrical portion 230, which is preferably seated in forward recess 226 of septa housing portion 130 and defines a rearwardly-directed forward septum surface 232, and a relatively narrow cylindrical portion 234, which extends forwardly of rearward cylindrical portion 230 and preferably extends through and forwardly of forward opening 224 in septa housing portion 130 and defines a forwardly-directed forward septum surface 236. Rearward septum 134 preferably is an integrally formed element formed of a polymer such as polyisoprene, has a disk like, flat cylindrical configuration and is seated in rearward recess 227 of septa housing portion 130.

Turning now specifically to FIGS. 5A-5D, which illustrate septa housing portion 130, it is seen that septa housing portion 130 has a generally cylindrical outer surface 238 having a radially outwardly protruding circumferential band 240 formed thereon. A pair of narrow protrusions 242 extend radially outwardly from circumferential band 240 of septa housing 130 for engaging septa housing guiding recesses 213 and forward stop-defining wall surfaces 214 and thus limiting the forward displacement of septa housing portion 130 in forward housing portion 110 and preventing azimuthal rotation of septa housing portion 130 about axis 101.

Figure 6A:
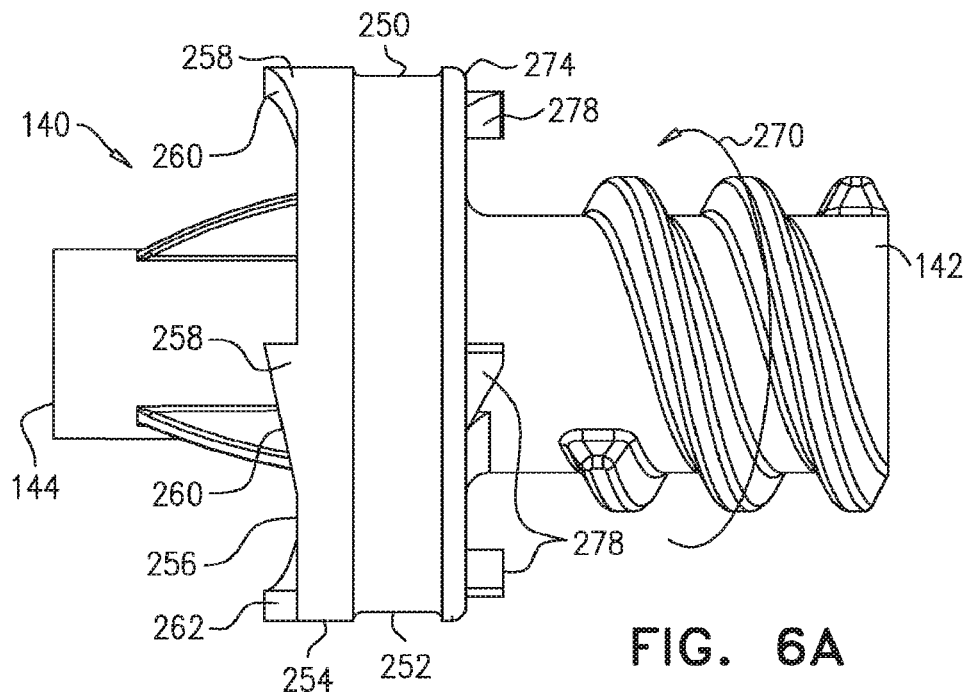
FIGS. 6A, 6B, 6C, 6D and 6E are simplified respective first and second side view, first and second perspective end view and sectional illustrations of a hub element forming part of the luer lock adaptor of FIGS. 1A-2, FIG. 6E being taken along lines VIE-VIE in FIG. 6C.
Figure 6B:
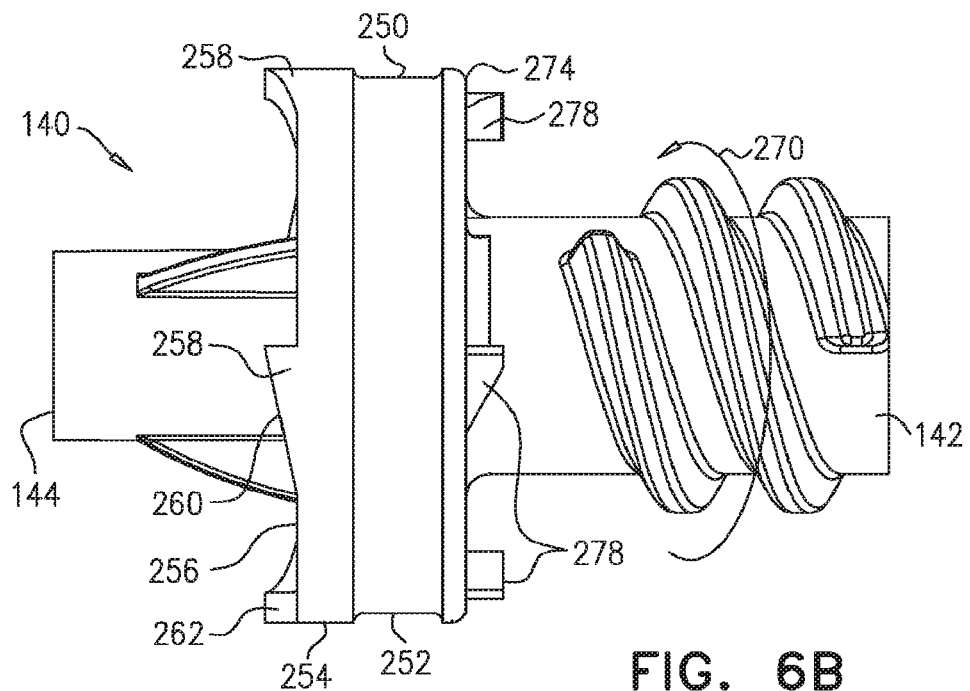
Figure 6C:
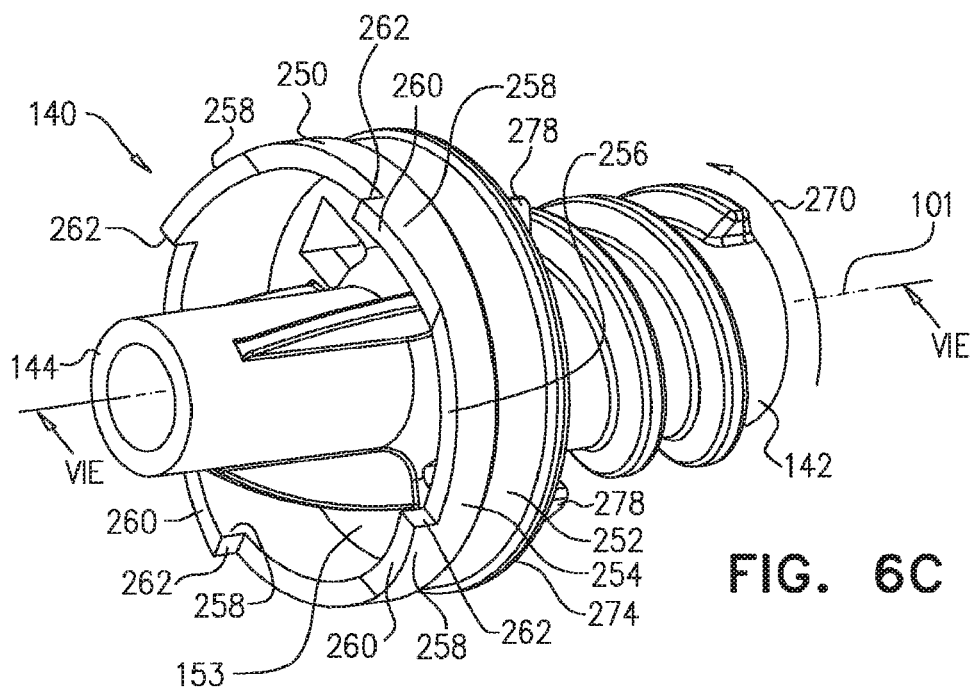
Figure 6D:
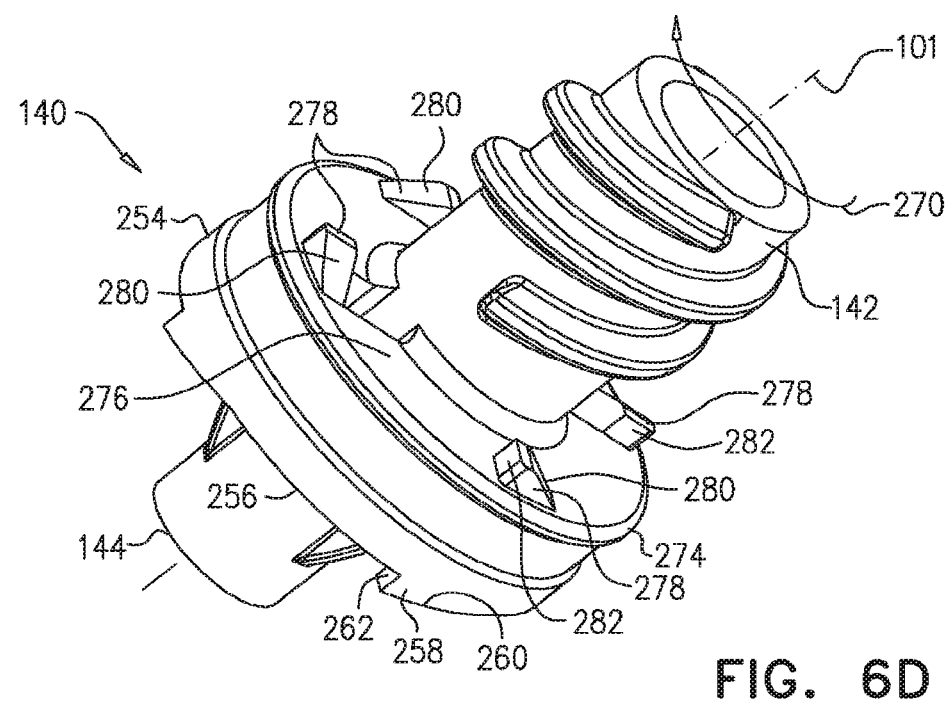
Figure 6E:
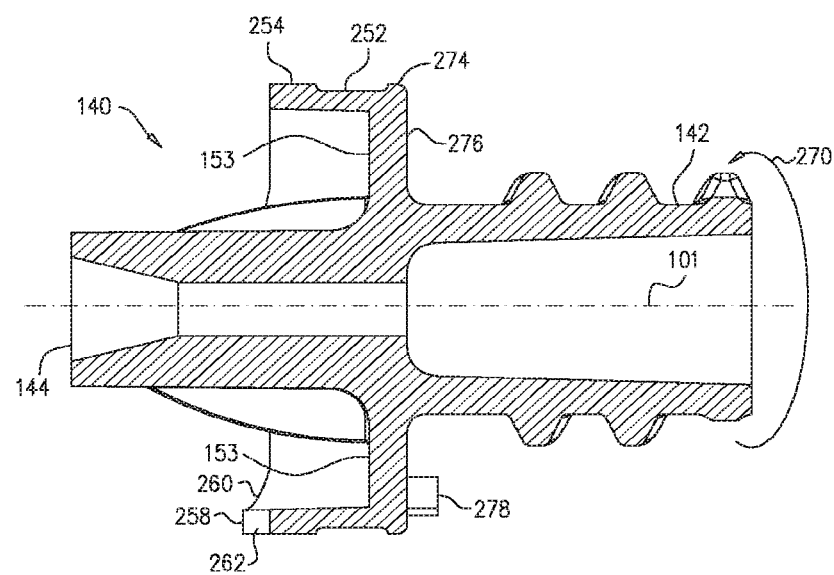

Reference is now made to FIGS. 6A, 6B, 6C, 6D and 6E, which are simplified respective first and second side view, first and second perspective end view, and a sectional view, taken along lines VIE-VIE in FIG. 6C, illustrations of hub element 140. As noted hereinabove, hub element 140 defines a female luer connector portion 142 at a rearward-facing end and a needle mounting portion 144 at a forward-facing end.

Disposed intermediate the female luer connector portion 142 and the needle mounting portion 144 is a doubly-toothed circumferential intermediate portion 250. Toothed circumferential intermediate portion 250 preferably includes an outwardly-facing circular cylindrical surface portion 252.

Forwardly of outwardly-facing circular cylindrical surface portion 252 is a forward-facing toothed portion 254 having a forward-facing toothed edge 256 having formed thereon a plurality of teeth 258, typically four in number, each including a forwardly and clockwise-facing inclined surface 260 and an axially extending, clockwise facing, locking surface 262, from a forward-facing perspective.

The arrangement of teeth 258 is such that when a male luer connector of a syringe or other element (not shown) is screwed onto female luer connector portion 142 in a clockwise direction of rotation from a forwardly-facing perspective, continued rotation of the syringe in the aforesaid clockwise direction produces corresponding rotation of hub element 140 in the aforesaid clockwise direction and causes clockwise facing, axially and radially directed locking surfaces 262 to lockingly engage corresponding counter-clockwise facing, axially and radially directed locking surfaces 219 of teeth 216 on rearwardly-facing toothed edge 215 of forward housing portion 110. The aforesaid clockwise direction of rotation is indicated by arrows 270 in FIGS. 6A-6E.

Rearwardly of outwardly-facing circular cylindrical surface portion 252 is a rearward-facing toothed portion 274 having a rearward-facing toothed surface 276 having formed thereon a plurality of teeth 278, typically four in number, each including a rearwardly and clockwise-facing inclined surface 280 and a clockwise-facing, axially and radially directed locking surface 282.

Figure 7A:
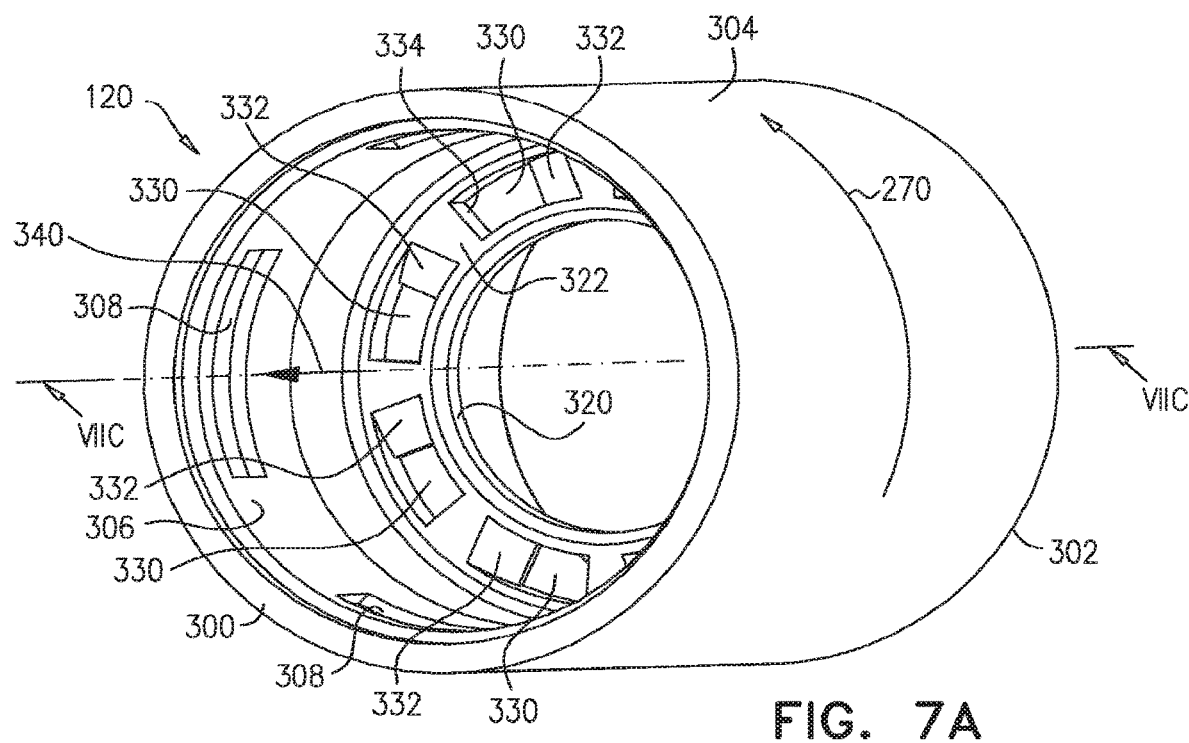
FIGS. 7A, 7B and 7C are simplified first and second perspective end view and a sectional illustration of a rearward housing portion forming part of the luer lock adaptor of FIGS. 1A-2, FIG. 7C being taken along lines VIIC-VIIC in FIG. 7A.
Figure 7B:
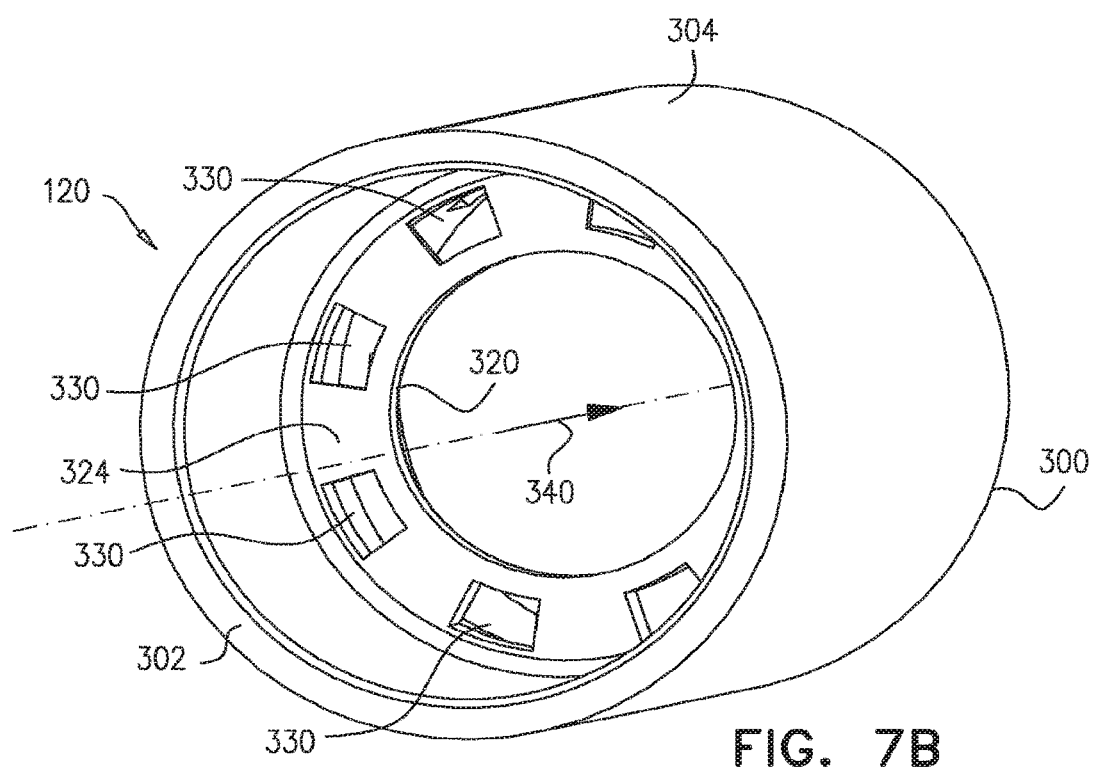
Figure 7C:
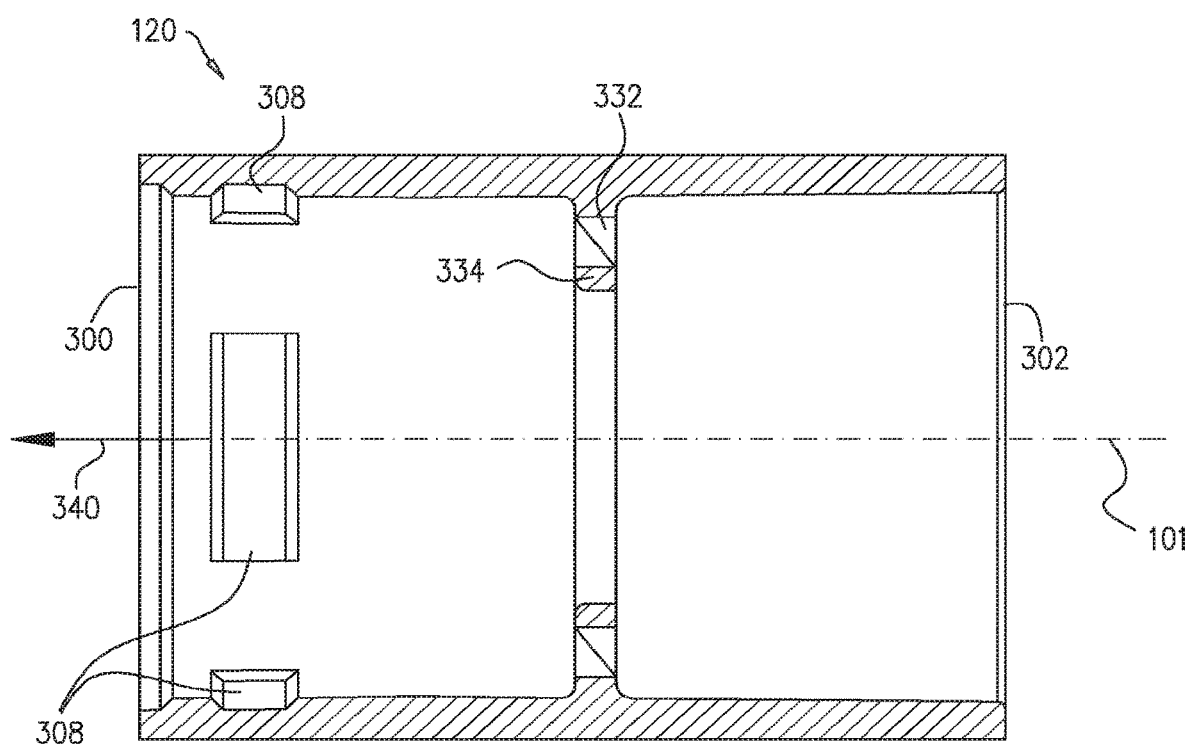

Reference is now additionally made to FIGS. 7A, 7B and 7C, which are simplified first and second perspective end view and sectional view illustrations of rearward housing portion 120.

As seen in FIGS. 2 and 7A-7C, rearward housing portion 120 is preferably an overall circular cylindrical element arranged along axis 101 and having a forward end 300, a rearward end 302 and a circular cylindrical outwardly-facing surface 304. Formed on an inwardly-facing surface 306 are a plurality of mutually azimuthally spaced circumferential recesses 308 which receive corresponding protrusions 221 of forward housing portion 110 in a snap fit engagement, thereby providing both axial and azimuthal locking between forward housing portion 110 and rearward housing portion 120.

Intermediate forward end 300 and rearward end 302 and extending radially inwardly of inwardly-facing surface 306 is an inwardly directed flange 320 having a forwardly-facing surface 322 and a rearwardly-facing surface 324. Forwardly-facing surface 322 is preferably formed with an azimuthal array of toothed recesses 330, preferably four or more in number, each of which includes a forwardly and clockwise-facing inclined surface 332 and an axial directed counter-clockwise-facing locking surface 334.

The aforesaid axial and azimuthal locking between forward housing portion 110 and rearward housing portion 120 retains hub element 140 between forward facing surface 322 of rearward housing portion 120 and compression spring 152, which urges hub element 140 against forward facing surface 322, such that teeth 278 of hub element 140 lockingly engage recesses 330 and clockwise-facing, axially and radially directed locking surfaces 282 of teeth 278 lockingly engage axial directed counter-clockwise-facing locking surfaces 334, thereby permitting counterclockwise, from a forwardly-facing perspective, rotation of hub element 140 relative to rearward housing portion 120 but preventing clockwise, from a forwardly-facing perspective, rotation of hub element 140 relative to rearward housing portion 120.

The arrangement of teeth 278 is such that when a male luer connector of a syringe or other element (not shown) is screwed onto female luer connector portion 142 in a clockwise direction of rotation, indicated by arrow 270, without the application of a forwardly-directed axial force along axis 101, indicated by an arrow 340, continued rotation of the syringe in the aforesaid clockwise direction does not produce corresponding rotation of hub element 140 in the aforesaid clockwise direction indicated by arrow 270 and enables tight engagement of the syringe with the hub 140. This arrangement is also such that when a user attempts to unscrew the male luer connector by rotating it in a counterclockwise direction, indicated by an arrow 342 (FIGS. 8A-8D), the hub 140 rotates about axis 101 together with the syringe, thereby preventing disengagement of the syringe from the hub 140.

Reference is now made to FIGS. 8A, 8B, 8C, 8D, 8E, 8F and 8G, which are simplified illustrations of the luer lock adaptor of FIGS. 1A-7C in respective first, second, third, fourth, fifth, sixth and seventh operative orientations with respect to a conventional luer lock syringe.

Figure 8A:
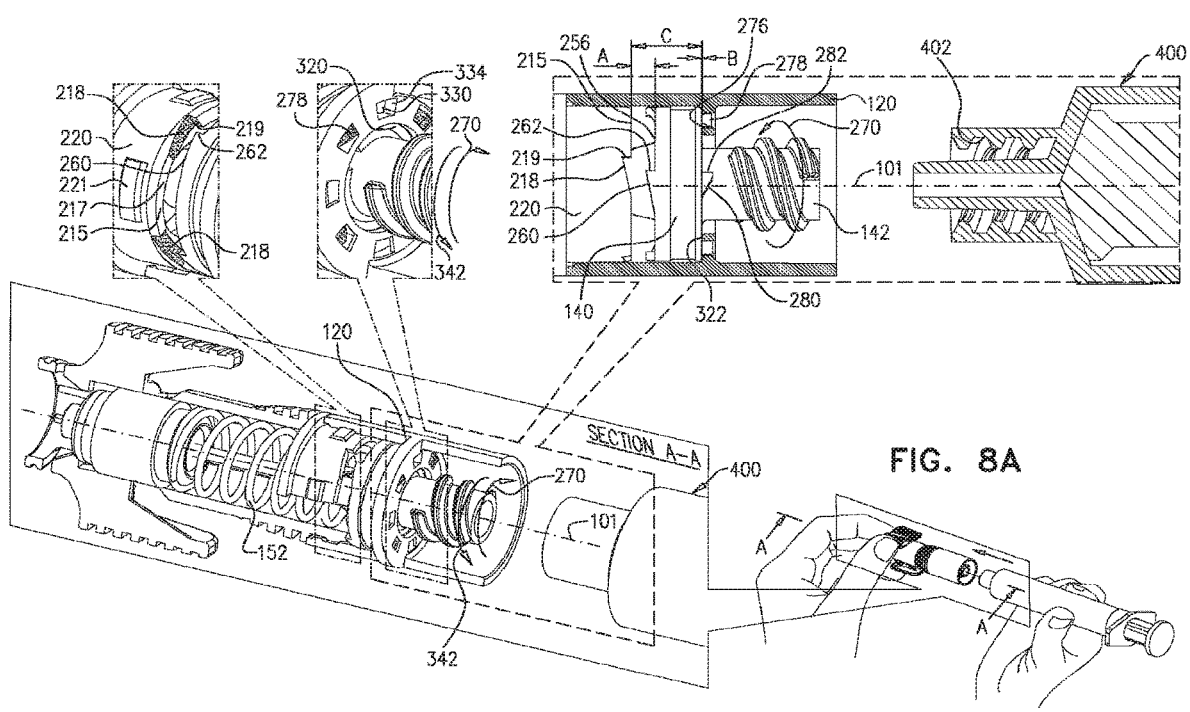

FIG. 8A shows a conventional luer lock syringe 400 having a male luer connector 402 about to be connected to the luer lock adaptor 100 of FIGS. 1A-7C. Prior to engagement of the luer lock syringe 400 with the luer lock adaptor 100, the compression action of compression spring 152 urges hub element 140 against forward facing surface 322 of flange 320 of rearward housing portion 120, such that teeth 278 of hub element 140 lockingly engage recesses 330 and clockwise-facing, axially and radially directed locking surfaces 282 of teeth 278 lockingly engage axial directed counter-clockwise-facing locking surfaces 334, thereby permitting counterclockwise, from a forwardly-facing perspective, rotation of hub element 140 relative to rearward housing portion 120, represented by arrow 342, but preventing clockwise, from a forwardly-facing perspective, rotation of hub element 140 relative to rearward housing portion 120, represented by arrow 270. It is noted that an axial separation, typically approximately 1.8 mm, indicated by the letter A, between rearwardly-facing toothed edge 215 of forward housing portion 110 and forward-facing toothed edge 256 of hub element 140 is greater than the axial extent of axially extending, clockwise facing, locking surface 262, typically approximately 0.7 mm, such that mutual rotation between the hub element 140 and the forward housing portion 110 in either rotational direction is not restricted. It is appreciated that rotation of the hub element 140 in a clockwise direction indicated by arrow 270 relative to forward housing portion 110 is nevertheless prevented by virtue of the fact that the rear housing portion 120 is fixed to the forward housing portion 110.

It is further noted that an axial separation between forward-facing surface 322 of the rearward housing portion 120 and the rearward-facing toothed surface of 276 of hub element 140 is indicated by the letter B. In the orientation shown in FIG. 8A, compression action of compression spring 152 urges hub element 140 against forward facing surface 322 of flange 320 of rearward housing portion 120, such that the axial separation B is zero.

It is appreciated that an axial separation between forward-facing surface 322 of the rearward housing portion 120 and rearwardly-facing toothed edge 215 of forward housing portion 110, indicated by the letter C, remains constant, typically approximately 5.4 mm, due to the snap fit engagement of forward housing portion 110 and rearward housing portion 120, providing axial and azimuthal locking between forward housing portion 110 and rearward housing portion 120, as described hereinabove. Additionally, the sum of axial separation A and axial separation B remains constant due to the snap fit engagement of forward housing portion 110 and rearward housing portion 120, providing axial and azimuthal locking between forward housing portion 110 and rearward housing portion 120, as described hereinabove.

Figure 8B:
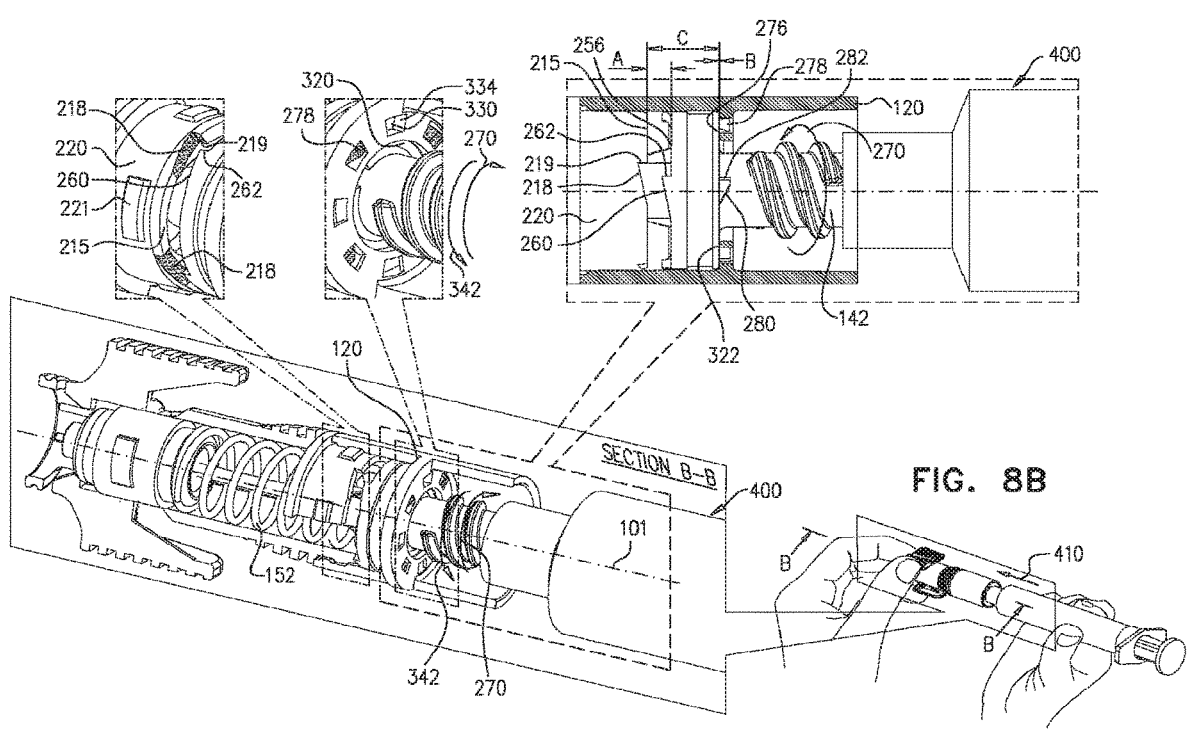

FIG. 8B illustrates initial forward axial displacement of syringe 400 relative to luer lock adaptor 100 along axis 101, as indicated by an arrow 410, such that the male luer connector 402 is in touching engagement with female luer connector portion 142 at a rearward-facing end thereof. The locking engagement of rearward housing portion 120 and teeth 278 of hub element 140 is unchanged from that described hereinabove with reference to FIG. 8A. It is noted that the axial separation A, between rearwardly-facing toothed edge 215 and forward-facing toothed edge 256 and axial separation B, between forward-facing surface 322 of the rearward housing portion 120 and the rearward-facing toothed surface of 276 of hub element 140 are unchanged from that described hereinabove with reference to FIG. 8A.

Figure 8C:
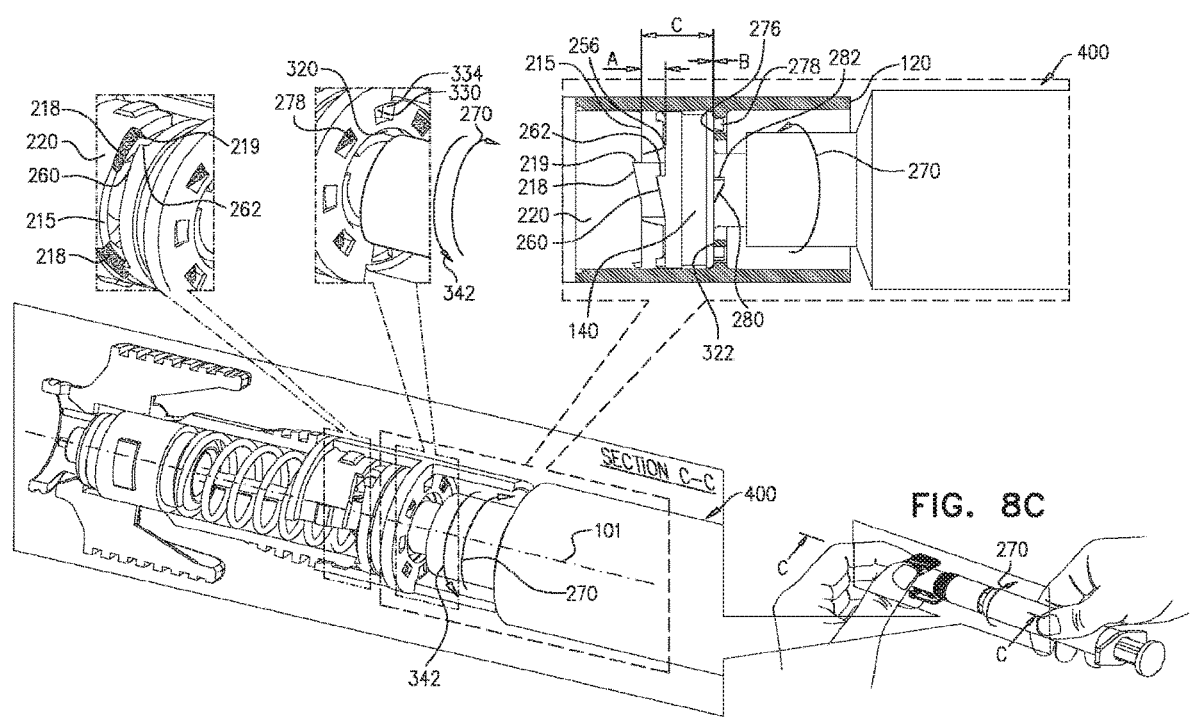

FIG. 8C illustrates clockwise rotation of the syringe 400 relative to luer lock adaptor 100 about axis 101, such that the male luer connector 402 is in full threaded frictional engagement with female luer connector portion 142 of hub element 140. This rotation takes place without application of an additional forward axial force along axis 101. This full threaded engagement is made possible by the aforementioned locking of rotation of hub element 140 against clockwise rotation relative to rearward housing portion 120. It is noted that axial separation A, between rearwardly-facing toothed edge 215 and forward-facing toothed edge 256, and axial separation B, between forward-facing surface 322 of the rearward housing portion 120 and the rearward-facing toothed surface of 276 of hub element 140, are unchanged from that described hereinabove with reference to FIGS. 8A and 8B.

FIG. 8D illustrates counterclockwise rotation of the syringe 400 relative to rearward housing portion 120 of luer lock adaptor 100 about axis 101, in an attempt to disengage the male luer connector 402 from the female luer connector portion 142 of hub element 140. This attempt is unsuccessful due to the frictional engagement of the male luer connector 402 with the female luer connector portion 142 of hub element 140 and due to the fact that the hub element 140 is free to rotate counterclockwise relative to the remainder of the luer lock adaptor 100 due to the fact that the axial separation A, between rearwardly-facing toothed edge 215 and forward-facing toothed edge 256, typically approximately 1.0 mm, is greater than the axial extent of axially extending, clockwise facing, locking surface 262, typically approximately 0.7 mm, such that mutual rotation between the hub element 140 and the forward housing portion 110 in the counterclockwise direction is not restricted. It is appreciated that axial separation A in FIG. 8D is less than the axial separation A in FIGS. 8A-8C, but still greater than the axial extent of axially extending, clockwise facing, locking surface 262.

It is also appreciated that due to the counterclockwise rotation of hub element 140 relative to the rearward housing portion 120, axial separation B, between forward-facing surface 322 of the rearward housing portion 120 and the rearward-facing toothed surface of 276 of hub element 140, which typically varies between 0 and 0.8 mm, has increased, typically to approximately 0.8 mm, from axial separation B shown in FIGS. 8A-8C corresponding to the decrease in axial separation A shown in FIG. 8D from axial separation A shown in FIGS. 8A-8C.

Figure 8E:
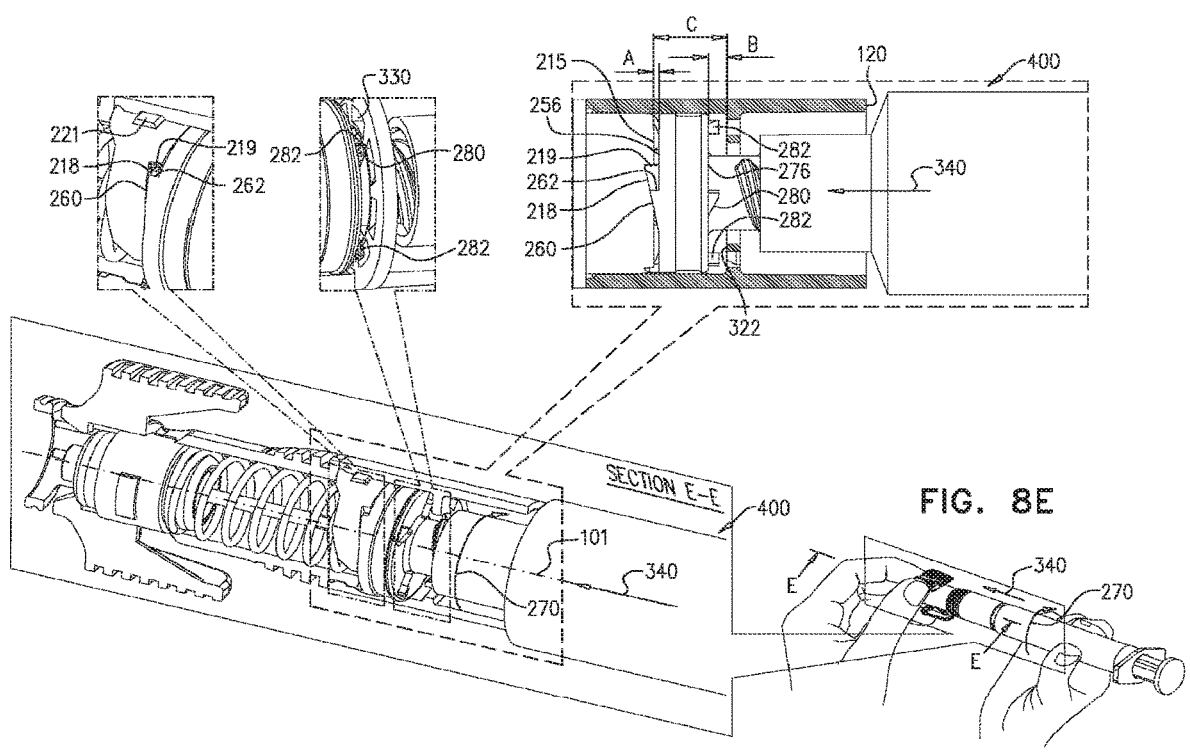

FIGS. 8E and 8F illustrate an alternative to the stage shown in FIG. 8C. FIG. 8E illustrates clockwise rotation of the syringe 400 relative to luer lock adaptor 100 about axis 101, as indicated by arrow 270, such that the male luer connector 402 is in full threaded frictional engagement with female luer connector portion 142 of hub element 140. As distinguished from FIG. 8C, here this rotation takes place with application of an additional forward axial force along axis 101 as indicated by arrow 340.

This forward axial force causes axial separation A, between rearwardly-facing toothed edge 215 and forward-facing toothed edge 256, to be less than the axial extent of axially extending, clockwise facing, locking surface 262, typically approximately 0.7 mm, such that clockwise rotation of the hub element 140 relative to forward housing portion 110 is restricted.

FIG. 8E shows partial threaded frictional engagement between male luer connector 402 and female luer connector portion 142 resulting from clockwise rotation of the syringe 400 combined with application of an axial force, as indicated by arrows 270 and 340. It is appreciated that at the stage shown in FIG. 8E, axial separation A, typically approximately 0.3 mm, is less than axial separation B, typically approximately 1.5 mm.

FIG. 8F shows full threaded frictional engagement between male luer connector 402 and female luer connector portion 142 resulting from further clockwise rotation of the syringe 400 combined with application of an axial force, as indicated by arrows 270 and 340. It is appreciated that at the stage shown in FIG. 8F, axial separation A is typically 0 mm and axial separation B is typically approximately 1.8 mm.

Figure 8G:
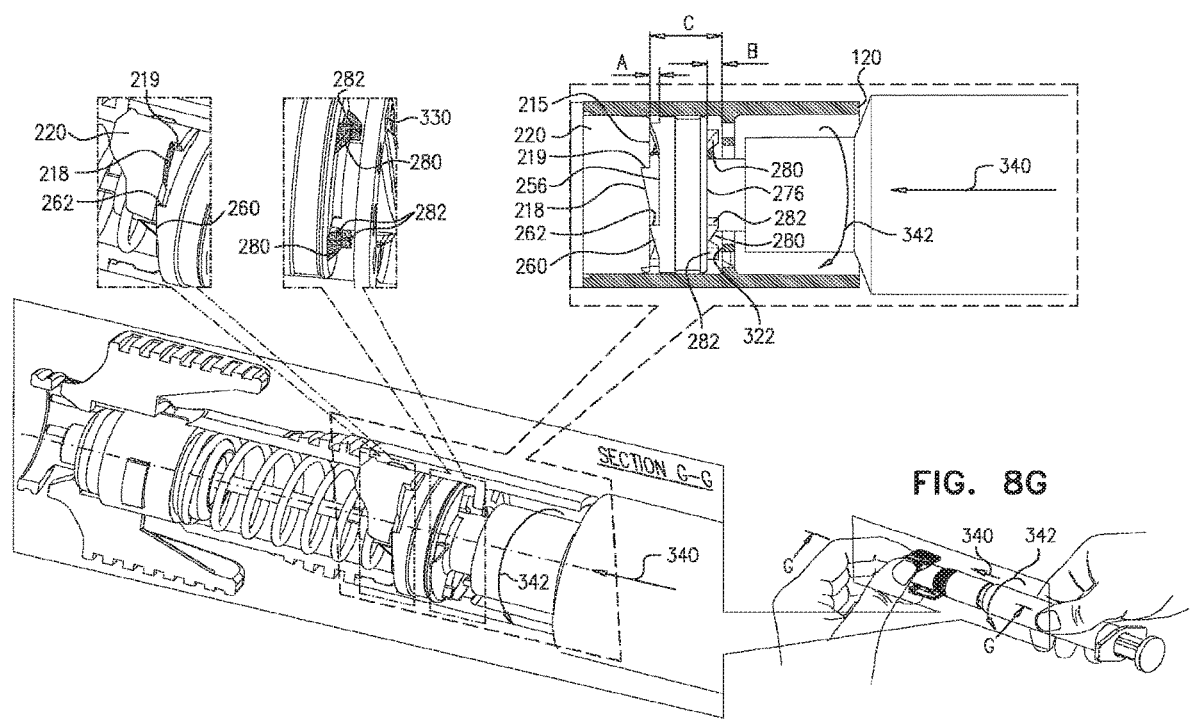

FIG. 8G illustrates counterclockwise rotation of the syringe 400 relative to rearward housing portion 120 of luer lock adaptor 100 about axis 101 combined with application of an axial force, as indicated by arrows 342 and 340, in an attempt to disengage the male luer connector 402 from the female luer connector portion 142 of hub element 140. This attempt is unsuccessful due to the frictional engagement of the male luer connector 402 with the female luer connector portion 142 of hub element 140 and due to the fact that the hub element 140 is free to rotate counterclockwise relative to the remainder of the luer lock adaptor 100 due to the fact that forward-facing toothed edge 256 of hub element 140, having formed thereon a plurality of teeth 258, typically four in number, each including a forwardly and clockwise-facing inclined surface 260 in counterclockwise rotation relative to the forward housing portion 110 slides over rearwardly-facing toothed edge 215 having formed thereon a plurality of teeth 216, typically four in number, each including, rearwardly-facing partially circumferential surface 217 and rearwardly and clockwise-facing inclined surface 218 such that rotation of the hub element 140 relative to the forward housing portion 110 in the counterclockwise direction is not restricted.

It is also appreciated that due to the counterclockwise rotation of hub element 140 relative to the rearward housing portion 120, axial separation B, between forward-facing surface 322 of the rearward housing portion 120 and the rearward-facing toothed surface of 276 of hub element 140, typically varies between 1.1 and 1.8 mm.

Reference is now made to FIGS. 9A, 9B, 9C, 9D, 9E, 9F and 9G, which are simplified illustrations of the luer lock adaptor of FIGS. 1A-7C in respective first, second, third, fourth fifth, sixth and seventh operative orientations with respect to a conventional luer lock connector.

Figure 9A:
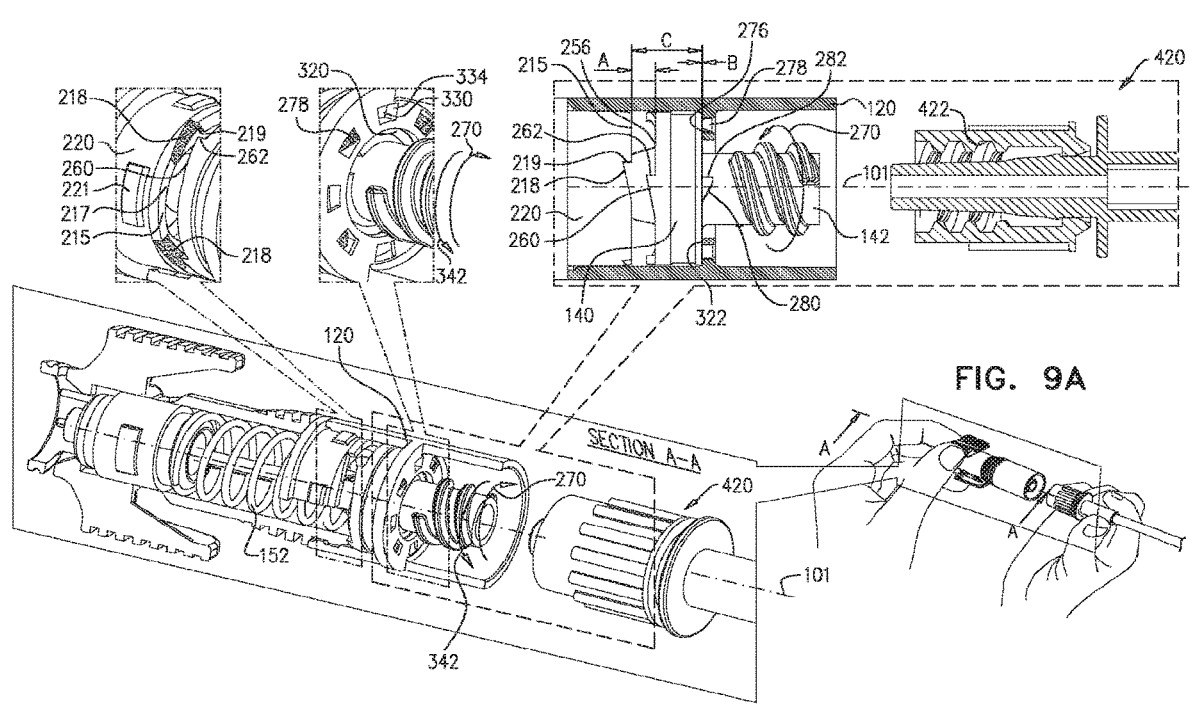

FIG. 9A shows a conventional luer lock connector 420 having a male luer connector 422 about to be connected to the luer lock adaptor 100 of FIGS. 1A-7C. Prior to engagement of the luer lock connector 420 with the luer lock adaptor 100, the compression action of compression spring 152 urges hub element 140 against forward facing surface 322 of flange 320 of rearward housing portion 120, such that teeth 278 of hub element 140 lockingly engage recesses 330 and clockwise-facing, axially and radially directed locking surfaces 282 of teeth 278 lockingly engage axial directed counter-clockwise-facing locking surfaces 334, thereby permitting counterclockwise, from a forwardly-facing perspective, rotation of hub element 140 relative to rearward housing portion 120, represented by arrow 342, but preventing clockwise, from a forwardly-facing perspective, rotation of hub element 140 relative to rearward housing portion 120, represented by arrow 270. It is noted that an axial separation, typically approximately 1.8 mm, indicated by the letter A, between rearwardly-facing toothed edge 215 of forward housing portion 110 and forward-facing toothed edge 256 of hub element 140 is greater than the axial extent of axially extending, clockwise facing, locking surface 262, typically approximately 0.7 mm, such that mutual rotation between the hub element 140 and the forward housing portion 110 in either rotational direction is not restricted. It is appreciated that rotation of the hub element 140 in a clockwise direction indicated by arrow 270 relative to forward housing portion 110 is nevertheless prevented by virtue of the fact that the rear housing portion 120 is fixed to the forward housing portion 110.

It is further noted that an axial separation between forward-facing surface 322 of the rearward housing portion 120 and the rearward-facing toothed surface of 276 of hub element 140 is indicated by the letter B. In the orientation shown in FIG. 8A, compression action of compression spring 152 urges hub element 140 against forward facing surface 322 of flange 320 of rearward housing portion 120, such that the axial separation B is zero.

It is appreciated that an axial separation between forward-facing surface 322 of the rearward housing portion 120 and rearwardly-facing toothed edge 215 of forward housing portion 110, indicated by the letter C, remains constant, typically approximately 5.4 mm, due to the snap fit engagement of forward housing portion 110 and rearward housing portion 120, providing axial and azimuthal locking between forward housing portion 110 and rearward housing portion 120, as described hereinabove. Additionally, the sum of axial separation A and axial separation B remains constant due to the snap fit engagement of forward housing portion 110 and rearward housing portion 120, providing axial and azimuthal locking between forward housing portion 110 and rearward housing portion 120, as described hereinabove.

FIG. 9B illustrates initial forward axial displacement of luer lock connector 420 relative to luer lock adaptor 100 along axis 101, as indicated by an arrow 430, such that the male luer connector 422 is in touching engagement with female luer connector portion 142 at a rearward-facing end thereof. The locking engagement of rearward housing portion 120 and teeth 278 of hub element 140 is unchanged from that described hereinabove with reference to FIG. 9A.

It is noted that the axial separation A, between rearwardly-facing toothed edge 215 and forward-facing toothed edge 256 and axial separation B, between forward-facing surface 322 of the rearward housing portion 120 and the rearward-facing toothed surface of 276 of hub element 140 are unchanged from that described hereinabove with reference to FIG. 9A.

Figure 9C:
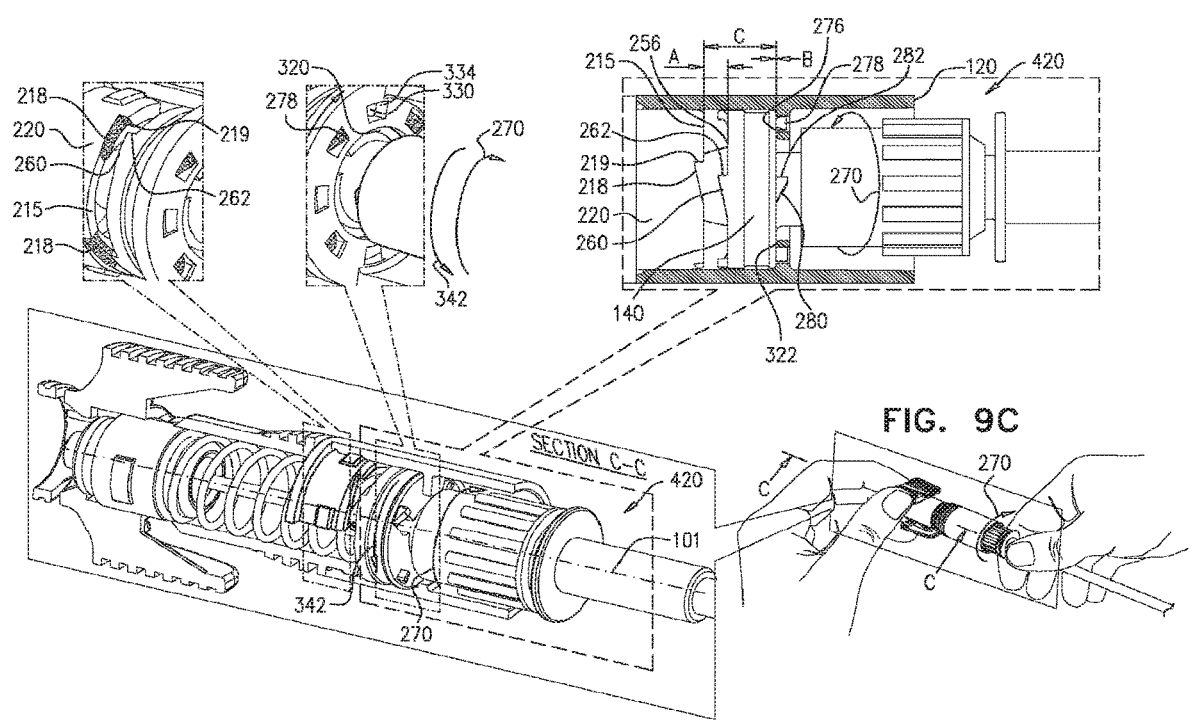

FIG. 9C illustrates clockwise rotation of the luer lock connector 420 relative to luer lock adaptor 100 about axis 101, such that the male luer connector 422 is in full threaded frictional engagement with female luer connector portion 142 of hub element 140. This rotation takes place without application of an additional forward axial force along axis 101. This full threaded engagement is made possible by the aforementioned locking of rotation of hub element 140 against clockwise rotation relative to rearward housing portion 120. It is noted that the axial separation A, between rearwardly-facing toothed edge 215 and forward-facing toothed edge 256, and axial separation B, between forward-facing surface 322 of the rearward housing portion 120 and the rearward-facing toothed surface of 276 of hub element 140, are is unchanged from that described hereinabove with reference to FIGS. 9A and 9B.

FIG. 9D illustrates counterclockwise rotation of the luer lock connector 420 relative to rearward housing portion 120 of luer lock adaptor 100 about axis 101, in an attempt to disengage the male luer connector 422 from the female luer connector portion 142 of hub element 140. This attempt is unsuccessful due to the frictional engagement of the male luer connector 422 with the female luer connector portion 142 of hub element 140 and due to the fact that the hub element 140 is free to rotate counterclockwise relative to the remainder of the luer lock adaptor 100 due to the fact that the axial separation A, between rearwardly-facing toothed edge 215 and forward-facing toothed edge 256, typically approximately 1.0 mm, is greater than the axial extent of axially extending, clockwise facing, locking surface 262, typically approximately 0.7 mm, such that mutual rotation between the hub element 140 and the forward housing portion 110 in the counterclockwise direction is not restricted. It is appreciated that axial separation a in FIG. 9D is less than axial separation A in FIGS. 9A-9C, but still greater than the axial extent of axially extending, clockwise facing, locking surface 262.

It is also appreciated that due to the counterclockwise rotation of hub element 140 relative to the rearward housing portion 120, axial separation B, between forward-facing surface 322 of the rearward housing portion 120 and the rearward-facing toothed surface of 276 of hub element 140, which typically varies between 0 and 0.8 mm, has increased, typically to approximately 0.8 mm, from axial separation B shown in FIGS. 9A-9C corresponding to the decrease in axial separation A shown in FIG. 9D from axial separation A shown in FIGS. 9A-9C.

Figure 9F:
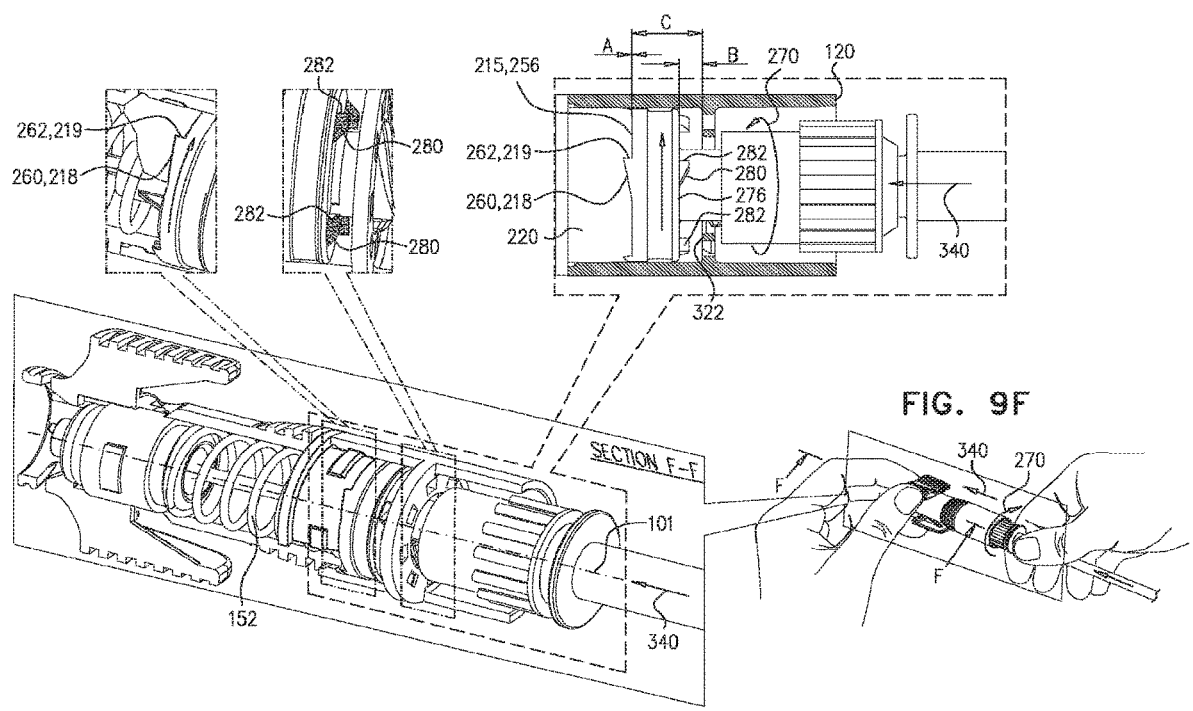

FIGS. 9E and 9F illustrate an alternative to the stage shown in FIG. 9C. FIG. 9E illustrates clockwise rotation of the luer lock connector 420 relative to luer lock adaptor 100 about axis 101, as indicated by arrow 270, such that the male luer connector 422 is in full threaded frictional engagement with female luer connector portion 142 of hub element 140. As distinguished from FIG. 9C, here this rotation takes place with application of an additional forward axial force along axis 101 as indicated by arrow 340.

This forward axial force causes axial separation A, between rearwardly-facing toothed edge 215 and forward-facing toothed edge 256, to be less than the axial extent of axially extending, clockwise facing, locking surface 262, typically approximately 0.7 mm, such that clockwise rotation of the hub element 140 relative to forward housing portion 110 is restricted.

FIG. 9E shows partial threaded frictional engagement between male luer connector 422 and female luer connector portion 142 resulting from clockwise rotation of the luer lock connector 420 combined with application of an axial force, as indicated by arrows 270 and 340. It is appreciated that at the stage shown in FIG. 9E, axial separation A, typically approximately 0.3 mm, is less than axial separation B, typically approximately 1.5 mm.

FIG. 9F shows full threaded frictional engagement between male luer connector 422 and female luer connector portion 142 resulting from further clockwise rotation of the luer lock connector 420 combined with application of an axial force, as indicated by arrows 270 and 340. It is appreciated that at the stage shown in FIG. 9F, axial separation A is typically 0 mm and axial separation B is typically approximately 1.8 mm.

Figure 9G:
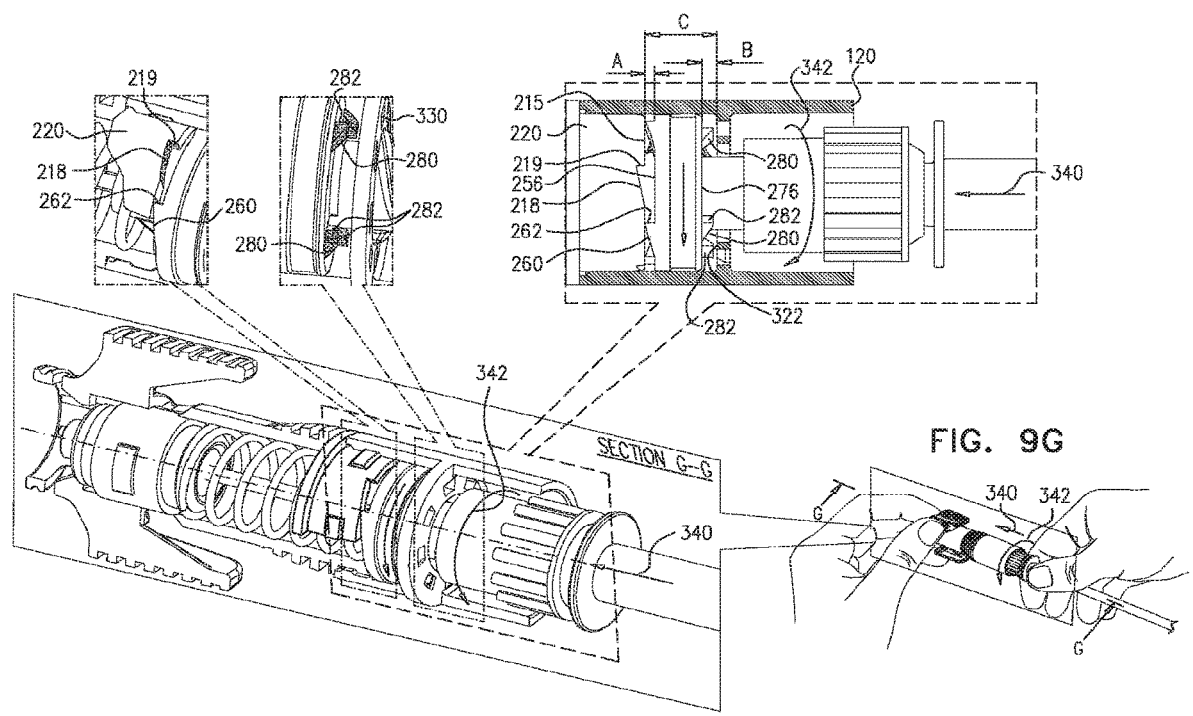

FIG. 9G illustrates counterclockwise rotation of the luer lock connector 420 relative to rearward housing portion 120 of luer lock adaptor 100 about axis 101 combined with application of an axial force, as indicated by arrows 342 and 340, in an attempt to disengage the male luer connector 422 from the female luer connector portion 142 of hub element 140. This attempt is unsuccessful due to the frictional engagement of the male luer connector 422 with the female luer connector portion 142 of hub element 140 and due to the fact that the hub element 140 is free to rotate counterclockwise relative to the remainder of the luer lock adaptor 100 due to the fact that forward-facing toothed edge 256 of hub element 140, having formed thereon a plurality of teeth 258, typically four in number, each including a forwardly and clockwise-facing inclined surface 260 in counterclockwise rotation relative to the forward housing portion 110 slides over rearwardly-facing toothed edge 215 having formed thereon a plurality of teeth 216, typically four in number, each including a rearwardly-facing partially circumferential surface 217, a rearwardly and clockwise-facing inclined surface 218 such that rotation of the hub element 140 relative to the forward housing portion 110 in the counterclockwise direction is not restricted.

It is also appreciated that due to the counterclockwise rotation of hub element 140 relative to the rearward housing portion 120, axial separation B, between forward-facing surface 322 of the rearward housing portion 120 and the rearward-facing toothed surface of 276 of hub element 140, typically varies between 1.1 and 1.8 mm.

Figure 10A:
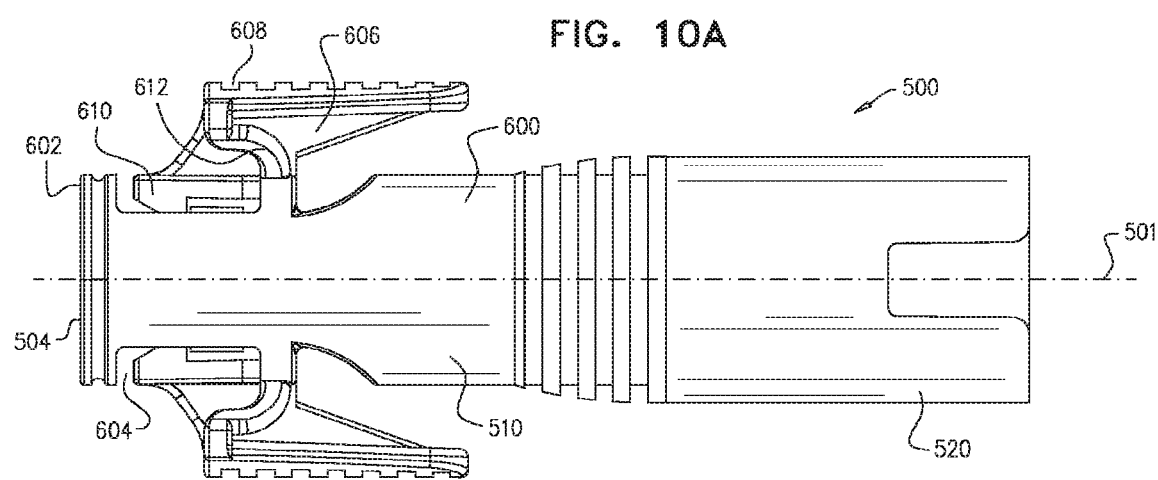
FIGS. 10A, 10B, 10C, 10D, 10E and 10F are simplified respective first and second side view, perspective view, first and second end view illustrations and a sectional illustration, taken along lines XF-XF in FIG. 10E, of a luer lock adaptor constructed and operative in accordance with another preferred embodiment of the present invention.
Figure 10B:
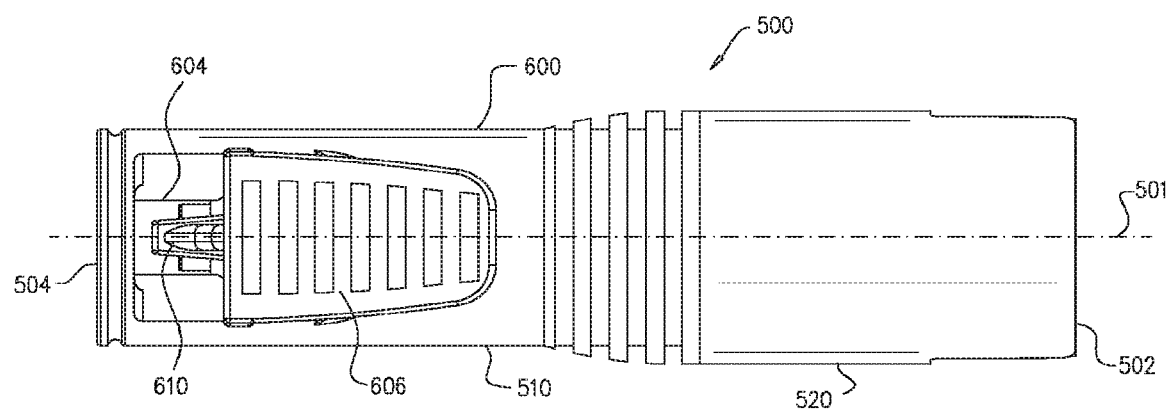
Figure 10C:
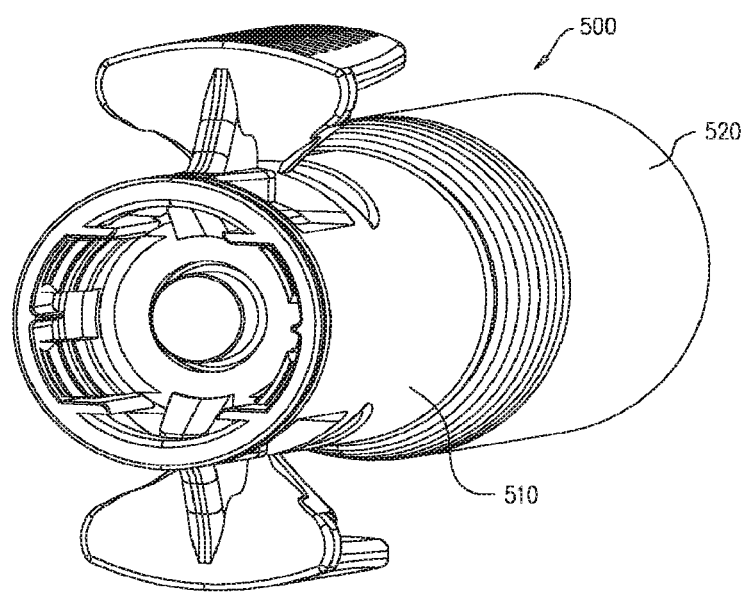
Figure 10D:
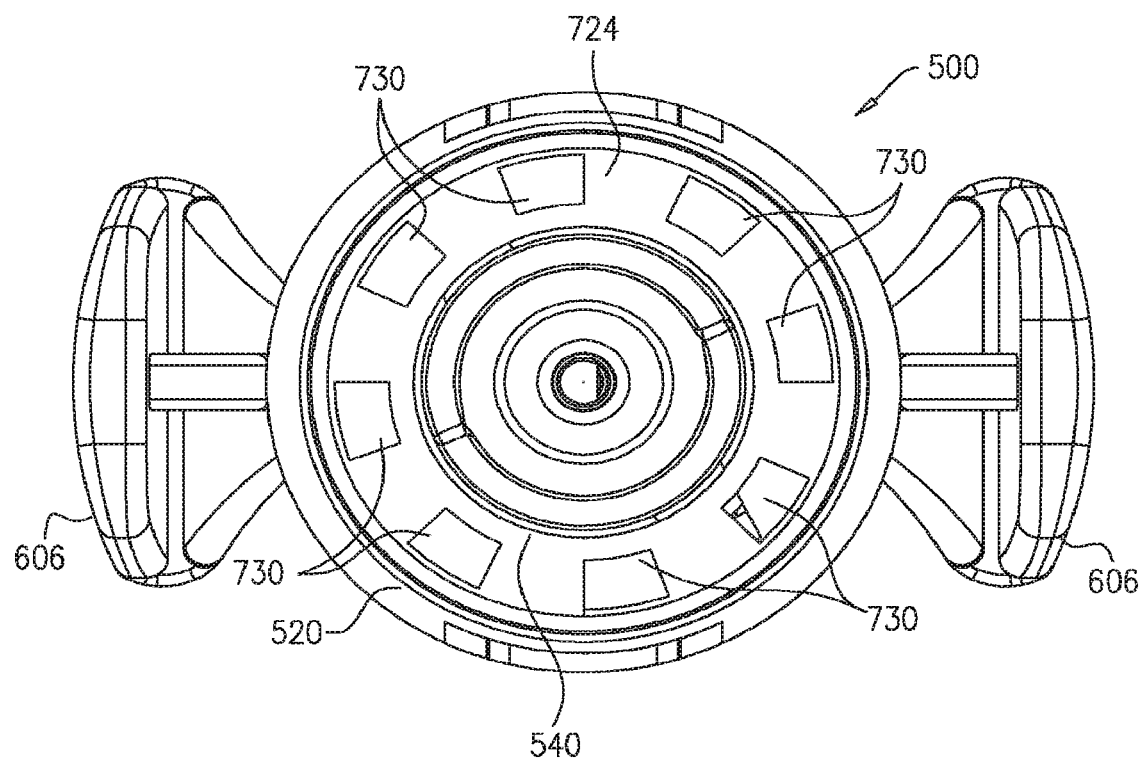
Figure 10E:
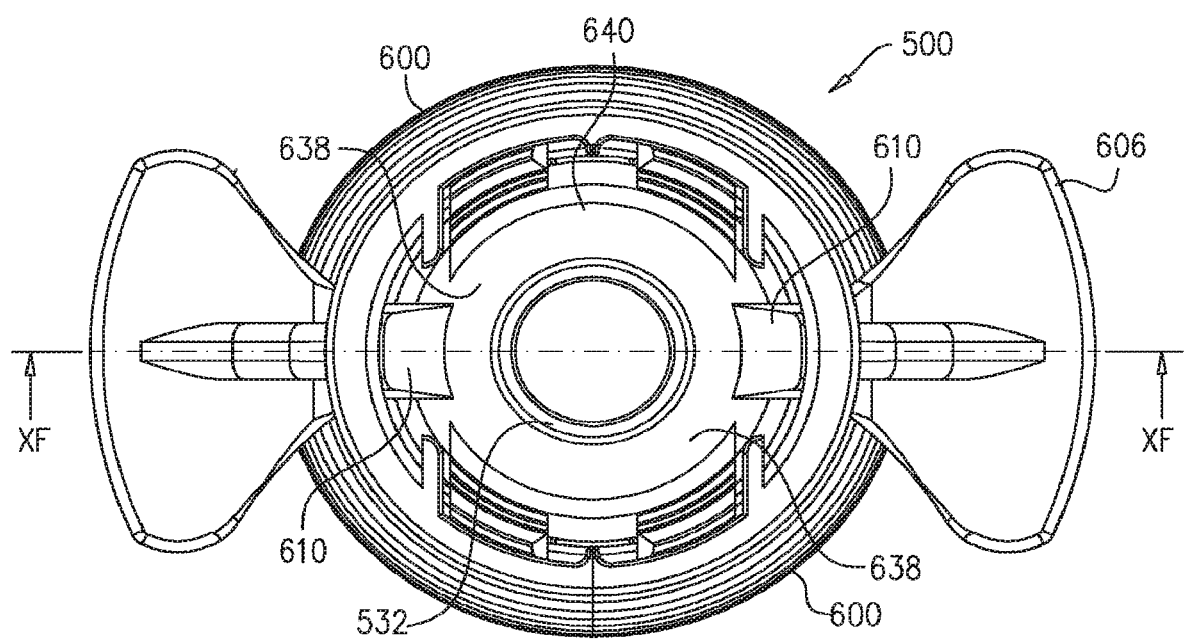
Figure 10F:
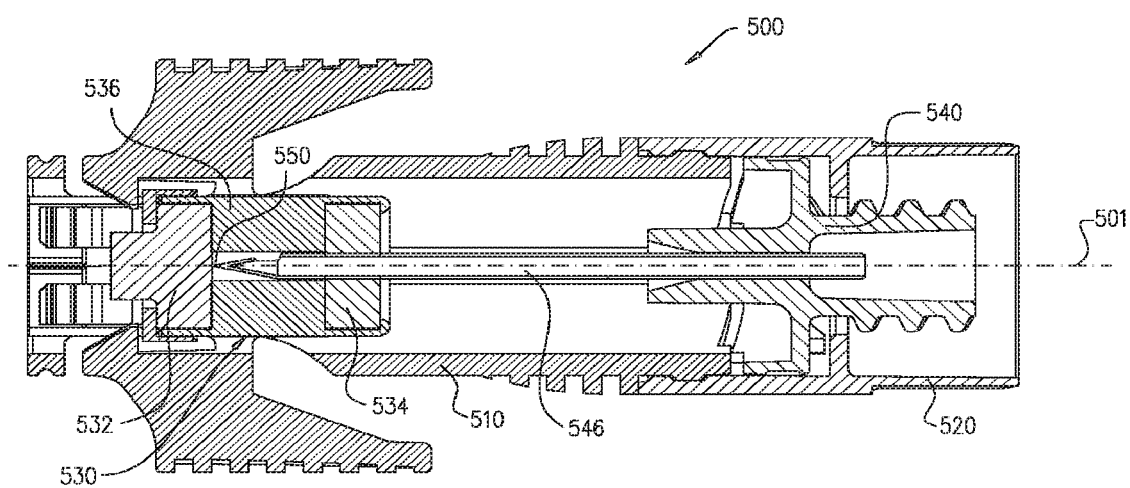
Figure 11:
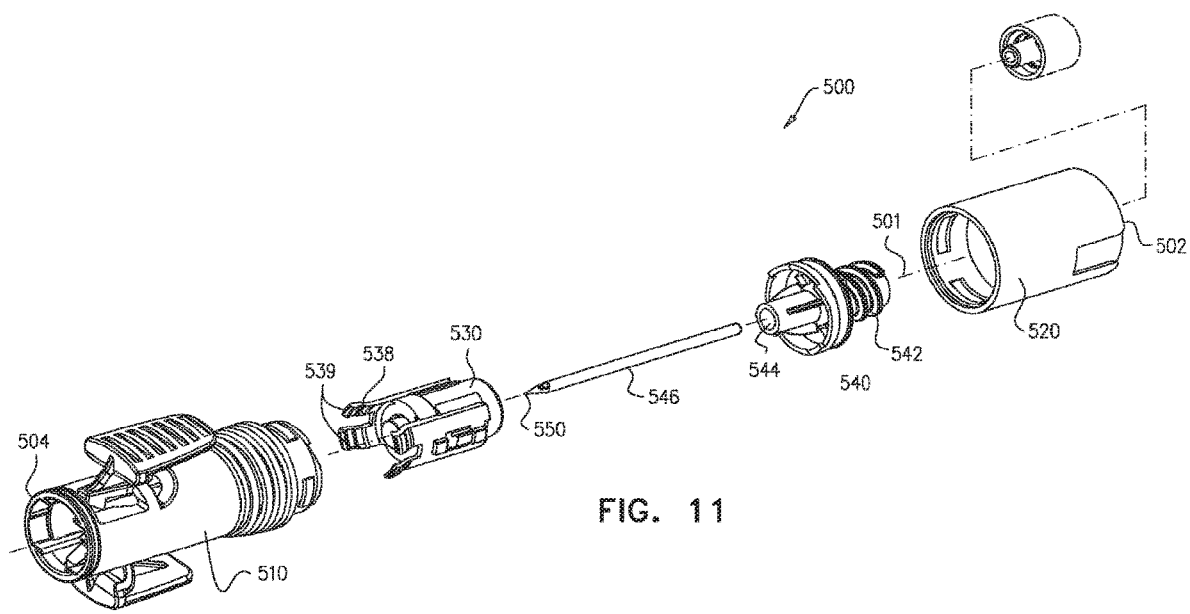
FIG. 11 is a simplified exploded view illustration of the luer lock adaptor of FIGS. 10A-10F.

Reference is now made to FIGS. 10A, 10B, 10C, 10D, 10E and 10F, which are simplified respective first and second side view, perspective view, first and second end view illustrations and a sectional illustration, taken along lines XF-XF in FIG. 10E, of a luer lock adaptor constructed and operative in accordance with another preferred embodiment of the present invention, and to FIG. 11, which is a simplified exploded view illustration of the luer lock adaptor of FIGS. 10A-10F.

As seen in FIGS. 10A-10F and 11, there is provided a luer lock adaptor 500, which extends generally along a longitudinal axis 501 and has a luer connection end 502 and a port connection end 504. The luer lock adaptor 500 preferably includes a forward housing portion 510 and a rearward housing portion 520, which are preferably fixedly snap-fit to each other so as to prevent both relative axial movement and relative azimuthal movement about axis 501 therebetween. Alternatively, forward housing portion 510 and rearward housing portion 520 may be formed as a single integral unit. The forward-facing direction is facing to the left in FIG. 10A.

Disposed within forward housing portion 510 is a septa housing assembly 530 including a forward septum 532 and a rearward septum 534, which are fixedly and sealingly retained in a septa mounting portion 536, preferably by ultrasonic swaging of forward and rearward edges of the septa mounting portion 536. Septa housing assembly 530 preferably includes a plurality of septa housing mounting legs 538, each including a forward engagement portion 539, which are typically snap mounted onto septa mounting portion 536.

Disposed within rearward housing portion 520 is a hub element 540, defining a female luer connector portion 542, at a rearward-facing end thereof, and, at a forward-facing end thereof, a needle mounting portion 544. A needle 546, mounted onto needle mounting portion 544, extends axially forwardly along longitudinal axis 501 into forward housing portion 510, such that in the absence of a port connection at the port connection end 504, a sharp tip 550 of needle 546 is located within the septa housing 530 between rearward septum 534 and forward septum 532. As distinct from the embodiment of FIGS. 1A-9G, no compression spring is provided and septa housing 530 is axially slidably mounted onto forward housing portion 510 via septa housing mounting legs 538.

It is a particular feature of an embodiment of the present invention that there is provided a luer lock adaptor, here luer lock adaptor 500, which includes a housing, here housing portions 510 and 520, which define an axis, here axis 501, and an internal luer lock element, here hub element 540, the internal luer lock element being located internally of the housing and being rotatably mounted thereto for rotation about the axis relative to the housing, in a manner which permits rotation of the luer lock element relative to the housing in a first rotation direction about the axis and limits rotation of the luer lock element relative to the housing in a second rotation direction about the axis, opposite to the first rotation direction, whereby the location of the internal luer lock element internally of the housing prevents manual access to the internal luer lock element for limiting rotation thereof in the first rotation direction.

Figure 12A:
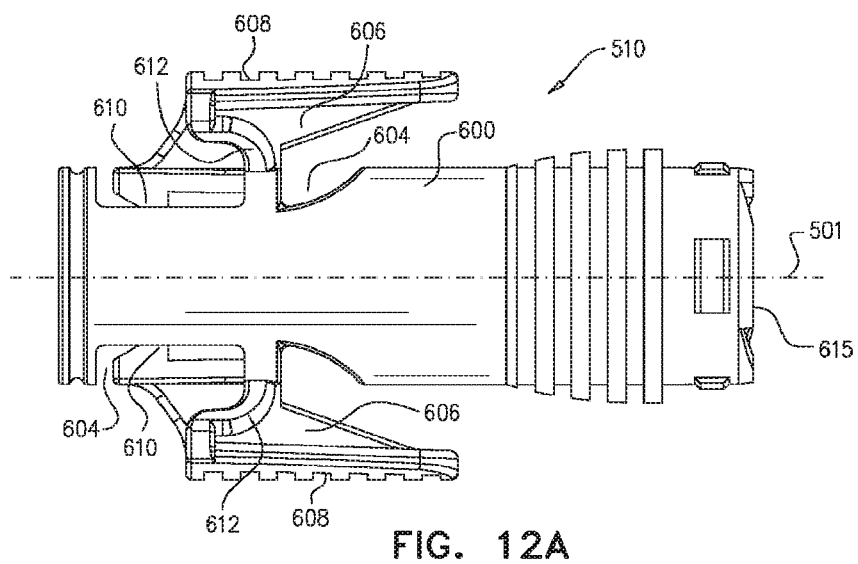
FIGS. 12A, 12B, 12C, 12D, 12E and 12F are simplified respective first and second side view, perspective luer connection end view and sectional view illustrations of a forward housing portion forming part of the luer lock adaptor of FIGS. 10A-11, FIGS. 12D, 12E and 12F being taken along respective lines XIID-XIID, XIIE-XIIE and XIIF-XIIF in FIG. 12C.
Figure 12B:
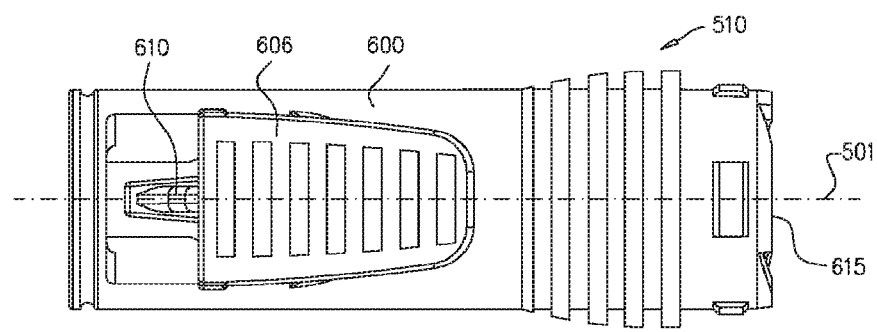
Figure 12C:
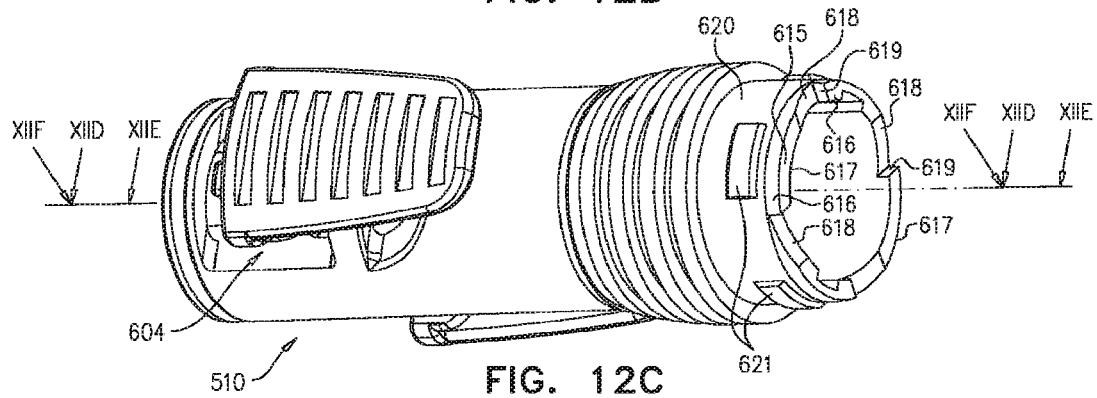

Reference is now additionally made to FIGS. 12A, 12B, 12C, 12D, 12E and 12F, which are simplified respective first and second side view, perspective luer connection end view and sectional view illustrations of a forward housing portion forming part of the luer lock adaptor of FIGS. 10A-11, FIGS. 12D, 12E and 12F being taken along respective lines XIID-XIID, XIIE-XIIE and XIIF-XIIF in FIG. 12C.

As seen in FIGS. 12A-12F, the forward housing portion 510 comprises a generally circular cylindrical main portion 600 having a forward circumferential rim 602 and a pair of opposite side cut outs 604 adjacent which are mounted a pair of oppositely directed port connector engagement portions 606.

Each of port connector engagement portions 606 preferably includes a ribbed finger engagement surface 608, which is connected to a retractable port connector engagement tooth 610. Each of port connector engagement portions 606 is flexibly mounted onto main portion 600 by means of a flexible mounting arch 612 which spans a corresponding cut out 604. Manual pressing on engagement surface 608 causes retraction of port connector engagement tooth 610, such that simultaneous manual pressing on engagement surfaces 608 of both of port connector engagement portions 606 enables disengagement of a port connector (not shown) from the interior of cylindrical main portion 600.

Figure 12D:
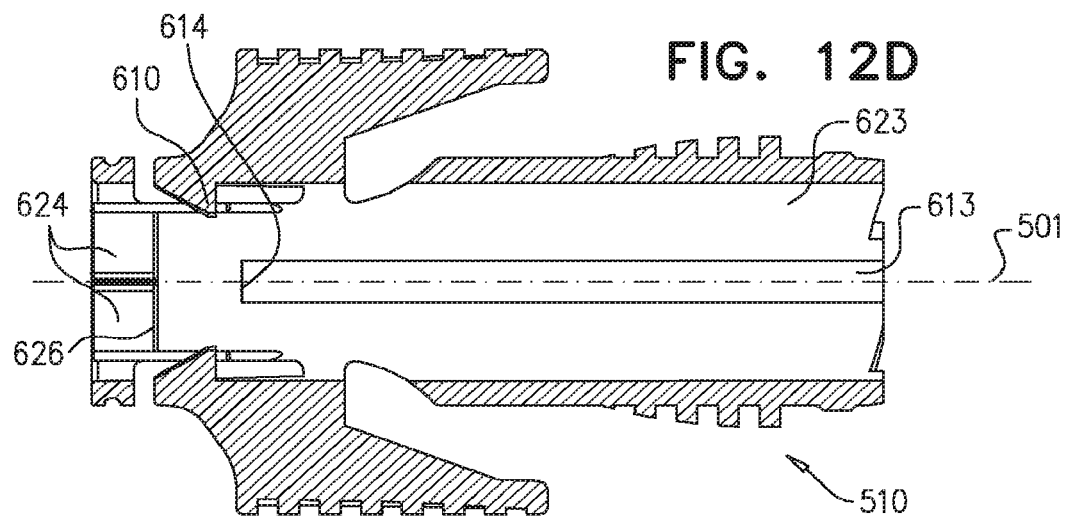

As seen clearly in FIG. 12D, opposite interior surfaces of main portion 600 each define a septa housing guiding recess 613 having a forward stop-defining wall surface 614, which limits the forward displacement of the septa housing 530 relative to the forward housing portion 510.

As seen particularly clearly in FIG. 12C, forward housing portion 510 includes a rearwardly-facing toothed edge 615 having formed thereon a plurality of teeth 616, typically four in number, each including a rearwardly-facing partially circumferential surface 617, a rearwardly and clockwise-facing inclined surface 618 and an axially extending, counter-clockwise facing, locking surface 619 from a forwardly-facing perspective.

Adjacent rearwardly-facing toothed edge 615 on a radially outward surface 620 of main portion 600 are a plurality of mutually spaced circumferential elongate protrusions 621.

Figure 12E:
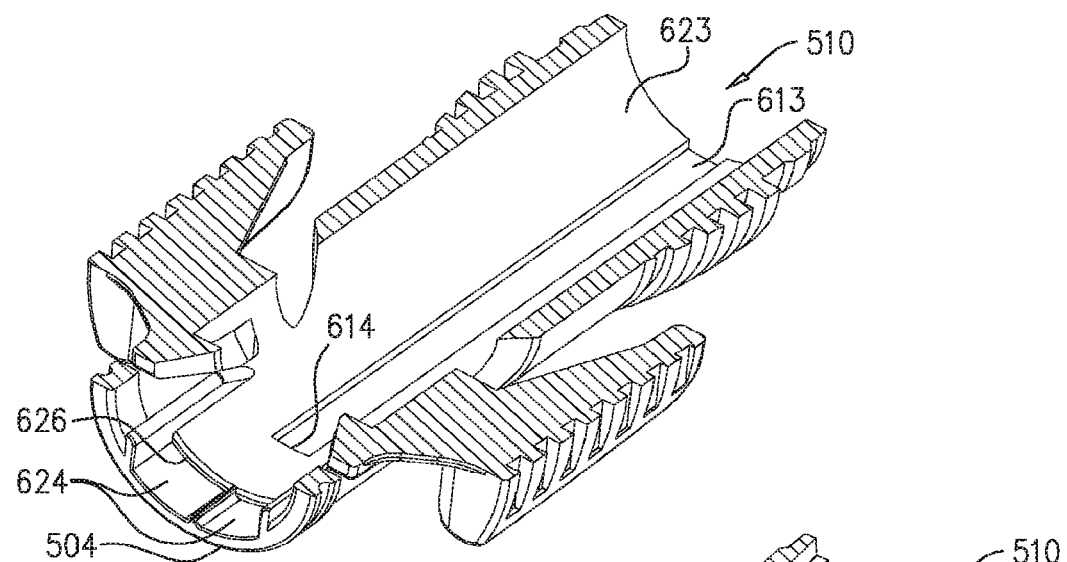
Figure 12F:
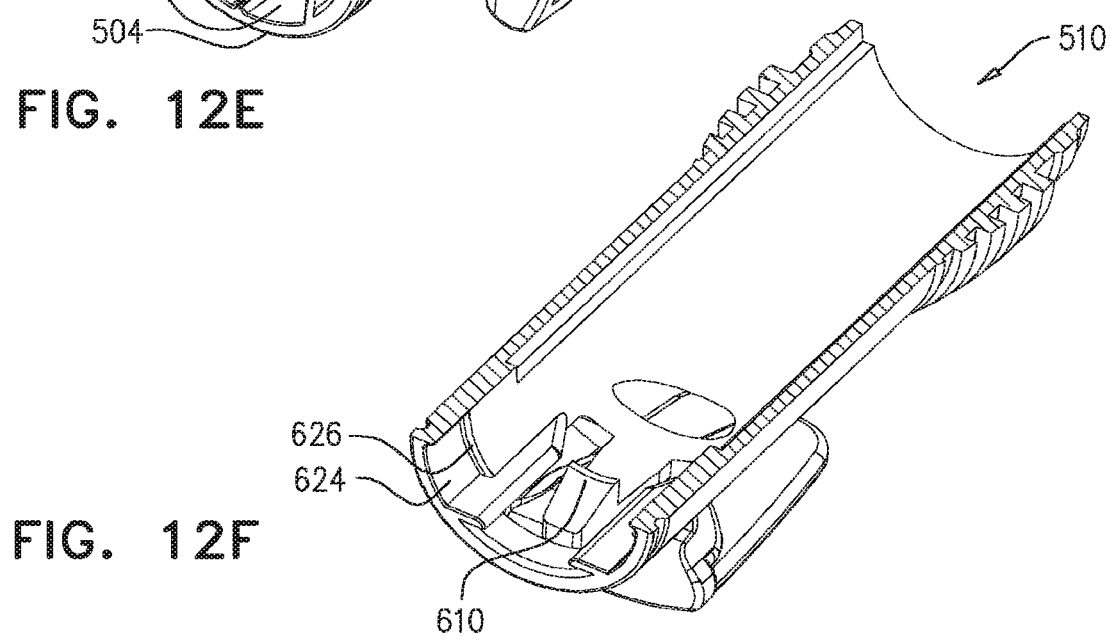

As seen in FIGS. 12D-12F, forwardly of an inwardly-facing circumferential wall surface 623 of the forward housing portion 510 there are provided a plurality of recesses 624, each having an inwardly-facing wall surface which is disposed radially outwardly with respect to inwardly-facing circumferential wall surface 623 as well as being forward thereof. Recesses 624 are each separated from inwardly-facing circumferential wall surface 623 by a tapered shoulder 626.

It is appreciated that forward engagement portions 539 of septa housing mounting legs 538 are seated in corresponding recesses 624 when the port connection end 504 is not engaged by a port adaptor, such as, for example a vial adaptor. Engagement of a port adaptor with port connection end 504 typically forces forward engagement portions 539 radially inwardly and rearwardly out of recesses 624, over respective tapered shoulders 626 and into engagement with inwardly-facing circumferential wall surface 623.

Figure 13A:
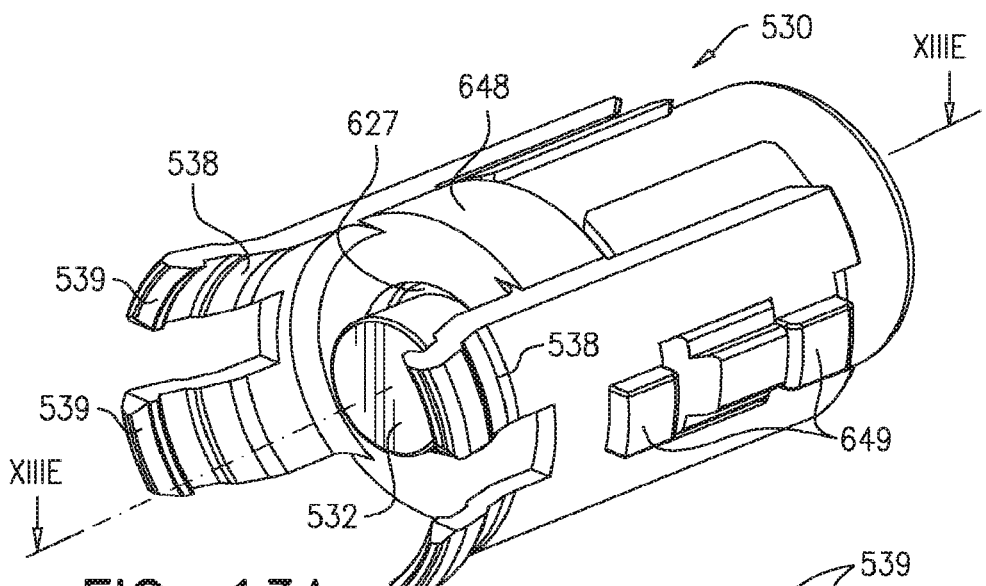
FIGS. 13A, 13B, 13C, 13D and 13E are simplified respective rearward-facing and forward-facing perspective view, side view, forward-facing end view and sectional view illustrations of a septa housing portion forming part of the luer lock adaptor of FIGS. 10A-11, FIG. 13E being taken along lines XIIIE-XIIIE in FIG. 13A.
Figure 13B:
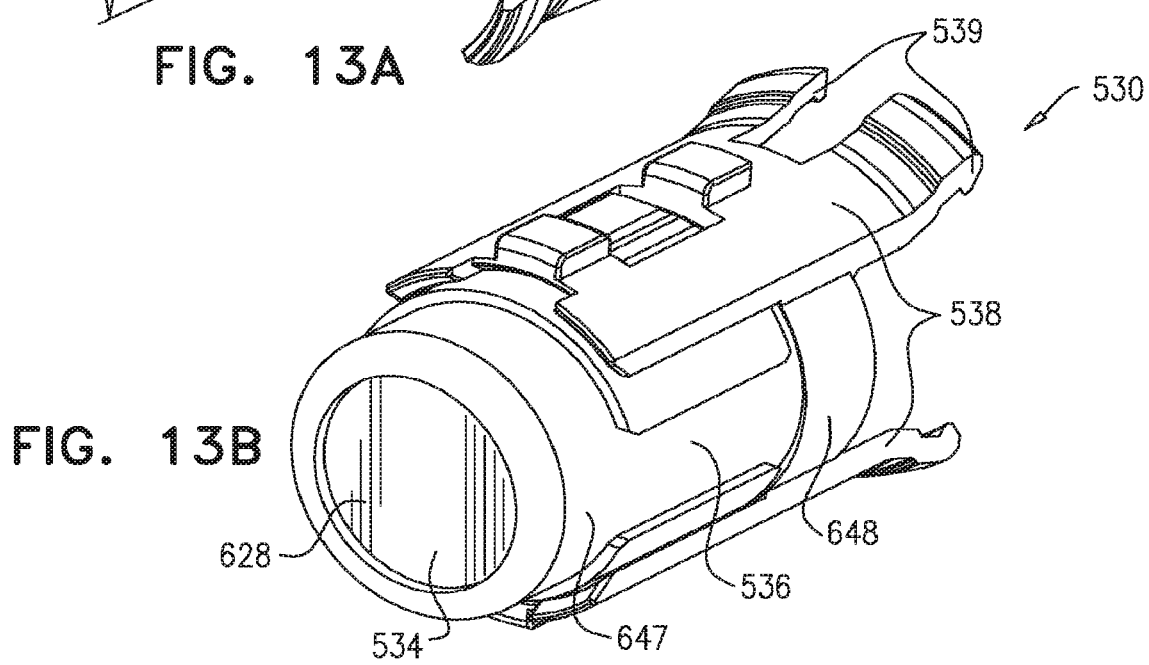
Figure 13C:
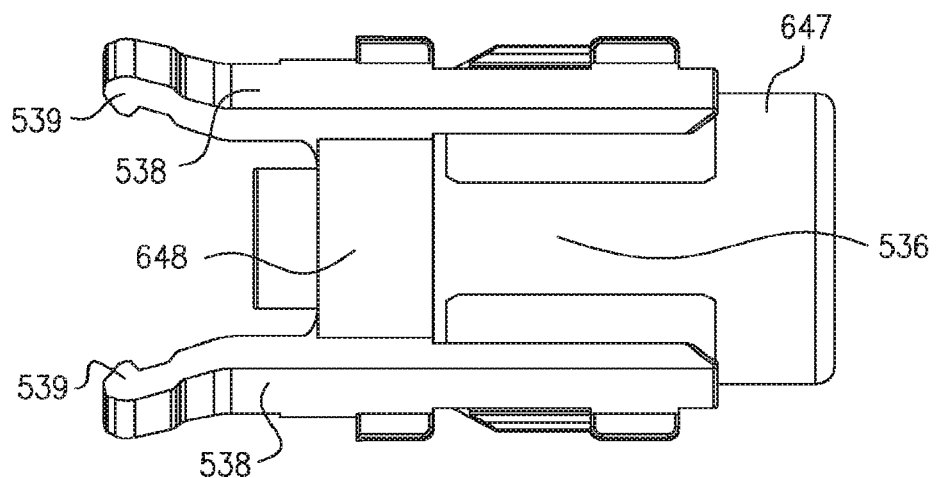
Figure 13D:
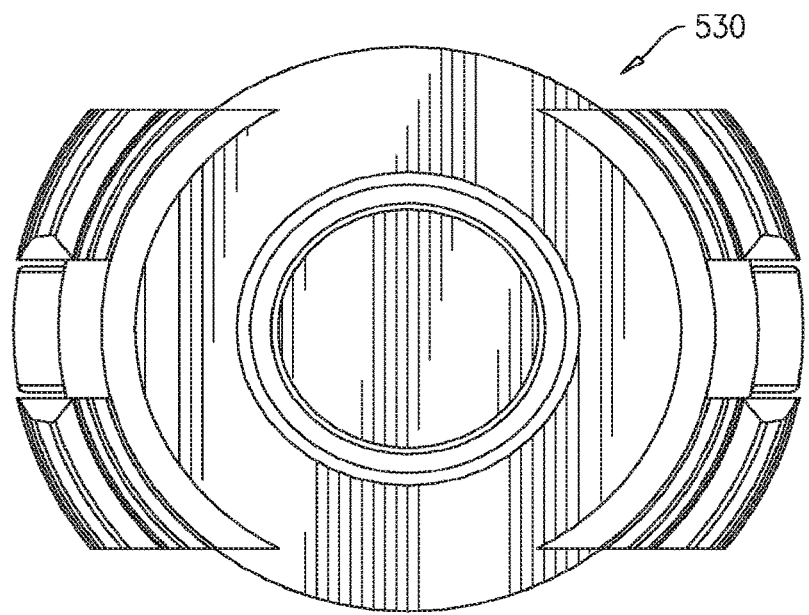
Figure 13E:
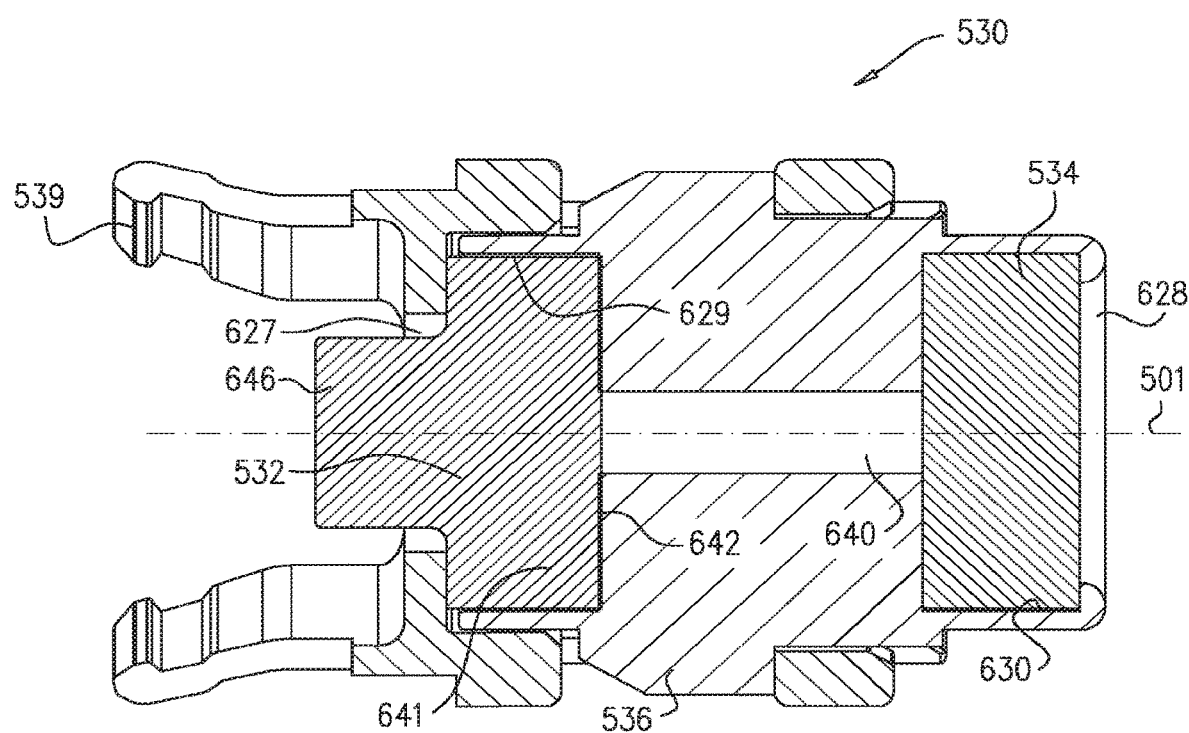

Reference is now made to FIGS. 13A, 13B, 13C, 13D and 13E, which are simplified respective rearward-facing and forward-facing perspective view, side view, forward-facing end view and sectional view illustrations of a septa housing assembly forming part of the luer lock adaptor of FIGS. 10A-11, FIG. 13E being taken along lines XIIIE-XIIIE in FIG. 13A.

As noted above, septa housing assembly 530 including a forward septum 532 and a rearward septum 534, which are fixedly and sealingly retained in a septa mounting portion 536, preferably by ultrasonic swaging of forward and rearward edges of the septa mounting portion 536. Septa housing assembly 530 preferably includes a plurality of septa housing mounting legs 538, each including a forward engagement portion 539, which are typically snap mounted onto septa mounting portion 536.

As seen in FIGS. 13A-13E, the septa housing assembly 530 is a generally cylindrical element having generally rounded respective forward and rearward openings 627 and 628 leading to respective forward and rearward recesses 629 and 630, which accommodate respective forward and rearward septa 532 and 534. An open needle accommodating channel 640 extends longitudinally along axis 501 between forward and rearward recesses 629 and 630.

As seen particularly in FIGS. 13A-13E, forward septum 532 preferably is an integrally formed element formed of a polymer such as polyisoprene and includes a relatively wide, rearward cylindrical portion 641, which is preferably seated in forward recess 629 of septa mounting portion 536 and defines a rearwardly-directed forward septum surface 642, and a relatively narrow cylindrical portion 644, which extends forwardly of rearward cylindrical portion 641 and preferably extends through and forwardly of forward opening 627 in septa housing assembly 530 and defines a forwardly-directed forward septum surface 646. Rearward septum 534 preferably is an integrally formed element formed of a polymer such as polyisoprene, is of a disk like, flat cylindrical configuration and is seated in rearward recess 630 of septa housing assembly 530.

It is seen that septa mounting portion 536 has a generally cylindrical outer surface 647 onto which is snap mounted or otherwise secured a radially outwardly protruding circumferential band 648 from which septa housing mounting legs 538 extend forwardly. A pair of narrow protrusions 649 extend radially outwardly from circumferential band 648 for engaging septa housing guiding recesses 613 and forward stop-defining wall surfaces 614 and thus limiting the forward displacement of septa housing assembly 530 in forward housing portion 510 and preventing the azimuthal rotation of septa housing portion 530 about axis 501.

Figure 14A:
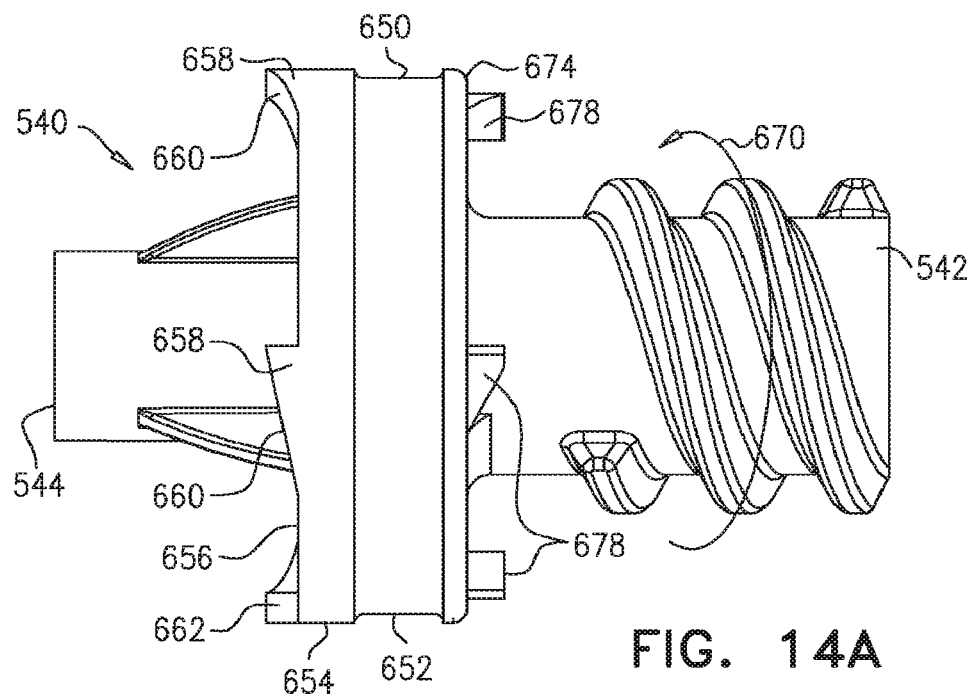
FIGS. 14A, 14B, 14C, 14D and 14E are simplified respective first and second side view, first and second perspective end view and sectional illustrations of a hub element forming part of the luer lock adaptor of FIGS. 10A-11, FIG. 14E being taken along lines XIVE-XIVE in FIG. 14C.
Figure 14B:
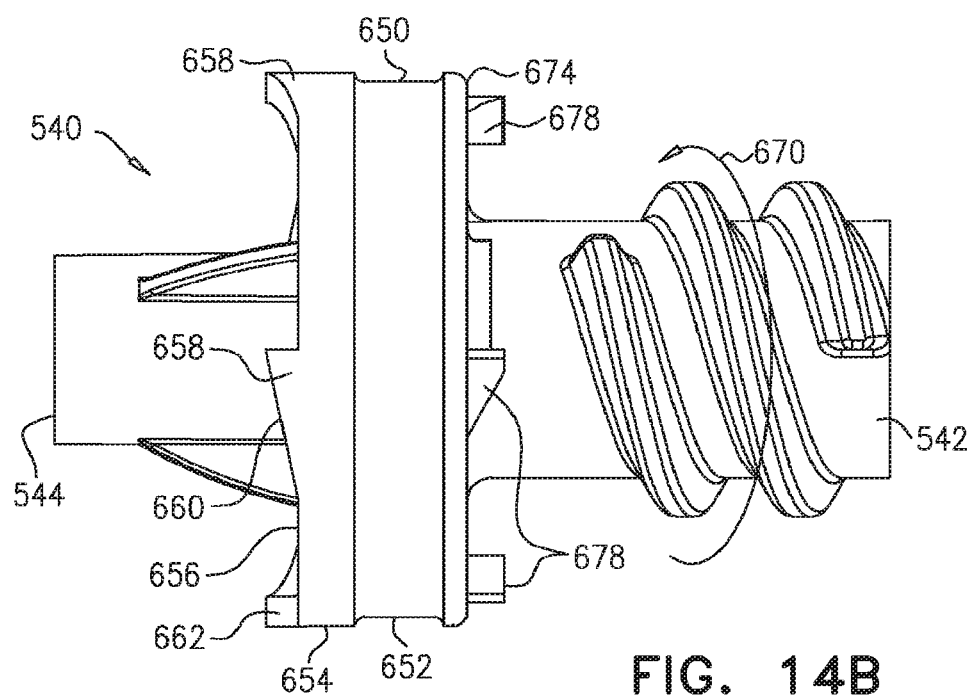
Figure 14C:
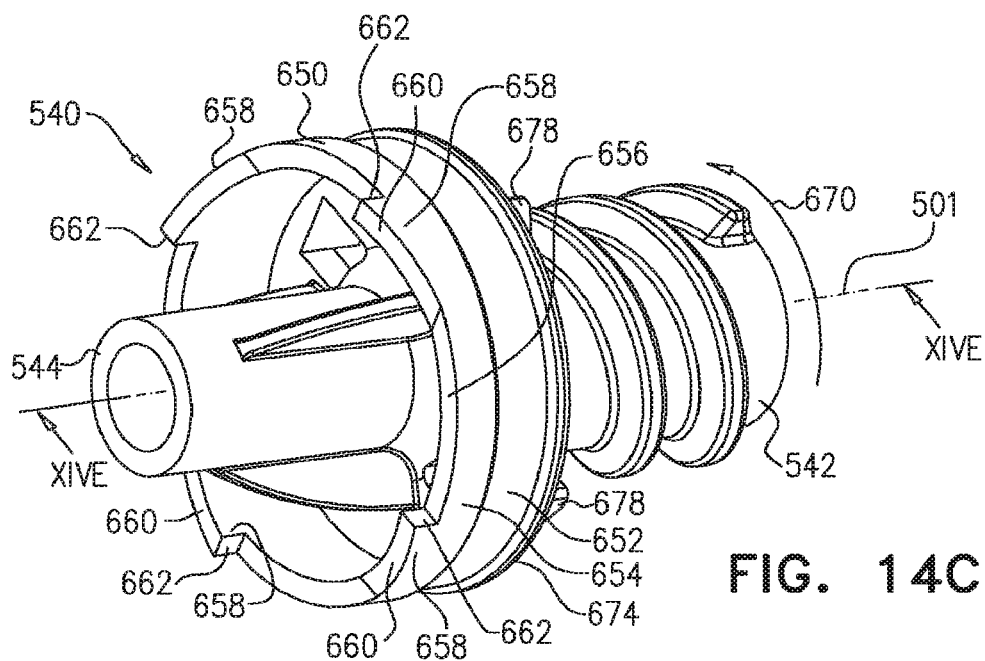
Figure 14D:
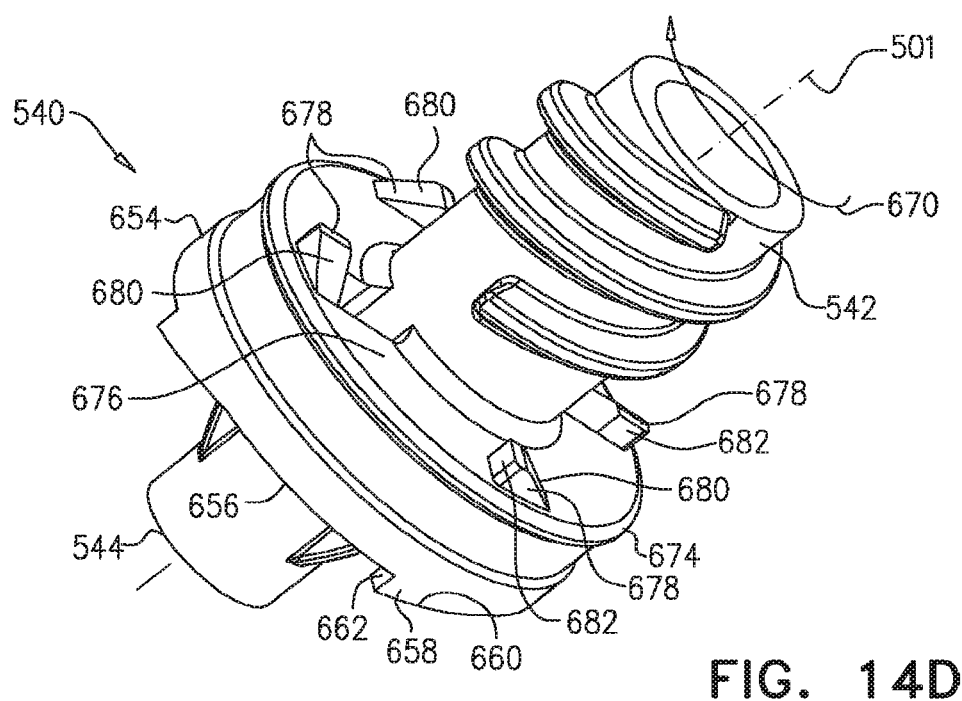
Figure 14E:
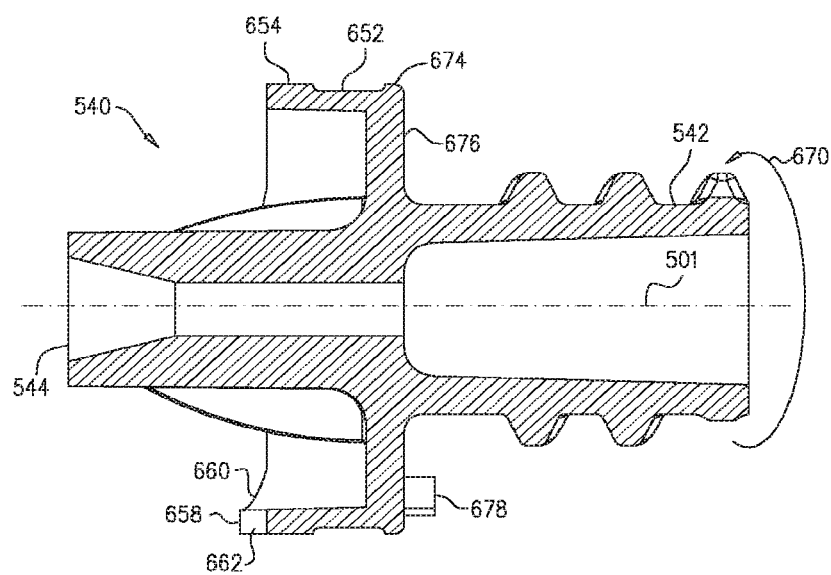

Reference is now made to FIGS. 14A, 14B, 14C, 14D and 14E, which are simplified respective first and second side view, first and second perspective end view and sectional illustrations of hub element 540 forming part of the luer lock adaptor of FIGS. 10A-11, FIG. 14E being taken along lines XIVE-XIVE in FIG. 14C. As noted hereinabove, hub element 540 defines a female luer connector portion 542 at a rearward-facing end and a needle mounting portion 544 at a forward-facing end.

Disposed intermediate the female luer connector portion 542 and the needle mounting portion 544 is a doubly-toothed circumferential intermediate portion 650. Toothed circumferential intermediate portion 650 preferably includes an outwardly-facing circular cylindrical surface portion 652.

Forwardly of outwardly-facing circular cylindrical surface portion 652 is a forward-facing toothed portion 654 having a forward-facing toothed edge 656 having formed thereon a plurality of teeth 658, typically four in number, each including a forwardly and clockwise-facing inclined surface 660 and an axially extending, clockwise facing, locking surface 662, from a forward-facing perspective.

The arrangement of teeth 658 is such that when a male luer connector of a syringe or other element (not shown) is screwed onto female luer connector portion 542 in a clockwise direction of rotation from a forwardly-facing perspective, continued rotation of the syringe in the aforesaid clockwise direction produces corresponding rotation of hub element 540 in the aforesaid clockwise direction and causes clockwise facing, axially and radially directed locking surfaces 662 to lockingly engage corresponding counter-clockwise facing, axially and radially directed locking surfaces 619 of teeth 616 on rearwardly-facing toothed edge 615 of forward housing portion 510. The aforesaid clockwise direction of rotation is indicated by arrows 670 in FIGS. 14A-14E.

Rearwardly of outwardly-facing circular cylindrical surface portion 652 is a rearward-facing toothed portion 674 having a rearward-facing toothed surface 676 having formed thereon a plurality of teeth 678, typically four in number, each including a rearwardly and clockwise-facing inclined surface 680 and a clockwise-facing, axially and radially directed locking surface 682.

Figure 15A:
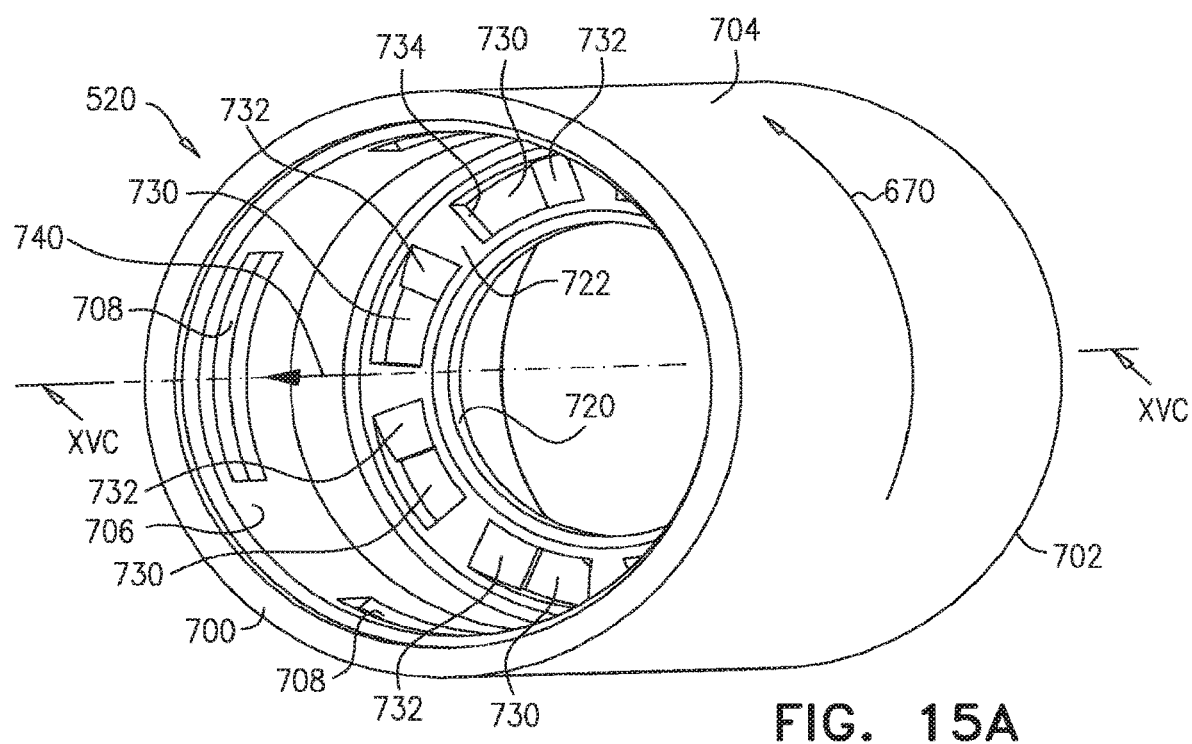
FIGS. 15A, 15B and 15C are simplified first and second perspective end view and a sectional illustration of a rearward housing portion forming part of the luer lock adaptor of FIGS. 10A-11.
Figure 15B:
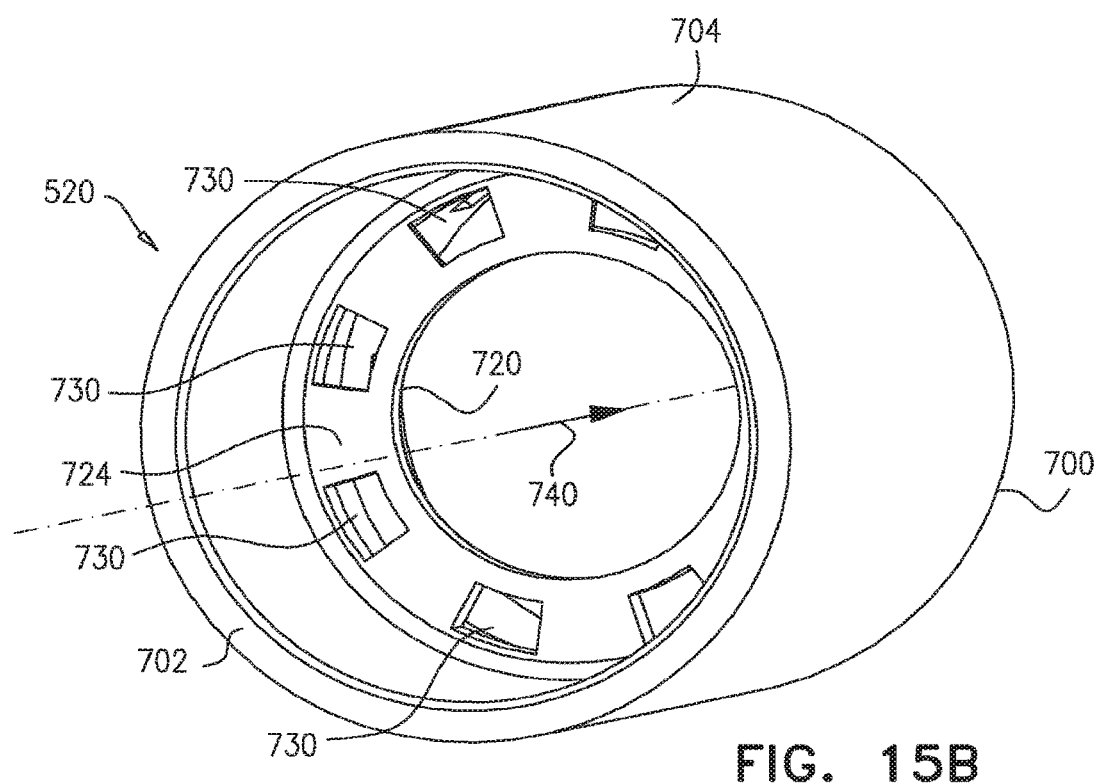
Figure 15C:
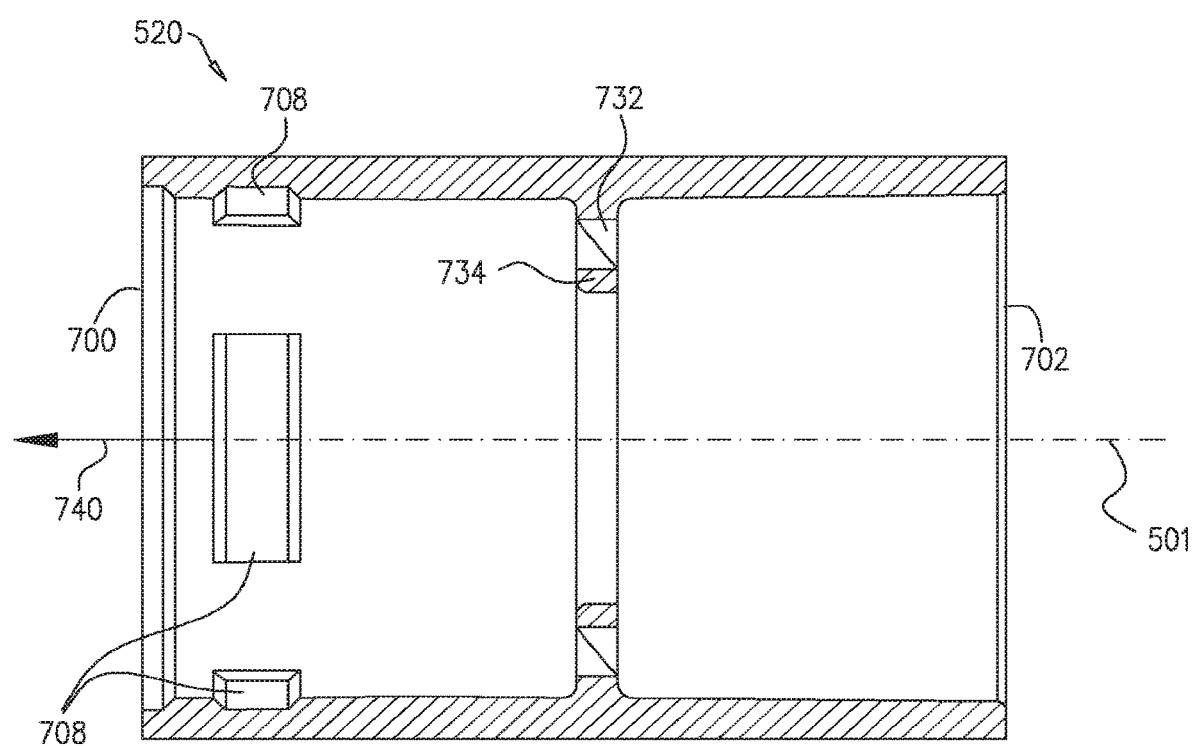

Reference is now additionally made to FIGS. 15A, 15B and 15C, which are simplified first and second perspective end view, and sectional view illustrations of rearward housing portion 520.

As seen in FIGS. 11 and 15A-15C, rearward housing portion 520 is preferably an overall circular cylindrical element arranged along axis 501 and having a forward end 700, a rearward end 702 and a circular cylindrical outwardly-facing surface 704. Formed on an inwardly-facing surface 706 are a plurality of mutually azimuthally spaced circumferential recesses 708 which receive corresponding protrusions 621 of forward housing portion 510 in a snap fit engagement, thereby providing both axial and azimuthal locking between forward housing portion 510 and rearward housing portion 520.

Intermediate forward end 700 and rearward end 702 and extending radially inwardly of inwardly-facing surface 706 is an inwardly directed flange 720 having a forwardly-facing surface 722 and a rearwardly-facing surface 724. Forwardly-facing surface 722 is preferably formed with an azimuthal array of toothed recesses 730, preferably four or more in number, each of which includes a forwardly and clockwise-facing inclined surface 732 and an axial directed counter-clockwise-facing locking surface 734.

The arrangement of teeth 658 is such that when a male luer connector of a syringe or other element (not shown) is screwed onto female luer connector portion 542 in a clockwise direction of rotation, indicated by arrow 670, together with the application of a forwardly-directed axial force along axis 501, indicated by an arrow 740, continued rotation of the syringe in the aforesaid clockwise direction does not produce corresponding rotation of hub element 540 in the aforesaid clockwise direction indicated by arrow 670 and enables tight engagement of the syringe with the hub 540. This arrangement is also such that when a user attempts to unscrew the male luer connector by rotating it in a counterclockwise direction, indicated by an arrow 742 (FIGS. 16A-16D), the hub 540 rotates about axis 501 together with the syringe, thereby preventing disengagement of the syringe from the hub 540.

Reference is now made to FIGS. 16A, 16B, 16C, 16D, 16E and 16F, which are simplified illustrations of the luer lock adaptor of FIGS. 10A-15C in respective first, second, third, fourth, fifth and sixth operative orientations with respect to a conventional luer lock syringe.

Figure 16A:
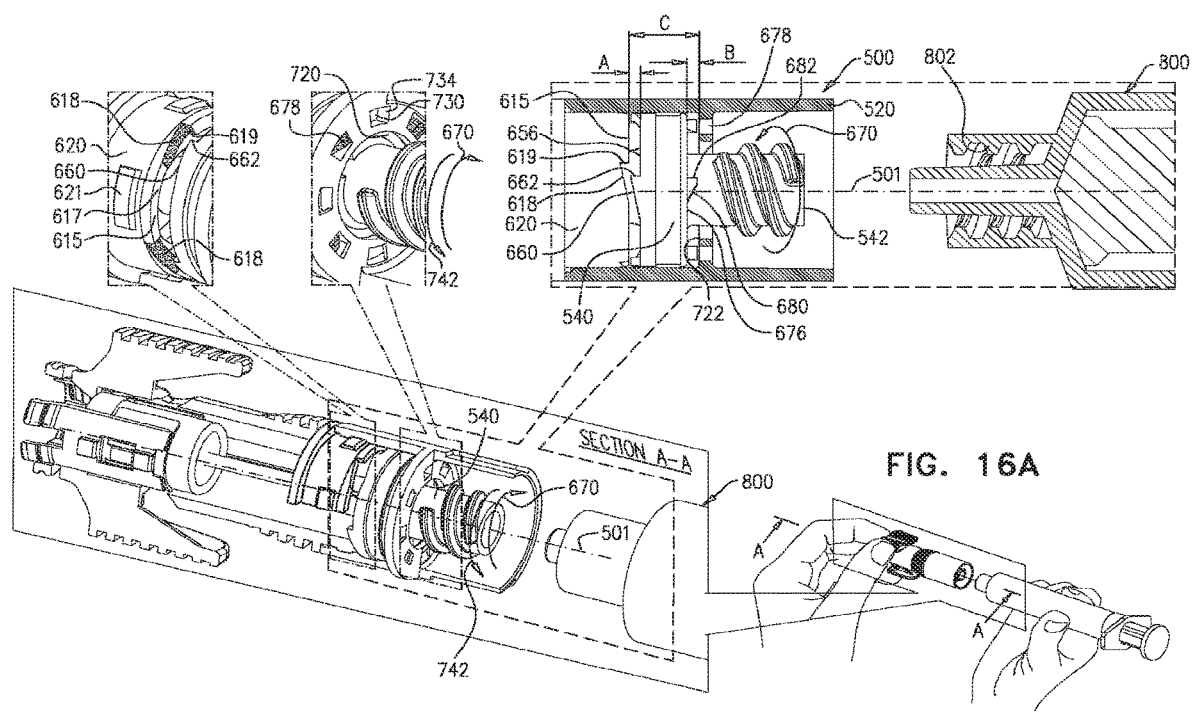

FIG. 16A shows a conventional luer lock syringe 800 having a male luer connector 802 about to be connected to the luer lock adaptor 500 of FIGS. 10A-15C.

It is noted that in the embodiment of FIGS. 1A-9G, prior to engagement of the luer lock syringe 400 with the luer lock adaptor 100, the compression action of compression spring 152 urges hub element 140 against forward facing surface 322 of flange 320 of rearward housing portion 120, such that teeth 278 of hub element 140 lockingly engage recesses 330 and clockwise-facing, axially and radially directed locking surfaces 282 of teeth 278 lockingly engage axial directed counter-clockwise-facing locking surfaces 334, thereby permitting counterclockwise, from a forwardly-facing perspective, rotation of hub element 140 relative to rearward housing portion 120, represented by arrow 342, but preventing clockwise, from a forwardly-facing perspective, rotation of hub element 140 relative to rearward housing portion 120, represented by arrow 270.

In the embodiment of FIGS. 10A-16F, no compression spring is provided and thus, prior to engagement of the luer lock syringe 800 with the luer lock adaptor 500, hub element 540 is not urged against forward facing surface 722 of flange 720 of rearward housing portion 520, such that teeth 678 of hub element 540 do not necessarily and usually do not lockingly engage recesses 730 and clockwise-facing, axially and radially directed locking surfaces 682 of teeth 678 do not necessarily and usually do not lockingly engage axial directed counter-clockwise-facing locking surfaces 734, thereby permitting counterclockwise, from a forwardly-facing perspective, rotation of hub element 540 relative to rearward housing portion 520, represented by arrow 742, but usually also permitting clockwise, from a forwardly-facing perspective, rotation of hub element 540 relative to rearward housing portion 520, represented by arrow 670.

It is noted that an axial separation, indicated by the letter A, between rearwardly-facing toothed edge 615 of forward housing portion 510 and forward-facing toothed edge 656 of hub element 540 may or may not be greater than the axial extent of axially extending, clockwise facing, locking surface 662, such that mutual rotation between the hub element 540 and the forward housing portion 510 in either rotational direction may or may not be restricted. In the illustrated embodiment shown in FIG. 16A, axial separation A is typically between approximately 0.7 mm and 1.0 mm and an axial separation, indicated by the letter B, between forward-facing surface 722 of the rearward housing portion 520 and the rearward-facing toothed surface of 676 of hub element 540, is typically between 0.8 mm and 1.1 mm.

It is appreciated that an axial separation between forward-facing surface 722 of the rearward housing portion 520 and rearwardly-facing toothed edge 615 of forward housing portion 510, indicated by the letter C, remains constant, typically approximately 5.4 mm, due to the snap fit engagement of forward housing portion 510 and rearward housing portion 520, providing axial and azimuthal locking between forward housing portion 510 and rearward housing portion 520, as described hereinabove. Additionally, the sum of axial separation A and axial separation B remains constant, typically approximately 1.8 mm, due to the snap fit engagement of forward housing portion 510 and rearward housing portion 520, providing axial and azimuthal locking between forward housing portion 510 and rearward housing portion 520, as described hereinabove.

Figure 16B:
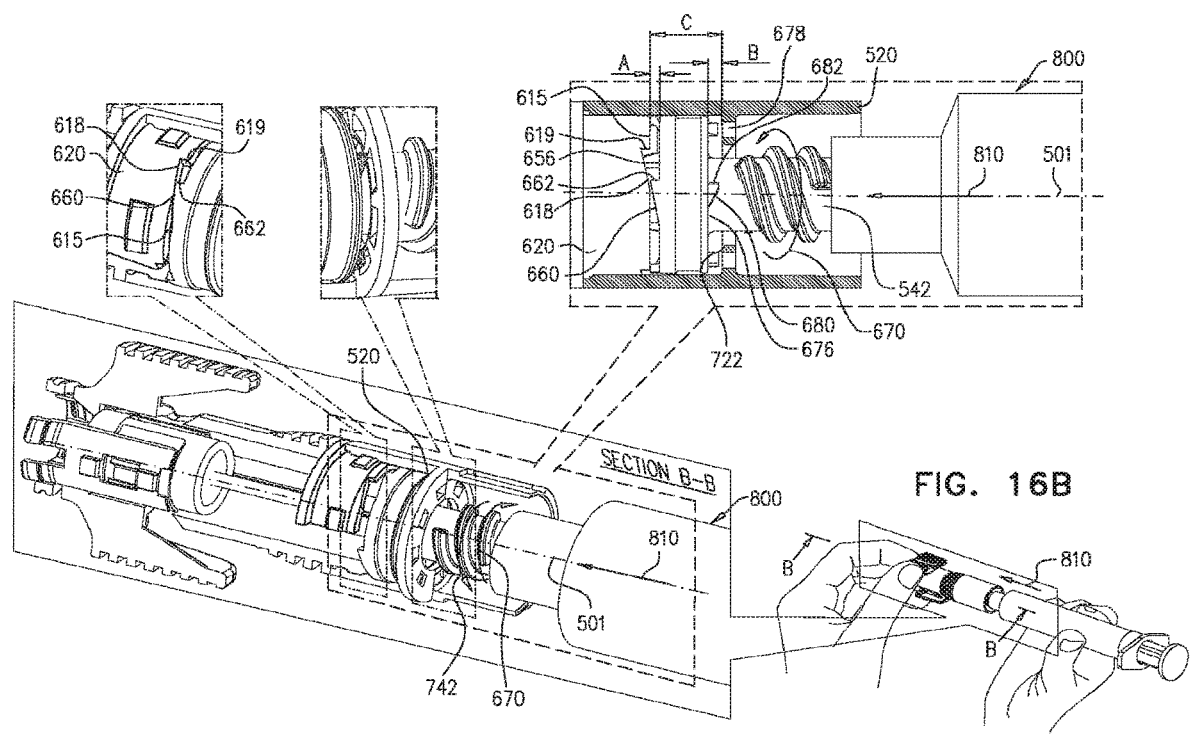

FIG. 16B illustrates initial forward axial displacement of syringe 800 relative to luer lock adaptor 500 along axis 501 such that the male luer connector 802 is in touching engagement with female luer connector portion 542 at a rearward-facing end thereof. The touching engagement pushes hub element 540 forward, as indicated by an arrow 810, relative to rearward housing portion 520 until teeth 658 of hub element 540 are in touching engagement with inclined surfaces 618 of teeth 616 which stops rotation of hub element 540 and allows syringe 800 to be rotated relative to hub element 540.

In the illustrated embodiment shown in FIG. 16B, axial separation A is less than the axial extent of axially extending, clockwise facing locking surface 662, approximately 0.7 mm, and axial separation B, is greater than 1.1 mm, which is greater than the axial extent of clockwise-facing, axially and radially directed locking surface 682, which is typically approximately 0.8 mm.

FIG. 16C illustrates clockwise rotation of the syringe 800 relative to luer lock adaptor 500 about axis 501, as indicated by arrow 670, such that the male luer connector 802 is in partial threaded frictional engagement with female luer connector portion 542 of hub element 540. This rotation takes place together with application of an additional forward axial force along axis 501 as indicated by arrow 740.

In the illustrated embodiment shown in FIG. 16C, due to the clockwise rotation of hub element 540 relative to forward housing portion 510 and rearward housing portion 520 from the position shown in FIG. 16B, axial separation A shown in FIG. 16C, approximately 0.4 mm, is less than axial separation A shown in FIG. 16B, and axial separation B shown in FIG. 16C, approximately 1.4 mm, is greater than axial separation B shown in FIG. 16B.

FIG. 16D illustrates clockwise rotation of the syringe 800 relative to luer lock adaptor 500 about axis 501, such that the male luer connector 802 is in full threaded frictional engagement with female luer connector portion 542 of hub element 540. This rotation takes place together with application of an additional forward axial force along axis 501 as indicated by arrow 740.

This forward axial force causes axial separation A to decrease to zero and axial separation B to increase to approximately 1.8 mm as rearwardly-facing toothed edge 615 of forward housing portion 510 lockingly engages forward-facing toothed edge 656 of hub element 540 and prevents further clockwise rotation of the hub element 540 relative to forward housing portion 510, notwithstanding the absence of a compression spring.

Figure 16E:
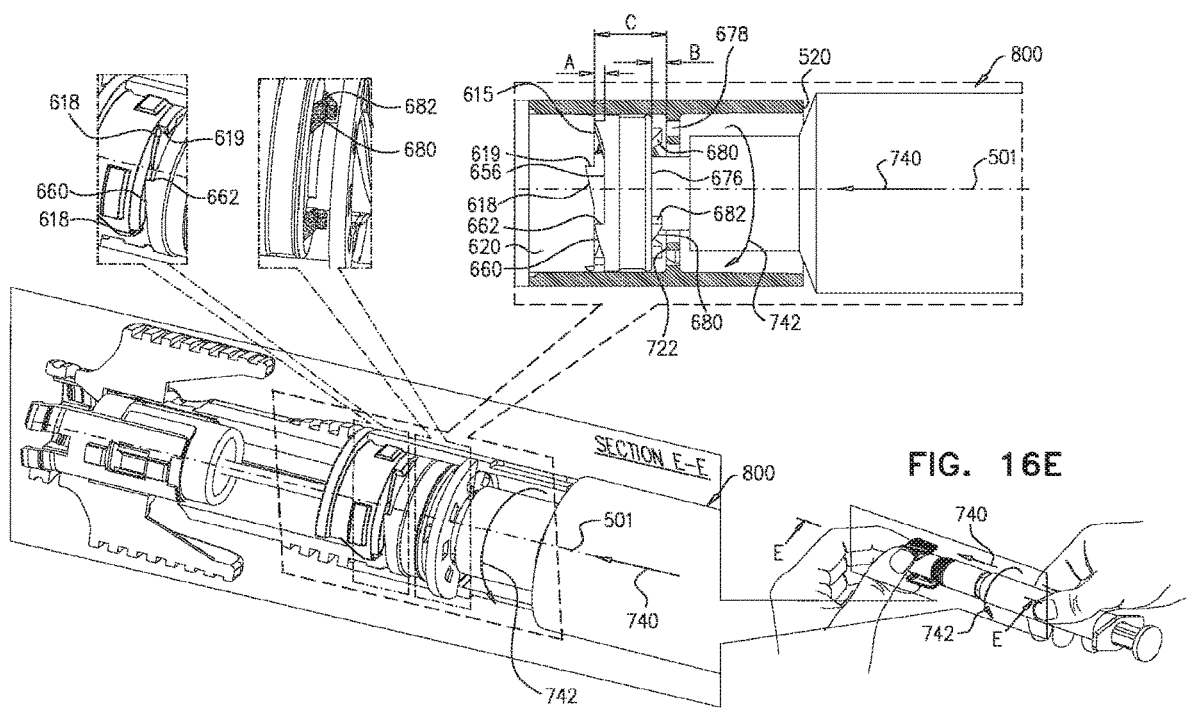

FIG. 16E illustrates counterclockwise rotation of the syringe 800 relative to rearward housing portion 520 of luer lock adaptor 500 about axis 501 combined with application of a forwardly-directed axial force, as indicated by arrows 742 and 740, in an attempt to disengage the male luer connector 802 from the female luer connector portion 542 of hub element 540. This attempt is unsuccessful due to the frictional engagement of the male luer connector 802 with the female luer connector portion 542 of hub element 540 and due to the fact that the hub element 540 is free to rotate counterclockwise relative to the remainder of the luer lock adaptor 500 due to the fact that forward-facing toothed edge 656 of hub element 540, having formed thereon a plurality of teeth 658, typically four in number, each including a forwardly and clockwise-facing inclined surface 660 in counterclockwise rotation relative to the forward housing portion 510 slides over rearwardly-facing toothed edge 615 having formed thereon a plurality of teeth 616, typically four in number, each including, a rearwardly-facing partially circumferential surface 617 and a rearwardly and clockwise-facing inclined surface 618, such that rotation of the hub element 540 relative to the forward housing portion 510 in the counterclockwise direction is not restricted.

In the illustrated embodiment shown in FIG. 16E, due to the counter-clockwise rotation of hub element 540 relative to forward housing portion 510 and rearward housing portion 520 from the position shown in FIG. 16D, axial separation A is approximately equal to the axial extent of axially extending, clockwise facing locking surface 662, approximately 0.7 mm, and axial separation B is approximately 1.1 mm.

FIG. 16F illustrates counterclockwise rotation of the syringe 800 relative to rearward housing portion 520 of luer lock adaptor 500 about axis 501 combined with application of a rearwardly-directed axial force, as indicated by arrows 742 and 820, in an attempt to disengage the male luer connector 802 from the female luer connector portion 542 of hub element 540. This attempt is unsuccessful due to the frictional engagement of the male luer connector 802 with the female luer connector portion 542 of hub element 540 and due to the fact that the hub element 540 is free to rotate counterclockwise relative to the remainder of the luer lock adaptor 500 due to the fact that rearward-facing toothed edge 674 of hub element 540, having formed thereon a plurality of teeth 678, typically four in number, each including rearwardly and clockwise-facing inclined surface 680, in counterclockwise rotation relative to the rearward housing portion 520 slides over forwardly-facing surface 722 having formed thereon a plurality of teethed recesses 730, typically four in number, each including, forwardly and clockwise-facing inclined surface 732 and an axial directed counter-clockwise-facing locking surface 734, such that rotation of the hub element 540 relative to the forward housing portion 510 in the counterclockwise direction is not restricted.

In the illustrated embodiment shown in FIG. 16F, due to the combination of rearwardly-directed axial force, indicated by arrow 820, and counter-clockwise rotation of hub element 540 relative to forward housing portion 510 and rearward housing portion 520 from the position shown in FIG. 16D, axial separation A is approximately 1.0 mm and axial separation B is approximately equal to the axial extent of clockwise-facing, axially and radially directed locking surface 682, approximately 0.8 mm.

Reference is now made to FIGS. 17A, 17B, 17C, 17D, 17E and 17F, which are simplified illustrations of the luer lock adaptor of FIGS. 10A-15C in respective first, second, third, fourth, fifth and sixth operative orientations with respect to a conventional luer lock syringe.

Figure 17A:
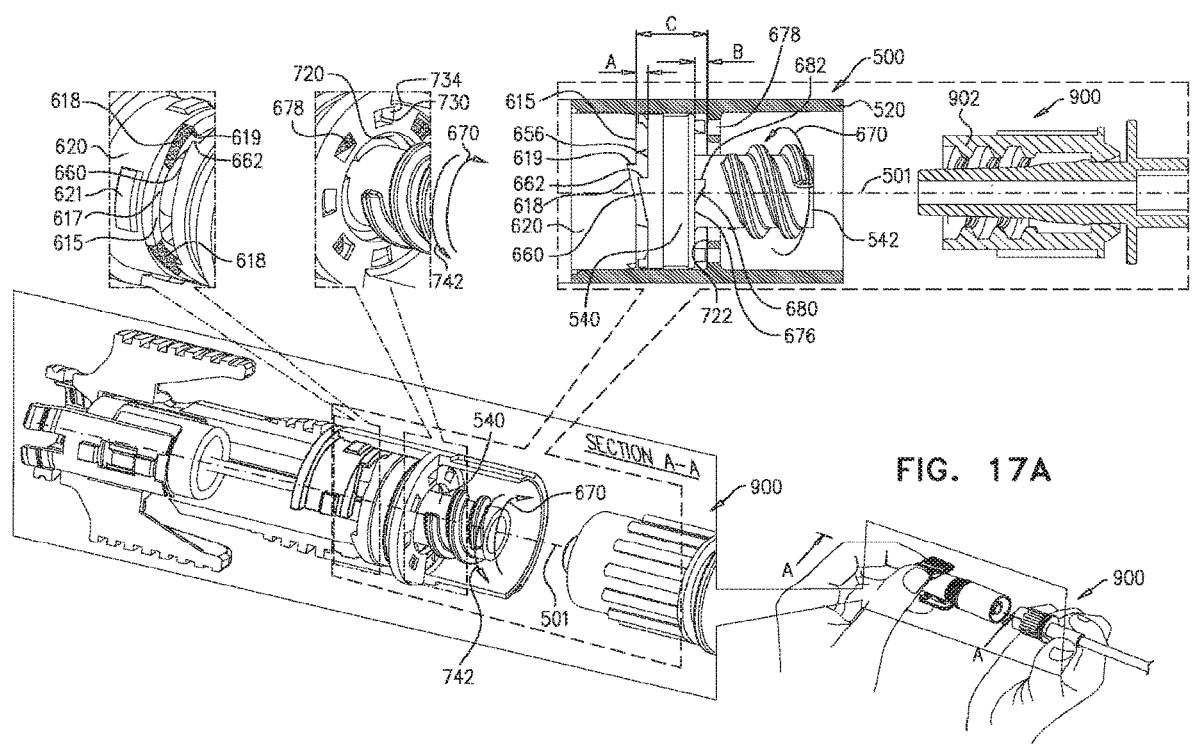

FIG. 17A shows a conventional luer lock connector 900 having a male luer connector 902 about to be connected to the luer lock adaptor 500 of FIGS. 10A-15C.

It is noted that in the embodiment of FIGS. 1A-9G, prior to engagement of the luer lock connector 420 with the luer lock adaptor 100, the compression action of compression spring 152 urges hub element 140 against forward facing surface 322 of flange 320 of rearward housing portion 120, such that teeth 278 of hub element 140 lockingly engage recesses 330 and clockwise-facing, axially and radially directed locking surfaces 282 of teeth 278 lockingly engage axial directed counter-clockwise-facing locking surfaces 334, thereby permitting counterclockwise, from a forwardly-facing perspective, rotation of hub element 140 relative to rearward housing portion 120, represented by arrow 342, but preventing clockwise, from a forwardly-facing perspective, rotation of hub element 140 relative to rearward housing portion 120, represented by arrow 270.

In the embodiment of FIGS. 10A-17F, no compression spring is provided and thus, prior to engagement of the luer lock connector 900 with the luer lock adaptor 500, hub element 540 is not urged against forward facing surface 722 of flange 720 of rearward housing portion 520, such that teeth 678 of hub element 540 do not necessarily and usually do not lockingly engage recesses 730 and clockwise-facing, axially and radially directed locking surfaces 682 of teeth 678 do not necessarily and usually do not lockingly engage axial directed counter-clockwise-facing locking surfaces 734, thereby permitting counterclockwise, from a forwardly-facing perspective, rotation of hub element 540 relative to rearward housing portion 520, represented by arrow 742, but usually also permitting clockwise, from a forwardly-facing perspective, rotation of hub element 540 relative to rearward housing portion 520, represented by arrow 670.

It is noted that an axial separation, indicated by the letter A, between rearwardly-facing toothed edge 615 of forward housing portion 510 and forward-facing toothed edge 656 of hub element 540 may or may not be greater than the axial extent of axially extending, clockwise facing, locking surface 662, such that mutual rotation between the hub element 540 and the forward housing portion 510 in either rotational direction may or may not be restricted. In the illustrated embodiment shown in FIG. 17A, axial separation A is typically between approximately 0.7 mm and 1.0 mm and an axial separation, indicated by the letter B, between forward-facing surface 722 of the rearward housing portion 520 and the rearward-facing toothed surface of 676 of hub element 540, is typically between 0.8 mm and 1.1 mm.

It is appreciated that an axial separation between forward-facing surface 722 of the rearward housing portion 520 and rearwardly-facing toothed edge 615 of forward housing portion 510, indicated by the letter C, remains constant, typically approximately 5.4 mm, due to the snap fit engagement of forward housing portion 510 and rearward housing portion 520, providing axial and azimuthal locking between forward housing portion 510 and rearward housing portion 520, as described hereinabove. Additionally, the sum of axial separation A and axial separation B remains constant, typically approximately 1.8 mm, due to the snap fit engagement of forward housing portion 510 and rearward housing portion 520, providing axial and azimuthal locking between forward housing portion 510 and rearward housing portion 520, as described hereinabove.

FIG. 17B illustrates initial forward axial displacement of luer lock connector 900 relative to luer lock adaptor 500 along axis 501 such that the male luer connector 902 is in touching engagement with female luer connector portion 542 at a rearward-facing end thereof. The touching engagement pushes hub element 540 forward, as indicated by an arrow 910, relative to rearward housing portion 520 until teeth 658 of hub element 540 are in touching engagement with inclined surfaces 618 of teeth 616 which stops rotation of hub element 540 and allows luer lock connector 900 to be rotated relative to hub element 540.

In the illustrated embodiment shown in FIG. 17B, axial separation A is less than the axial extent of axially extending, clockwise facing locking surface 662, approximately 0.7 mm, and axial separation B, is greater than 1.1 mm, which is greater than the axial extent of clockwise-facing, axially and radially directed locking surface 682, which is typically approximately 0.8 mm.

FIG. 17C illustrates clockwise rotation of the luer lock connector 900 relative to luer lock adaptor 500 about axis 501, as indicated by arrow 670, such that the male luer connector 902 is in partial threaded frictional engagement with female luer connector portion 542 of hub element 540. This rotation takes place together with application of an additional forward axial force along axis 501 as indicated by arrow 740.

In the illustrated embodiment shown in FIG. 17C, due to the clockwise rotation of hub element 540 relative to forward housing portion 510 and rearward housing portion 520 from the position shown in FIG. 17B, axial separation A shown in FIG. 17C, approximately 0.4 mm, is less than axial separation A shown in FIG. 17B, and axial separation B shown in FIG. 17C, approximately 1.4 mm, is greater than axial separation B shown in FIG. 17B.

Figure 17D:
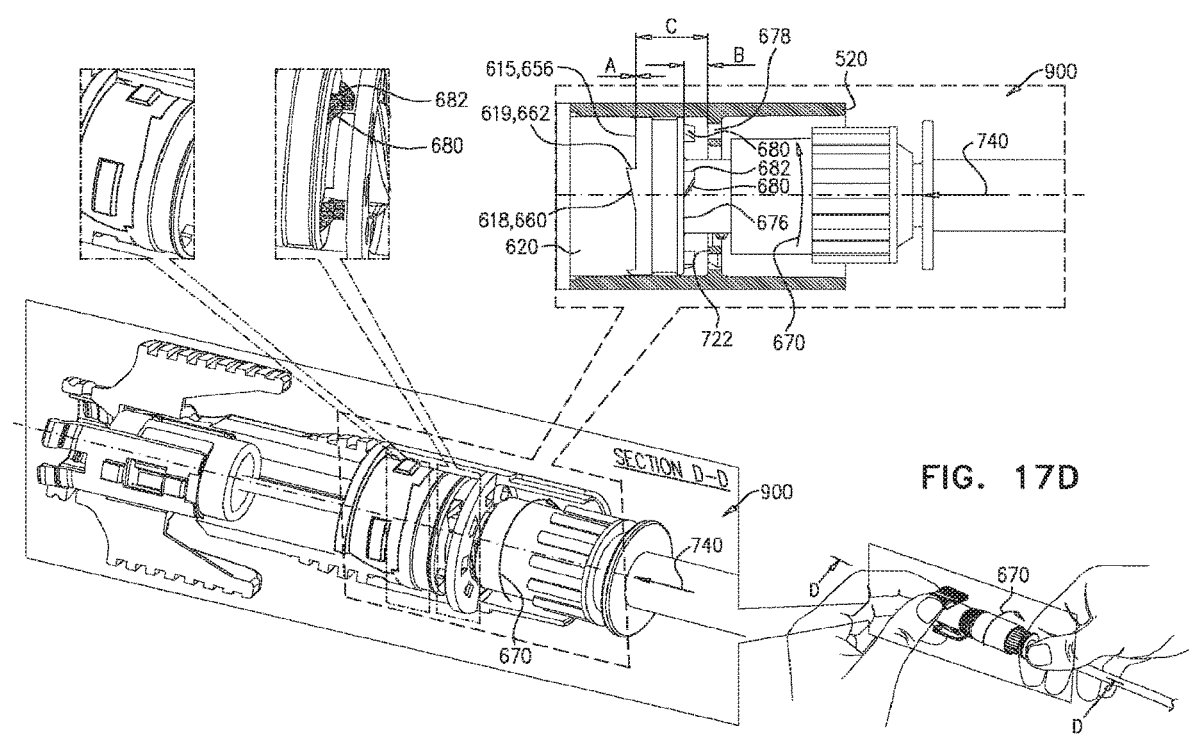

FIG. 17D illustrates clockwise rotation of the luer lock connector 900 relative to luer lock adaptor 500 about axis 501, such that the male luer connector 902 is in full threaded frictional engagement with female luer connector portion 542 of hub element 540. This rotation takes place together with application of an additional forward axial force along axis 501 as indicated by arrow 740.

This forward axial force causes axial separation A to decrease to zero and axial separation B to increase to approximately 1.8 mm as rearwardly-facing toothed edge 615 of forward housing portion 510 lockingly engages forward-facing toothed edge 656 of hub element 540 and prevents further clockwise rotation of the hub element 540 relative to forward housing portion 510, notwithstanding the absence of a compression spring.

Figure 17E:
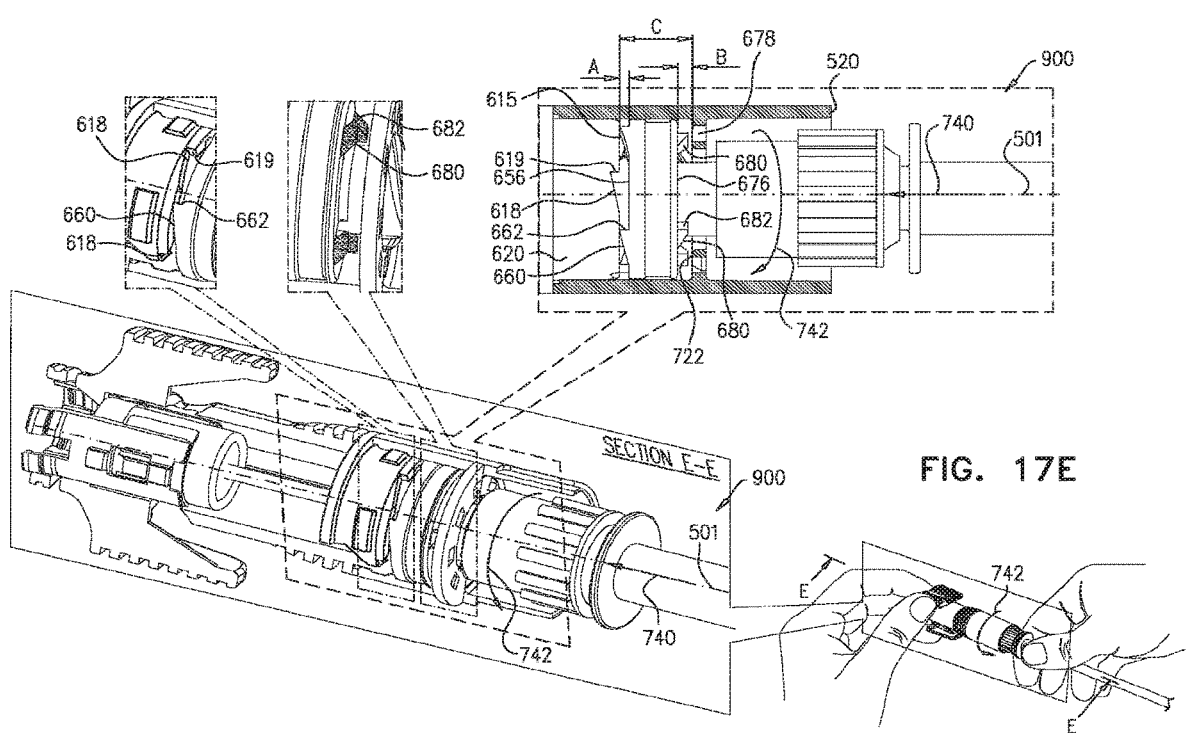

FIG. 17E illustrates counterclockwise rotation of the luer lock connector 900 relative to rearward housing portion 520 of luer lock adaptor 500 about axis 501 combined with application of a forwardly-directed axial force, as indicated by arrows 742 and 740, in an attempt to disengage the male luer connector 902 from the female luer connector portion 542 of hub element 540. This attempt is unsuccessful due to the frictional engagement of the male luer connector 902 with the female luer connector portion 542 of hub element 540 and due to the fact that the hub element 540 is free to rotate counterclockwise relative to the remainder of the luer lock adaptor 500 due to the fact that forward-facing toothed edge 656 of hub element 540, having formed thereon a plurality of teeth 658, typically four in number, each including a forwardly and clockwise-facing inclined surface 660 in counterclockwise rotation relative to the forward housing portion 510 slides over rearwardly-facing toothed edge 615 having formed thereon a plurality of teeth 616, typically four in number, each including, a rearwardly-facing partially circumferential surface 617 and a rearwardly and clockwise-facing inclined surface 618, such that rotation of the hub element 540 relative to the forward housing portion 510 in the counterclockwise direction is not restricted.

In the illustrated embodiment shown in FIG. 17E, due to the counter-clockwise rotation of hub element 540 relative to forward housing portion 510 and rearward housing portion 520 from the position shown in FIG. 17D, axial separation A is approximately equal to the axial extent of axially extending, clockwise facing locking surface 662, approximately 0.7 mm, and axial separation B is approximately 1.1 mm.

Figure 17F:
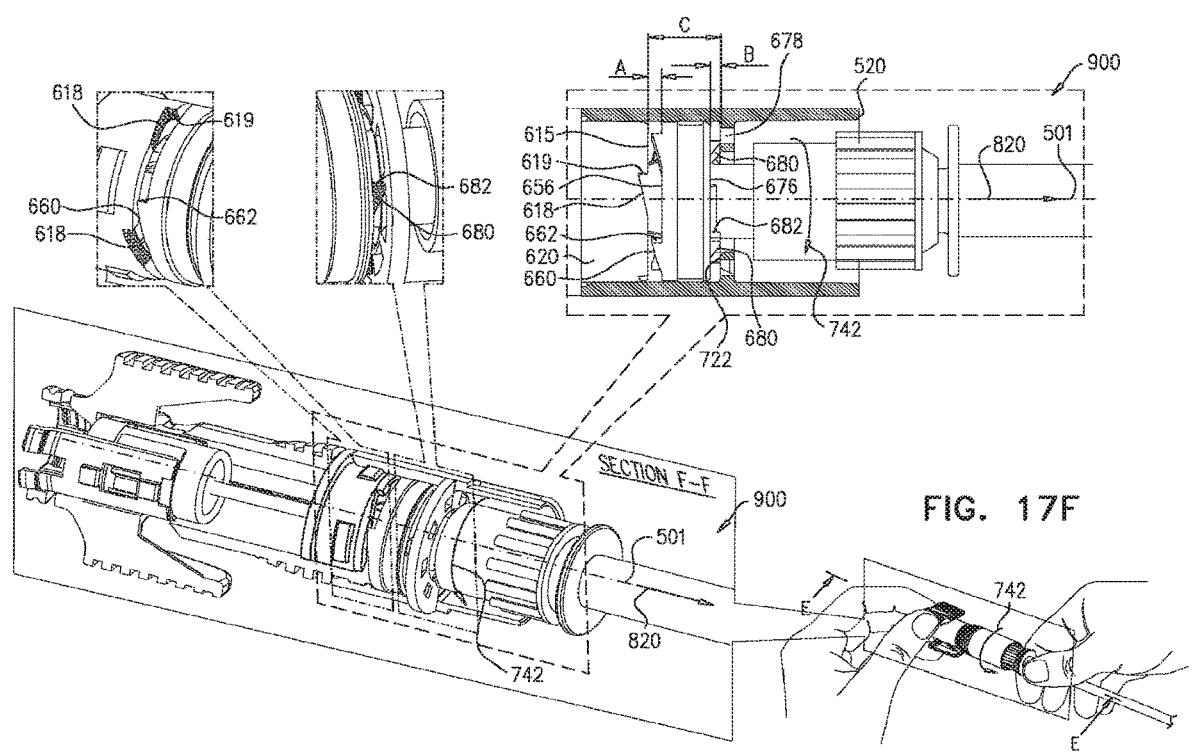

FIG. 17F illustrates counterclockwise rotation of luer lock connector 900 relative to rearward housing portion 520 of luer lock adaptor 500 about axis 501 combined with application of a rearwardly-directed axial force, as indicated by arrows 742 and 920, in an attempt to disengage the male luer connector 902 from the female luer connector portion 542 of hub element 540. This attempt is unsuccessful due to the frictional engagement of the male luer connector 902 with the female luer connector portion 542 of hub element 540 and due to the fact that the hub element 540 is free to rotate counterclockwise relative to the remainder of the luer lock adaptor 500 due to the fact that rearward-facing toothed edge 674 of hub element 540, having formed thereon a plurality of teeth 678, typically four in number, each including rearwardly and clockwise-facing inclined surface 680, in counterclockwise rotation relative to the rearward housing portion 520 slides over forwardly-facing surface 722 having formed thereon a plurality of teethed recesses 730, typically four in number, each including, forwardly and clockwise-facing inclined surface 732 and an axial directed counter-clockwise-facing locking surface 734, such that rotation of the hub element 540 relative to the forward housing portion 510 in the counterclockwise direction is not restricted.

In the illustrated embodiment shown in FIG. 17F, due to the combination of rearwardly-directed axial force, indicated by arrow 820, and counter-clockwise rotation of hub element 540 relative to forward housing portion 510 and rearward housing portion 520 from the position shown in FIG. 17D, axial separation A is approximately 1.0 mm and axial separation B is approximately equal to the axial extent of clockwise-facing, axially and radially directed locking surface 682, approximately 0.8 mm.

Figure 18A:
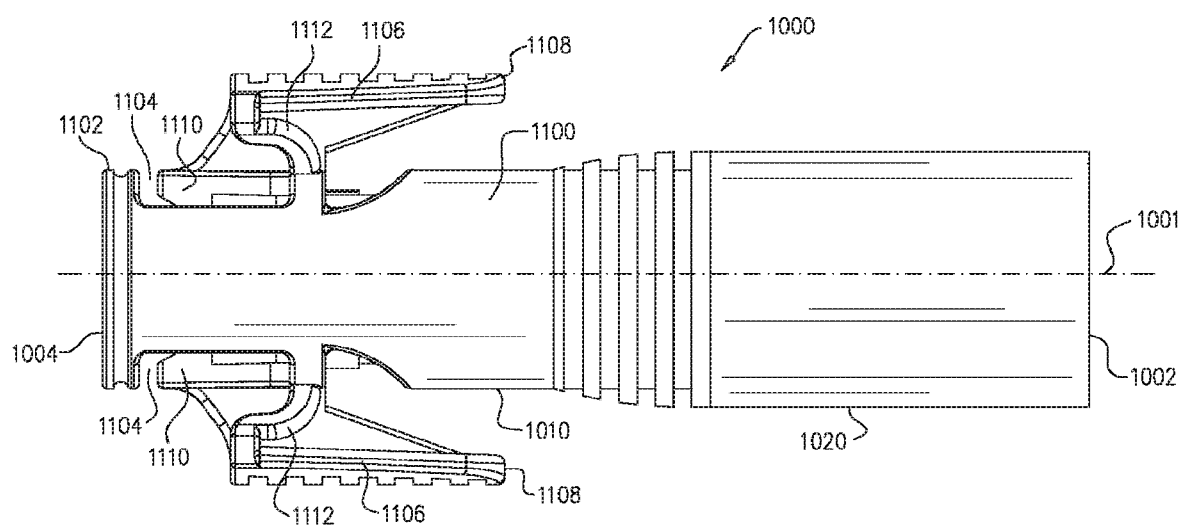
FIGS. 18A, 18B, 18C, 18D and 18E are simplified respective first and second side view, first and second end view illustrations and a sectional illustration, taken along lines XVIIIE-XVIIIE in FIG. 18D, of a luer lock adaptor constructed and operative in accordance with another preferred embodiment of the present invention.
Figure 18B:
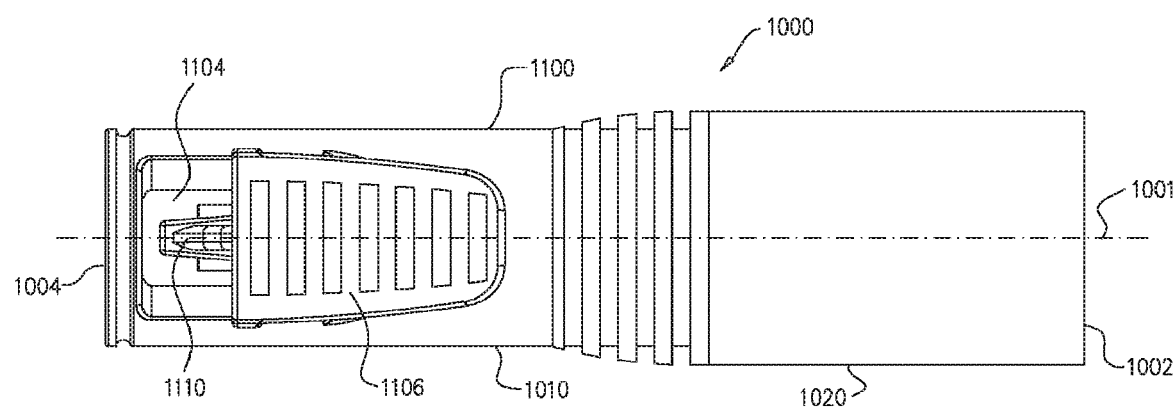
Figure 18C:
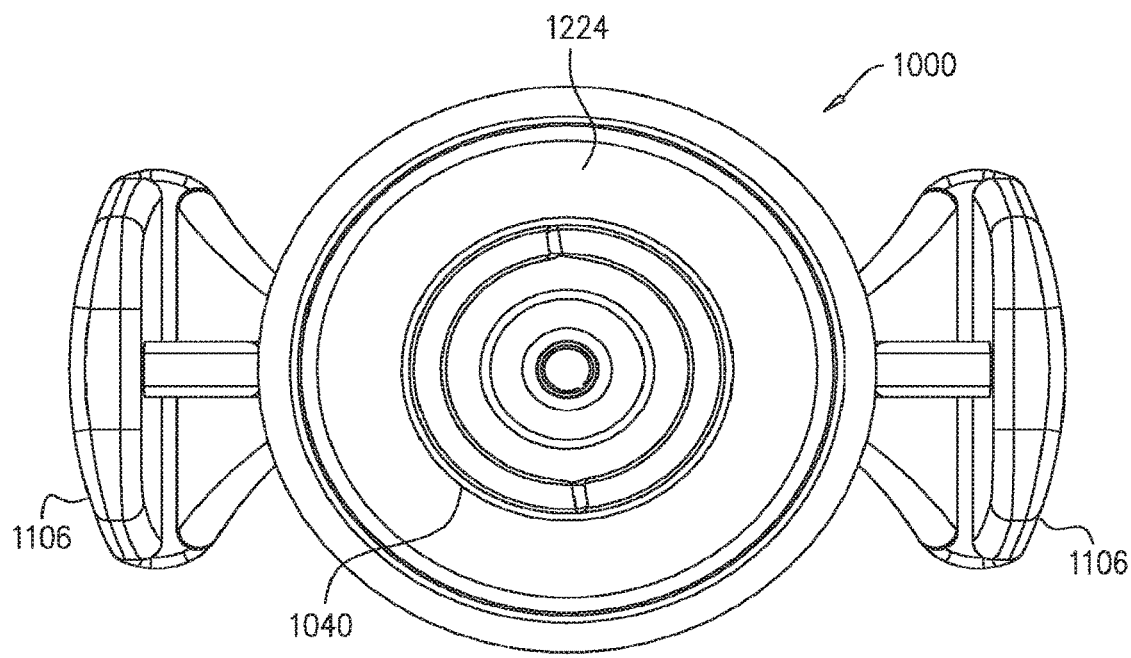
Figure 18D:
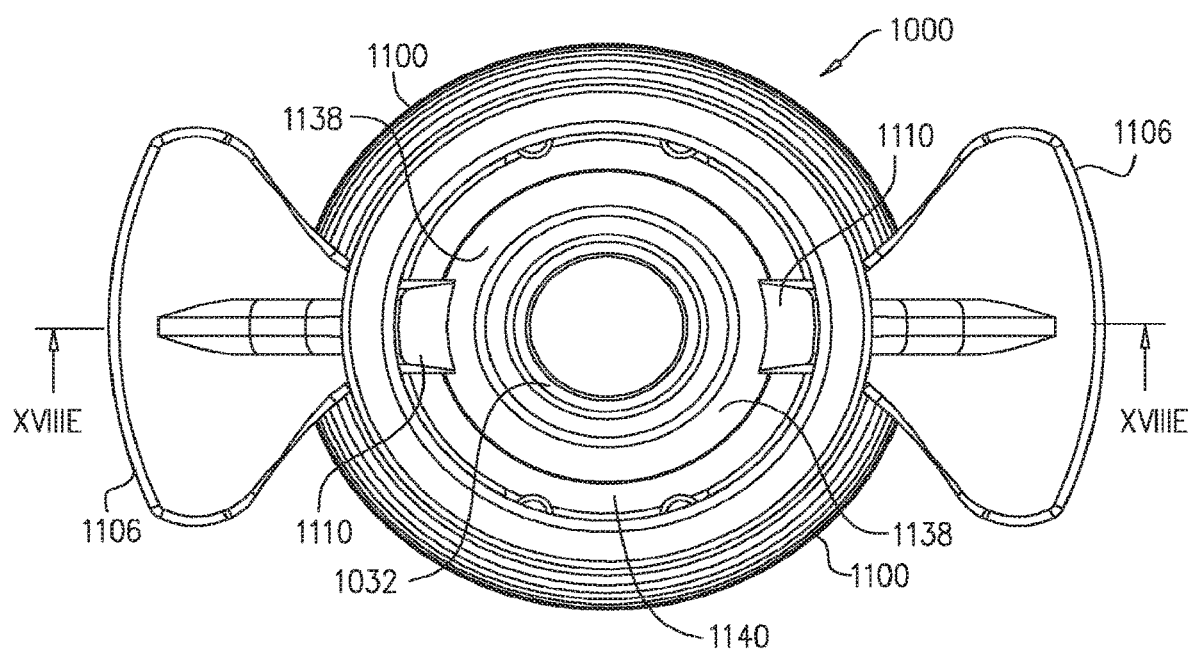
Figure 18E:
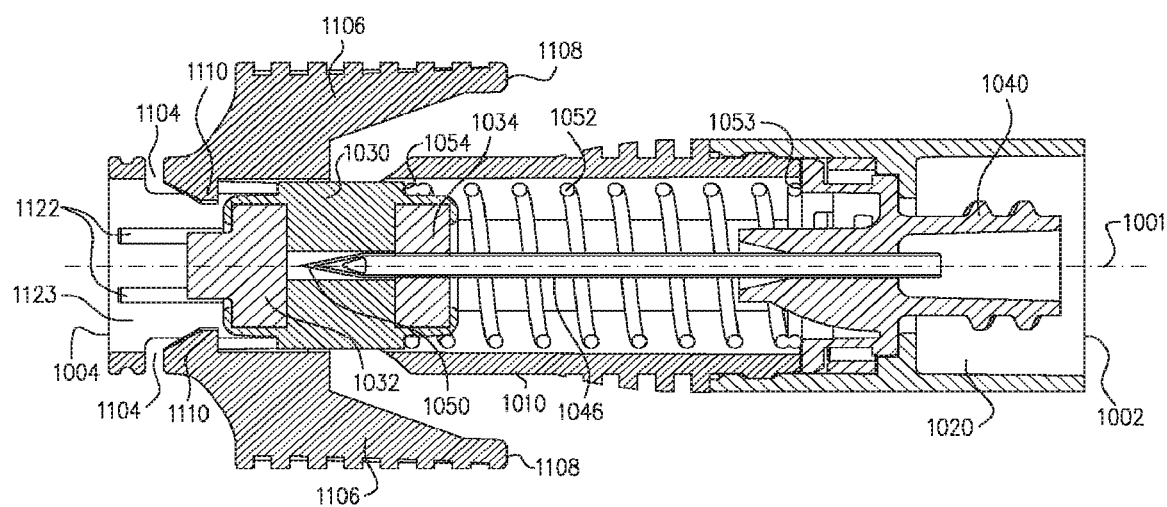
Figure 19:
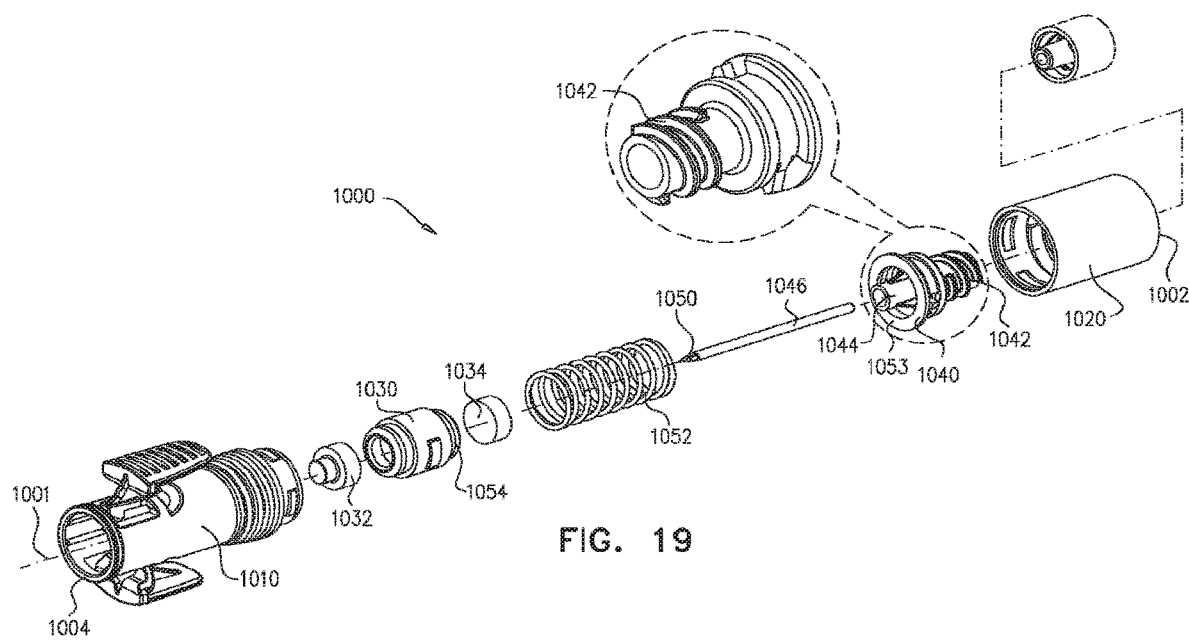
FIG. 19 is a simplified exploded view illustration of the luer lock adaptor of FIGS. 18A-18E.

Reference is now made to FIGS. 18A, 18B, 18C, 18D and 18E, which are simplified respective first and second side view and first and second end view illustrations and a sectional illustration, taken along lines XVIIIE-XVIIIE in FIG. 18D, of a luer lock adaptor constructed and operative in accordance with a preferred embodiment of the present invention, and to FIG. 19, which is a simplified exploded view illustration of the luer lock adaptor of FIGS. 18A-18E.

As seen in FIGS. 18A-18E and 19, there is provided a luer lock adaptor 1000, which extends generally along a longitudinal axis 1001 and has a luer connection end 1002 and a port connection end 1004. Although a female luer connection end 1002 is shown, the luer connection end may be any suitable luer connection end. Although a specific port connection end 1004 is shown, the port connection end 1004 may be any suitable port connection end.

The luer lock adaptor 1000 preferably includes a forward housing portion 1010 and a rearward housing portion 1020, which are preferably fixedly snap-fit to each other so as to prevent both relative axial movement and relative azimuthal movement about axis 1001 therebetween. Alternatively, forward housing portion 1010 and rearward housing portion 1020 may be formed as a single integral unit. The forward-facing direction is facing to the left in FIG. 18A.

Disposed within forward housing portion 1010 is a septa housing portion 1030 onto which is fixedly mounted a forward septum 1032 and a rearward septum 1034, which are retained in the septa housing portion 1030, preferably by ultrasonic swaging of forward and rearward edges of the septa housing portion 1030.

Disposed within rearward housing portion 1020 is a hub element 1040, defining a female luer connector portion 1042, at a rearward-facing end thereof, and, at a forward-facing end thereof, a needle mounting portion 1044. A needle 1046, mounted onto needle mounting portion 1044, extends axially forwardly along longitudinal axis 1001 into forward housing portion 1010, such that in the absence of a port connection at the port connection end 1004, a sharp tip 1050 of needle 1046 is located within the septa housing 1030 between rearward septum 1034 and forward septum 1032. A compression spring 1052 urges septa housing 1030 forwardly with respect to hub element 1040 and needle 1046. Compression spring 1052 is seated between a forward-facing surface 1053 of hub element 1040 and a rearward facing surface 1054 of septa housing 1030.

It is a particular feature of an embodiment of the present invention that there is provided a luer lock adaptor, here luer lock adaptor 1000, which includes a housing, here housing portions 1010 and 1020, which define an axis, here axis 1001, and an internal luer lock element, here hub element 1040, the internal luer lock element being located internally of the housing and being rotatably mounted thereto for rotation about the axis relative to the housing, in a manner which permits rotation of the luer lock element relative to the housing in a first rotation direction about the axis and limits rotation of the luer lock element relative to the housing in a second rotation direction about the axis, opposite to the first rotation direction, whereby the location of the internal luer lock element internally of the housing prevents manual access to the internal luer lock element for limiting rotation thereof in the first rotation direction.

Reference is now additionally made to FIGS. 20A, 20B, 20C and 20D, which are simplified respective first and second side view, perspective luer connection end view, and sectional view illustrations of forward housing portion 1010, forming part of the luer lock adaptor of FIGS. 18A-19.

As seen in FIGS. 20A-20D, the forward housing portion 1010 comprises a generally circular cylindrical main portion 1100 having a forward circumferential rim 1102 and a pair of opposite side cut outs 1104 adjacent which are mounted a pair of oppositely directed port connector engagement portions 1106.

Each of port connector engagement portions 1106 preferably includes a ribbed finger engagement surface 1108, which is connected to a retractable port connector engagement tooth 1110. Each of port connector engagement portions 1106 is flexibly mounted onto main portion 1100 by means of a flexible mounting arch 1112 which spans a corresponding cut out 1104. Manual pressing on engagement surface 1108 causes retraction of port connector engagement tooth 1110, such that simultaneous manual pressing on engagement surfaces 1108 of both of port connector engagement portions 1106 enables disengagement of a port connector (not shown) from the interior of cylindrical main portion 1100.

Figure 20A:
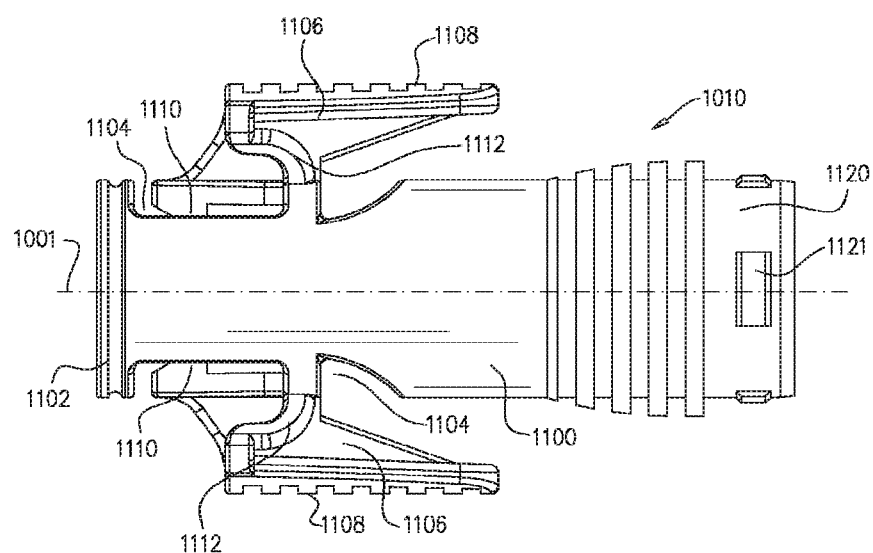
FIGS. 20A, 20B, 20C and 20D are simplified respective first and second side view, perspective luer connection end view and sectional view illustrations of a forward housing portion forming part of the luer lock adaptor of FIGS. 18A-19, FIG. 20D being taken along lines XXD-XXD in FIG. 20C.
Figure 20B:
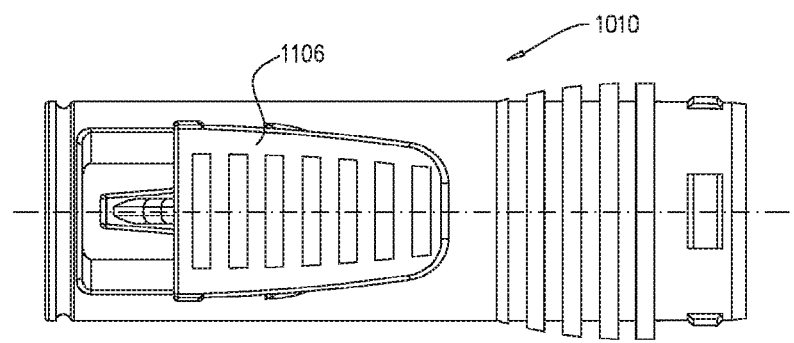
Figure 20C:
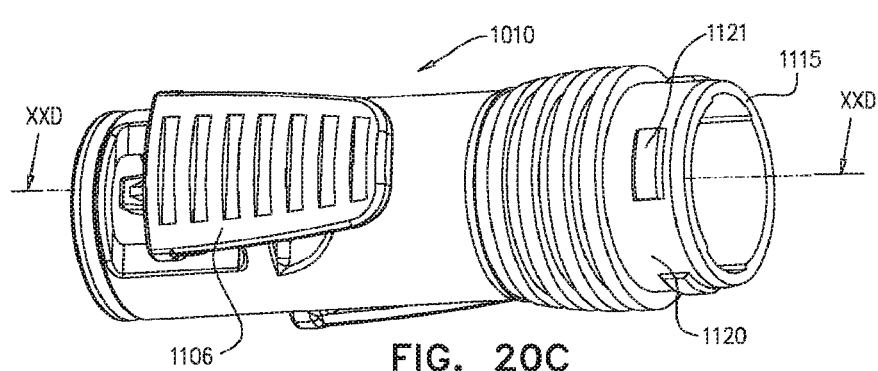
Figure 20D:
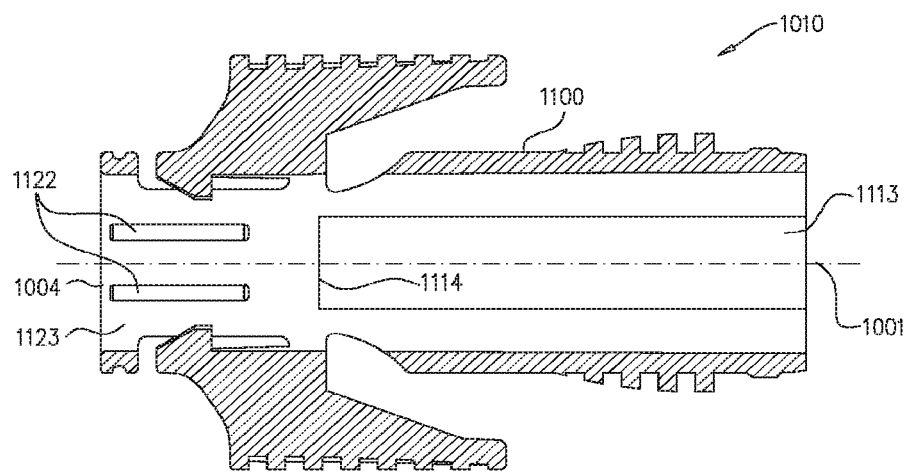

As seen clearly in FIG. 20D, opposite interior surfaces of main portion 1100 each define a septa housing guiding recess 1113 having a forward stop-defining wall surface 1114, which limits the forward displacement of the septa housing 1030 relative to the forward housing portion 1010.

As seen particularly clearly in FIG. 20C, forward housing portion 1010 includes a rearwardly-facing edge 1115. Adjacent rearwardly-facing edge 1115 on a radially outward surface 1120 of main portion 1100 are a plurality of mutually spaced circumferential elongate protrusions 1121.

As seen in FIG. 20D, a plurality of protrusions 1122, preferably a pair on either side, lie on opposite sides of an inwardly-facing circumferential wall surface 1123 of the hollow port connection end 1004 of the luer lock adaptor 1000.

Figure 21A:
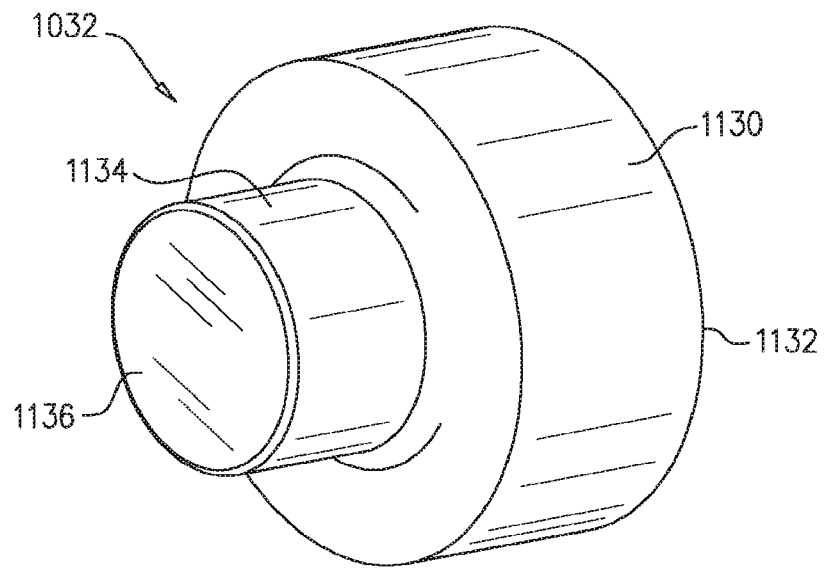
FIGS. 21A and 21B are simplified pictorial illustrations of a forward septum, forming part of the luer lock adaptor of FIGS. 18A-19.
Figure 21B:
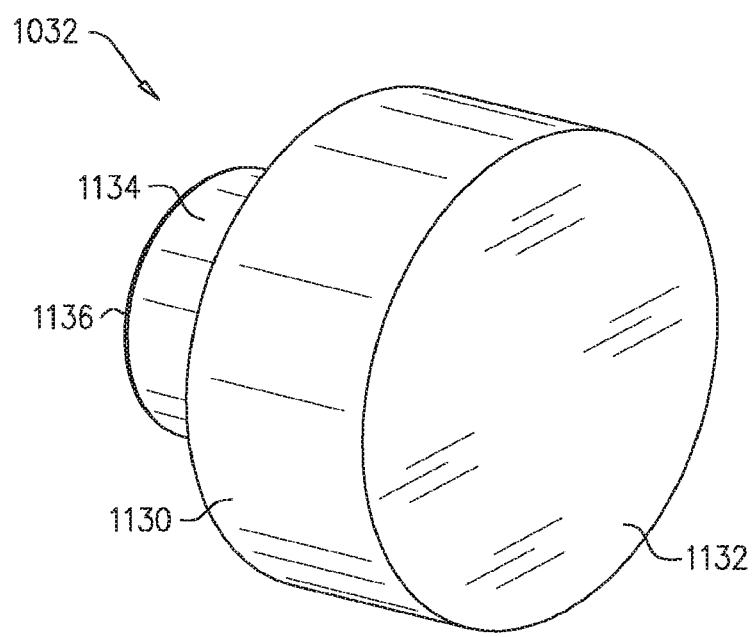
Figure 22A:
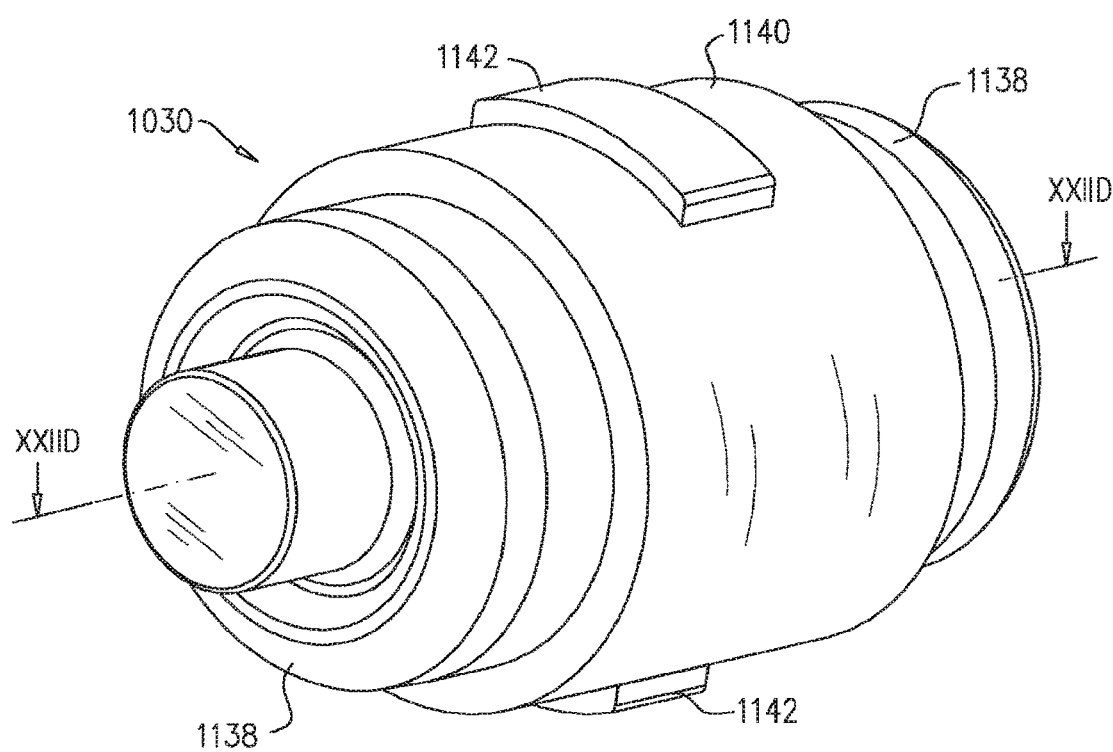
FIGS. 22A, 22B, 22C and 22D are simplified respective first and second side view, end view and sectional view illustrations of a septa housing portion forming part of the luer lock adaptor of FIGS. 18A-19, FIG. 22D being taken along lines XXIID-XXIID in FIG. 22A.
Figure 22B:
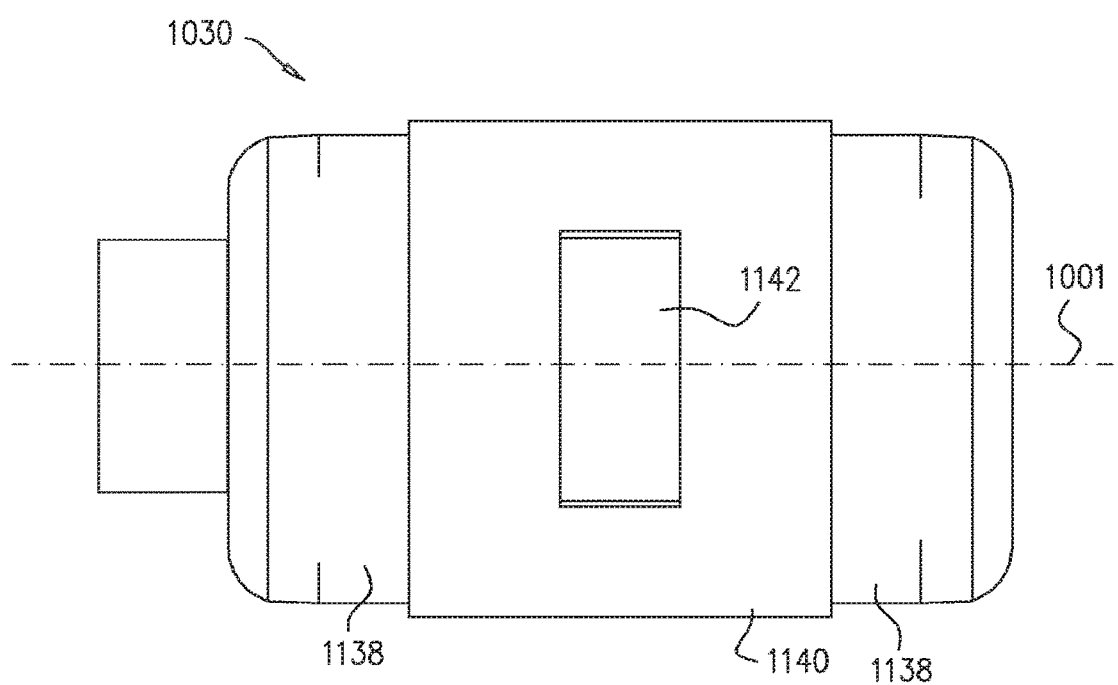
Figure 22C:
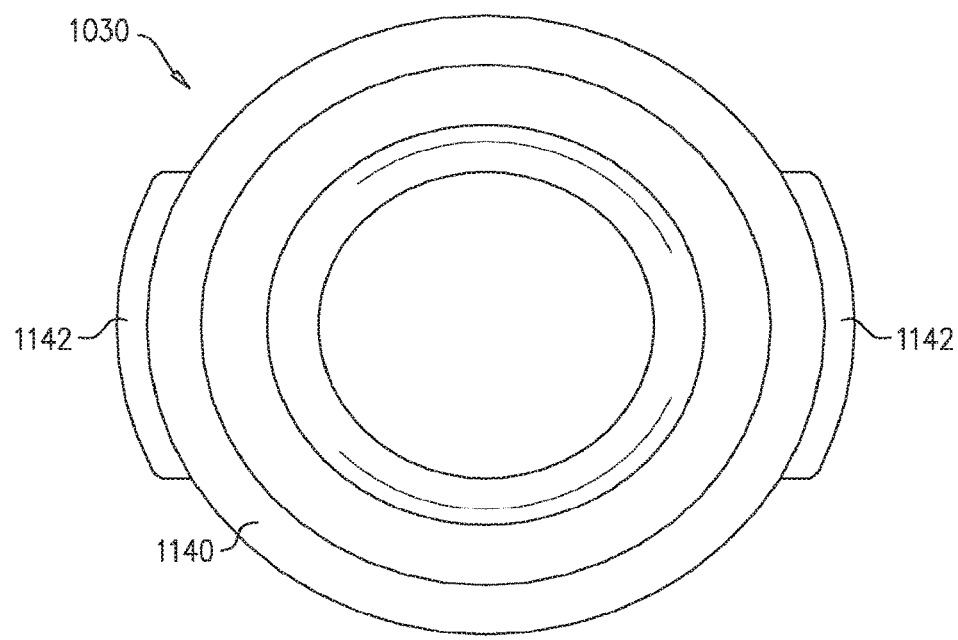
Figure 22D:
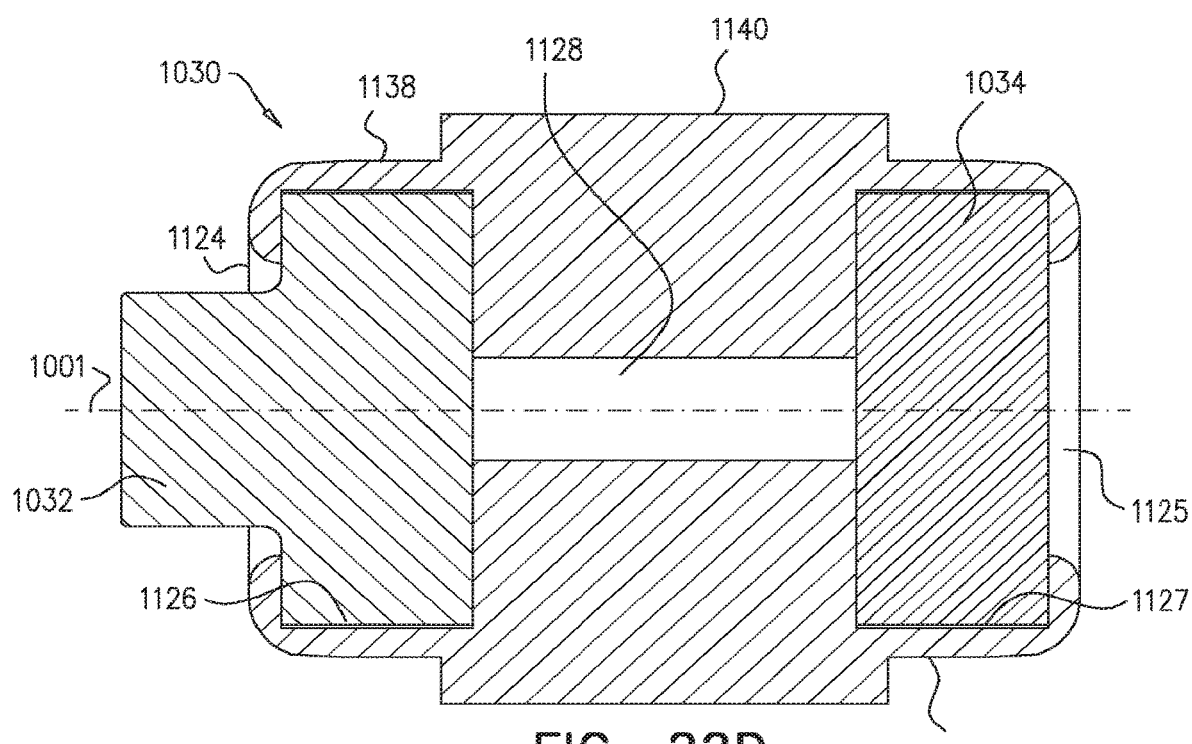

Reference is now additionally made to FIGS. 21A and 21B, which are simplified pictorial illustrations of forward septum 1032, and to FIGS. 22A, 22B, 22C and 22D, which are simplified respective first and second side view, end view, and a sectional view, taken along lines XXIID-XXIID in FIG. 22A, illustrations of septa housing portion 1030.

As seen in FIGS. 21A-22D, the septa housing portion 1030 is a generally cylindrical element having generally rounded respective forward and rearward openings 1124 and 1125 leading to respective forward and rearward recesses 1126 and 1127, which accommodate respective forward and rearward septa 1032 and 1034. An open needle accommodating channel 1128 extends longitudinally along axis 1001 between forward and rearward recesses 1126 and 1127.

As seen particularly in FIGS. 21A & 21B, forward septum 1032 preferably is an integrally formed element formed of a polymer, such as polyisoprene, and includes a relatively wide, rearward cylindrical portion 1130, which is preferably seated in forward recess 1126 of septa housing portion 1030 and defines a rearwardly-directed forward septum surface 1132, and a relatively narrow cylindrical portion 1134, which extends forwardly of rearward cylindrical portion 1130 and preferably extends through and forwardly of forward opening 1124 in septa housing portion 1030 and defines a forwardly-directed forward septum surface 1136. Rearward septum 1034 preferably is an integrally formed element formed of a polymer, such as polyisoprene, is of a disk like, flat cylindrical configuration and is seated in rearward recess 1127 of septa housing portion 1030.

Turning now specifically to FIGS. 22A-22D, which illustrate septa housing portion 1030, it is seen that septa housing portion 1030 has a generally cylindrical outer surface 1138 having a radially outwardly protruding circumferential band 1140 formed thereon. A pair of narrow protrusions 1142 extend radially outwardly from circumferential band 1140 of septa housing 1030 for engaging septa housing guiding recesses 1113 and forward stop-defining wall surfaces 1114 and thus limiting the forward displacement of septa housing portion 1030 in forward housing portion 1010 and preventing azimuthal rotation of septa housing portion 1030 about axis 1001.

Figure 23A:
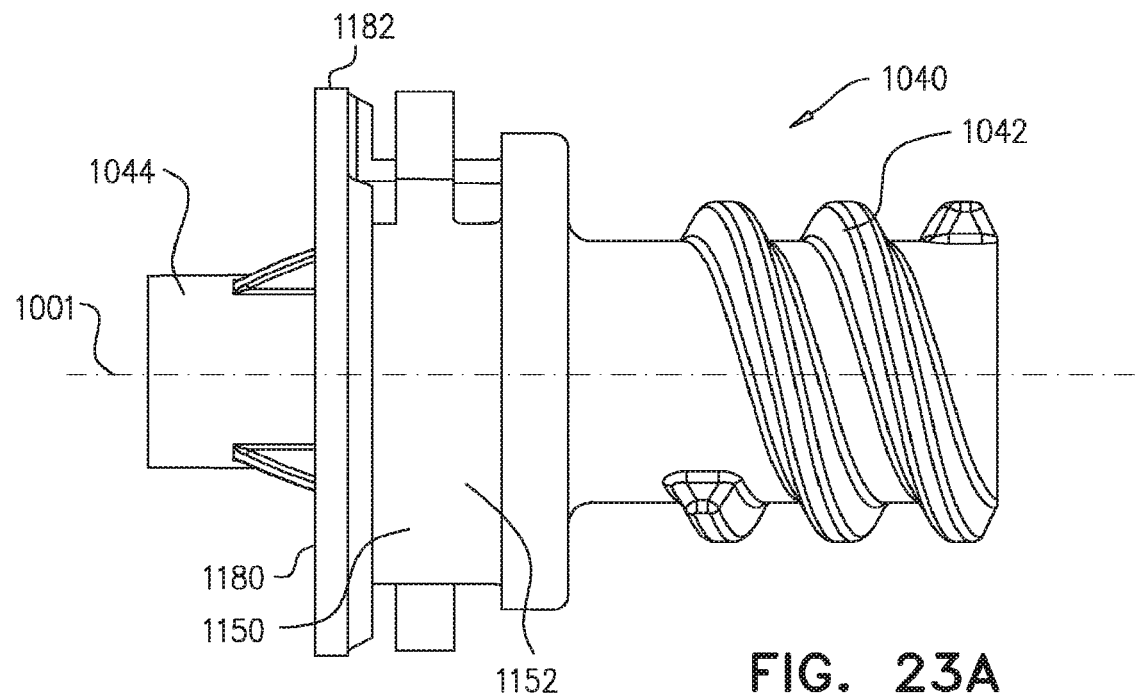
FIGS. 23A, 23B, 23C, 23D and 23E are simplified respective first and second side view, first and second perspective end view and sectional illustrations of a hub element forming part of the luer lock adaptor of FIGS. 18A-19, FIG. 23E being taken along lines XXIIIE-XXIIIE in FIG. 23C.
Figure 23B:
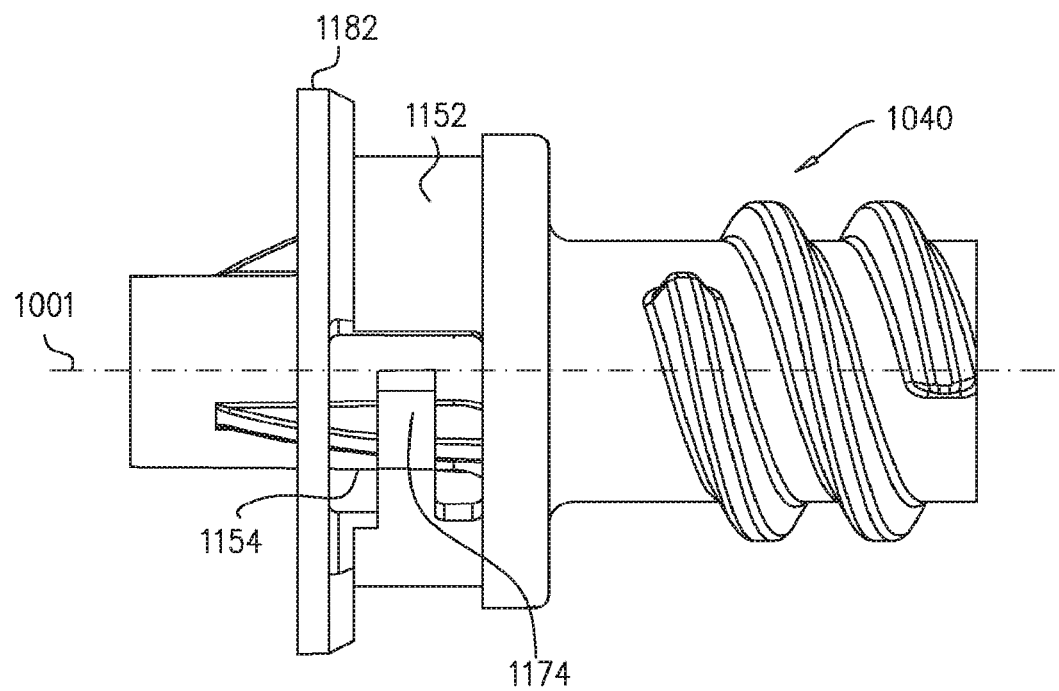
Figure 23C:
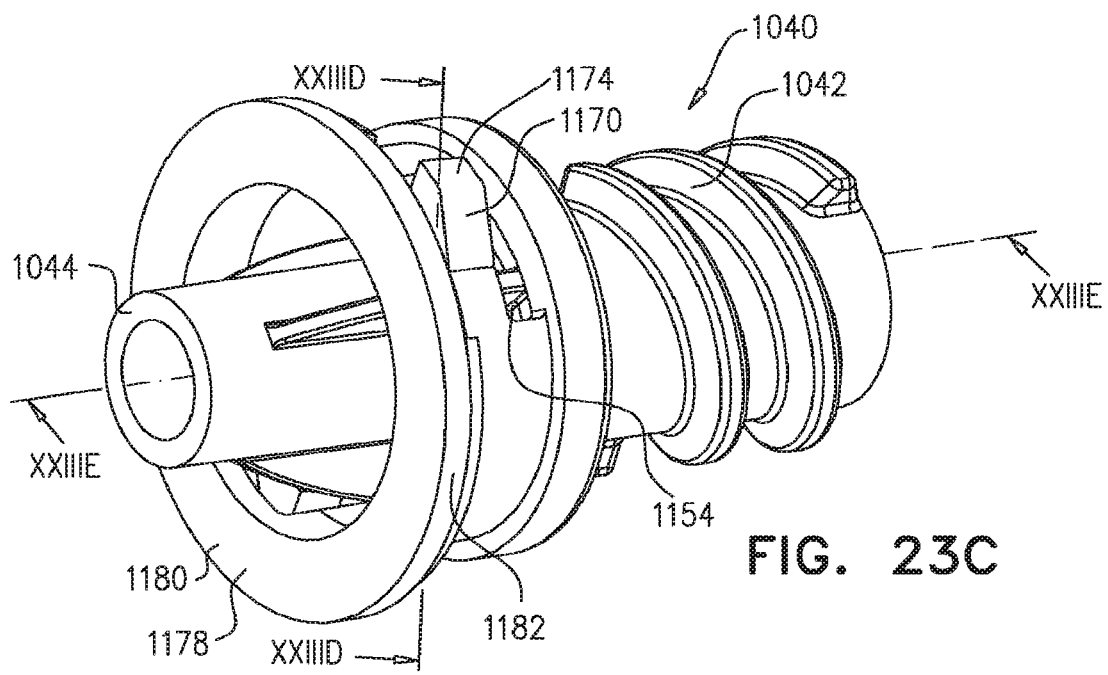
Figure 23D:
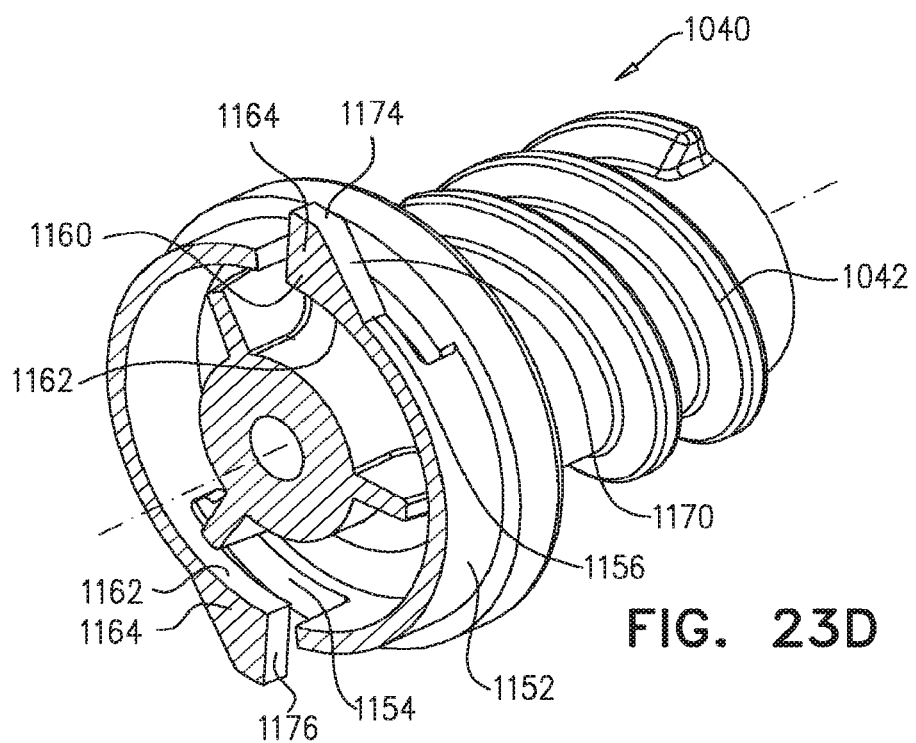
Figure 23E:
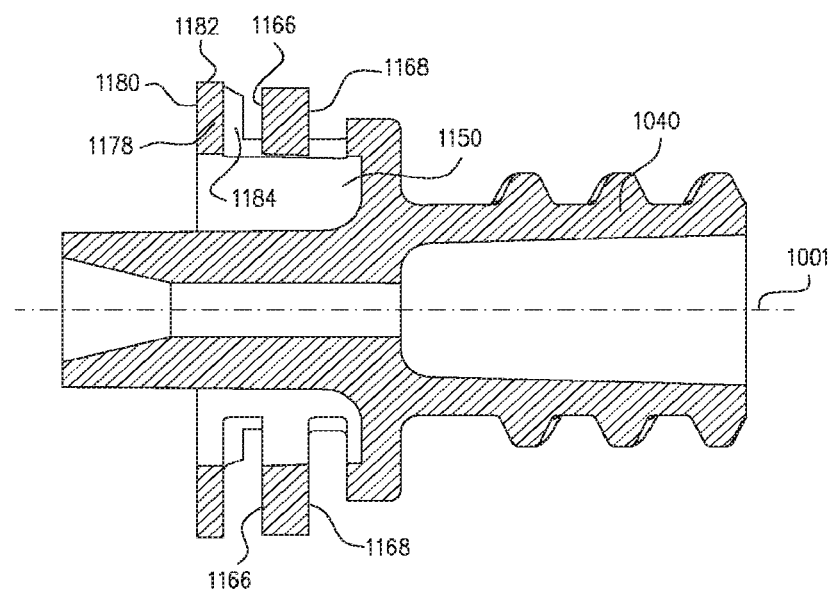

Reference is now made to FIGS. 23A, 23B, 23C, 23D and 23E, which are simplified respective first and second side view, first and second perspective end view, and a sectional view, taken along lines XXIIIE-XXIIIE in FIG. 23C, illustrations of hub element 1040. As noted hereinabove, hub element 1040 defines a female luer connector portion 1042 at a rearward-facing end and a needle mounting portion 1044 at a forward-facing end.

Disposed intermediate the female luer connector portion 1042 and the needle mounting portion 1044 is a radially-toothed circumferential intermediate portion 1150. Radially-toothed circumferential intermediate portion 1150 preferably includes a pair of generally opposite, outwardly-facing circular cylindrical surface portions 1152 which are separated by a pair of generally opposite circumferential gaps 1154.

Extending circumferentially into respective gaps 1154 and radially outwardly from circumferential edges 1156 of outwardly-facing circular cylindrical surface portions 1152 are a pair of preferably evenly circumferentially spaced, cantilevered toothed arms 1160, each including a generally circumferential arm portion 1162 and a tooth portion 1164.

Tooth portion 1164 preferably includes a forward-facing surface 1166 and a rearward-facing surface 1168 parallel to surface 1166, a circumferentially and radially outwardly inclined surface 1170 which preferably extends perpendicularly to surfaces 1166 and 1168, a radially outward-facing engagement surface 1174 and a clockwise-facing radially directed locking surface 1176.

Forwardly of radially-toothed circumferential intermediate portion 1150 is a forward-facing flange 1178 having a forward facing surface 1180, an outer facing cylindrical edge surface 1182 and a rearward-facing surface 1184.

Figure 24A:
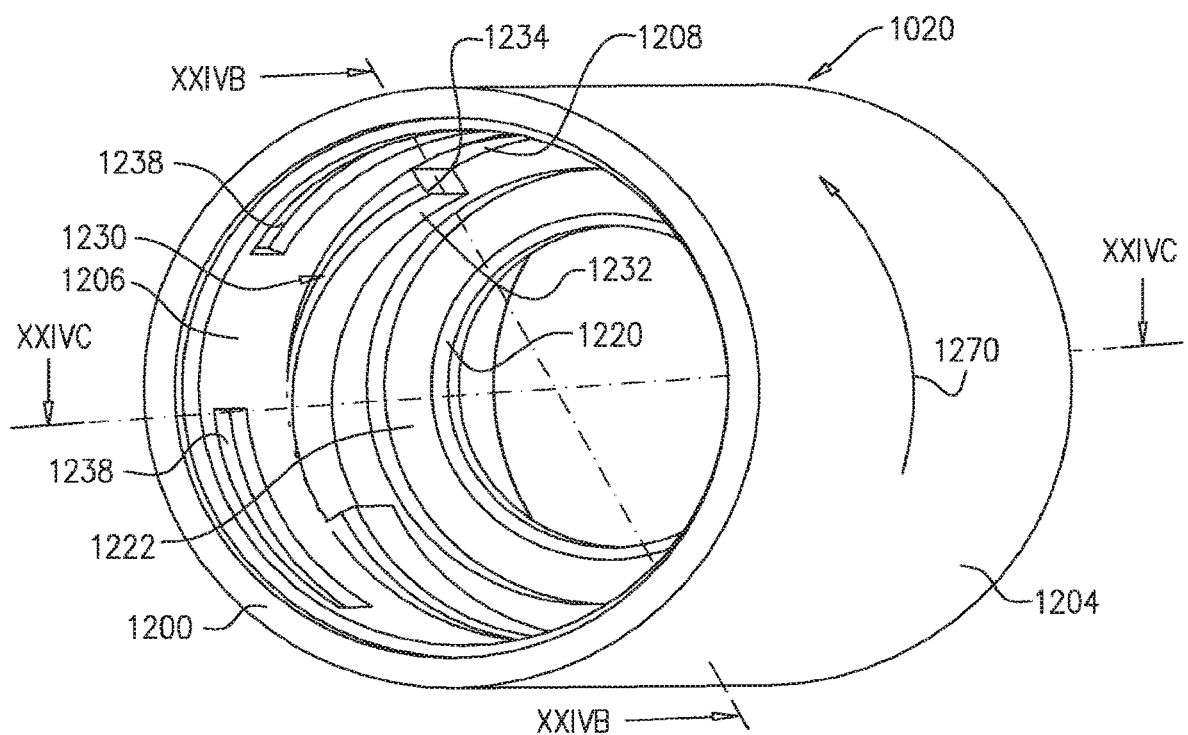
FIGS. 24A, 24B and 24C are simplified perspective end view, cut away perspective end view and sectional illustrations of a rearward housing portion forming part of the luer lock adaptor of FIGS. 18A-19.
Figure 24B:
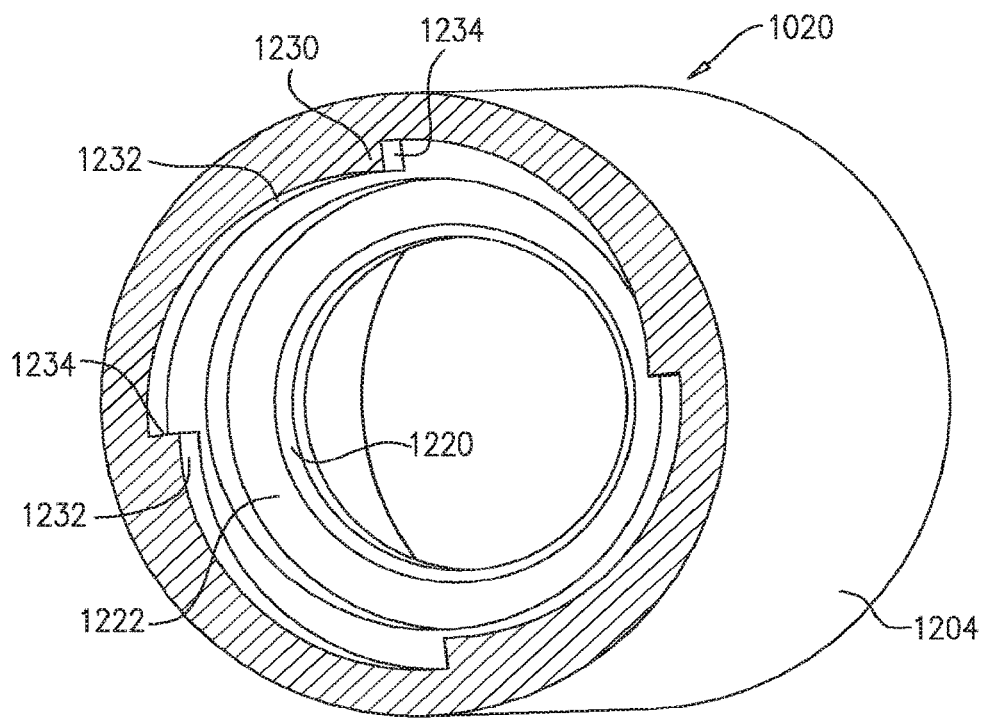
Figure 24C:
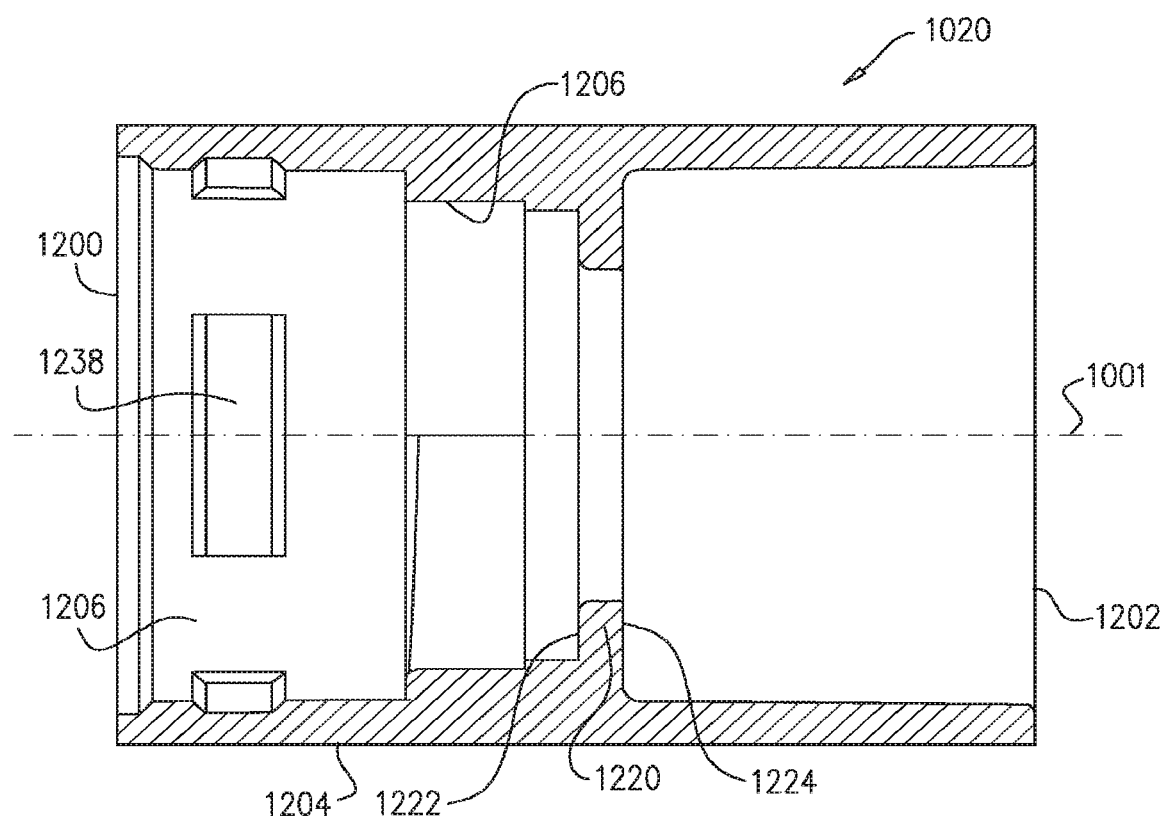

Reference is now additionally made to FIGS. 24A, 24B and 24C, which are simplified perspective end view, cut away perspective end view and sectional view illustrations of rearward housing portion 1020.

As seen in FIGS. 19 and 24A-24C, rearward housing portion 1020 is preferably an overall circular cylindrical element arranged along axis 1001 and having a forward end 1200, a rearward end 1202, a circular cylindrical outwardly-facing surface 1204 and a circular cylindrical inwardly-facing surface 1206. Intermediate forward end 1200 and rearward end 1202 and extending radially inwardly of inwardly-facing surface 1206 is an inwardly directed flange 1220 having a forwardly-facing surface 1222 and a rearwardly-facing surface 1224.

Extending circumferentially and radially inwardly of circular cylindrical inwardly-facing surface 1206 forwardly of inwardly directed flange 1220 are a plurality of generally evenly spaced teeth 1230, preferably four, each having an gradually inclined radially facing surface 1232 and a counterclockwise-facing, radially directed locking surface 1234. The radially inward extent of each of teeth 1230 increases counterclockwise from inwardly-facing surface 1206 to counterclockwise-facing locking surface 1234.

The arrangement of tooth portions 1164 on hub element 1040 and of teeth 1230 on rearward housing portion 1020 is preferably such that when a male luer connector of a syringe or other element (not shown) is screwed onto female luer connector portion 1042 in a clockwise direction of rotation from a forwardly-facing perspective, continued rotation of the syringe in the aforesaid clockwise direction produces corresponding rotation of hub element 1040 in the aforesaid clockwise direction and causes clockwise facing, radially directed locking surfaces 1176 to lockingly engage corresponding counter-clockwise facing, radially directed locking surfaces 1234 of two of teeth 1230 of rearward housing portion 1020. The aforesaid clockwise direction of rotation is indicated by an arrow 1270 in FIG. 24A.

Formed on inwardly-facing surface 1206 are a plurality of mutually azimuthally spaced circumferential recesses 1238 which receive corresponding protrusions 1121 of forward housing portion 1010 in a snap fit engagement, thereby providing both axial and azimuthal locking between forward housing portion 1010 and rearward housing portion 1020.

It is appreciated that, although in the embodiments shown in FIGS. 1A-9G and 10A-17F respective hub elements 140 and 540 are able to move axially relative to respective forward housing portions 110 and 510 and relative to respective rearward housing portions 120 and 520, in the embodiment shown in FIGS. 18A-24C the above referenced axial and azimuthal locking of forward housing portion 1010 and rearward housing portion 1020 also axially locks hub element 1040 relative to forward housing portion 1010 and relative to rearward housing portion 1020, but allows azimuthal movement of hub element 1040 about axis 1001 relative to forward housing portion 1010 and relative to rearward housing portion 1020.

Reference is now made to FIGS. 23F-23I, which illustrate the relative positions of radially directed locking surfaces 1176 of hub element 1040 and corresponding locking surfaces 1234 of rearward housing portion 1020 in four different rotational orientations.

Figure 23F:
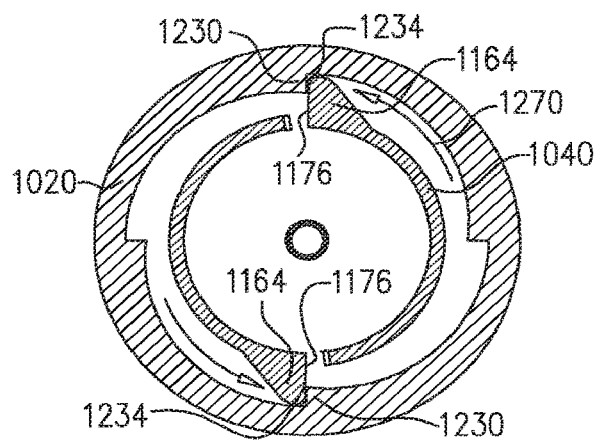
FIGS. 23F, 23G, 23H and 23I are simplified sectional illustrations of relative positioning of a hub element and a rearward housing portion of the luer lock adaptor of FIGS. 18A-19 in four different rotational orientations, taken along lines XXIIIF-XXIIIF in FIG. 18E.

As seen in FIG. 23F, in a first rotational orientation, radially directed locking surfaces 1176 of hub element 1040 are in a locked clockwise operative engagement with locking surfaces 1234 of rearward housing portion 1020 and prevent clockwise, from a forwardly-facing perspective, rotation, as shown by arrow 1270, of hub element 1040 relative to rearward housing portion 1020. It is appreciated that in this orientation counterclockwise movement of the hub element 1040 relative to the rearward housing portion 1020 is permitted.

Figure 23G:
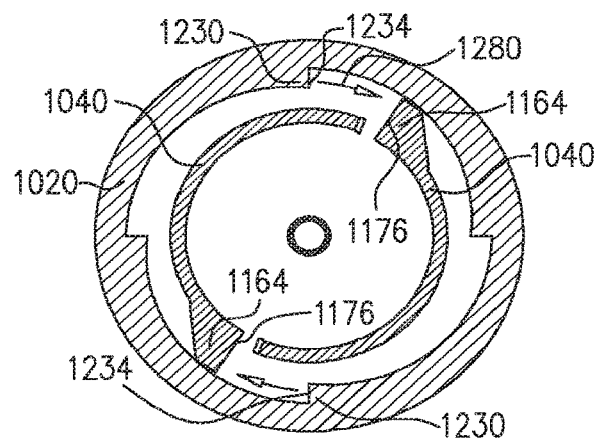
Figure 23H:
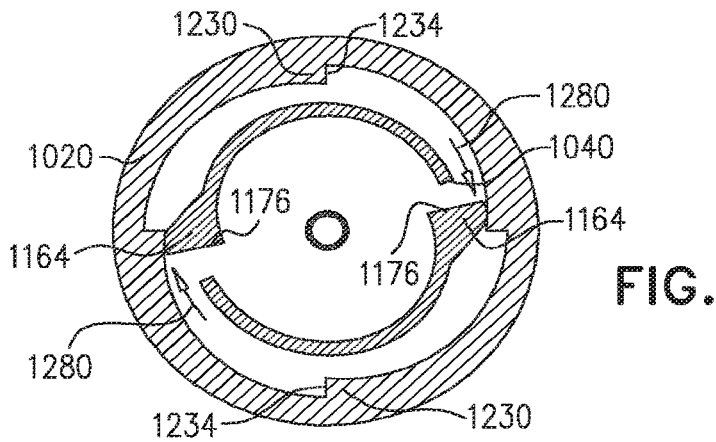

As seen in FIGS. 23G and 23H, in a second and a third rotational orientation, hub element 1040 has been rotated counterclockwise, from a forwardly-facing perspective, relative to rearward housing portion 1020, from the orientation shown in FIG. 23F. Radially directed locking surfaces 1176 of hub element 1040 are not in a locked clockwise operative engagement with locking surfaces 1234 of rearward housing portion 1020. It is appreciated that in these orientations counterclockwise, from a forwardly-facing perspective, rotation of the hub element 1040 relative to the rearward housing portion 1020, as shown by arrows 1280, is permitted. It is also appreciated that limited clockwise, from a forwardly-facing perspective, rotation of hub element 1040 relative to rearward housing portion 1020, to return to the first rotational orientation shown in FIG. 23F, is possible.

Figure 23I:
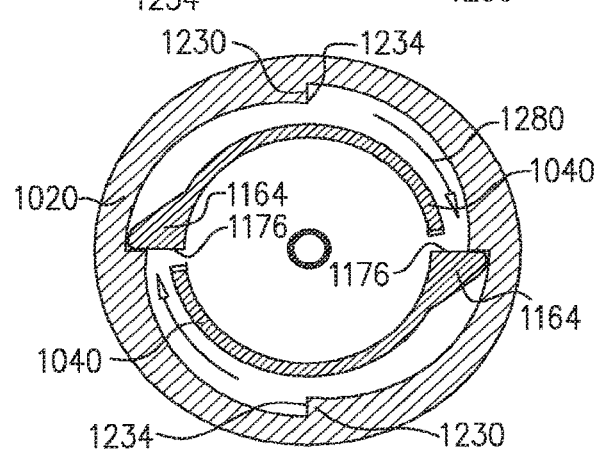

As seen in FIG. 23I, in a fourth rotational orientation, hub element 1040 has been rotated by 90° counterclockwise, as indicated by arrows 1280, from a forwardly-facing perspective, from the orientation shown in FIG. 23F. Radially directed locking surfaces 1176 of hub element 1040 are in a locked clockwise operative engagement with locking surfaces 1234 of rearward housing portion 1020 and prevent clockwise, from a forwardly-facing perspective, rotation of hub element 1040 relative to rearward housing portion 1020. It is appreciated that in this orientation, counterclockwise movement of the hub element 1040 relative to the rearward housing portion 1020 is permitted.

Reference is now made to FIGS. 25A, 25B, 25C, 25D, 25E and 25F, which are simplified illustrations of the luer lock adaptor of FIGS. 18A-24C in respective first, second, third, fourth, fifth and sixth operative orientations with respect to a conventional luer lock syringe.

Figure 25A:
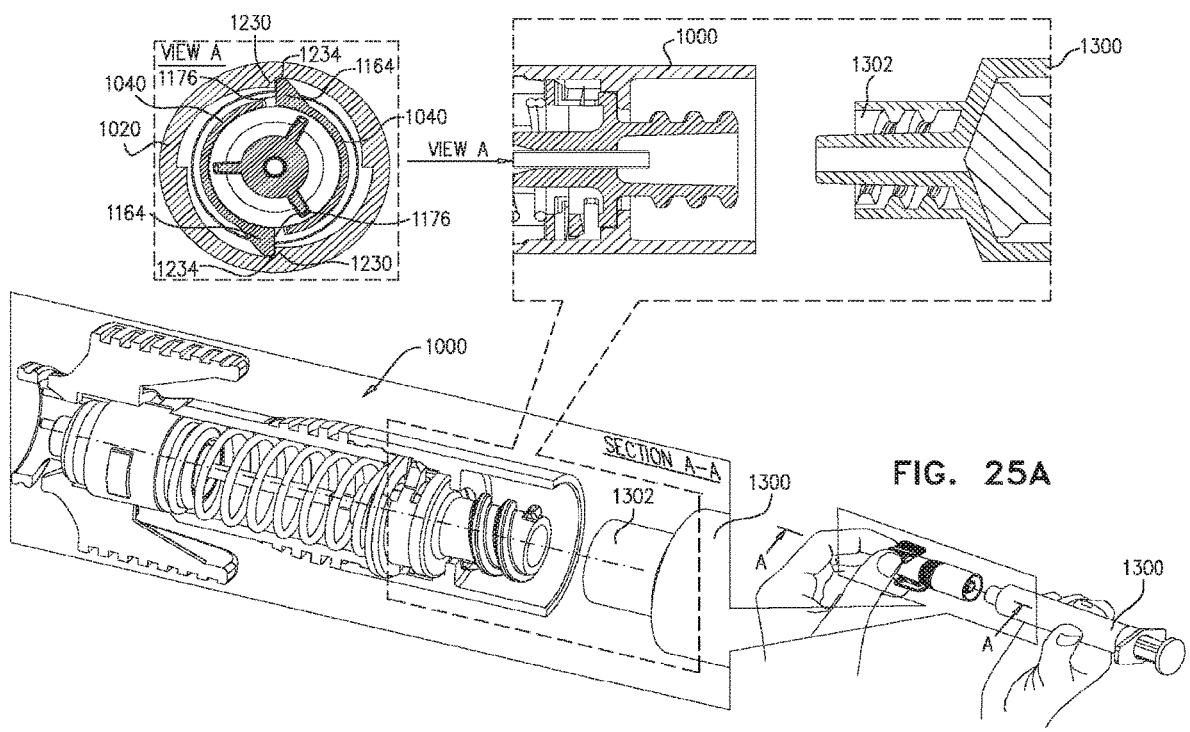

FIG. 25A shows a conventional luer lock syringe 1300 having a male luer connector 1302 about to be connected to the luer lock adaptor 1000 of FIGS. 18A-24C. Prior to engagement of the luer lock syringe 1300 with the luer lock adaptor 1000, snap-fit engagement between the forward housing portion 1010 and the rearward housing portion 1020, and more specifically between mutually azimuthally spaced circumferential recesses 1238 of rearward housing portion, which receive corresponding protrusions 1121 of forward housing portion 1010, retains the hub element 1040, as seen in FIG. 18E, such that tooth portions 1164 on hub element 1040 are generally coplanar with and in operative engagement with teeth 1230 on rearward housing portion 1020, as seen in sectional enlargement at View A in FIG. 25A.

Typically, clockwise-facing, radially directed locking surfaces 1176 of tooth elements 1164 lockingly engage counterclockwise-facing, radially directed locking surfaces 1234 of teeth 1230 of rearward housing portion 1020, thereby permitting counterclockwise, from a forwardly-facing perspective, rotation of hub element 1040 relative to rearward housing portion 1020, represented by arrow 1280, but preventing clockwise, from a forwardly-facing perspective, rotation of hub element 1040 relative to rearward housing portion 1020, represented by arrow 1270.

FIG. 25B illustrates initial forward axial displacement of syringe 1300 relative to luer lock adaptor 1000 along axis 1001 such that the male luer connector 1302 is in touching engagement with female luer connector portion 1042 at a rearward-facing end thereof. The locking engagement of rearward housing portion 1020 and hub element 1040 is unchanged from that described hereinabove with reference to FIG. 25A.

Figure 25C:
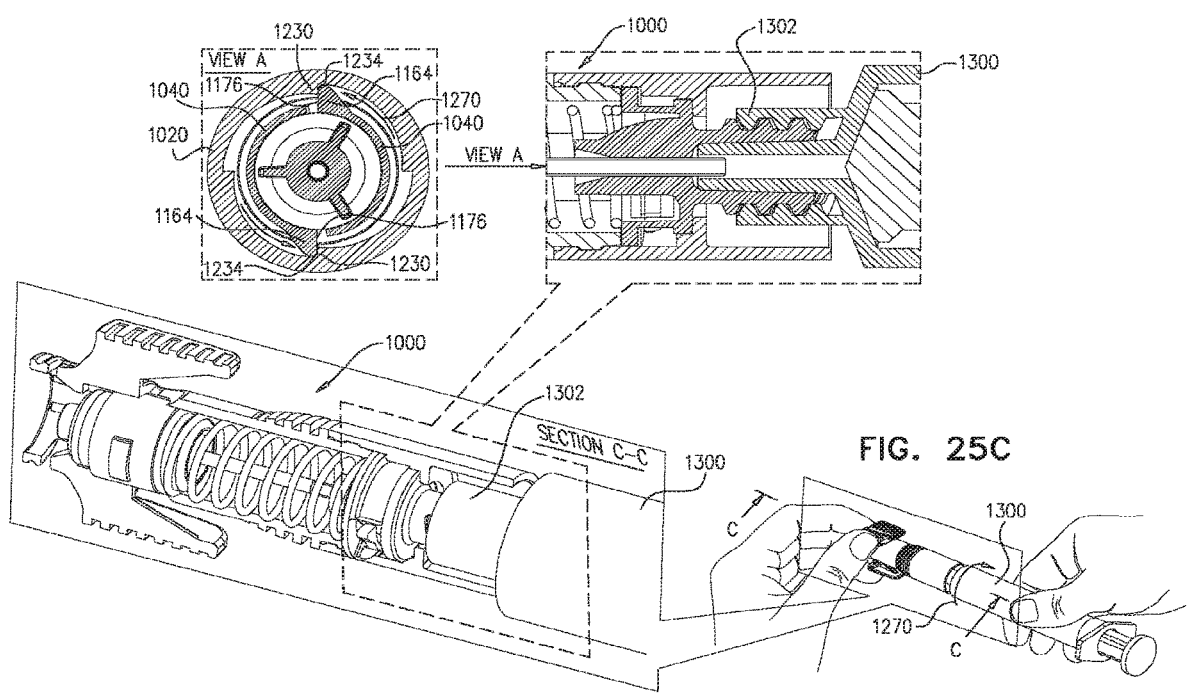

FIG. 25C illustrates clockwise rotation of the syringe 1300 relative to luer lock adaptor 1000 about axis 1001, as indicated by arrow 1270, such that the male luer connector 1302 is in full threaded frictional engagement with female luer connector portion 1042 of hub element 1040. This rotation takes place without application of an additional forward axial force along axis 1001. This full threaded engagement is made possible by the aforementioned locking of rotation of hub element 1040 against clockwise rotation relative to rearward housing portion 1020.

Figure 25D:
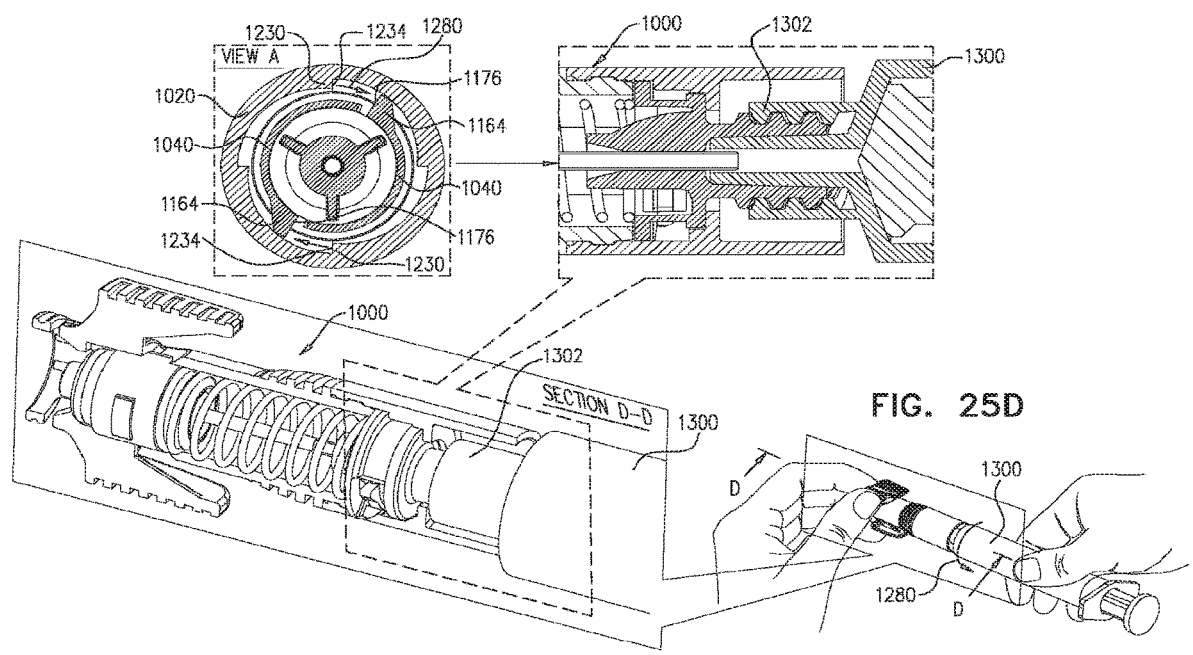
Figure 25E:
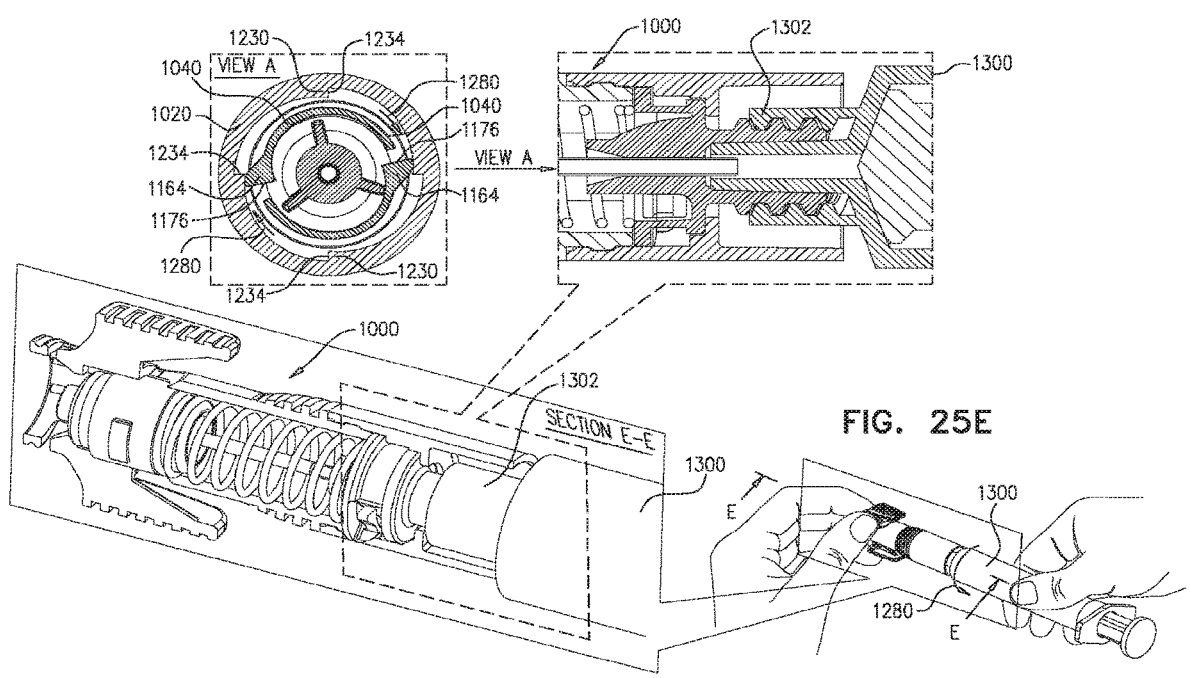
Figure 25F:
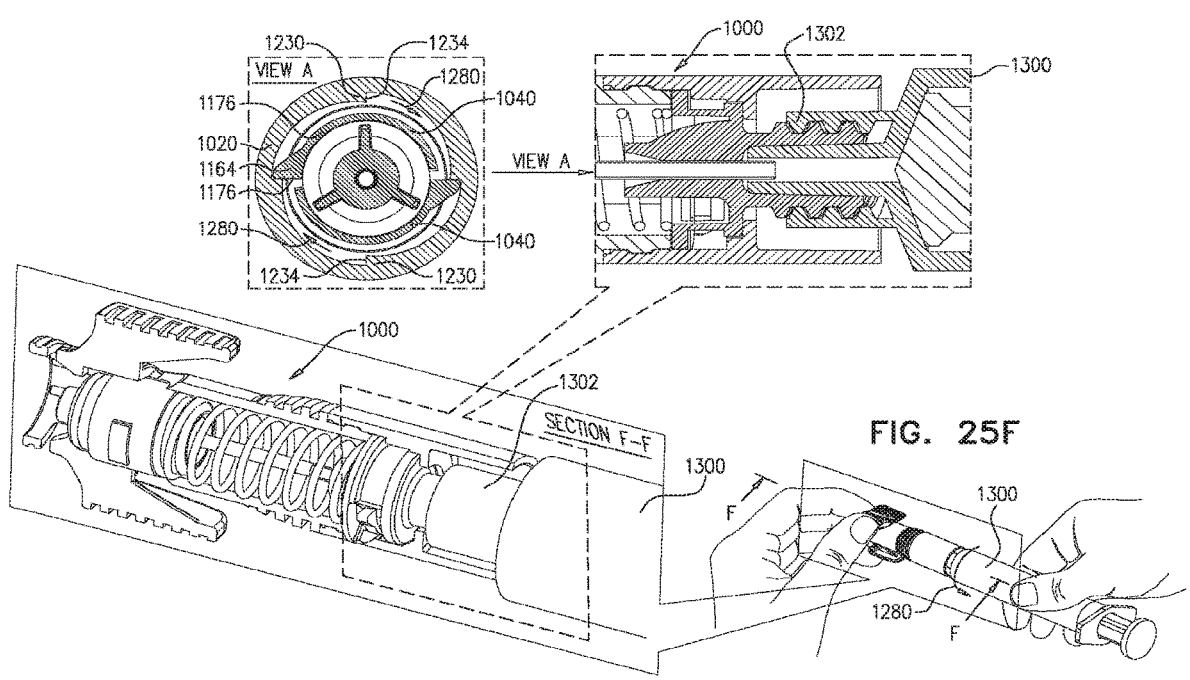

FIGS. 25D, 25E and 25F illustrate counterclockwise rotation of the syringe 1300 relative to rearward housing portion 1020 of luer lock adaptor 1000 about axis 1001, as indicated by arrows 1280, in an attempt to disengage the male luer connector 1302 from the female luer connector portion 1042 of hub element 1040. This attempt is unsuccessful due to the frictional engagement of the male luer connector 1302 with the female luer connector portion 1042 of hub element 1040 and due to the fact that the hub element 1040 is free to rotate counterclockwise relative to the remainder of the luer lock adaptor 1000. It is seen in the sectional enlargement at View A in FIGS. 25D and 25E that radially directed locking surfaces 1176 of tooth elements 1164 no longer lockingly engage counterclockwise-facing, radially directed locking surfaces 1234 of teeth 1230 of rearward housing portion 1020 due to counterclockwise movement of the hub element 1040 relative to the rearward housing portion 1020. As seen in the sectional enlargement at View A in FIG. 25F, following a 90° rotation of syringe 1300 and hub element 1040 relative to rearward housing portion 1020, radially directed locking surfaces 1176 of tooth elements 1164 again lockingly engage counterclockwise-facing, radially directed locking surfaces 1234 of teeth 1230 of rearward housing portion 1020 and prevent clockwise movement of the hub element 1040 relative to the rearward housing portion 1020 while allowing counterclockwise movement of the hub element 1040 relative to the rearward housing portion 1020.

Reference is now made to FIGS. 26A, 26B, 26C, 26D, 26E and 26F, which are simplified illustrations of the luer lock adaptor of FIGS. 18A-24C in respective first, second, third, fourth, fifth and sixth operative orientations with respect to a conventional luer lock connector.

FIG. 26A shows a conventional luer lock connector 1400 having a male luer connector 1402 about to be connected to the luer lock adaptor 1000 of FIGS. 18A-24C. Prior to engagement of the luer lock connector 1400 with the luer lock adaptor 1000, snap-fit engagement between the forward housing portion 1010 and the rearward housing portion 1020, and more specifically between mutually azimuthally spaced circumferential recesses 1238 of rearward housing portion, which receive corresponding protrusions 1121 of forward housing portion 1010, retains the hub element 1040, as seen in FIG. 18E, such that tooth portions 1164 on hub element 1040 are generally coplanar with and in operative engagement with teeth 1230 on rearward housing portion 1020, as seen in sectional enlargement at View A in FIG. 26A.

Typically clockwise-facing, radially directed locking surfaces 1176 of tooth elements 1164 lockingly engage counterclockwise-facing, radially directed locking surfaces 1234 of teeth 1230 of rearward housing portion 1020, thereby permitting counterclockwise, from a forwardly-facing perspective, rotation of hub element 1040 relative to rearward housing portion 1020, represented by an arrow 1320, but preventing clockwise, from a forwardly-facing perspective, rotation of hub element 1040 relative to rearward housing portion 1020, represented by arrow 1270.

Figure 26B:
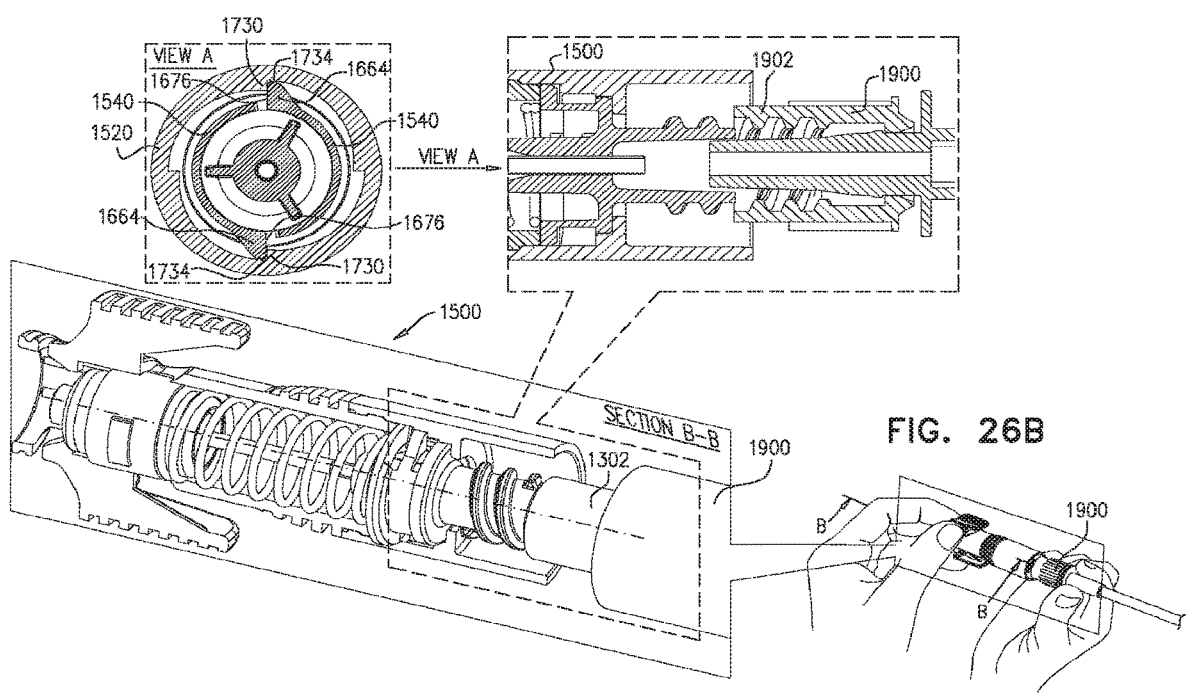

FIG. 26B illustrates initial forward axial displacement of luer lock connector 1400 relative to luer lock adaptor 1000 along axis 1001 such that the male luer connector 1402 is in touching engagement with female luer connector portion 1042 at a rearward-facing end thereof. The locking engagement of rearward housing portion 1020 and hub element 1040 is unchanged from that described hereinabove with reference to FIG. 26A.

Figure 26C:
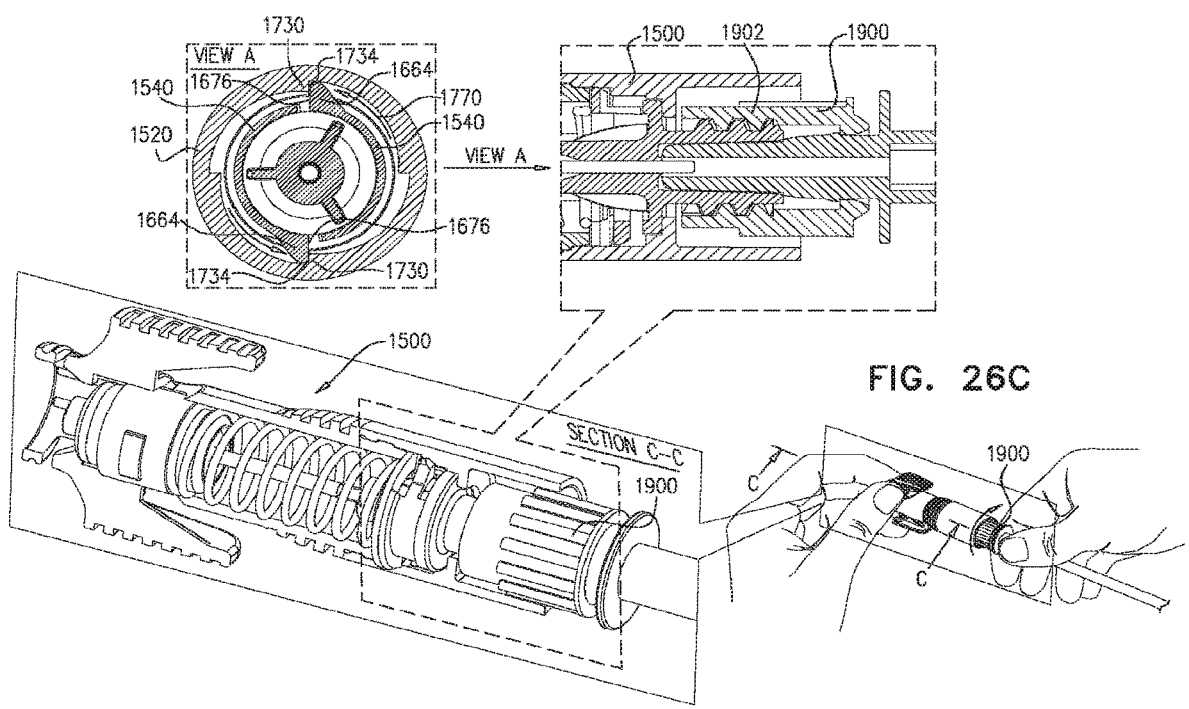

FIG. 26C illustrates clockwise rotation of the luer lock connector 1400 relative to luer lock adaptor 1000 about axis 1001, as indicated by arrow 1270, such that the male luer connector 1402 is in full threaded frictional engagement with female luer connector portion 1042 of hub element 1040. This rotation takes place without application of an additional forward axial force along axis 1001. This full threaded engagement is made possible by the aforementioned locking of rotation of hub element 1040 against clockwise rotation relative to rearward housing portion 1020.

Figure 26D:
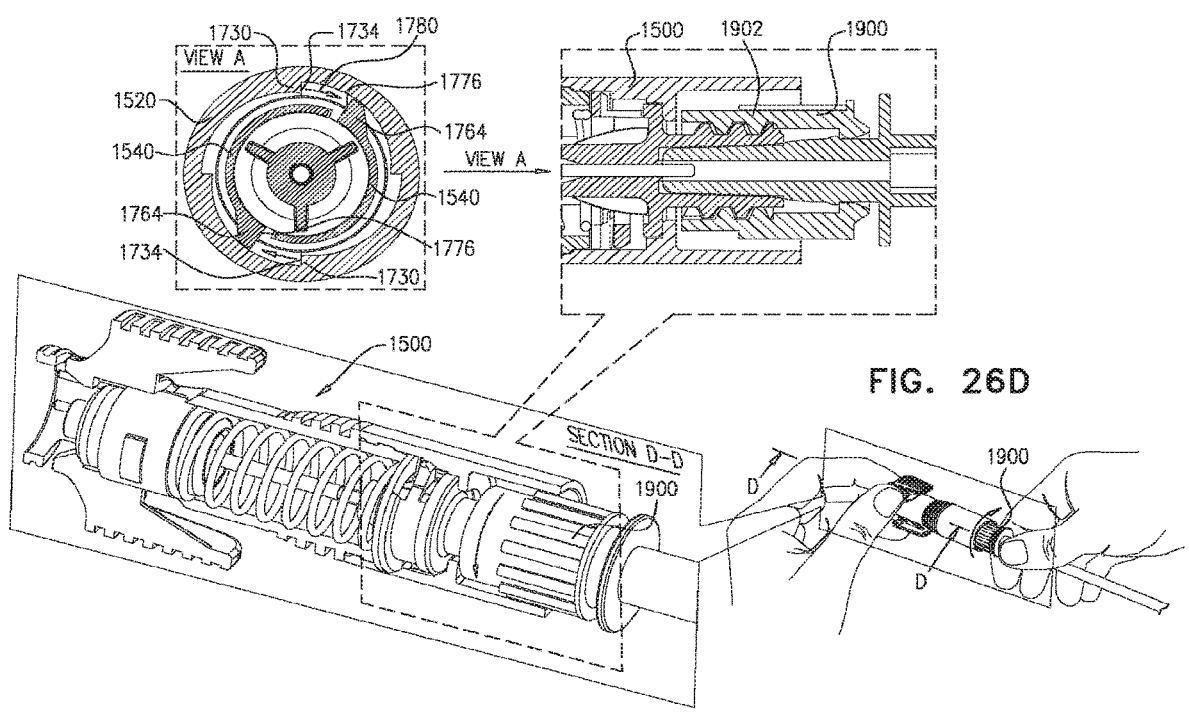
Figure 26E:
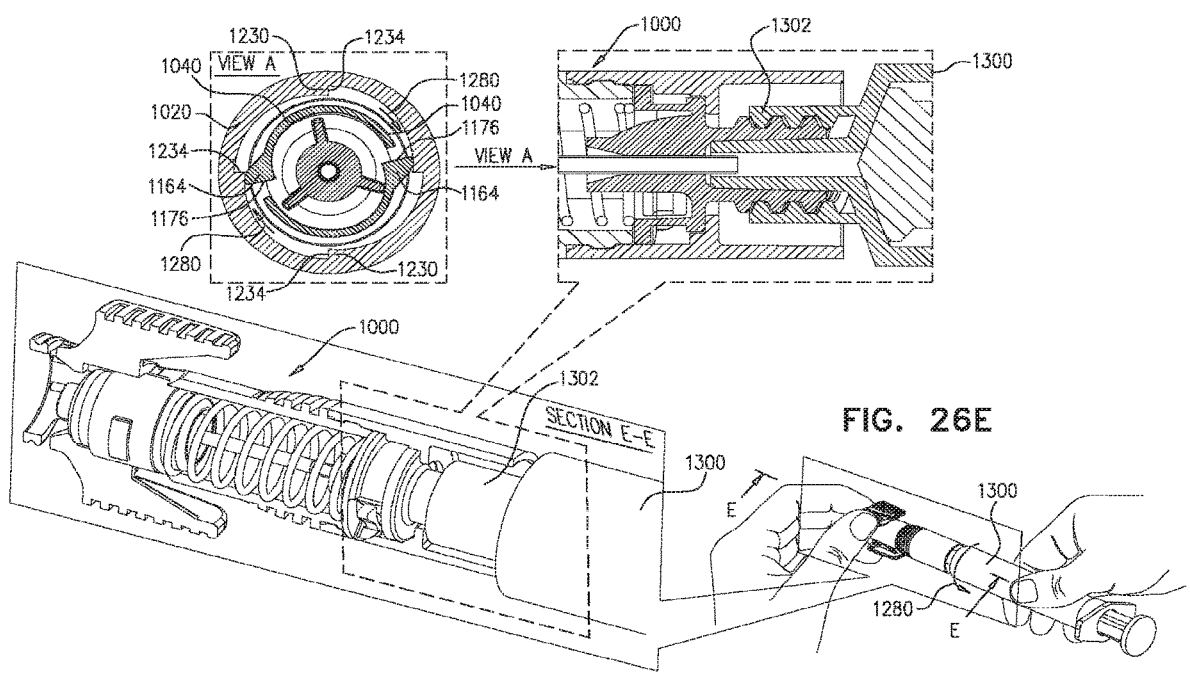
Figure 26F:
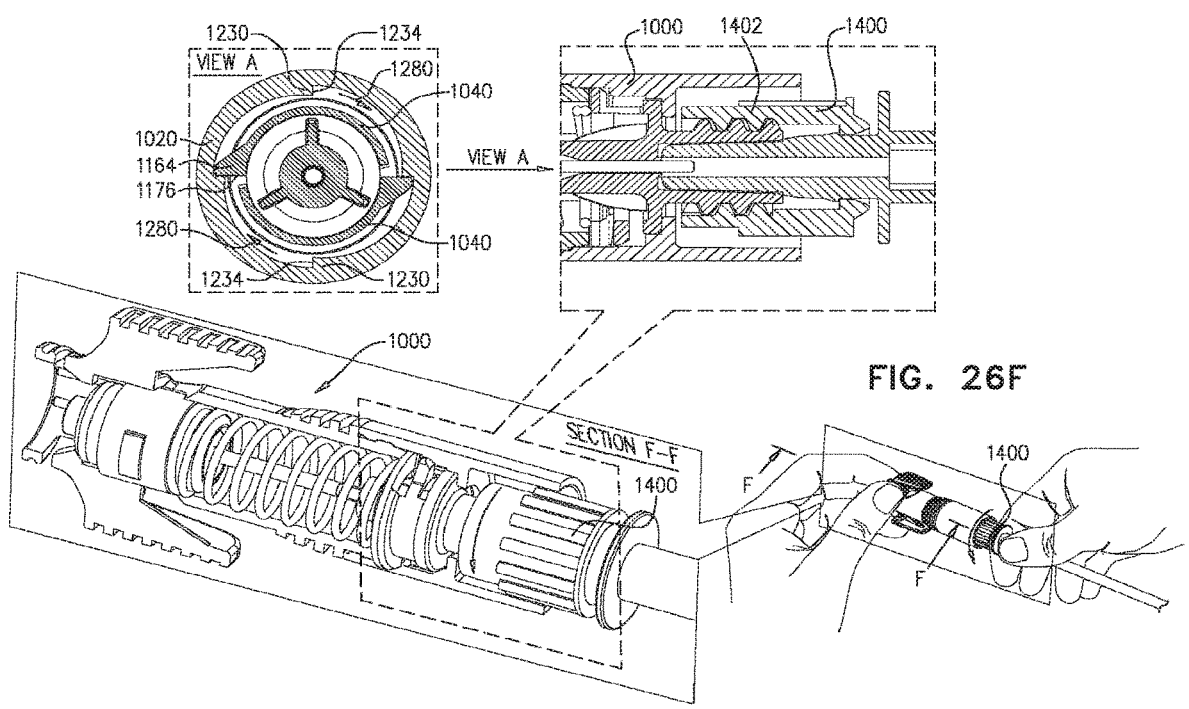

FIGS. 26D, 26E and 26F illustrate counterclockwise rotation of the luer lock connector 1400 relative to rearward housing portion 1020 of luer lock adaptor 1000 about axis 1001, as indicated by arrows 1320, in an attempt to disengage the male luer connector 1402 from the female luer connector portion 1042 of hub element 1040. This attempt is unsuccessful due to the frictional engagement of the male luer connector 1402 with the female luer connector portion 1042 of hub element 1040 and due to the fact that the hub element 1040 is free to rotate counterclockwise relative to the remainder of the luer lock adaptor 1000. It is seen in the sectional enlargement at View A in FIGS. 26D and 26E that radially directed locking surfaces 1176 of tooth elements 1164 no longer lockingly engage counterclockwise-facing, radially directed locking surfaces 1234 of teeth 1230 of rearward housing portion 1020 due to counterclockwise movement of the hub element 1040 relative to the rearward housing portion 1020. As seen in the sectional enlargement at View A in FIG. 26F, following a 90° rotation of luer lock connector 1400 and hub element 1040 relative to rearward housing portion 1020, radially directed locking surfaces 1176 of tooth elements 1164 again lockingly engage counterclockwise-facing, radially directed locking surfaces 1234 of teeth 1230 of rearward housing portion 1020 and prevent clockwise movement of the hub element 1040 relative to the rearward housing portion 1020 while allowing counterclockwise movement of the hub element 1040 relative to the rearward housing portion 1020.

Figure 27A:
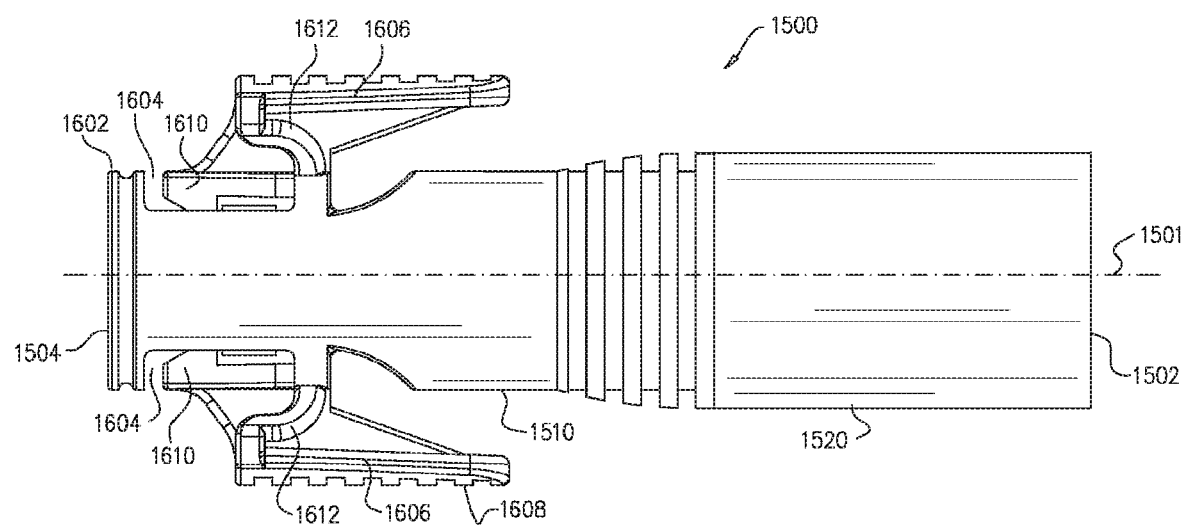
FIGS. 27A, 27B, 27C, 27D and 27E are simplified respective first and second side view, first and second end view illustrations and a sectional illustration, taken along lines XXVIIE-XXVIIE in FIG. 27D, of a luer lock adaptor constructed and operative in accordance with yet another preferred embodiment of the present invention.
Figure 27B:
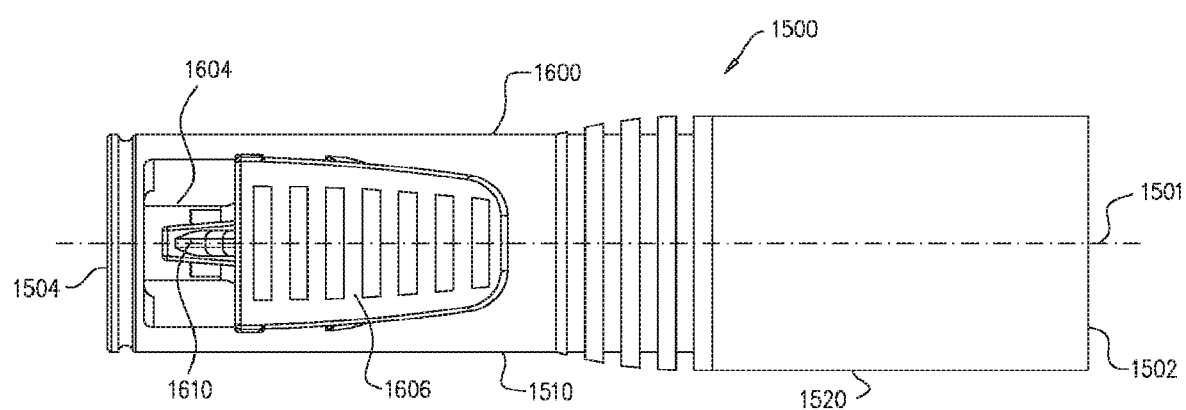
Figure 27C:
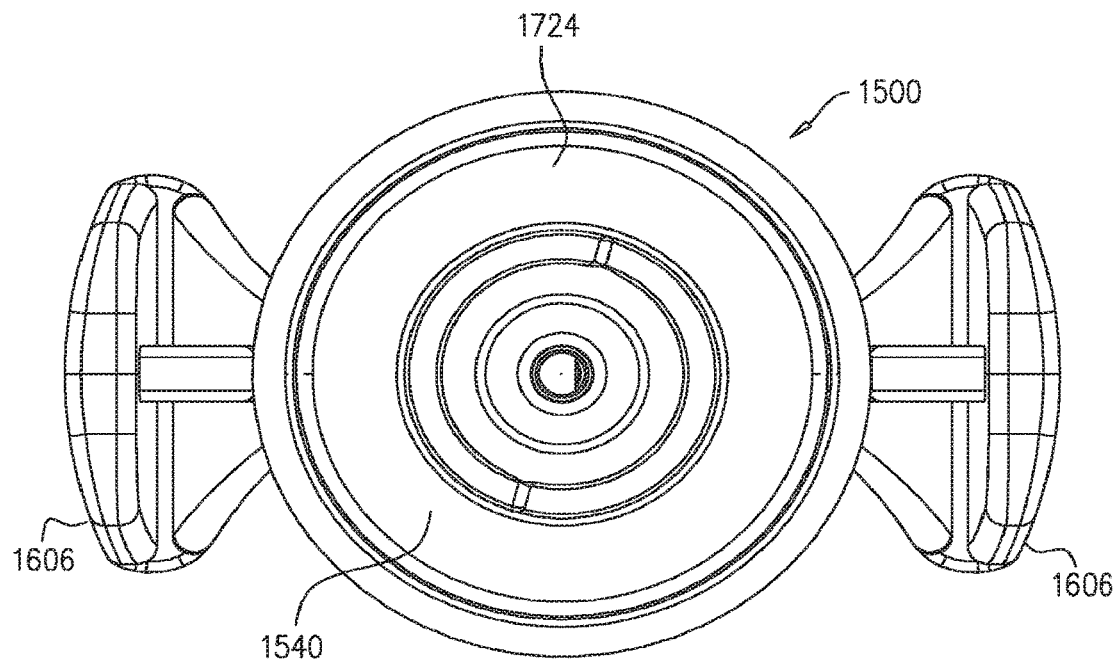
Figure 27D:
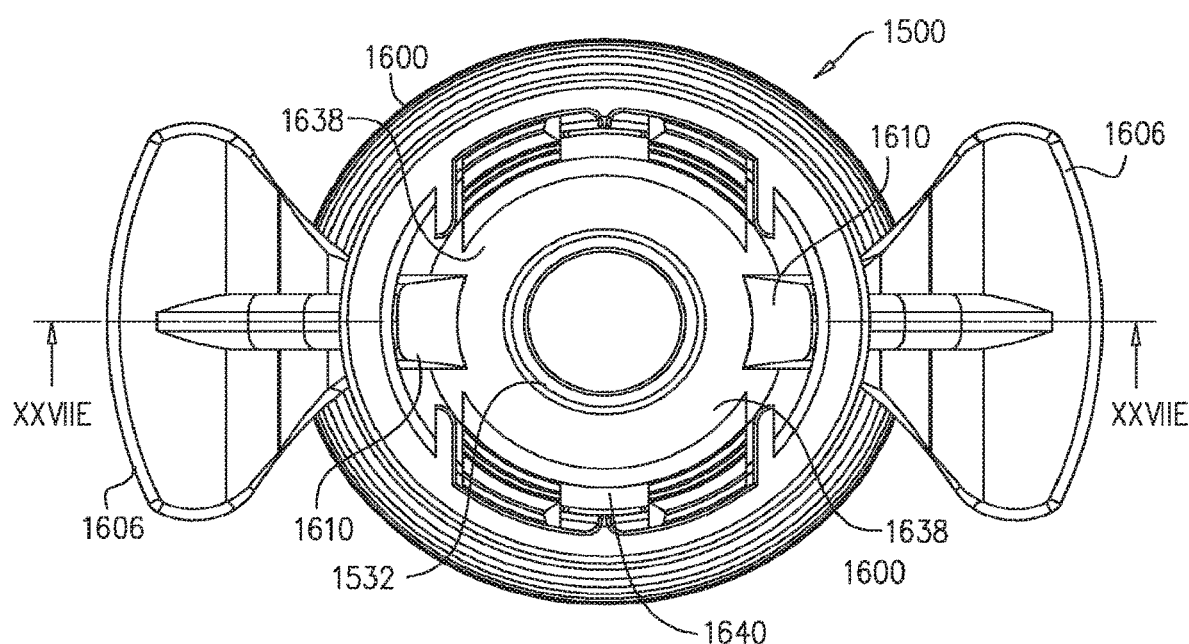
Figure 27E:
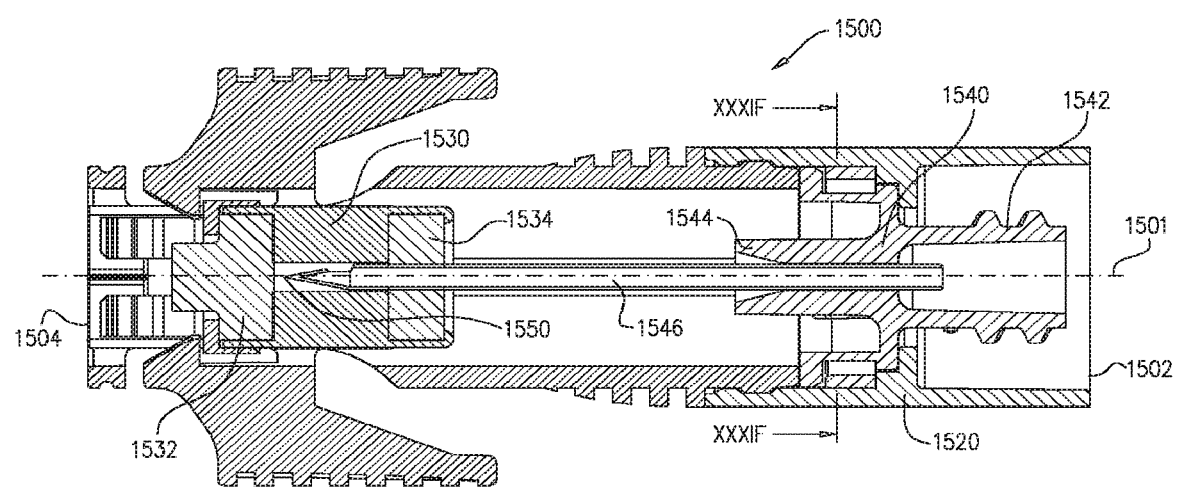
Figure 28:
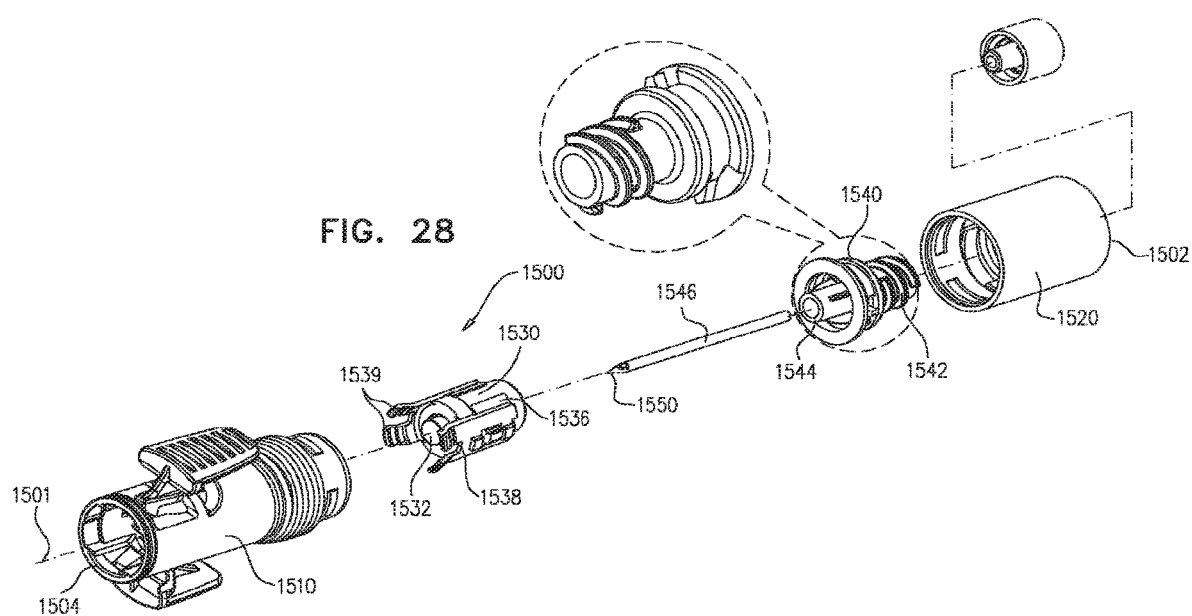
FIG. 28 is a simplified exploded view illustration of the luer lock adaptor of FIGS. 27A-27E.

Reference is now made to FIGS. 27A, 27B, 27C, 27D and 27E, which are simplified respective first and second side view, first and second end view illustrations and a sectional illustration, taken along lines XXVIIE-XXVIIE in FIG. 27D, of a luer lock adaptor constructed and operative in accordance with another preferred embodiment of the present invention and to FIG. 28, which is a simplified exploded view illustration of the luer lock adaptor of FIGS. 27A-27E.

As seen in FIGS. 27A-27E and 28, there is provided a luer lock adaptor 1500, which extends generally along a longitudinal axis 1501 and has a luer connection end 1502 and a port connection end 1504. The luer lock adaptor 1500 preferably includes a forward housing portion 1510 and a rearward housing portion 1520, which are preferably fixedly snap-fit to each other so as to prevent both relative axial movement and relative azimuthal movement about axis 1501 therebetween.

Alternatively, forward housing portion 1510 and rearward housing portion 1520 may be formed as a single integral unit. The forward-facing direction is facing to the left in FIG. 27A.

Disposed within forward housing portion 1510 is a septa housing assembly 1530 including a forward septum 1532 and a rearward septum 1534, which are fixedly and sealingly retained in a septa mounting portion 1536, preferably by ultrasonic swaging of forward and rearward edges of the septa mounting portion 1536. Septa housing assembly 1530 preferably includes a plurality of septa housing mounting legs 1538, each including a forward engagement portion 1539, which are typically snap mounted onto septa mounting portion 1536.

Disposed within rearward housing portion 1520 is a hub element 1540, defining a female luer connector portion 1542 at a rearward-facing end thereof and, at a forward-facing end thereof, defining a needle mounting portion 1544. A needle 1546, mounted onto needle mounting portion 1544, extends axially forwardly along longitudinal axis 1501 into forward housing portion 1510, such that in the absence of a port connection at the port connection end 1504, a sharp tip 1550 of needle 1546 is located within the septa housing 1530 between rearward septum 1534 and forward septum 1532. As distinct from the embodiment of FIGS. 18A-26F, no compression spring is provided and septa housing 1530 is axially slidably mounted onto forward housing portion 1510 via septa housing mounting legs 1538.

It is a particular feature of an embodiment of the present invention that there is provided a luer lock adaptor, here luer lock adaptor 1500, which includes a housing, here housing portions 1510 and 1520, which define an axis, here axis 1501, and an internal luer lock element, here hub element 1540, the internal luer lock element being located internally of the housing and being rotatably mounted thereto for rotation about the axis relative to the housing, in a manner which permits rotation of the luer lock element relative to the housing in a first rotation direction about the axis and limits rotation of the luer lock element relative to the housing in a second rotation direction about the axis, opposite to the first rotation direction, whereby the location of the internal luer lock element internally of the housing prevents manual access to the internal luer lock element for limiting rotation thereof in the first rotation direction.

Figure 29A:
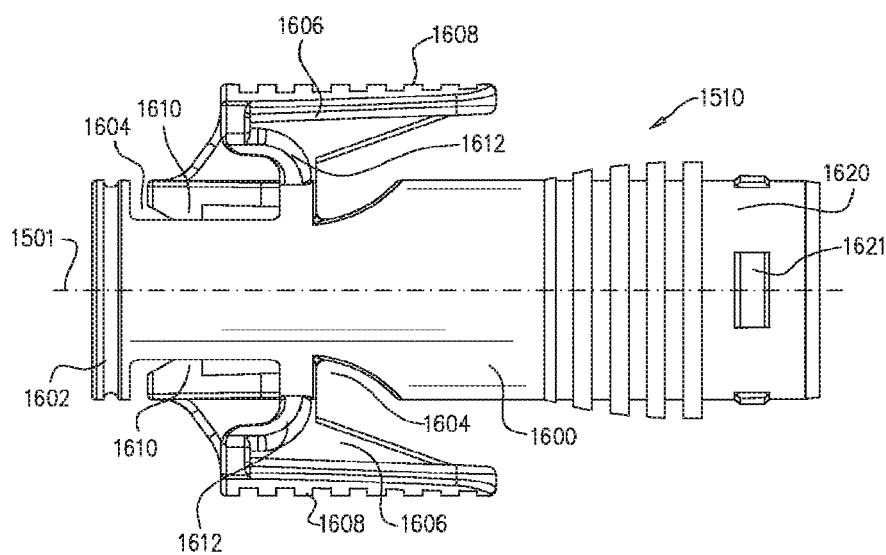
FIGS. 29A, 29B, 29C and 29D are simplified respective first and second side view, perspective luer connection end view and sectional view illustrations of a forward housing portion forming part of the luer lock adaptor of FIGS. 27A-28, FIG. 29D being taken along lines XXIXD-XXIXD in FIG. 29C.
Figure 29B:
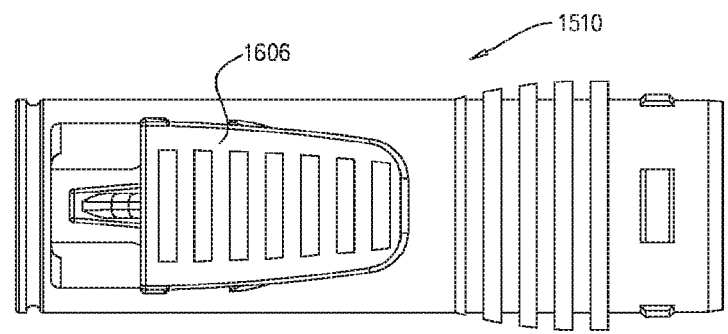
Figure 29C:
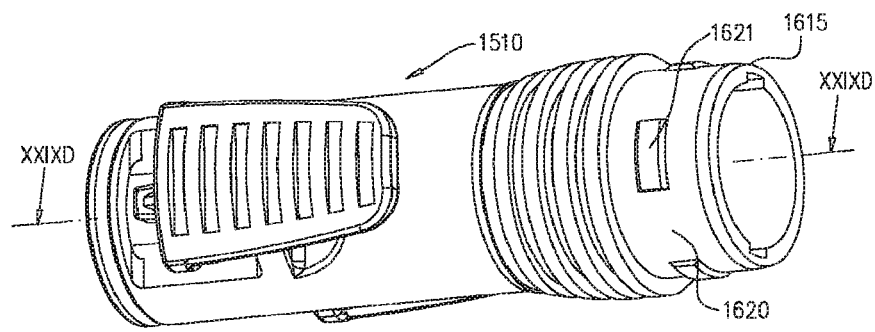

Reference is now additionally made to FIGS. 29A, 29B, 29C and 29D, which are simplified respective first and second side view, perspective luer connection end view and sectional view illustrations of a forward housing portion forming part of the luer lock adaptor of FIGS. 27A-28, FIG. 29D being taken along lines XXIXD-XXIXD in FIG. 29C.

As seen in FIGS. 29A-29D, the forward housing portion 1510 comprises a generally circular cylindrical main portion 1600 having a forward circumferential rim 1602 and a pair of opposite side cut outs 1604 adjacent which are mounted a pair of oppositely directed port connector engagement portions 1606.

Each of port connector engagement portions 1606 preferably includes a ribbed finger engagement surface 1608, which is connected to a retractable port connector engagement tooth 1610. Each of port connector engagement portions 1606 is flexibly mounted onto main portion 1600 by means of a flexible mounting arch 1612 which spans a corresponding cut out 1604. Manual pressing on engagement surface 1608 causes retraction of port connector engagement tooth 1610, such that simultaneous manual pressing on engagement surfaces 1608 of both of port connector engagement portions 1606 enables disengagement of a port connector (not shown) from the interior of cylindrical main portion 1600.

Figure 29D:
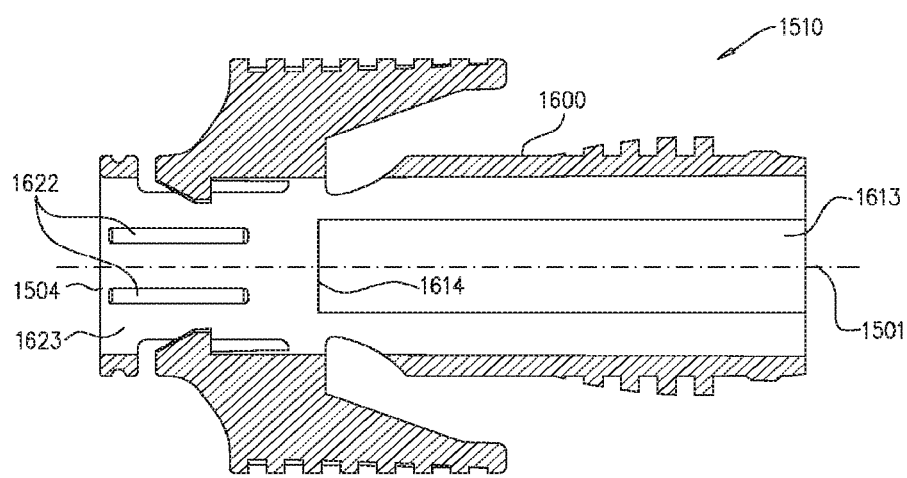

As seen clearly in FIG. 29D, opposite interior surfaces of main portion 1600 each define a septa housing guiding recess 1613 having a forward stop-defining wall surface 1614, which limits the forward displacement of the septa housing 1530 relative to the forward housing portion 1510.

As seen particularly clearly in FIG. 29C, forward housing portion 1510 includes a rearwardly-facing edge 1615. Adjacent rearwardly-facing edge 1615 on a radially outward surface 1620 of main portion 1600 are a plurality of mutually spaced circumferential elongate protrusions 1621.

As seen in FIG. 29D, forwardly of an inwardly-facing circumferential wall surface 1623 of the forward housing portion 1510 there are provided a plurality of recesses 1624, each having an inwardly-facing wall surface which is disposed radially outwardly with respect to inwardly-facing circumferential wall surface 1623 as well as being forward thereof. Recesses 1624 are each separated from inwardly-facing circumferential wall surface 1623 by a tapered shoulder 1626.

It is appreciated that forward engagement portions 1539 of septa housing mounting legs 1538 are seated in corresponding recesses 1624 when the port connection end 1504 is not engaged by a port adaptor, such as, for example a vial adaptor. Engagement of a port adaptor with port connection end 1504 typically forces forward engagement portions 1539 radially inwardly and rearwardly out of recesses 1624, over respective tapered shoulders 1626 and into engagement with inwardly-facing circumferential wall surface 1623.

Figure 30A:
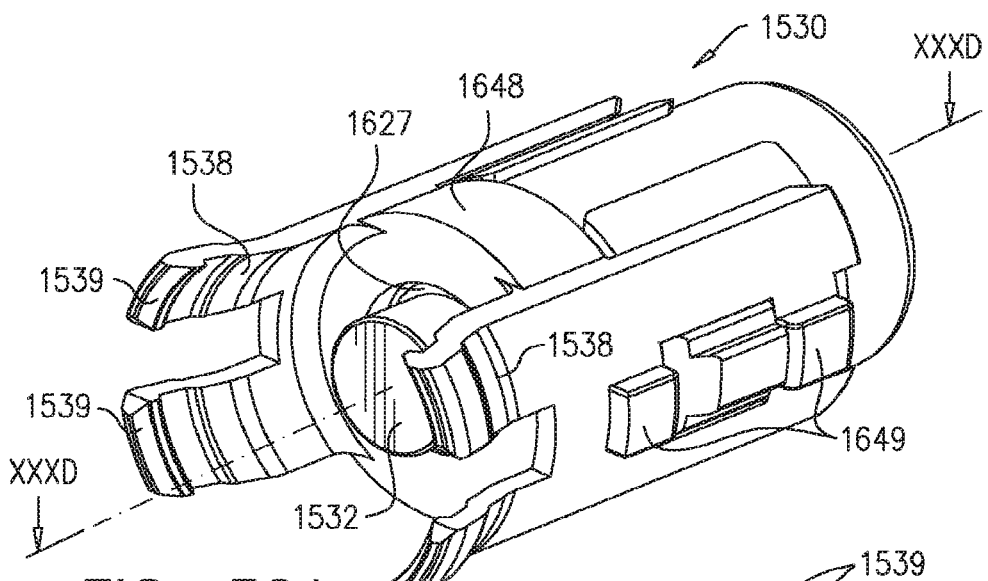
FIGS. 30A, 30B, 30C, 30D and 30E are simplified respective rearward-facing and forward-facing perspective view, side view, forward-facing end view and sectional view illustrations of a septa housing portion forming part of the luer lock adaptor of FIGS. 27A-28, FIG. 30D being taken along lines XXXD-XXXD in FIG. 30A.
Figure 30B:
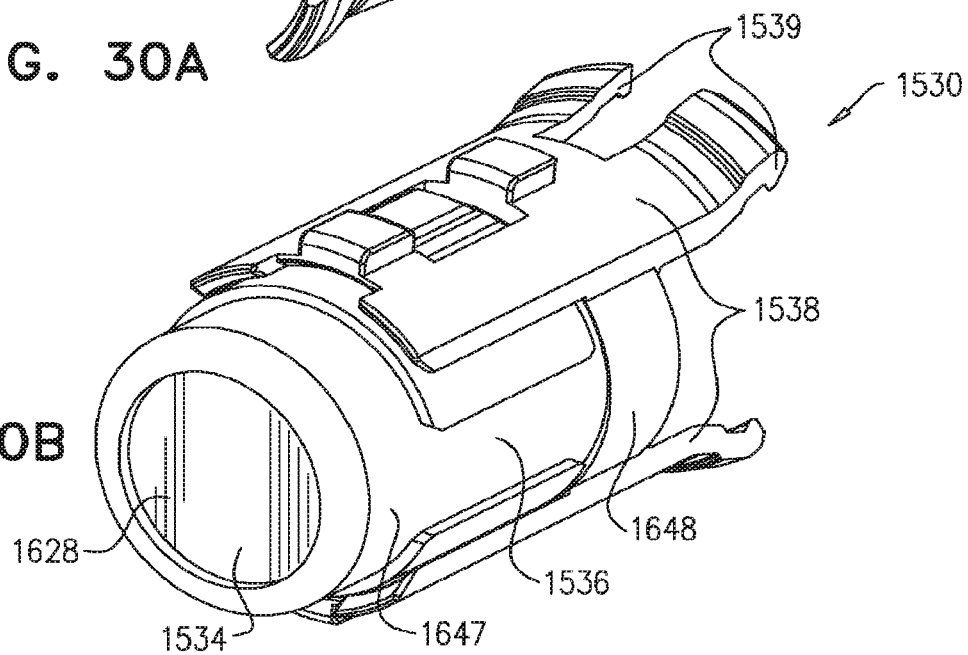
Figure 30C:
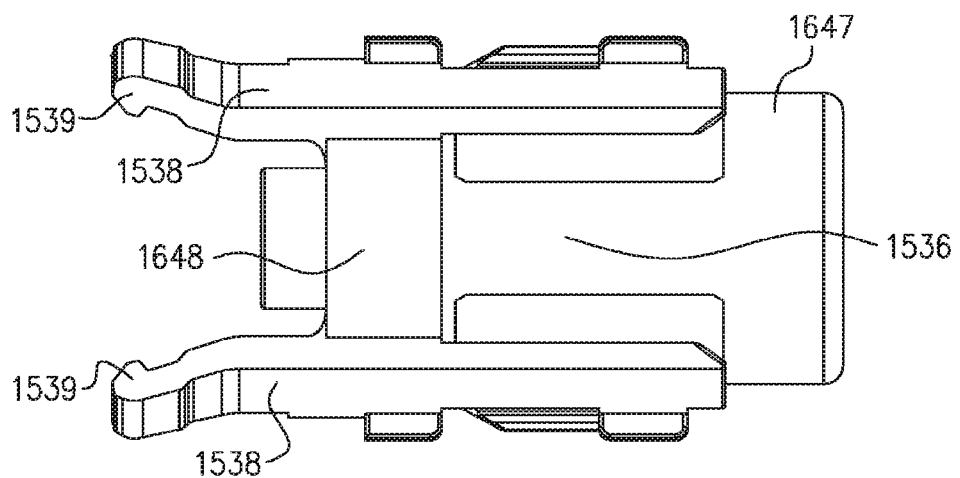
Figure 30D:
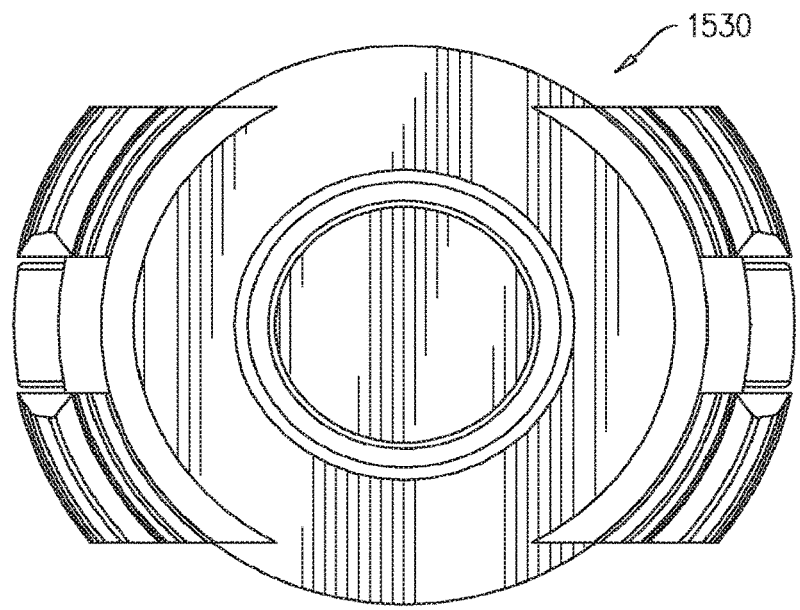
Figure 30E:
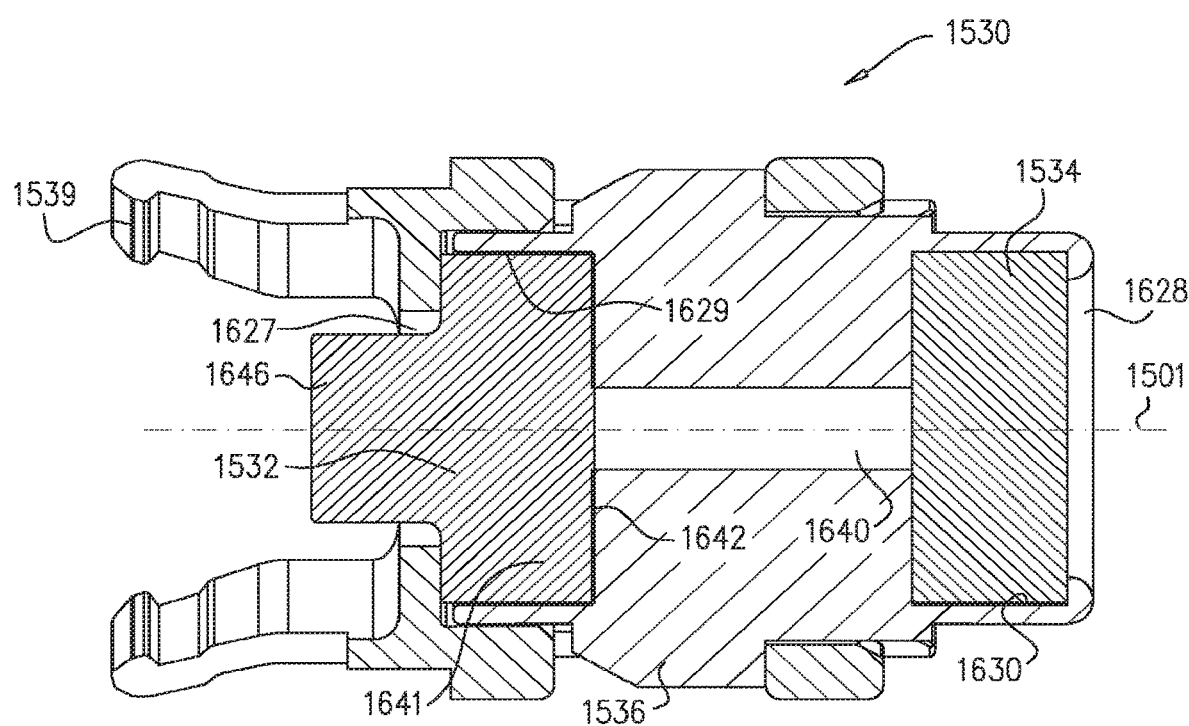

Reference is now made to FIGS. 30A, 30B, 30C, 30D and 30E, which are simplified respective rearward-facing and forward-facing perspective view, side view, forward-facing end view and sectional view illustrations of a septa housing assembly forming part of the luer lock adaptor of FIGS. 27A-28, FIG. 30D being taken along lines XXXD-XXXD in FIG. 30A.

As noted above, septa housing assembly 1530 including a forward septum 1532 and a rearward septum 1534, which are fixedly and sealingly retained in a septa mounting portion 1536, preferably by ultrasonic swaging of forward and rearward edges of the septa mounting portion 1536. Septa housing assembly 1530 preferably includes a plurality of septa housing mounting legs 1538, each including a forward engagement portion 1539, which are typically snap mounted onto septa mounting portion 1536.

As seen in FIGS. 30A-30E, the septa housing assembly 1530 is a generally cylindrical element having generally rounded respective forward and rearward openings 1627 and 1628 leading to respective forward and rearward recesses 1629 and 1630, which accommodate respective forward and rearward septa 1532 and 1534. An open needle accommodating channel 1640 extends longitudinally along axis 501 between forward and rearward recesses 1629 and 1630.

As seen particularly in FIGS. 30A-30E, forward septum 1532 preferably is an integrally formed element formed of a polymer, such as polyisoprene, and includes a relatively wide, rearward cylindrical portion 1641, which is preferably seated in forward recess 1629 of septa mounting portion 1536 and defines a rearwardly-directed forward septum surface 1642, and a relatively narrow cylindrical portion 1644, which extends forwardly of rearward cylindrical portion 1641 and preferably extends through and forwardly of forward opening 1627 in septa housing assembly 1530 and defines a forwardly-directed forward septum surface 1646. Rearward septum 1534 preferably is an integrally formed element formed of a polymer, such as polyisoprene, is of a disk like, flat cylindrical configuration and is seated in rearward recess 1630 of septa housing assembly 1530.

It is seen that septa mounting portion 1536 has a generally cylindrical outer surface 1647 onto which is snap mounted or otherwise secured a radially outwardly protruding circumferential band 1648 from which septa housing mounting legs 1538 extend forwardly. A pair of narrow protrusions 1649 extend radially outwardly from circumferential band 1648 for engaging septa housing guiding recesses 1613 and forward stop-defining wall surfaces 1614 and thus limiting the forward displacement of septa housing assembly 1530 in forward housing portion 1510 and preventing the azimuthal rotation of septa housing portion 1530 about axis 1501.

Figure 31A:
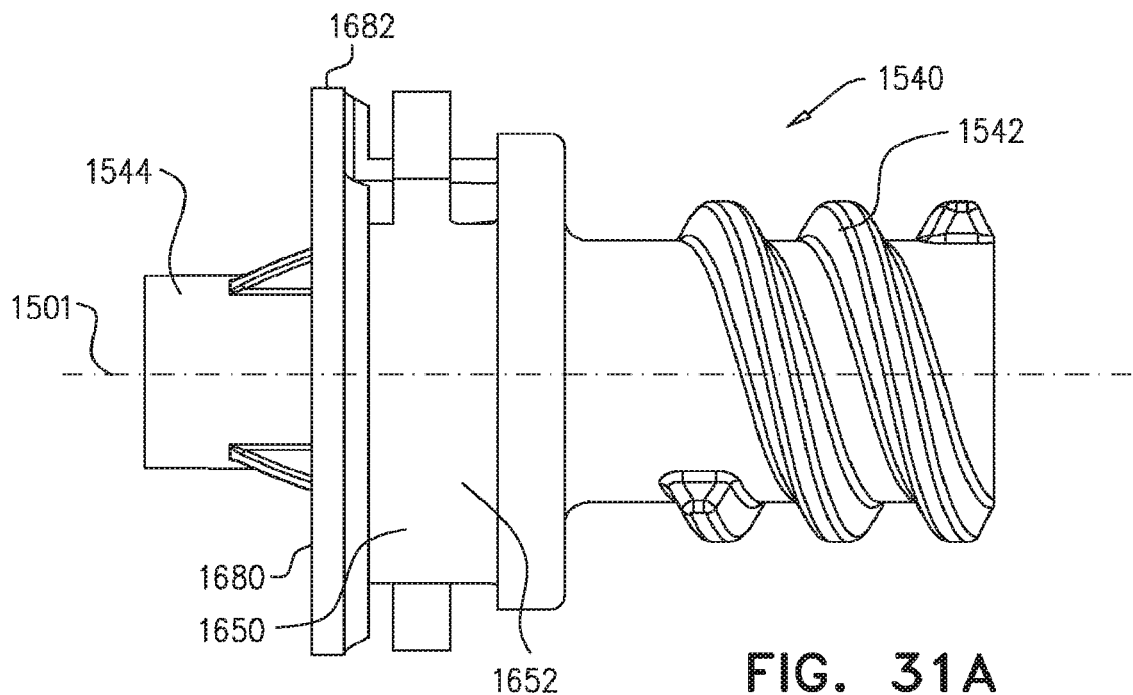
FIGS. 31A, 31B, 31C, 31D and 31E are simplified respective first and second side view, first and second perspective end view and sectional illustrations of a hub element forming part of the luer lock adaptor of FIGS. 27A-28, FIG. 31E being taken along lines XXXIE-XXXIE in FIG. 31C.
Figure 31B:
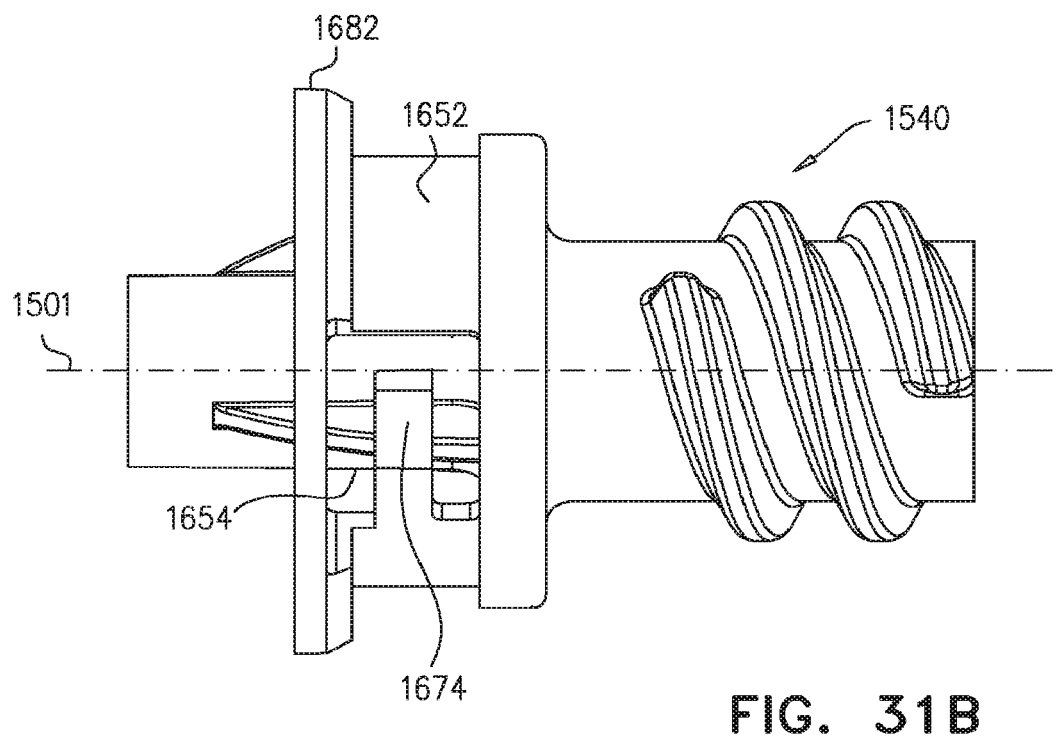
Figure 31C:
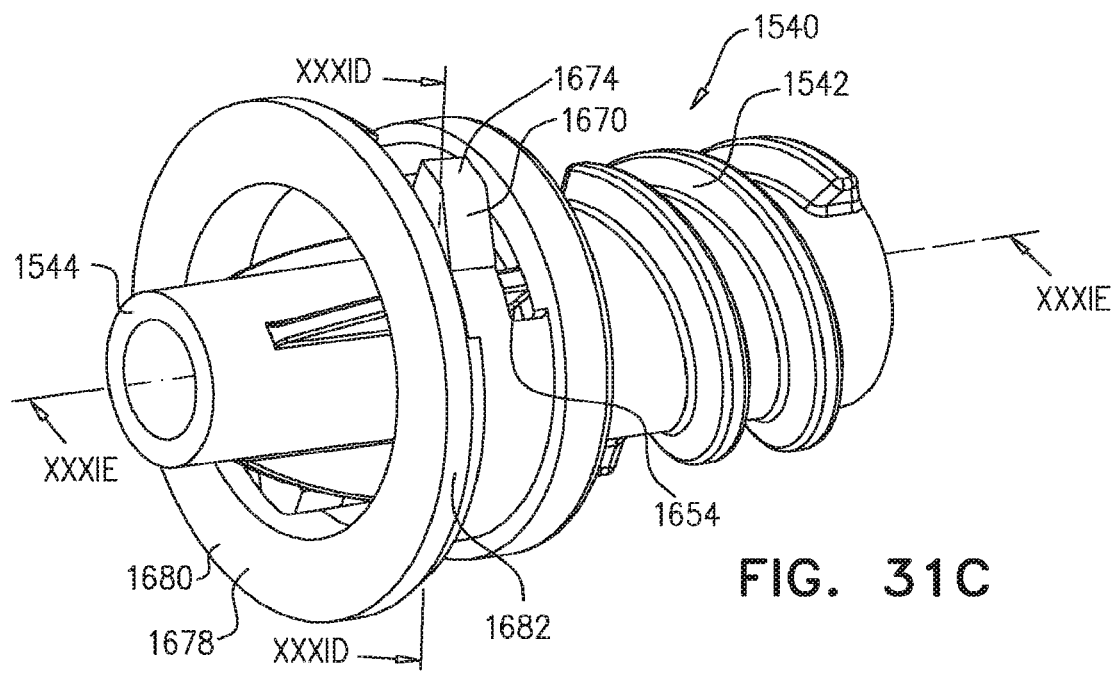
Figure 31D:
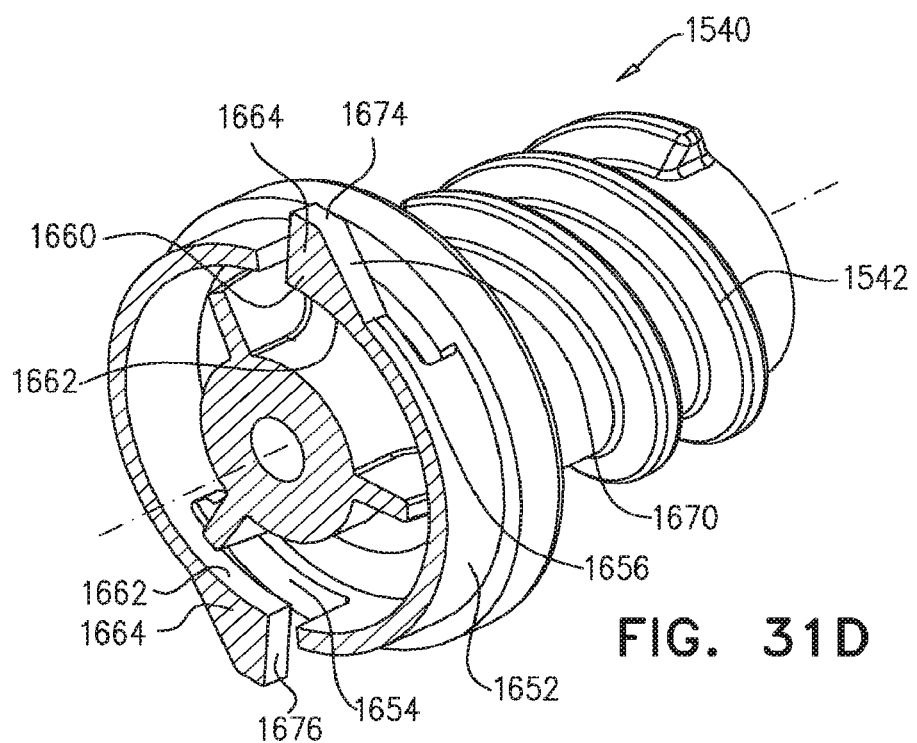
Figure 31E:
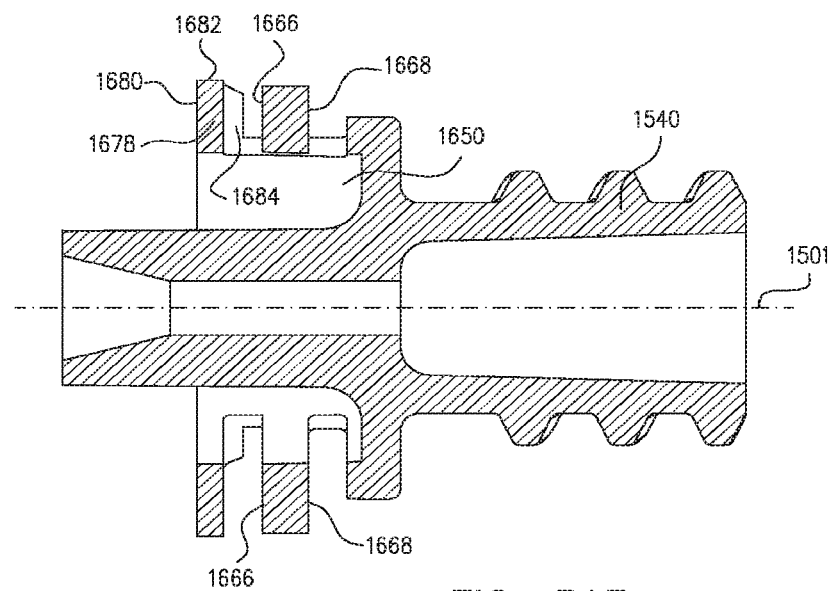

Reference is now made to FIGS. 31A, 31B, 31C, 31D and 31E, which are simplified respective first and second side view, first and second perspective end view, and a sectional view, taken along lines XXXIE-XXXIE in FIG. 31C, illustrations of hub element 1540. As noted hereinabove, hub element 1540 defines a female luer connector portion 1542 at a rearward-facing end and a needle mounting portion 1544 at a forward-facing end.

Disposed intermediate the female luer connector portion 1542 and the needle mounting portion 1544 is a radially-toothed circumferential intermediate portion 1650. Radially-toothed circumferential intermediate portion 1650 preferably includes a pair of generally opposite, outwardly-facing circular cylindrical surface portions 1652 which are separated by a pair of generally opposite circumferential gaps 1654.

Extending circumferentially into respective gaps 1654 and radially outwardly from circumferential edges 1656 of outwardly-facing circular cylindrical surface portions 1652 are a pair of preferably evenly circumferentially spaced, cantilevered toothed arms 1660, each including a generally circumferential arm portion 1662 and a tooth portion 1664.

Tooth portion 1664 preferably includes a forward-facing surface 1666 and a rearward-facing surface 1668 parallel to surface 1666, a circumferentially and radially outwardly inclined surface 1670 which preferably extends perpendicularly to surfaces 1666 and 1668, a radially outward-facing engagement surface 1674 and a clockwise-facing radially directed locking surface 1676.

Forwardly of radially-toothed circumferential intermediate portion 1650 is a forward-facing flange 1678 having a forward facing surface 1680, an outer facing cylindrical edge surface 1682 and a rearward-facing surface 1684.

Figure 32A:
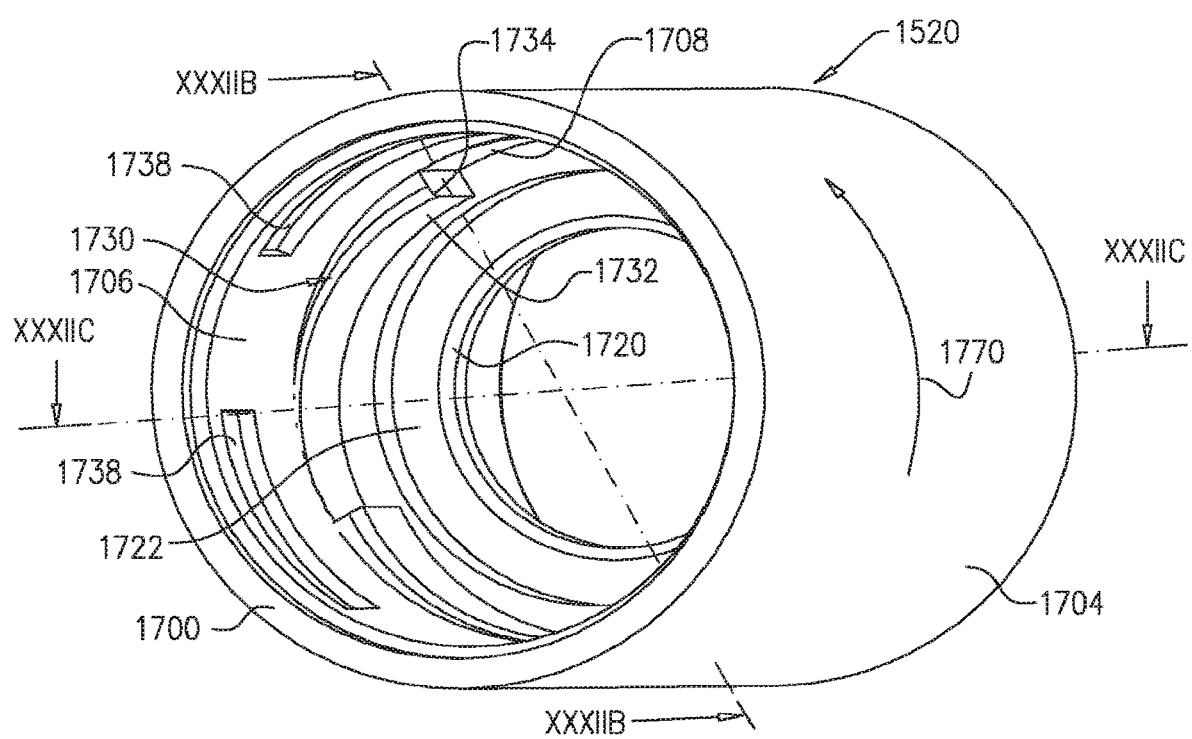
FIGS. 32A, 32B and 32C are simplified perspective end view, cut away perspective end view and sectional illustrations of a rearward housing portion forming part of the luer lock adaptor of FIGS. 27A-28.
Figure 32B:
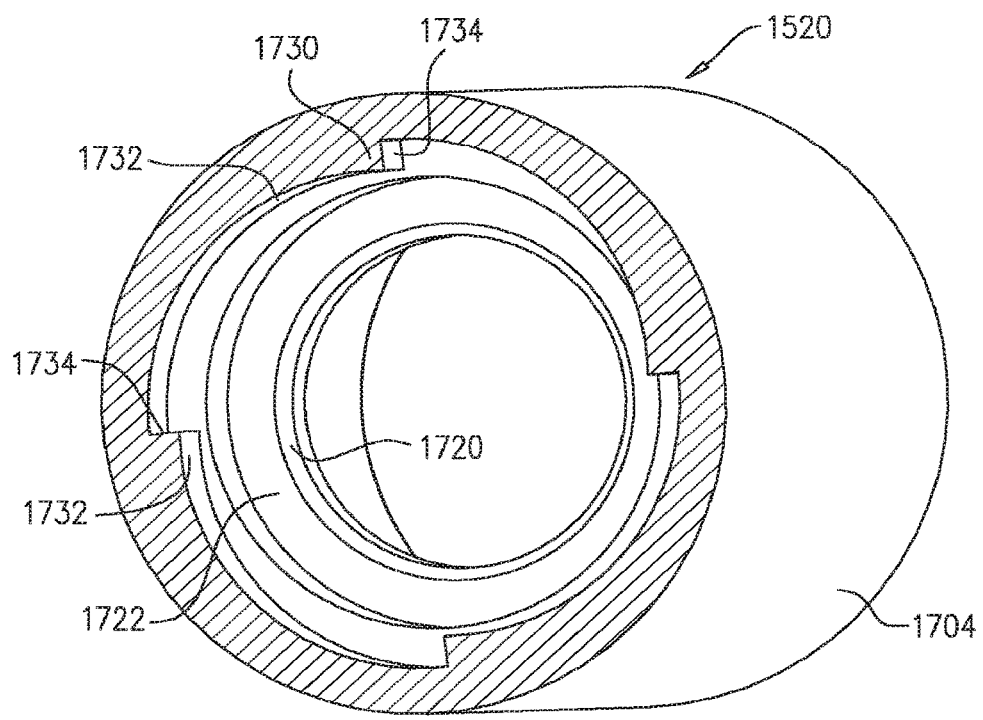
Figure 32C:
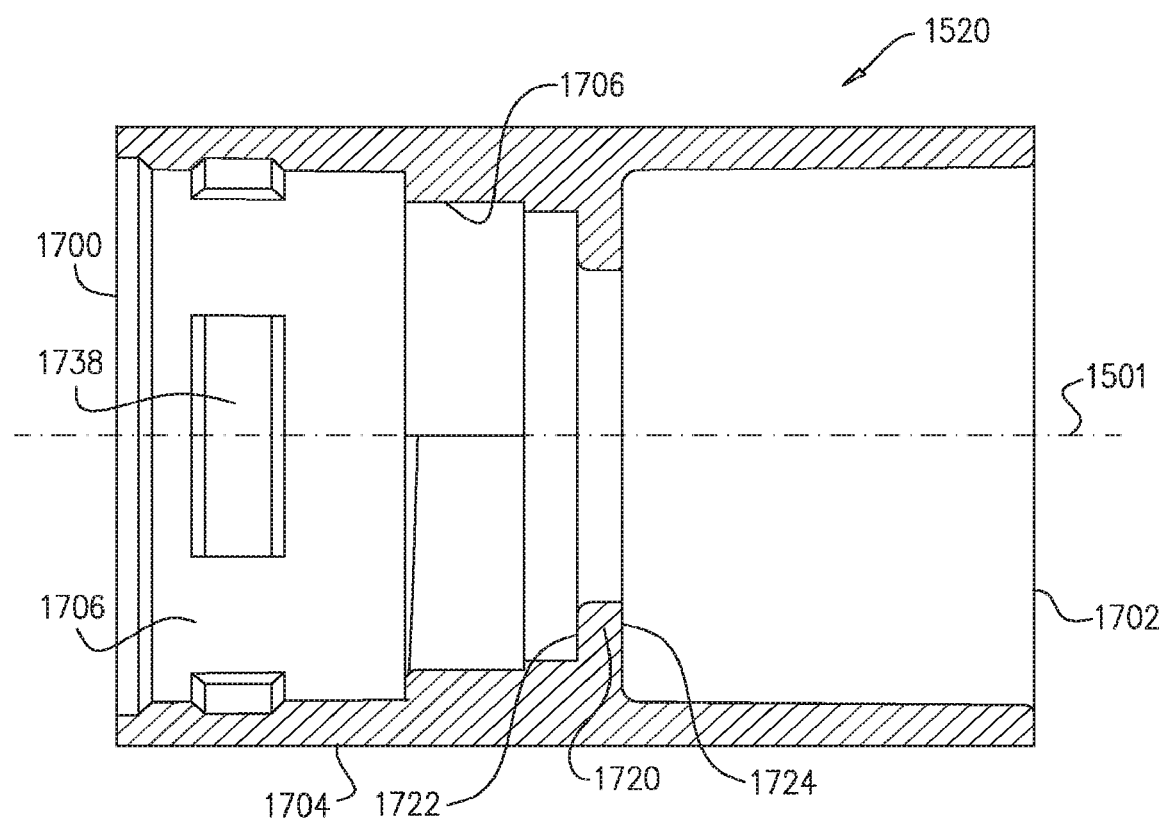

Reference is now additionally made to FIGS. 32A, 32B and 32C, which are simplified perspective end view, cut away perspective end view and sectional view illustrations of rearward housing portion 1520.

As seen in FIGS. 28 and 32A-32C, rearward housing portion 1520 is preferably an overall circular cylindrical element arranged along axis 1501 and having a forward end 1700, a rearward end 1702, a circular cylindrical outwardly-facing surface 1704 and a circular cylindrical inwardly-facing surface 1706. Intermediate forward end 1700 and rearward end 1702 and extending radially inwardly of inwardly-facing surface 1706 is an inwardly directed flange 1720 having a forwardly-facing surface 1722 and a rearwardly-facing surface 1724.

Extending circumferentially and radially inwardly of circular cylindrical inwardly-facing surface 1706 forwardly of inwardly directed flange 1720 are a plurality of generally evenly spaced teeth 1730, preferably four, each having an gradually inclined radially facing surface 1732 and a counterclockwise-facing, radially directed locking surface 1734. The radially inward extent of each of teeth 1730 increases counterclockwise from inwardly-facing surface 1706 to counterclockwise-facing locking surface 1734.

The arrangement of tooth portions 1664 on hub element 1540 and of teeth 1730 on rearward housing portion 1520 is preferably such that when a male luer connector of a syringe or other element (not shown) is screwed onto female luer connector portion 1542 in a clockwise direction of rotation from a forwardly-facing perspective, continued rotation of the syringe in the aforesaid clockwise direction produces corresponding rotation of hub element 1540 in the aforesaid clockwise direction and causes clockwise facing, radially directed locking surfaces 1676 to lockingly engage corresponding counter-clockwise facing, radially directed locking surfaces 1734 of two of teeth 1730 of rearward housing portion 1520. The aforesaid clockwise direction of rotation is indicated by an arrow 1770 in FIG. 32A.

Formed on inwardly-facing surface 1706 are a plurality of mutually azimuthally spaced circumferential recesses 1738 which receive corresponding protrusions 1621 of forward housing portion 1510 in a snap fit engagement of forward housing portion 1510 and rearward housing portion 1520, thereby providing both axial and azimuthal locking between forward housing portion 1510 and rearward housing portion 1520.

It is appreciated that, although in the embodiments shown in FIGS. 1A-9G and 10A-17F respective hub elements 140 and 540 are able to move axially relative to respective forward housing portions 110 and 510 and relative to respective rearward housing portions 120 and 520, in the embodiment shown in FIGS. 27A-32C, similar to the embodiment shown in FIGS. 18A-24C, the above referenced axial and azimuthal locking of forward housing portion 1510 and rearward housing portion 1520 also axially locks hub element 1540 relative to forward housing portion 1510 and relative to rearward housing portion 1520, but allows azimuthal movement of hub element 1540 about axis 1501 relative to forward housing portion 1510 and relative to rearward housing portion 1520.

Reference is now made to FIGS. 31F-31I, which illustrate the relative positions of radially directed locking surfaces 1676 of hub element 1540 and corresponding locking surfaces 1734 of rearward housing portion 1520 in four different rotational orientations.

Figure 31F:
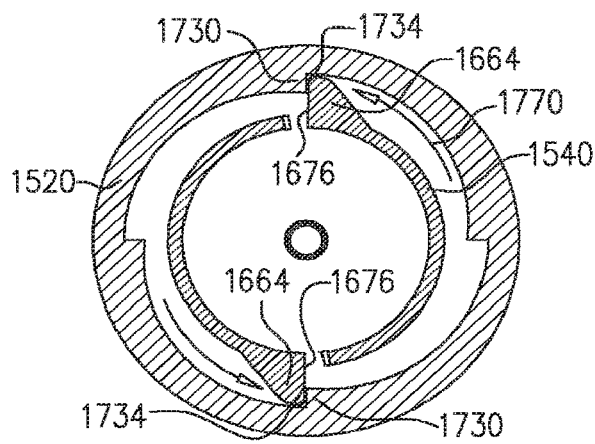
FIGS. 31F, 31G, 31H and 31I are simplified sectional illustrations of relative positioning of a hub element and a rearward housing portion of the luer lock adaptor of FIGS. 27A-28 in four different rotational orientations, taken along lines XXXIF-XXXIF in FIG. 27E.

As seen in FIG. 31F, in a first rotational orientation, radially directed locking surfaces 1676 of hub element 1540 are in a locked clockwise operative engagement with locking surfaces 1734 of rearward housing portion 1520 and prevent clockwise, from a forwardly-facing perspective, rotation, as shown by arrow 1770, of hub element 1540 relative to rearward housing portion 1520. It is appreciated that in this orientation counterclockwise movement of the hub element 1540 relative to the rearward housing portion 1520 is permitted.

Figure 31G:
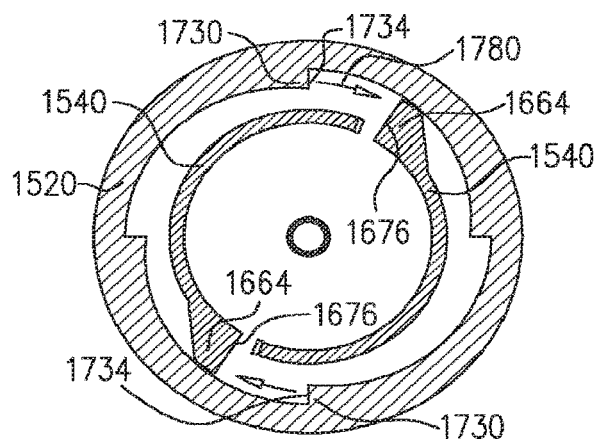
Figure 31H:
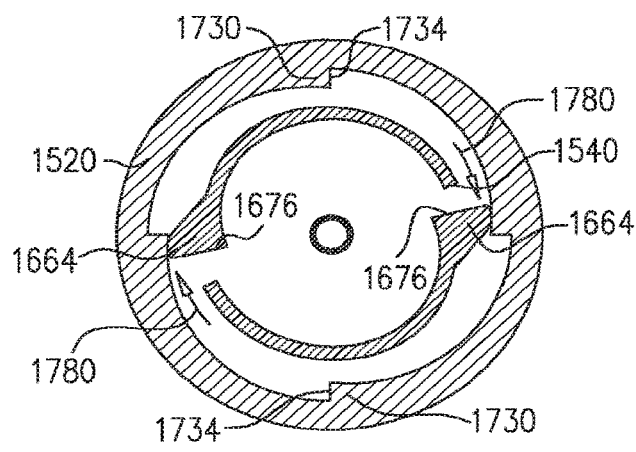

As seen in FIGS. 31G and 31H, in a second and a third rotational orientation, hub element 1540 has been rotated counterclockwise, from a forwardly-facing perspective, relative to rearward housing portion 1520, from the orientation shown in FIG. 31F. Radially directed locking surfaces 1676 of hub element 1540 are not in a locked clockwise operative engagement with locking surfaces 1734 of rearward housing portion 1520. It is appreciated that in these orientations counterclockwise, from a forwardly-facing perspective, rotation of the hub element 1540 relative to the rearward housing portion 1520, as shown by arrows 1780, is permitted, It is also appreciated that limited clockwise, from a forwardly-facing perspective, rotation of hub element 1540 relative to rearward housing portion 1520, to return to the first rotational orientation shown in FIG. 31F, is possible.

Figure 31I:
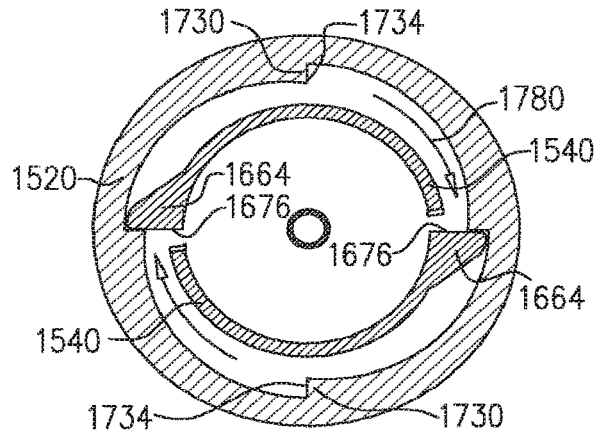

As seen in FIG. 31I, in a fourth rotational orientation, hub element 1540 has been rotated by 90° counterclockwise, as indicated by arrows 1780, from a forwardly-facing perspective, from the orientation shown in FIG. 31F. Radially directed locking surfaces 1676 of hub element 1540 are in a locked clockwise operative engagement with locking surfaces 1734 of rearward housing portion 1520 and prevent clockwise, from a forwardly-facing perspective, rotation of hub element 1540 relative to rearward housing portion 1520. It is appreciated that in this orientation counterclockwise movement of the hub element 1540 relative to the rearward housing portion 1520 is permitted, Reference is now made to FIGS. 33A, 33B, 33C, 33D, 33E and 33F, which are simplified illustrations of the luer lock adaptor of FIGS. 27A-32C in respective first, second, third, fourth, fifth and sixth operative orientations with respect to a conventional luer lock syringe.

FIG. 33A shows a conventional luer lock syringe 1800 having a male luer connector 1802 about to be connected to the luer lock adaptor 1500 of FIGS. 27A-32C. Prior to engagement of the luer lock syringe 1800 with the luer lock adaptor 1500, snap-fit engagement between the forward housing portion 1510 and the rearward housing portion 1520, and more specifically between mutually azimuthally spaced circumferential recesses 1738 of rearward housing portion, which receive corresponding protrusions 1621 of forward housing portion 1510, retains the hub element 1540, as seen in FIG. 27E, such that tooth portions 1664 on hub element 1540 are generally coplanar with and in operative engagement with teeth 1730 on rearward housing portion 1520, as seen in sectional enlargement at View A in FIG. 33A.

Typically, clockwise-facing, radially directed locking surfaces 1676 of tooth elements 1664 lockingly engage counterclockwise-facing, radially directed locking surfaces 1734 of teeth 1730 of rearward housing portion 1520, thereby permitting counterclockwise, from a forwardly-facing perspective, rotation of hub element 1540 relative to rearward housing portion 1520, represented by arrow 1780, but preventing clockwise, from a forwardly-facing perspective, rotation of hub element 1540 relative to rearward housing portion 1520, represented by arrow 1770.

Figure 33B:
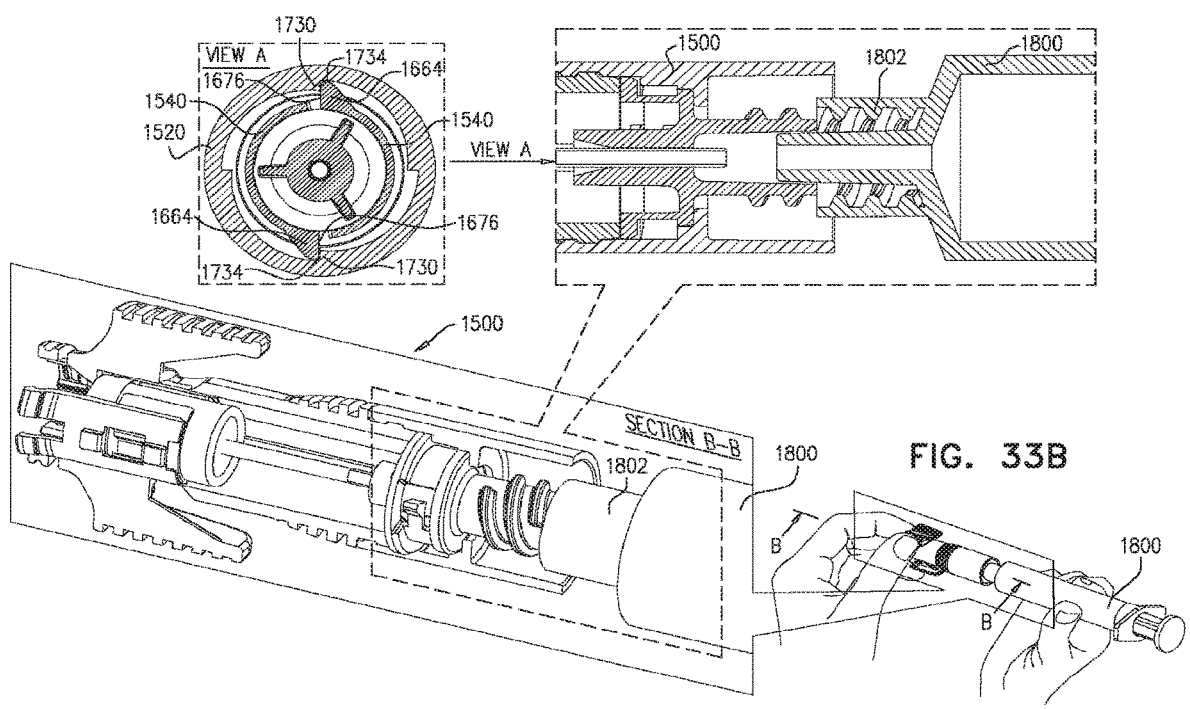

FIG. 33B illustrates initial forward axial displacement of syringe 1800 relative to luer lock adaptor 1500 along axis 1501 such that the male luer connector 1802 is in touching engagement with female luer connector portion 1542 at a rearward-facing end thereof. The locking engagement of rearward housing portion 1520 and hub element 1540 is unchanged from that described hereinabove with reference to FIG. 33A.

FIG. 33C illustrates clockwise rotation of the syringe 1800 relative to luer lock adaptor 1500 about axis 1501, as indicated by arrow 1770, such that the male luer connector 1802 is in full threaded frictional engagement with female luer connector portion 1542 of hub element 1540. This rotation takes place without application of an additional forward axial force along axis 1501. This full threaded engagement is made possible by the aforementioned locking of rotation of hub element 1540 against clockwise rotation relative to rearward housing portion 1520.

Figure 33D:
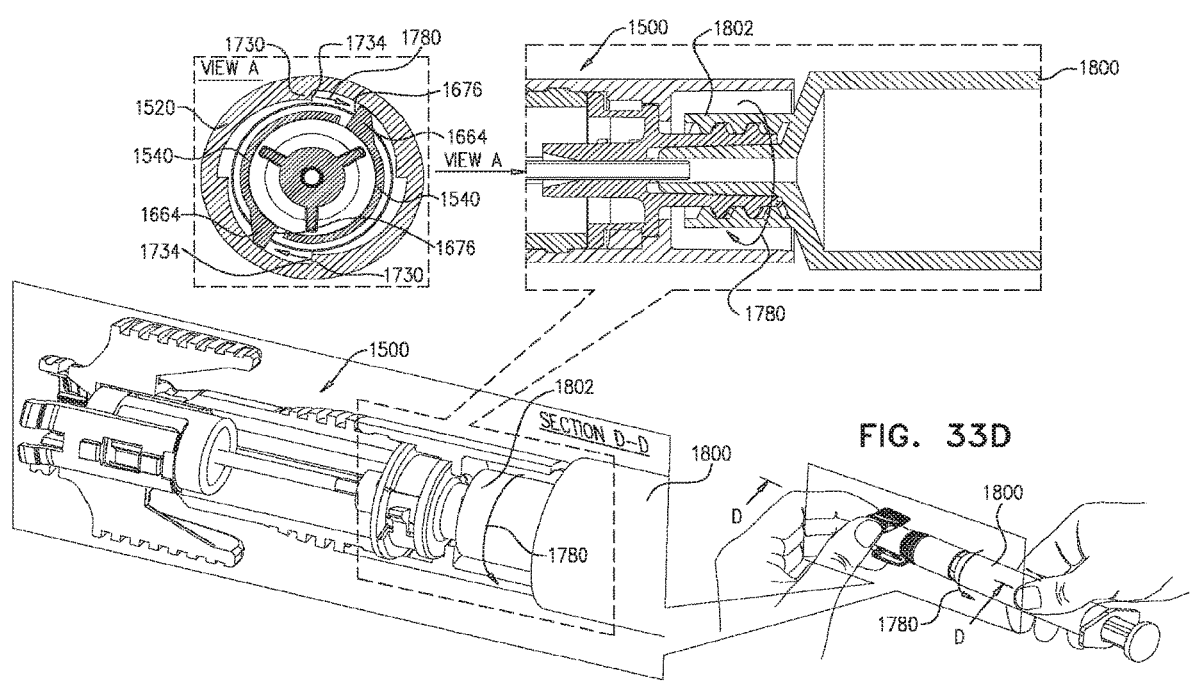
Figure 33E:
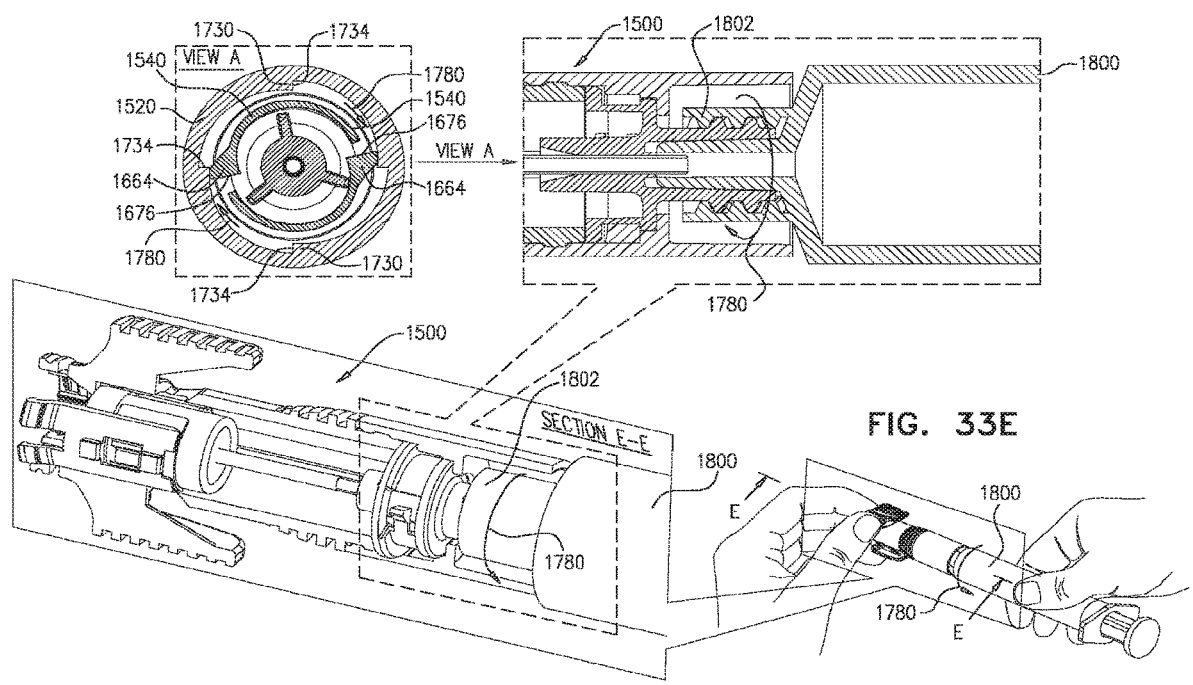
Figure 33F:
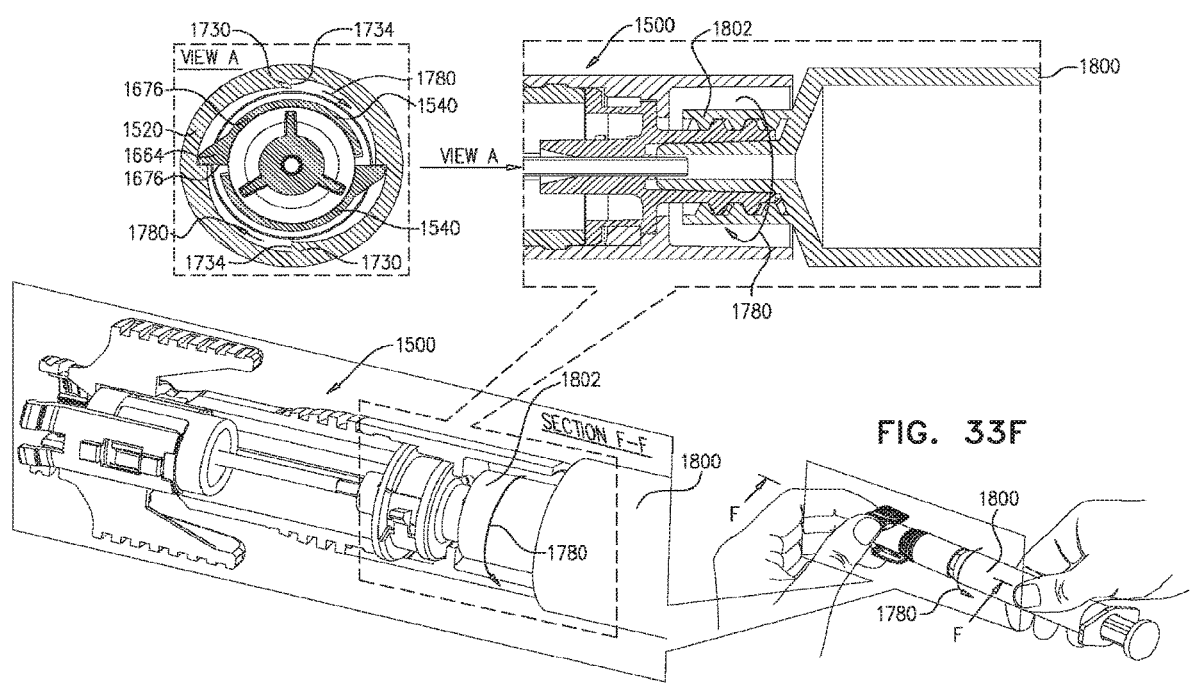

FIGS. 33D, 33E and 33F illustrate counterclockwise rotation of the syringe 1800 relative to rearward housing portion 1520 of luer lock adaptor 1500 about axis 1501, as indicated by arrows 1780, in an attempt to disengage the male luer connector 1802 from the female luer connector portion 1542 of hub element 1540. This attempt is unsuccessful due to the frictional engagement of the male luer connector 1802 with the female luer connector portion 1542 of hub element 1540 and due to the fact that the hub element 1540 is free to rotate counterclockwise relative to the remainder of the luer lock adaptor 1500. It is seen in the sectional enlargement at View A in FIGS. 33D and 33E that radially directed locking surfaces 1676 of tooth elements 1664 no longer lockingly engage counterclockwise-facing, radially directed locking surfaces 1734 of teeth 1730 of rearward housing portion 1520 due to counterclockwise movement of the hub element 1540 relative to the rearward housing portion 1520. As seen in the sectional enlargement at View A in FIG. 33F, following a 90° rotation of syringe 1800 and hub element 1540 relative to rearward housing portion 1520, radially directed locking surfaces 1676 of tooth elements 1664 again lockingly engage counterclockwise-facing, radially directed locking surfaces 1734 of teeth 1730 of rearward housing portion 1520 and prevent clockwise movement of the hub element 1540 relative to the rearward housing portion 1520 while allowing counterclockwise movement of the hub element 1540 relative to the rearward housing portion 1520.

Reference is now made to FIGS. 34A, 34B, 34C, 34D, 34E and 34F, which are simplified illustrations of the luer lock adaptor of FIGS. 27A-32C in respective first, second, third, fourth, fifth and sixth operative orientations with respect to a conventional luer lock connector.

Figure 34A:
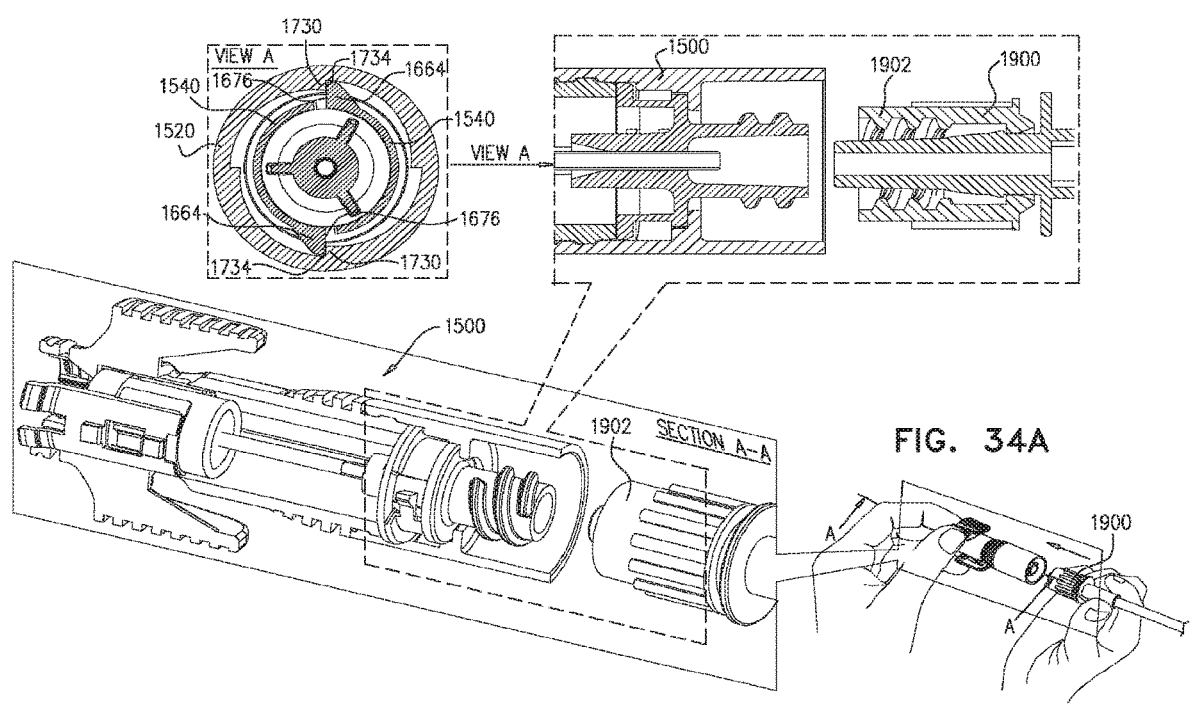
FIGS. 34A, 34B, 34C, 34D, 34E and 34F are simplified illustrations of the luer lock adaptor of FIGS. 1A-7C in respective first, second, third, fourth, fifth and sixth operative orientations with respect to a conventional luer lock connector.

FIG. 34A shows a conventional luer lock connector 1900 having a male luer connector 1902 about to be connected to the luer lock adaptor 1500 of FIGS. 27A-32C. Prior to engagement of the luer lock connector 1900 with the luer lock adaptor 1500, snap-fit engagement between the forward housing portion 1510 and the rearward housing portion 1520, and more specifically between mutually azimuthally spaced circumferential recesses 1738 of rearward housing portion, which receive corresponding protrusions 1621 of forward housing portion 1510, retains the hub element 1540, as seen in FIG. 27E, such that tooth portions 1664 on hub element 1540 are generally coplanar with and in operative engagement with teeth 1730 on rearward housing portion 1520, as seen in sectional enlargement at View A in FIG. 34A.

Typically clockwise-facing, radially directed locking surfaces 1676 of tooth elements 1664 lockingly engage counterclockwise-facing, radially directed locking surfaces 1734 of teeth 1730 of rearward housing portion 1520, thereby permitting counterclockwise, from a forwardly-facing perspective, rotation of hub element 1540 relative to rearward housing portion 1520, represented by an arrow 1820, but preventing clockwise, from a forwardly-facing perspective, rotation of hub element 1540 relative to rearward housing portion 1520, represented by arrow 1770.

Figure 34B:
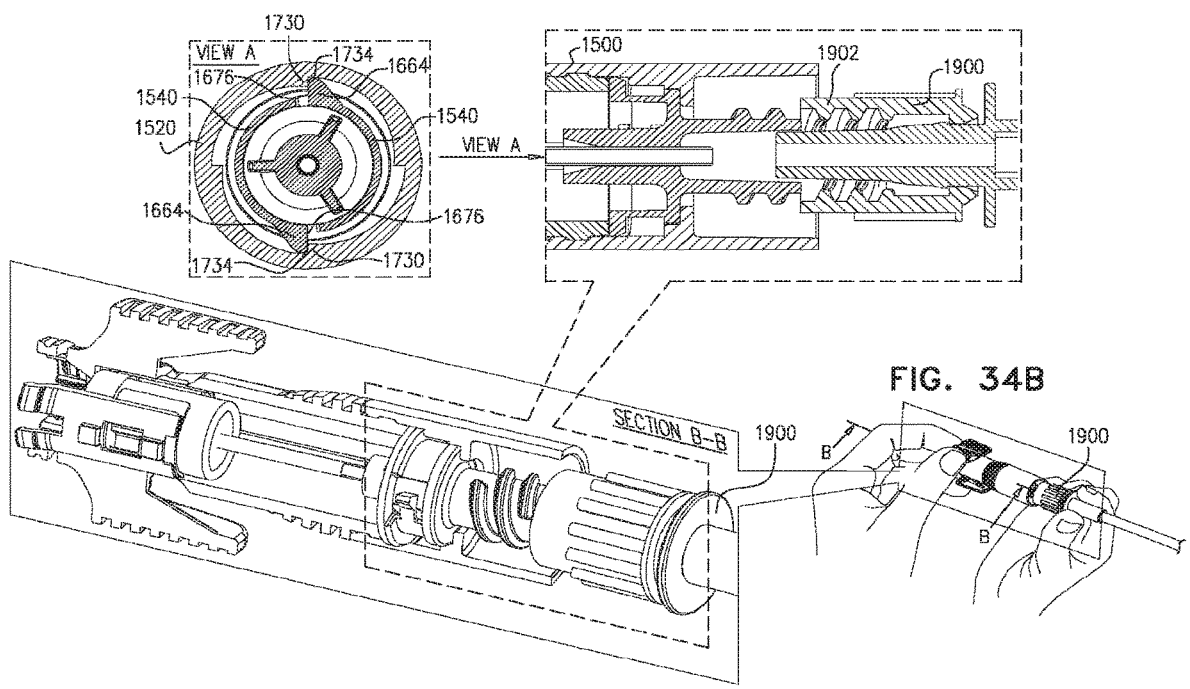

FIG. 34B illustrates initial forward axial displacement of luer lock connector 1900 relative to luer lock adaptor 1500 along axis 1501 such that the male luer connector 1902 is in touching engagement with female luer connector portion 1542 at a rearward-facing end thereof. The locking engagement of rearward housing portion 1520 and hub element 1540 is unchanged from that described hereinabove with reference to FIG. 34A.

Figure 34C:
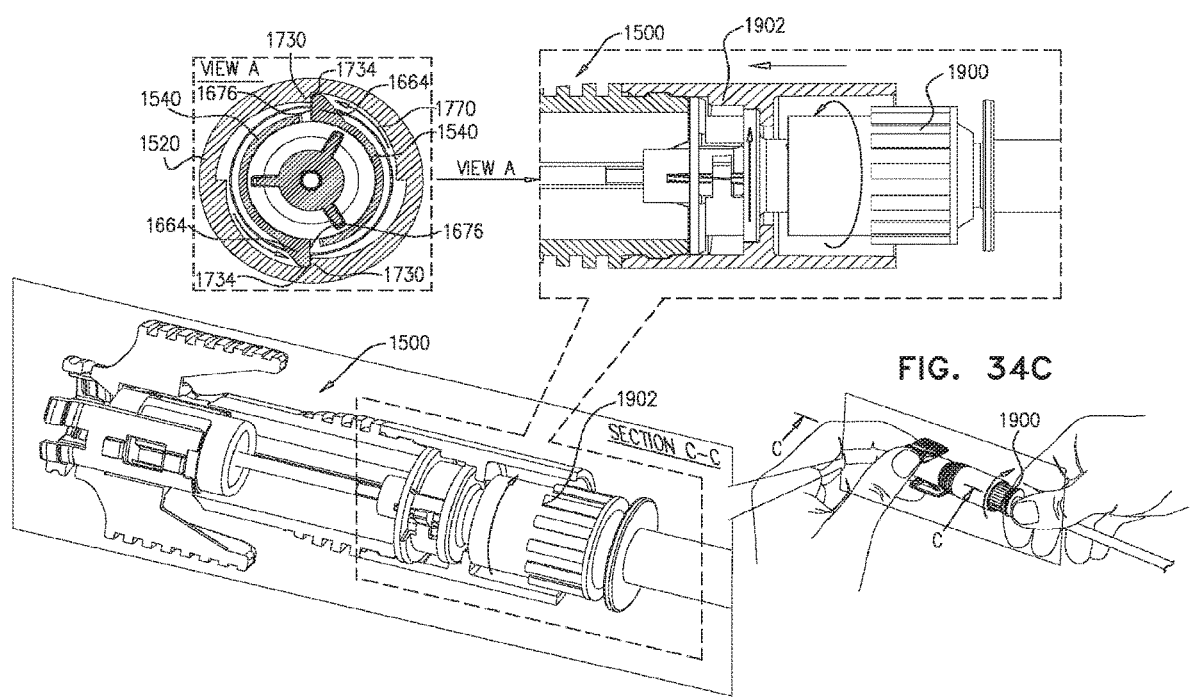

FIG. 34C illustrates clockwise rotation of the luer lock connector 1900 relative to luer lock adaptor 1500 about axis 1501, as indicated by arrow 1770, such that the male luer connector 1902 is in full threaded frictional engagement with female luer connector portion 1542 of hub element 1540. This rotation takes place without application of an additional forward axial force along axis 1501. This full threaded engagement is made possible by the aforementioned locking of rotation of hub element 1540 against clockwise rotation relative to rearward housing portion 1520.

Figure 34D:
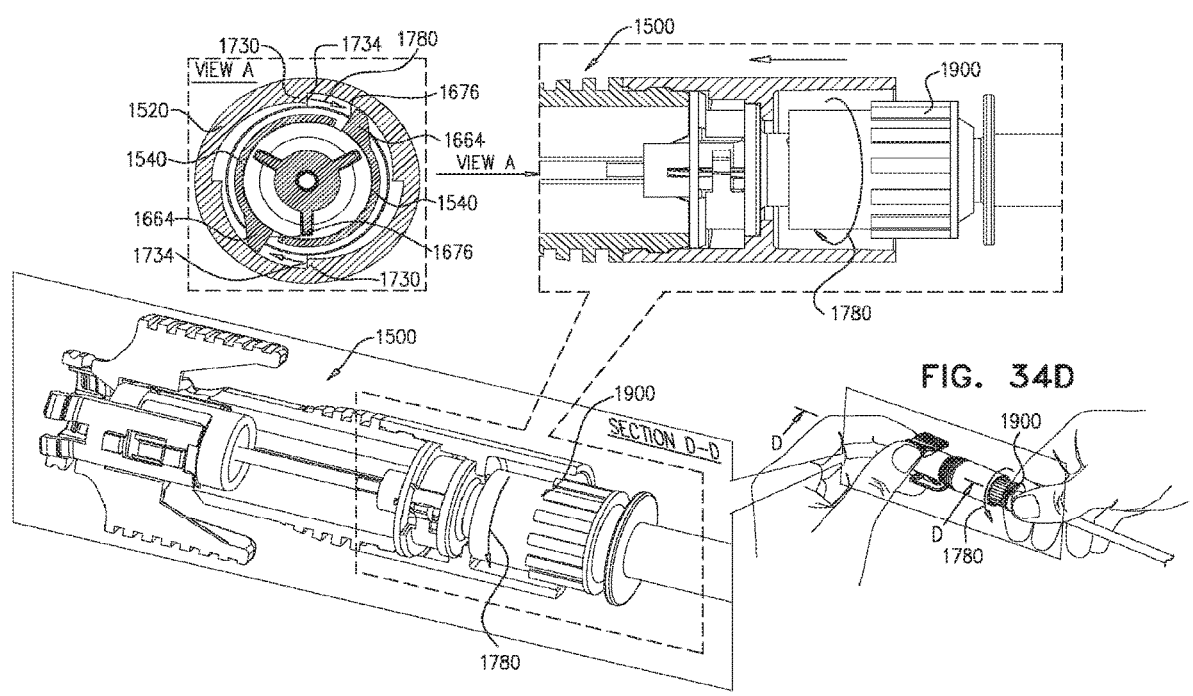
Figure 34E:
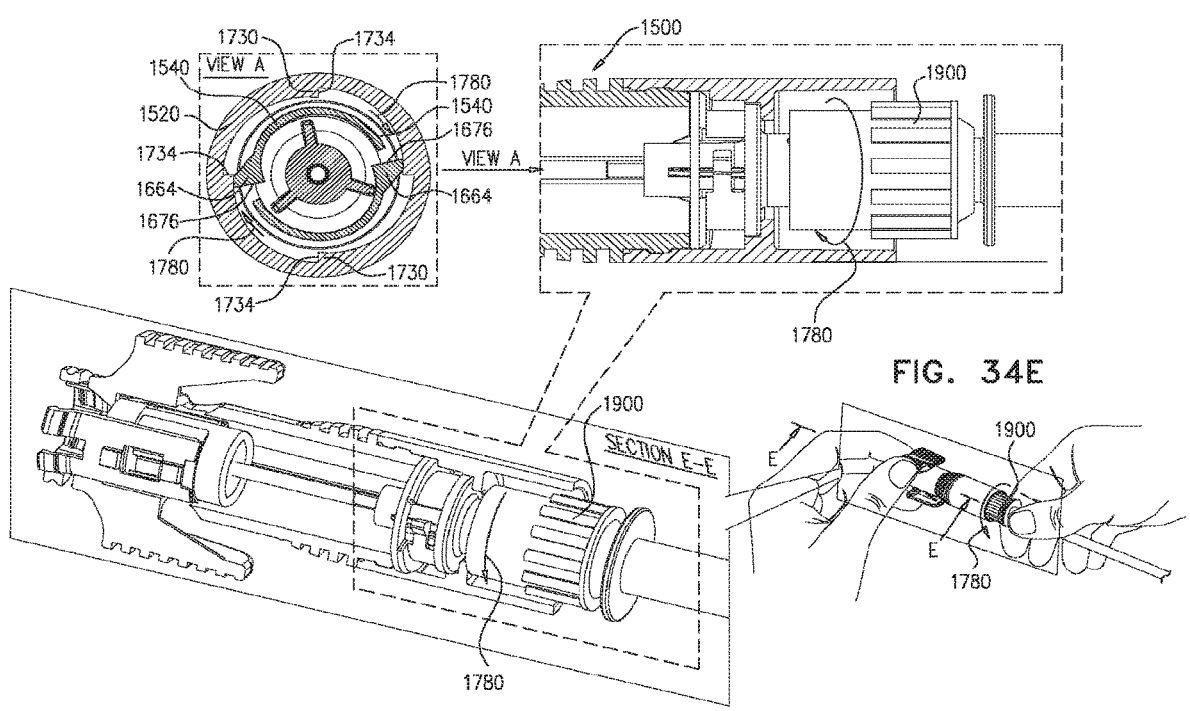
Figure 34F:
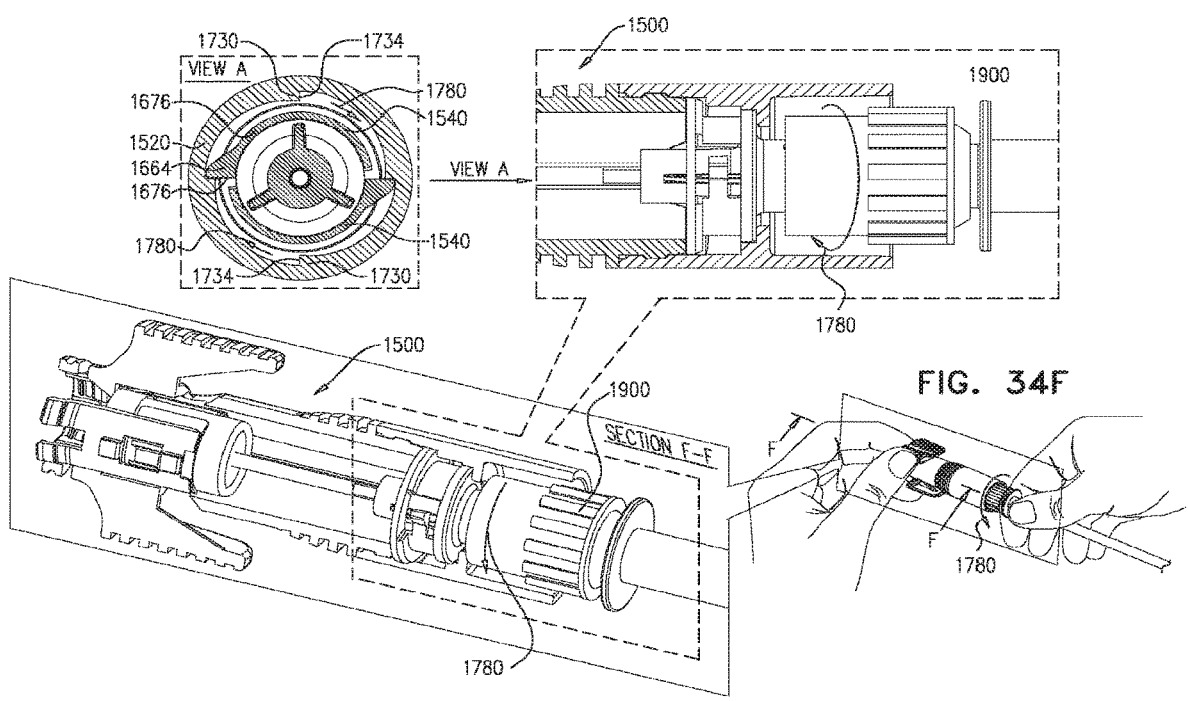

FIGS. 34D, 34E and 34F illustrate counterclockwise rotation of the luer lock connector 1900 relative to rearward housing portion 1520 of luer lock adaptor 1500 about axis 1501, as indicated by arrows 1820, in an attempt to disengage the male luer connector 1902 from the female luer connector portion 1542 of hub element 1540. This attempt is unsuccessful due to the frictional engagement of the male luer connector 1902 with the female luer connector portion 1542 of hub element 1540 and due to the fact that the hub element 1540 is free to rotate counterclockwise relative to the remainder of the luer lock adaptor 1500. It is seen in the sectional enlargement at View A in FIGS. 34D and 34E that radially directed locking surfaces 1676 of tooth elements 1664 no longer lockingly engage counterclockwise-facing, radially directed locking surfaces 1734 of teeth 1730 of rearward housing portion 1520 due to counterclockwise movement of the hub element 1540 relative to the rearward housing portion 1520. As seen in the sectional enlargement at View A in FIG. 34F, following a 90° rotation of luer lock connector 1900 and hub element 1540 relative to rearward housing portion 1520, radially directed locking surfaces 1676 of tooth elements 1664 again lockingly engage counterclockwise-facing, radially directed locking surfaces 1734 of teeth 1730 of rearward housing portion 1520 and prevent clockwise movement of the hub element 1540 relative to the rearward housing portion 1520 while allowing counterclockwise movement of the hub element 1540 relative to the rearward housing portion 1520.

It will be appreciated by persons skilled in the art that the present invention is not limited by what has been particularly shown and described hereinabove. Rather the scope of the present invention includes modifications and variations of the various features shown or described hereinabove as well as combinations and sub-combinations thereof which are not in the prior art.

What is claimed is:

1. A luer lock adaptor comprising:
   a housing defining an axis and comprising:
      a forward housing portion defining a port connection end; and
      a rearward housing portion defining a luer connection end;
   a first luer lock element comprising:
      a first locking surface located proximate the port connection end and comprising a needle mounting portion extending axially outward from the first locking surface;
      a second locking surface located proximate the luer connection end and comprising:
         a plurality of teeth; and
         a connector portion, each extending axially outward from the second locking surface; and
      an intermediate portion disposed between the first locking surface and the second locking surface;
   the first luer lock element being located internal to the rearward housing portion to prevent manual access to the first luer lock element, the first luer lock element being rotatably mounted to the axis in a manner that permits rotation of the first luer lock element relative to the housing in a first rotation direction about the axis and limits rotation of the first luer lock element relative to the housing in a second rotation direction about the axis, the first rotation direction being opposite the second rotation direction; and
   the connector portion of the first luer lock element being configured to form an irreversible connection with a mating component of a second luer lock element being located externally at an end of a syringe responsive to rotating the second luer lock element in a threaded engagement with the first luer lock element in the second rotation direction.

2. The luer lock adaptor of claim 1, wherein, in response to forming the irreversible connection between the first luer lock element and the second luer lock element, the second luer lock element cannot be disconnected from the first luer lock element by rotation of the second luer lock element in the first rotation direction, since the threaded engagement between the first luer lock element and the second luer lock element causes the first luer lock element to rotate in the first rotation direction together with the second luer lock element when the second luer lock element is rotated in the first rotation direction.

3. The luer lock adaptor of claim 1, wherein:
   the forward housing portion comprises:
      a first end disposed near the port connection end; and
      a second end disposed near the luer connection end, the second end comprising:
         an toothed edge comprising an axially-extending locking surface and a plurality of teeth; and
         an outward surface comprising protrusions; and
   the rearward housing portion comprises:
      a cylindrical element arranged along the axis;
      a first end located proximate the port connection end and disposed opposite a second end located proximate the luer connection end; and
      an inwardly directed flange intermediate the first end and the second end, the inwardly directed flange comprising a first end facing surface disposed opposite a second end facing surface, the first end facing surface comprising recesses, each of which comprises an inclined surface and an axial locking surface.

4. The luer lock adaptor of claim 3, wherein a quantity of the recesses of the first end facing surface is at least four.

5. The luer lock adaptor of claim 3, further comprising:
   a septa housing portion disposed within the forward housing portion.

6. The luer lock adaptor of claim 5, wherein the septa housing portion comprises:
   a cylindrical element comprising:
      a first end located proximate the port connection end and disposed opposite a second end located proximate the luer connection end;
      the first end comprising a first opening;
      the second end comprising a second opening; and
      a circumferential band disposed thereon, the circumferential band comprising protrusions extending radially outward from the cylindrical element.

7. The luer lock adaptor of claim 6, wherein the protrusions of the circumferential band engage recesses and forward stop-defining wall surfaces of an interior of the forward housing portion to limit displacement of the septa housing portion in the forward housing portion and to prevent azimuthal rotation of the septa housing portion about the axis.

8. The luer lock adaptor of claim 6, further comprising:
   a compression spring disposed between the first luer lock element and the septa housing portion.

9. The luer lock adaptor of claim 8, wherein the recesses on the first end facing surface of the inwardly directed flange associated with the rearward housing portion are configured to receive the protrusions of the forward housing portion to affix the first housing portion to the rearward housing portion and to prevent axial movement and azimuthal movement relative to the axis.

10. The luer lock adaptor of claim 9, wherein affixing the first housing portion to the rearward housing portion retains the first luer lock element between the first end facing surface of the rearward housing portion and the compression spring.

11. The luer lock adaptor of claim 9, wherein affixing the first housing portion to the rearward housing portion causes the plurality of teeth of the second locking surface associated with the first luer element to engage the recesses on the first end facing surface of the inwardly directed flange associated with the rearward housing portion and the second locking surface associated with the first luer element to engage the axial locking surface of the inwardly directed flange associated with the rearward housing portion.

12. The luer lock adaptor of claim 9, wherein:
   an axial separation between the first end facing surface of the rearward housing portion and the toothed edge of the forward housing portion is approximately 5.4 mm, and the axial separation between the first end facing surface of the rearward housing portion and the toothed edge of the forward housing portion remains constant due to affixing the forward housing portion to the rearward housing portion.

13. The luer lock adaptor of claim 5, wherein the septa housing portion is axially slidably mounted onto the forward housing portion via septa housing mounting legs.

14. The luer lock adaptor of claim 5, wherein:
the septa housing portion comprises a first end disposed opposite a second end and is configured to receive a forward septum and a rearward septum, and
the forward septum and the rearward septum are retained within the septa housing portion via ultrasonic swaging of edges located on the first end and the second end of septa housing portion.

15. The luer lock adaptor of claim 14, further comprising:
a needle mounted onto the needle mounting portion of the first luer lock element such that the needle extends along the axis into forward housing portion, wherein in an absence of a port connection at the port connection end, a sharp tip of the needle is located within the septa housing between the rearward septum and the forward septum.

16. The luer lock adaptor of claim 3, wherein, prior to connection of the second luer lock element, an axial separation between the toothed edge of the second end associated with the forward housing portion and the first locking surface of the first luer lock element is approximately 1.8 mm.

17. The luer lock adaptor of claim 3, wherein, prior to connection of the second luer lock element, an axial separation between the first end facing surface of the rearward housing portion and the second locking surface of the first luer lock element is in a range of approximately 0 mm to approximately 0.8 mm.

18. The luer lock adapter of claim 1, wherein the irreversible connection between the connector portion of the first luer lock element and the mating component of the second luer lock element is formed responsive to rotating the second luer lock element in the threaded engagement with the first luer lock element in the second rotation direction and applying an axial force.

19. The luer lock adapter of claim 18, wherein, responsive to the irreversible connection between the connector portion of the first luer lock element and the mating component of the second luer lock element, an axial separation between the toothed edge of the second end associated with the forward housing portion and the first locking surface of the first luer lock element is approximately 0 mm.

20. The luer lock adapter of claim 19, wherein, responsive to the irreversible connection between the connector portion of the first luer lock element and the mating component of the second luer lock element, an axial separation between the first end facing surface of the rearward housing portion and the second locking surface of the first luer lock element is approximately 1.8 mm.

\* \* \* \* \*